(12) United States Patent
Cao et al.

(10) Patent No.: US 11,701,385 B2
(45) Date of Patent: Jul. 18, 2023

(54) MODULATION OF CELL FUNCTION FOR IMMUNOTHERAPY

(71) Applicant: Innovative Cellular Therapeutics Holdings, Ltd., George Town (KY)

(72) Inventors: Zhiyuan Cao, Shanghai (CN); Chengfei Pu, Shanghai (CN); Lei Xiao, Shanghai (CN); Zhao Wu, Shanghai (CN)

(73) Assignee: Innovative Cellular Therapeutics Holdings, Ltd., George Town (KY)

( * ) Notice: Subject to any disclaimer, the term of this patent is extended or adjusted under 35 U.S.C. 154(b) by 838 days.

(21) Appl. No.: 16/555,198

(22) Filed: Aug. 29, 2019

(65) Prior Publication Data

US 2020/0069732 A1 Mar. 5, 2020

Related U.S. Application Data

(60) Provisional application No. 62/725,895, filed on Aug. 31, 2018.

(51) Int. Cl.
| | |
|---|---|
| *A61K 35/17* | (2015.01) |
| *C07K 16/28* | (2006.01) |
| *C07K 14/725* | (2006.01) |
| *A61K 47/65* | (2017.01) |
| *C07K 14/47* | (2006.01) |

(52) U.S. Cl.
CPC .............. *A61K 35/17* (2013.01); *A61K 47/65* (2017.08); *C07K 14/4748* (2013.01); *C07K 14/7051* (2013.01); *C07K 16/2803* (2013.01); *C07K 2317/53* (2013.01); *C07K 2317/622* (2013.01); *C07K 2319/03* (2013.01)

(58) Field of Classification Search
CPC .... A61K 35/17; A61K 47/65; C07K 14/4748; C07K 14/7051; C07K 16/2803; C07K 2317/53; C07K 2317/622; C07K 2319/03; C07K 14/7158
See application file for complete search history.

(56) References Cited

FOREIGN PATENT DOCUMENTS

WO    WO-2016109410 A2 * 7/2016 ............. A61K 35/17

OTHER PUBLICATIONS

Gowrishankar et al. Manipulating the tumor microenvironment by adoptive cell transfer of CAR T-cellsMammalian Genome. (2018) 29:739-756.Received: Mar. 30, 2018 / Accepted: Jun. 28, 2018 / Published online: Jul. 9, 2018 (Year: 2018).*

* cited by examiner

*Primary Examiner* — Amy E Juedes
*Assistant Examiner* — Brian Hartnett
(74) *Attorney, Agent, or Firm* — Lee & Hayes, P.C.

(57) ABSTRACT

Embodiments relate to a modified cell comprising an antigen binding molecule, and the expression and/or function of one or more genes in the modified cell has been enhanced or reduced or eliminated. The one or more genes include CXCR3, SLC1A3, YAP, TIGIT, S1P1, and IL-35. In embodiments, the cell is a T cell, a dendritic cell, a NK cell, or a macrophage cell. In embodiments, the antigen binding molecule comprises a chimeric antigen receptor (CAR) and/or the second antigen binding molecule is a T Cell Receptor (TCR).

14 Claims, 10 Drawing Sheets
Specification includes a Sequence Listing.

MODULATION OF CELL FUNCTION FOR IMMUNOTHERAPY

CROSS REFERENCE TO RELATED PATENT APPLICATIONS

This application claims the benefit of U.S. Provisional Application 62/725,895, filed on Aug. 31, 2018, which is hereby incorporated by reference in its entirety.

SEQUENCE LISTING INFORMATION

A computer readable textfile, entitled "SDS1.0062US Sequence Listing_ST25.K" created on or about Aug. 14, 2019, with a file size of about 320 KB, contains the sequence listing for this application and is hereby incorporated by reference in its entirety.

TECHNICAL FIELD

The present disclosure relates to compositions and methods of using CAR T cell therapy to treat diseases including cancer.

BACKGROUND

T cells genetically targeted to certain malignancies have demonstrated tremendous clinical outcomes. During CAR-T cell therapy, physicians draw patients' blood and harvest her cytotoxic T cells. The cells are re-engineered in a lab to attack her particular cancer. Recent progress in genome editing technologies allow scientists to disrupt gene expression in T-cells in order to enhance effector functions or to bypass tumor immune suppression and metabolically hostile tumor microenvironment. Thus, there is a need to modulate T cell to overcome these problems.

SUMMARY

Embodiments relate to a modified cell comprising an antigen binding molecule, and expression and/or function of one or more genes in the modified cell has been enhanced or reduced or eliminated. The one or more genes include CXCR3, SLC1A3, YAP, TIGIT, S1P1, and IL-35. In embodiments, the cell is a T cell, a dendritic cell, a NK cell, or a macrophage cell. In embodiments, the antigen binding molecule comprises a chimeric antigen receptor (CAR) and/or the second antigen binding molecule is a T Cell Receptor (TCR).

This Summary is not intended to identify key features or essential features of the claimed subject matter, nor is it intended to be used to limit the scope of the claimed subject matter.

BRIEF DESCRIPTION OF THE DRAWINGS

The Detailed Description is described with reference to the accompanying figures. The use of the same reference numbers in different figures indicates similar or identical items.

DETAILED DESCRIPTION

Figure 1:
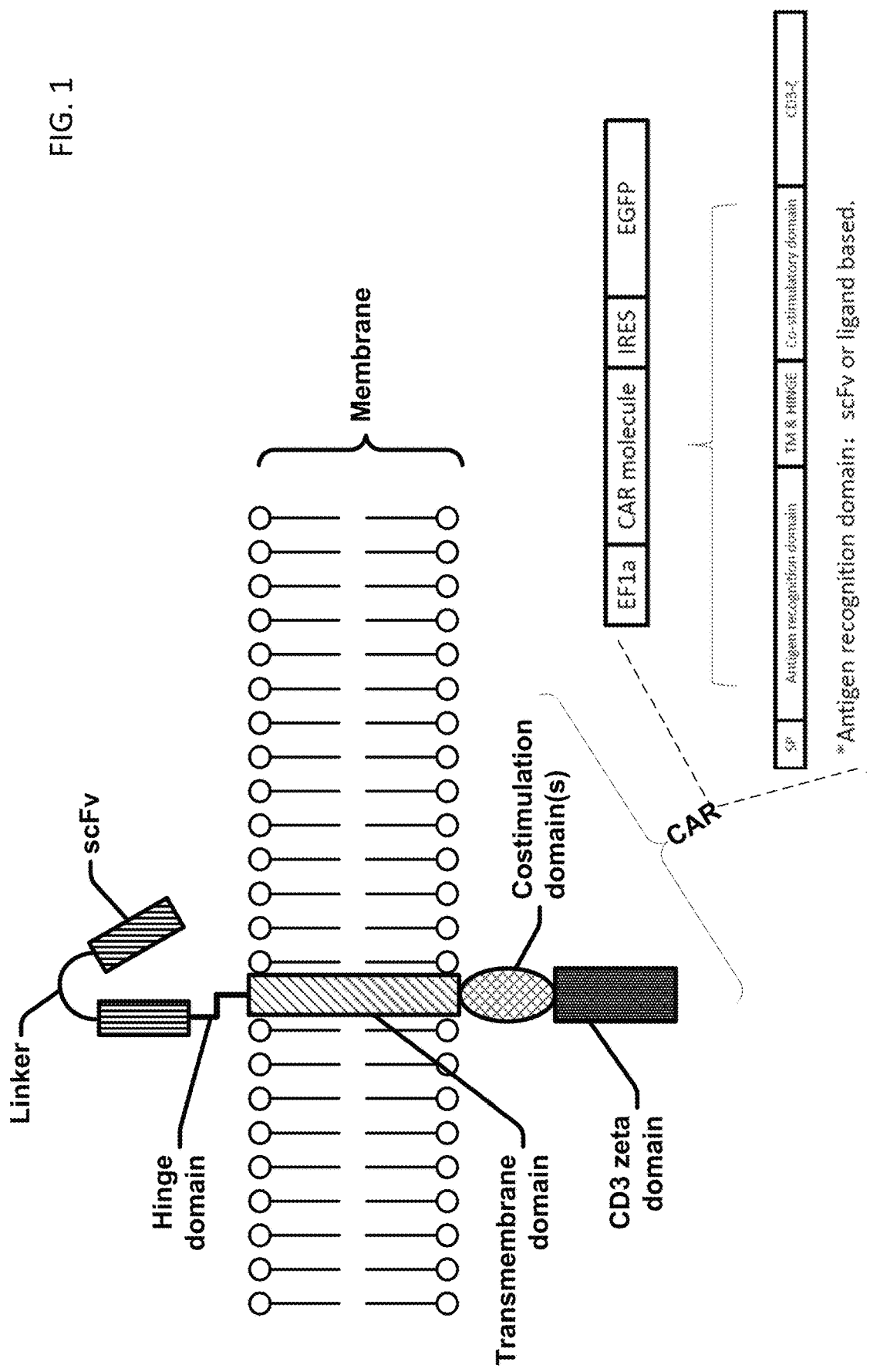
FIG. 1 shows an example of CAR structure.

Unless defined otherwise, all technical and scientific terms used herein have the same meaning as commonly understood by those of ordinary skill in the art to which the disclosure belongs. Although any methods and materials similar or equivalent to those described herein can be used in the practice or testing of the present disclosure, preferred methods and materials are described. For the purposes of the present disclosure, the following terms are defined below.

The articles "a" and "an" are used herein to refer to one or to more than one (i.e., to at least one) of the grammatical object of the article. By way of example, "an element" means one element or more than one element.

By "about" is meant a quantity, level, value, number, frequency, percentage, dimension, size, amount, weight or length that varies by as much as 20, 15, 10, 9, 8, 7, 6, 5, 4, 3, 2 or 1% to a reference quantity, level, value, number, frequency, percentage, dimension, size, amount, weight or length.

The term "activation," as used herein, refers to the state of a cell that has been sufficiently stimulated to induce detectable cellular proliferation. Activation can also be associated with induced cytokine production and detectable effector functions. The term "activated T cells" refers to, among other things, T cells that are undergoing cell division.

The term "antibody" is used in the broadest sense and refers to monoclonal antibodies (including full length monoclonal antibodies), polyclonal antibodies, multi-specific antibodies (e.g., bispecific antibodies), and antibody fragments so long as they exhibit the desired biological activity or function. The antibodies in the present disclosure may exist in a variety of forms including, for example, polyclonal antibodies, monoclonal antibodies, Fv, Fab and F(ab)$_2$, as well as single chain antibodies and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

The term "antibody fragments" refers to a portion of a full length antibody, for example, the antigen binding or variable region of the antibody. Other examples of antibody fragments include Fab, Fab', F(ab')2, and Fv fragments; diabodies; linear antibodies; single-chain antibody molecules; and multi-specific antibodies formed from antibody fragments.

The term "Fv" refers to the minimum antibody fragment which contains a complete antigen-recognition and -binding site. This fragment consists of a dimer of one heavy- and one light-chain variable region domain in tight, non-covalent association. From the folding of these two domains emanates six hypervariable loops (3 loops each from the H and L chain) that contribute the amino acid residues for antigen binding and confer antigen binding specificity to the antibody. However, even a single variable domain (or half of a Fv including only three complementarity determining regions (CDRs) specific for an antigen) has the ability to recognize and bind antigen, although at a lower affinity than the entire binding site (the dimer).

An "antibody heavy chain," as used herein, refers to the larger of the two types of polypeptide chains present in all antibody molecules in their naturally occurring conformations. An "antibody light chain," as used herein, refers to the smaller of the two types of polypeptide chains present in all antibody molecules in their naturally occurring conformations. K and λ light chains refer to the two major antibody light chain isotypes.

The term "synthetic antibody" refers to an antibody which is generated using recombinant DNA technology, such as, for example, an antibody expressed by a bacteriophage. The term also includes an antibody which has been generated by the synthesis of a DNA molecule encoding the antibody and the expression of the DNA molecule to obtain the antibody, or to obtain an amino acid encoding the antibody. The synthetic DNA is obtained using technology that is available and well known in the art.

The term "antigen" refers to a molecule that provokes an immune response, which may involve either antibody production, or the activation of specific immunologically-competent cells, or both. Antigens include any macromolecule, including all proteins or peptides, or molecules derived from recombinant or genomic DNA. For example, DNA including a nucleotide sequence or a partial nucleotide sequence encoding a protein or peptide that elicits an immune response, and therefore, encodes an "antigen" as the term is used herein. An antigen need not be encoded solely by a full-length nucleotide sequence of a gene. An antigen can be generated, synthesized or derived from a biological sample including a tissue sample, a tumor sample, a cell, or a biological fluid.

The term "anti-tumor effect" as used herein, refers to a biological effect associated with a decrease in tumor volume, a decrease in the number of tumor cells, a decrease in the number of metastases, decrease in tumor cell proliferation, decrease in tumor cell survival, an increase in life expectancy of a subject having tumor cells, or amelioration of various physiological symptoms associated with the cancerous condition. An "anti-tumor effect" can also be manifested by the ability of the peptides, polynucleotides, cells, and antibodies in the prevention of the occurrence of tumor in the first place.

The term "auto-antigen" refers to an antigen mistakenly recognized by the immune system as being foreign. Auto-antigens include cellular proteins, phosphoproteins, cellular surface proteins, cellular lipids, nucleic acids, glycoproteins, including cell surface receptors.

The term "autologous" is used to describe a material derived from a subject which is subsequently re-introduced into the same subject.

The term "allogeneic" is used to describe a graft derived from a different subject of the same species. As an example, a donor subject may be a related or unrelated or recipient subject, but the donor subject has immune system markers which are similar to the recipient subject.

The term "xenogeneic" is used to describe a graft derived from an subject of a different species. As an example, the donor subject is from a different species than a recipient subject and the donor subject and the recipient subject can be genetically and immunologically incompatible.

The term "cancer" as used to refer to a disease characterized by the rapid and uncontrolled growth of aberrant cells. Cancer cells can spread locally or through the bloodstream and lymphatic system to other parts of the body. Examples of various cancers include breast cancer, prostate cancer, ovarian cancer, cervical cancer, skin cancer, pancreatic cancer, colorectal cancer, renal cancer, liver cancer, brain cancer, lymphoma, leukemia, lung cancer, and the like.

Throughout this specification, unless the context requires otherwise, the words "comprise," "includes" and "including" will be understood to imply the inclusion of a stated step or element or group of steps or elements but not the exclusion of any other step or element or group of steps or elements.

The phrase "consisting of" is meant to include, and is limited to, whatever follows the phrase "consisting of." Thus, the phrase "consisting of" indicates that the listed elements are required or mandatory and that no other elements may be present.

The phrase "consisting essentially of" is meant to include any elements listed after the phrase and can include other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

The terms "complementary" and "complementarity" refer to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands.

The term "corresponds to" or "corresponding to" refers to (a) a polynucleotide having a nucleotide sequence that is substantially identical or complementary to all or a portion of a reference polynucleotide sequence or encoding an amino acid sequence identical to an amino acid sequence in a peptide or protein; or (b) a peptide or polypeptide having an amino acid sequence that is substantially identical to a sequence of amino acids in a reference peptide or protein.

The term "co-stimulatory ligand," refers to a molecule on an antigen presenting cell (e.g., an APC, dendritic cell, B cell, and the like) that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including at least one of proliferation, activation, differentiation, and other cellular responses. A co-stimulatory ligand can include B7-1 (CD80), B7-2 (CD86), PD-L1, PD-L2, 4-1BBL, OX40L, inducible co-stimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, a ligand for CD7, an agonist or antibody that binds the Toll ligand receptor and a ligand that specifically binds with B7-H3. A co-stimulatory ligand also includes, inter alia, an agonist or an antibody that specifically binds with a co-stimulatory molecule present on a T cell, such as CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds CD83.

The term "co-stimulatory molecule" refers to the cognate binding partner on a T cell that specifically binds with a co-stimulatory ligand, thereby mediating a co-stimulatory response by the T cell, such as proliferation. Co-stimulatory molecules include an MHC class I molecule, BTLA, and a Toll-like receptor.

The term "co-stimulatory signal" refers to a signal, which in combination with a primary signal, such as TCR/CD3 ligation, leads to T cell proliferation and/or upregulation or downregulation of key molecules. The terms "disease" and "condition" may be used interchangeably or may be different in that the particular malady or condition may not have a known causative agent (so that etiology has not yet been worked out), and it is therefore not yet recognized as a disease but only as an undesirable condition or syndrome, wherein a more or less specific set of symptoms have been identified by clinicians. The term "disease" is a state of health of a subject wherein the subject cannot maintain homeostasis, and wherein if the disease is not ameliorated then the subject's health continues to deteriorate. In contrast, a "disorder" in a subject is a state of health in which the animal is able to maintain homeostasis, but in which the animal's state of health is less favorable than it would be in the absence of the disorder. Left untreated, a disorder does not necessarily cause a further decrease in the animal's state of health.

The term "effective" refers to adequate to accomplish a desired, expected, or intended result. For example, an "effective amount" in the context of treatment may be an amount of a compound sufficient to produce a therapeutic or prophylactic benefit.

The term "encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence (except that a "T" is replaced by a "U") and is usually provided in sequence listings, and the non-coding strand, used as the template for transcription of a gene or cDNA, can be referred to as encoding the protein or other product of that gene or cDNA.

The term "exogenous" refers to a molecule that does not naturally occur in a wild-type cell or organism but is typically introduced into the cell by molecular biological techniques. Examples of exogenous polynucleotides include vectors, plasmids, and/or man-made nucleic acid constructs encoding the desired protein. With regard to polynucleotides and proteins, the term "endogenous" or "native" refers to naturally-occurring polynucleotide or amino acid sequences that may be found in a given wild-type cell or organism. Also, a particular polynucleotide sequence that is isolated from a first organism and transferred to a second organism by molecular biological techniques is typically considered an "exogenous" polynucleotide or amino acid sequence with respect to the second organism. In specific embodiments, polynucleotide sequences can be "introduced" by molecular biological techniques into a microorganism that already contains such a polynucleotide sequence, for instance, to create one or more additional copies of an otherwise naturally-occurring polynucleotide sequence, and thereby facilitate overexpression of the encoded polypeptide.

In embodiments, the polynucleotide may integrate into the genome of the modified cell and descendants of the modified cell will also express the polynucleotide, resulting in a stably transfected modified cell. In embodiments, the modified cell may express the polynucleotide encoding the CAR but the polynucleotide does not integrate into the genome of the modified cell such that the modified cell expresses the transiently transfected polynucleotide for a finite period of time (e.g., several days), after which the polynucleotide is lost through cell division or other factors. For example, the polynucleotide is present in the modified cell in a recombinant DNA construct, in an mRNA, or in a viral vector, and/or the polynucleotide is an mRNA, which is not integrated into the genome of the modified cell.

The term "expression" refers to the transcription and/or translation of a particular nucleotide sequence driven by its promoter.

The term "expression vector" refers to a vector including a recombinant polynucleotide including expression control sequences operably linked to a nucleotide sequence to be expressed. An expression vector includes sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

The term "homologous" refers to sequence similarity or sequence identity between two polypeptides or between two polynucleotides when a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared× 100. For example, if 6 of 10 of the positions in two sequences are matched or homologous then the two sequences are 60% homologous. By way of example, the DNA sequences ATTGCC and TATGGC share 50% homology. A comparison is made when two sequences are aligned to give maximum homology.

The term "immunoglobulin" or "Ig," refers to a class of proteins, which function as antibodies. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses, and is important in defense against bacteria and viruses. IgD is the immunoglobulin that has no known antibody function but may serve as an antigen receptor. IgE is the immunoglobulin that mediates immediate hypersensitivity by causing the release of mediators from mast cells and basophils upon exposure to the allergen.

The term "isolated" refers to a material that is substantially or essentially free from components that normally accompany it in its native state. The material can be a cell or a macromolecule such as a protein or nucleic acid. For example, an "isolated polynucleotide," as used herein, refers to a polynucleotide, which has been purified from the sequences which flank it in a naturally-occurring state, e.g., a DNA fragment which has been removed from the sequences that are normally adjacent to the fragment. Alternatively, an "isolated peptide" or an "isolated polypeptide" and the like, as used herein, refer to in vitro isolation and/or purification of a peptide or polypeptide molecule from its natural cellular environment, and from association with other components of the cell.

The term "substantially purified" refers to a material that is substantially frr from components that normally associated with it in its native state. For example, a substantially purified cell refers to a cell that has been separated from other cell types with which it is normally associated in its naturally occurring or native state. In some instances, a population of substantially purified cells refers to a homogenous population of cells. In other instances, this term refers simply to a cell that has been separated from the cells with which they are naturally associated in their natural state. In some embodiments, the cells are cultured in vitro. In other embodiments, the cells are not cultured in vitro.

In the context of the present disclosure, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "lentivirus" refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. Moreover, the use of lentiviruses enables integration of the genetic information into the host chromosome resulting in stably transduced genetic information. HIV, SIV, and FIV are all examples of lentiviruses. Vectors derived from lentiviruses offer the means to achieve significant levels of gene transfer in vivo.

The term "modulating," refers to mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation.

The term "under transcriptional control" refers to a promoter being operably linked to and in the correct location and orientation in relation to a polynucleotide to control the initiation of transcription by RNA polymerase and expression of the polynucleotide.

The term "overexpressed" tumor antigen or "overexpression" of the tumor antigen is intended to indicate an abnormal level of expression of the tumor antigen in a cell from a disease area such as a solid tumor within a specific tissue or organ of the patient relative to the level of expression in a normal cell from that tissue or organ. Patients having solid tumors or a hematological malignancy characterized by overexpression of the tumor antigen can be determined by standard assays known in the art.

The term "parenteral administration" of a composition includes, e.g., subcutaneous (s.c.), intravenous (i.v.), intramuscular (i.m.), intrasternal injection, or infusion techniques.

The terms "patient," "subject," and "individual," and the like are used interchangeably herein, and refer to any human, animal, or living organism, amenable to the methods described herein. In certain non-limiting embodiments, the patient, subject, or individual is a human or animal. In some embodiments, the term "subject" is intended to include living organisms in which an immune response can be elicited (e.g., mammals). Examples of subjects include humans, and animals such as dogs, cats, mice, rats, and transgenic species thereof.

A subject in need of a treatment or in need thereof includes a subject having a disease, condition, or disorder that needs to be treated. A subject in need thereof also includes a subject that needs treatment for prevention of a disease, condition, or disorder.

The term "polynucleotide" or "nucleic acid" refers to mRNA, RNA, cRNA, rRNA, cDNA or DNA. The term typically refers to a polymeric form of nucleotides of at least 10 bases in length, either ribonucleotides or deoxynucleotides or a modified form of either type of nucleotide. The term includes all forms of nucleic acids including single and double stranded forms of nucleic acids.

The terms "polynucleotide variant" and "variant" and the like refer to polynucleotides displaying substantial sequence identity with a reference polynucleotide sequence or polynucleotides that hybridize with a reference sequence under stringent conditions that are defined hereinafter. These terms also encompass polynucleotides that are distinguished from a reference polynucleotide by the addition, deletion or substitution of at least one nucleotide. Accordingly, the terms "polynucleotide variant" and "variant" include polynucleotides in which one or more nucleotides have been added or deleted or replaced with different nucleotides. In this regard, it is well understood in the art that certain alterations inclusive of mutations, additions, deletions, and substitutions can be made to a reference polynucleotide whereby the altered polynucleotide retains the biological function or activity of the reference polynucleotide or has increased activity in relation to the reference polynucleotide (i.e., optimized). Polynucleotide variants include, for example, polynucleotides having at least 50% (and at least 51% to at least 99% and all integer percentages in between, e.g., 90%, 95%, or 98%) sequence identity with a reference polynucleotide sequence described herein. The terms "polynucleotide variant" and "variant" also include naturally-occurring allelic variants and orthologs.

The terms "polypeptide," "polypeptide fragment," "peptide," and "protein" are used interchangeably herein to refer to a polymer of amino acid residues and to variants and synthetic analogues of the same. Thus, these terms apply to amino acid polymers in which one or more amino acid residues are synthetic non-naturally occurring amino acids, such as a chemical analogue of a corresponding naturally occurring amino acid, as well as to naturally-occurring amino acid polymers. In certain aspects, polypeptides may include enzymatic polypeptides, or "enzymes," which typically catalyze (i.e., increase the rate of) various chemical reactions.

The term "polypeptide variant" refers to polypeptides that are distinguished from a reference polypeptide sequence by the addition, deletion, or substitution of at least one amino acid residue. In certain embodiments, a polypeptide variant is distinguished from a reference polypeptide by one or more substitutions, which may be conservative or non-conservative. In certain embodiments, the polypeptide variant comprises conservative substitutions and, in this regard, it is well understood in the art that some amino acids may be changed to others with broadly similar properties without changing the nature of the activity of the polypeptide. Polypeptide variants also encompass polypeptides in which one or more amino acids have been added or deleted or replaced with different amino acid residues.

The term "promoter" refers to a DNA sequence recognized by the synthetic machinery of the cell or introduced synthetic machinery, required to initiate the specific transcription of a polynucleotide sequence. The term "expression control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

The term "bind," "binds," or "interacts with" refers to a molecule recognizing and adhering to a particular second molecule in a sample or organism but does not substantially recognize or adhere to other structurally unrelated molecules in the sample. The term "specifically binds," as used herein with respect to an antibody, refers to an antibody which recognizes a specific antigen, but does not substantially recognize or bind other molecules in a sample. For example, an antibody that specifically binds an antigen from one species may also bind that antigen from one or more species. But, such cross-species reactivity does not itself alter the classification of an antibody as specific. In another example, an antibody that specifically binds an antigen may also bind different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds a specific protein structure rather than to any protein. If an antibody is specific for epitope "A," the presence of a molecule containing epitope A (or free, unlabeled A), in a reaction containing labeled "A" and the antibody, will reduce the amount of labeled A bound to the antibody.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding, and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

Zinc finger binding domains can be "engineered" to bind to a predetermined nucleotide sequence, for example via engineering (altering one or more amino acids) of the recognition helix region of a naturally occurring zinc finger protein. Further, a Zinc finger binding domain may be fused a DNA-cleavage domain to form a Zinc finger nuclease (ZFN) targeting a specific desired DNA sequence. For example, a pair of ZFNs (e.g., a ZFN-left arm and a ZFN-right arm) may be engineered to target and cause modifications of specific desired DNA sequences (e.g., TRAC genes), as illustrated in FIG. 1.

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "target site" or "target sequence" is a nucleic acid sequence that defines a portion of a nucleic acid to which a binding molecule will bind, provided sufficient conditions for binding exist. For example, the sequence 5' GAATTC 3' is a target site for the Eco RI restriction endonuclease. Exemplary target sites for various targeted ZFPs are shown in Table 1.

A "fusion" molecule is a molecule in which two or more subunit molecules are linked, preferably covalently. The subunit molecules can be the same chemical type of molecule or can be different chemical types of molecules. Examples of the first type of fusion molecule include, but are not limited to, fusion proteins (for example, a fusion between a ZFP DNA-binding domain and one or more activation domains) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage, and polypeptide ligation can also be involved in the expression of the protein in a cell. Methods for polynucleotide and polypeptide delivery to cells are presented elsewhere in this disclosure.

"Modulation" of gene expression refers to a change in the activity of a gene. Modulation of expression can include but is not limited to, gene activation and gene repression. Genome editing (e.g., cleavage, alteration, inactivation, random mutation) can be used to modulate expression. Gene inactivation refers to any reduction in gene expression as compared to a cell that does not include a ZFP as described herein. Thus, gene inactivation may be partial or complete.

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

By "statistically significant," it is meant that the result was unlikely to have occurred by chance. Statistical significance can be determined by any method known in the art. Commonly used measures of significance include the p-value, which is the frequency or probability with which the observed event would occur if the null hypothesis were true. If the obtained p-value is smaller than the significance level, then the null hypothesis is rejected. In simple cases, the significance level is defined at a p-value of 0.05 or less. A "decreased" or "reduced" or "lesser" amount is typically a "statistically significant" or a physiologically significant amount, and may include a decrease that is about 1.1, 1.2, 1.3, 1.4, 1.5, 1.6 1.7, 1.8, 1.9, 2, 2.5, 3, 3.5, 4, 4.5, 5, 6, 7, 8, 9, 10, 15, 20, 30, 40, or 50 or more times (e.g., 100, 500, 1000 times) (including all integers and decimal points in between and above 1, e.g., 1.5, 1.6, 1.7. 1.8, etc.) an amount or level described herein.

The term "stimulation," refers to a primary response induced by binding of a stimulatory molecule (e.g., a TCR/CD3 complex) with its cognate ligand thereby mediating a signal transduction event, such as signal transduction via the TCR/CD3 complex. Stimulation can mediate altered expression of certain molecules, such as downregulation of TGF-β, and/or reorganization of cytoskeletal structures. CD3 zeta is not the only suitable primary signaling domain for a CAR construct with respect to the primary response. For example, back in 1993, both CD3 zeta and FcR gamma were shown as functional primary signaling domains of CAR molecules. Eshhar et al., "Specific activation and targeting of cytotoxic lymphocytes through chimeric single chains consisting of antibody-binding domains and the gamma or zeta subunits of the immunoglobulin and T-cell receptors" PNAS, 1993 Jan. 15; 90(2):720-4, showed that two CAR constructs in which an scFv was fused to "either the FcR y chain or the CD3 complex s chain" triggered T cell activation and target cell. Notably, as demonstrated in Eshhar et al., CAR constructs containing only the primary signaling domain CD3 zeta or FcR gamma are functional without the co-presence of co-stimulatory domains. Additional non-CD3 zeta based CAR constructs have been developed over the years. For example, Wang et al., "A Chimeric Antigen Receptor (CARs) Based Upon a Killer Immunoglobulin-Like Receptor (KIR) Triggers Robust Cytotoxic Activity in Solid Tumors" Molecular Therapy, vol. 22, no. Suppl.1, May 2014, page S57, tested a CAR molecule in which an scFv was fused to "the transmembrane and cytoplasmic domain of" a killer immunoglobulin-like receptor (KIR). Wang et al. states that, "a KIR-based CAR targeting mesothelin (SS 1-KIR) triggers antigen-specific cytotoxic activity and cytokine production that is comparable to CD3~-based CARs." A second publication from the same group, Wang et al., "Generation of Potent T-cell Immunotherapy for Cancer Using DAP12-Based, Multichain, Chimeric Immunoreceptors" Cancer Immunol Res. 2015 July; 3(7):815-26, showed that a CAR molecule in which "a single-chain variable fragment for antigen recognition [was fused] to the transmembrane and cytoplasmic domains of KIR2DS2, a stimulatory killer immunoglobulin-like receptor (KIR)" functioned both in vitro and in vivo "when introduced into human T cells with DAP12, an immunotyrosine-based activation motifs-containing adaptor."

The term "stimulatory molecule" refers to a molecule on a T cell that specifically binds a cognate stimulatory ligand present on an antigen presenting cell. For example, a functional signaling domain derived from a stimulatory molecule is the zeta chain associated with the T cell receptor complex.

The term "stimulatory ligand" refers to a ligand that when present on an antigen presenting cell (e.g., an APC, a dendritic cell, a B-cell, and the like.) can specifically bind with a cognate binding partner (referred to herein as a "stimulatory molecule") on a cell, for example a T cell, thereby mediating a primary response by the T cell, including activation, initiation of an immune response, proliferation, and similar processes. Stimulatory ligands are well-known in the art and encompass, inter alia, an MHC Class I molecule loaded with a peptide, an anti-CD3 antibody, a superagonist anti-CD28 antibody, and a superagonist anti-CD2 antibody.

The term "therapeutic" refers to a treatment and/or prophylaxis. A therapeutic effect is obtained by suppression, remission, or eradication of a disease state or alleviating the symptoms of a disease state.

The term "therapeutically effective amount" refers to the amount of the subject compound that will elicit the biological or medical response of a tissue, system, or subject that is being sought by the researcher, veterinarian, medical doctor or another clinician. The term "therapeutically effective amount" includes that amount of a compound that, when administered, is sufficient to prevent the development of, or alleviate to some extent, one or more of the signs or symptoms of the disorder or disease being treated. The therapeutically effective amount will vary depending on the compound, the disease and its severity and the age, weight, etc., of the subject to be treated.

The term "treat a disease" refers to the reduction of the frequency or severity of at least one sign or symptom of a disease or disorder experienced by a subject.

The term "transfected" or "transformed" or "transduced" refers to a process by which an exogenous nucleic acid is transferred or introduced into the host cell. A "transfected" or "transformed" or "transduced" cell is one which has been transfected, transformed, or transduced with exogenous nucleic acid. The cell includes the primary subject cell and its progeny.

The term "vector" refers to a polynucleotide that comprises an isolated nucleic acid and which can be used to deliver the isolated nucleic acid to the interior of a cell. Numerous vectors are known in the art including linear polynucleotides, polynucleotides associated with ionic or amphiphilic compounds, plasmids, and viruses. Thus, the term "vector" includes an autonomously replicating plasmid or a virus. The term also includes non-plasmid and non-viral compounds which facilitate transfer of nucleic acid into cells, such as, for example, polylysine compounds, liposomes, and the like. Examples of viral vectors include, adenoviral vectors, adeno-associated virus vectors, retroviral vectors, and others. For example, lentiviruses are complex retroviruses, which, in addition to the common retroviral genes gag, pol, and env, contain other genes with regulatory or structural function. Lentiviral vectors are well known in the art. Some examples of lentivirus include the Human Immunodeficiency Viruses: HIV-1, HIV-2, and the Simian Immunodeficiency Virus: SIV. Lentiviral vectors have been generated by multiply attenuating the HIV virulence genes, for example, the genes env, vif, vpr, vpu, and nef are deleted making the vector biologically safe.

Ranges: throughout this disclosure, various aspects of the disclosure can be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Embodiments relate to a modified cell comprising: an antigen binding molecule; and a disruption in an endogenous gene or an addition of an exogenous gene that are associated with a biosynthesis or transportation pathway of at least one of CXCR3, SLC1A3, YAP, TIGIT, S1P1, and IL-35. In some embodiments, the cell is a T cell, a dendritic cell, a NK cell, or a macrophage cell. In some embodiments, the antigen binding molecule comprises a chimeric antigen receptor (CAR) and/or the second antigen binding molecule is a T Cell Receptor (TCR).

Modified T-cells may be derived from a stem cell. The stem cells may be adult stem cells, embryonic stem cells, more particularly non-human stem cells, cord blood stem cells, progenitor cells, bone marrow stem cells, induced pluripotent stem cells, totipotent stem cells or hematopoietic stem cells. A modified cell may also be a dendritic cell, a NK-cell, a B-cell or a T-cell selected from the group consisting of inflammatory T-lymphocytes, cytotoxic T-lymphocytes, regulatory T-lymphocytes or helper T-lymphocytes. In another embodiment, Modified cells may be derived from the group consisting of CD4+T-lymphocytes and CD8+T-lymphocytes. Prior to expansion and genetic modification of the cells of the invention, a source of cells may be obtained from a subject through a variety of non-limiting methods. T cells may be obtained from a number of non-limiting sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T cell lines available and known to those skilled in the art, may be used. In embodiments, modified cells may be derived from a healthy donor, from a patient diagnosed with cancer or from a patient diagnosed with an infection. In embodiments, modified cell is part of a mixed population of cells which present different phenotypic characteristics.

The term "stem cell" refers to any of certain types of cell which have the capacity for self-renewal and the ability to differentiate into other kind(s) of cell. For example, a stem cell gives rise either to two daughter stem cells (as occurs in vitro with embryonic stem cells in culture) or to one stem cell and a cell that undergoes differentiation (as occurs e.g. in hematopoietic stem cells, which give rise to blood cells). Different categories of stem cell may be distinguished on the basis of their origin and/or on the extent of their capacity for differentiation into other types of cell. For example, stem cell may include embryonic stem (ES) cells (i.e., pluripotent stem cells), somatic stem cells, Induced pluripotent stem cells, and any other types stem cells.

The pluripotent embryonic stem cells may be found in the inner cell mass of a blastocyst and have high innate capacity for differentiation. For example, pluripotent embryonic stem cells may have the potential to form any type of cell in the body. When grown in vitro for long periods of time, ES cells maintain pluripotency: progeny cells retain the potential for multilineage differentiation.

Somatic stem cells may include the fetal stem cells (from the fetus) and adult stem cells (found in various tissues, such as bone marrow). These cells have been regarded as having a capacity for differentiation lower than that of the pluripotent ES cells—with the capacity of fetal stem cells being greater than that of adult stem cells; they apparently differentiate into only a limited range of types of cell and have been described as multipotent. The 'tissue-specific' stem cells normally give rise to only one type of cell. For example, embryonic stem cells may be differentiated into blood stem cells (e.g., Hematopoietic stem cells (HSCs)), which may be further differentiated into various blood cells (e.g., red blood cells, platelets, white blood cells, etc.).

Induced pluripotent stem cells (i.e., iPS cells or iPSCs) may include a type of pluripotent stem cell artificially derived from a non-pluripotent cell (e.g., an adult somatic cell) by inducing a expression of specific genes. Induced pluripotent stem cells are similar to natural pluripotent stem cells, such as embryonic stem (ES) cells, in many aspects, such as the expression of certain stem cell genes and proteins, chromatin methylation patterns, doubling time, embryoid body formation, teratoma formation, viable chimera formation, and potency and differentiability. Induced pluripotent cells may be made from adult stomach, liver, skin cells and blood cells.

In embodiments, the modified cell is a T cell, NK cell, dendritic cell, or a macrophage.

In some embodiments, the antigen binding molecule is the CAR comprising an extracellular domain, a transmembrane domain, and an intracellular domain, the extracellular domain binds an antigen.

In some embodiments, the intracellular domain comprises a co-stimulatory signaling region that comprises an intracellular domain of a co-stimulatory molecule selected from the group consisting of CD27, CD28, 4-1BB, OX40, CD30, CD40, PD-1, ICOS, lymphocyte function-associated antigen-1 (LFA-1), CD2, CD7, LIGHT, NKG2C, B7-H3, and any combination thereof. In some embodiments, the antigen is Epidermal growth factor receptor (EGFR), Variant III of the epidermal growth factor receptor (EGFRvIII), Human epidermal growth factor receptor 2 (HER2), Mesothelin (MSLN), Prostate-specific membrane antigen (PSMA), Carcinoembryonic antigen (CEA), Disialoganglioside 2 (GD2), Interleukin-13Ra2 (IL13Rα2), Glypican-3 (GPC3), Carbonic anhydrase IX (CAIX), L1 cell adhesion molecule (L1-CAM), Cancer antigen 125 (CA125), Cluster of differentiation 133 (CD133), Fibroblast activation protein (FAP), Cancer/testis antigen 1B (CTAG1B), Mucin 1 (MUC1), Folate receptor-α (FR-α) CD19, FZD10, TSHR, PRLR, Muc 17, GUCY2C, CD207, CD3, CD5, B-Cell Maturation Antigen (BCMA), or CD4.

In some embodiments, the antigen binding molecule is a modified TCR. In some embodiments, the TCR is derived from spontaneously occurring tumor-specific T cells in patients. In some embodiments, the TCR binds to a tumor antigen. In some embodiments, the tumor antigen comprises CEA, gp100, MART-1, p53, MAGE-A3, or NY-ESO-1. In some embodiments, the TCR comprises TCRγ and TCRδ Chains or TCRα and TCRβ chains, or a combination thereof. In some embodiments, the TCR comprises TCRγ and TCRδ Chains or TCRα and TCRβ chains. In some embodiments, a T cell clone that expresses a TCR with high affinity for the target antigen may be isolated. In certain embodiments, tumor-infiltrating lymphocytes (TILs) or peripheral blood mononuclear cells (PBMCs) may be cultured in the presence of antigen-presenting cells (APCs) pulsed with a peptide representing an epitope known to elicit a dominant T cell response when presented in the context of a defined HLA allele. High-affinity clones may be then selected on the basis of MHC-peptide tetramer staining and/or the ability to recognize and lyse target cells pulsed with low titrated concentrations of cognate peptide antigen. After the clone has been selected, the TCRα and TCRβ chains or TCRγ and TCRδ Chains are identified and isolated by molecular cloning. For example, for TCRα and TCRβ chains, the TCRα and TCRβ gene sequences are then used to generate an expression construct that ideally promotes stable, high-level expression of both TCR chains in human T cells. The transduction vehicle (e.g., a gammaretrovirus or lentivirus) may be then generated and tested for functionality (antigen specificity and functional avidity) and used to produce a clinical lot of the vector. An aliquot of the final product is then used to transduce the target T cell population (generally purified from patient PBMCs), which is expanded before infusion into the patient. Various methods may be implemented to obtain genes encoding tumor-reactive TCR. More information is provided in Kershaw et al., Clin Transl Immunology. 2014 May; 3(5): e16.

In some embodiments, specific TCR can be derived from spontaneously occurring tumor-specific T cells in patients. Antigens included in this category include the melanocyte differentiation antigens MART-1 and gp100, as well as the MAGE antigens and NY-ESO-1, with expression in a broader range of cancers. TCRs specific for viral-associated malignancies can also be isolated, as long as viral proteins are expressed by transformed cells. Malignancies in this category include liver and cervical cancer, associated with hepatitis and papilloma viruses, and Epstein-Barr virus-associated malignancies. In some embodiments, target antigens of the TCR may include CEA (e.g., for colorectal cancer), gp100, MART-1, p53 (e.g., for Melanoma), MAGE-A3 (e.g., Melanoma, esophageal and synovial sarcoma), NY-ESO-1 (e.g., for Melanoma and sarcoma as well as Multiple myelomas).

Some embodiments relate to the cell that has the disruption in an endogenous gene associated with a biosynthesis or transportation pathway of CXCR2 and a reduced amount of CXCR2 as compared to the corresponding wild-type of the cell. In some embodiments, the disruption is made by a nuclease.

In some embodiments, the disruption is made by a zinc finger nuclease (ZFN). In some embodiments, the disruption is made by a CRISPR associated protein 9 (Cas9). In some embodiments, the disruption is made by a Transcription activator-like effector nuclease (TALEN). In some embodiments, a target sequence of the TALEN is the amino acid sequence SEQ ID No: 29, or a left arm of the TALEN is the amino acid sequence SEQ ID No: 30, and a right arm of the TALEN is the amino acid sequence SEQ ID No: 31. In some embodiments, a target sequence of the TALEN is the amino acid sequence SEQ ID No: 32, or a left arm of the TALEN is the amino acid sequence SEQ ID No: 33, and a right arm of the TALEN is the amino acid sequence SEQ ID No: 34. In some embodiments, a target sequence of the TALEN is the amino acid sequence SEQ ID No: 35, or a left arm of the TALEN is the amino acid sequence SEQ ID No: 36, and a right arm of the TALEN is the amino acid sequence SEQ ID No: 37.

Some embodiments relate to the cell that has a nucleic acid sequence encoding modified CXCR2 that lacks a functional intracellular domain as compared to the corresponding wild-type receptor. In some embodiments, the modified CXCR2 is a dominant negative variant of CXCR2 such that the cell has an altered molecular function of CXCR2. In some embodiments, an intracellular domain of the modified CXCR2 consisting essentially of the amino acid sequence SEQ ID NO: 5 or comprising the amino acid sequence SEQ ID NO: 6.

Some embodiments relate to the cell that has the enhancement in an endogenous gene associated with a biosynthesis or transportation pathway of CXCR3 and an increased amount of CXCR2 as compared to the corresponding wild-type of the cell. In some embodiments, the CXCR3 is overexpressed as compared to the corresponding wild-type of the cell. In some embodiments, a level of expression of the CXCR3 is greater than the average level of expression of CXCR3 on the cell at least about 10%, 20%, 30%, 40%, or 50%. In some embodiments, the genome of the cell comprises a polynucleotide sequence encoding the CXCR3, the polynucleotide sequence operably linked to a promoter polynucleotide sequence. In some embodiments, the CAR an extracellular, a transmembrane domain; and an intracellular segment comprising a co-stimulatory domain and a CD3ζ intracellular signaling domain comprising a CXCL9/CXCL10-CXCR3 signaling motif such that CXCR3 overexpression is in an antigen-dependent manner.

CXCR2 is mainly expressed on the surface of cells such as neutrophils, monocytes, and T cells. It is a member of the G protein-coupled receptor superfamily and binds to CXCL1. CXCL1 can inhibit T cell infiltration of tumor microenvironment by binding to CXCR2 receptor. In some embodiments, CXCR2 can be expressed on the surface of T cells and bind to ligand CXCL1 to inhibit T cell infiltration in tumor microenvironment. By down-regulating the expression of CXCR2 in T cells, The CXCL1-CXCR2 signaling pathway inhibits the infiltration of T cells into the tumor microenvironment, thereby enhancing the effect of T cells, especially CAR-T cells, in immunotherapy. In some embodiments, the down-regulation of CXCR2 expression in T cells promotes the infiltration of T cells into the tumor microenvironment, and the modified CAR-T cells contribute to the improvement of immunotherapy. In some embodiments, the CXCR2 gene in T cells may be knocked out using a technique edited by Crisper et al., and T cells may be engineered into CXCR2-deficient CAR-T cells. In the mouse model, the efficacy of the modified CAR-T cells and common CAR-T cells may be compared, and the CXCR2-deficient CAR-T cells may be predicted to have a better tumor suppressing effect.

CXCR3 is mainly expressed on the surface of T cells, but not on related cells such as B cells, monocytes and granulocytes. CXCR3 and its ligand CXCL9/CXCL10 can help effect T cells to metastasize to tumor tissues, thereby achieving killing and control of tumor cells. CXCR3 can be expressed on the surface of T cells and binds to the ligand CXCL9/CXCL10 to promote T cell infiltration in the tumor microenvironment. The present invention enhances the promotion of T cell infiltration of the tumor microenvironment by overexpressing CXCR3 in T cells to enhance the CXCL9/

CXCL10-CXCR3 signaling pathway. Role, thereby enhancing the effect of T cells, especially CAR-T cells, in immunotherapy.

Some embodiments relate to the cell that comprises a nucleic acid sequence encoding SLC1A3. In some embodiments, the cell comprises a nucleic acid sequence SEQ ID NO: Construct of SLC1A3-CART. In some embodiments, the cell has enhanced capability of uptake of glutamate.

Aspartic acid is one of the basic amino acids that make up proteins. It is ubiquitous in biosynthesis and is essential for cell life activities. Recent studies have shown that in the hypoxic tumor microenvironment, the level of aspartic acid in tumor cells is reduced, which is the main limiting factor for tumor proliferation. Therefore, limiting the level of aspartic acid in tumor cells can be used as a tumor treatment. The new direction. Studies have shown that in some tumor cells, aspartate to intracellular transport requires a special transporter SLC1A3. The present invention competes for aspartic acid in tumor cells by expressing the SLC1A3 gene in T cells to inhibit aspartate levels in tumor cells. This invention can inhibit tumor growth by limiting aspartic acid, thereby enhancing the effect of T cells, particularly CAR-T cells, in immunotherapy.

The level of aspartic acid in tumor cells is the main limiting factor for tumor proliferation, so limiting the level of aspartate in tumor cells can serve as a new direction for tumor therapy. In some tumor cells, aspartate to intracellular transport requires a special transporter SLC1A3. The present invention inhibits aspartate levels in tumor cells by expressing TLC1A3 gene in T cells such that T cells compete for aspartic acid in tumor cells. This invention can inhibit tumor growth by limiting the level of aspartic acid in the tumor, thereby enhancing the effect of T cells, particularly CAR-T cells, in immunotherapy. The present invention inhibits aspartate levels in tumor cells by expressing TLC1A3 gene in T cells such that T cells compete for aspartic acid in tumor cells. This invention can inhibit tumor growth by limiting aspartic acid in the tumor, thereby enhancing the effect of T cells, particularly CAR-T cells, in immunotherapy. First, a CAR-T cell capable of expressing the SLC1A3 gene may be constructed. The lentiviral vector and the lentiviral packaging plasmid (Gag-pol and VSV-G) expressing the cDNA of SLC1A3 may be transfected into HEK293T cells, and 48 hours after transfection, virus particles may be obtained, and the virus particles may be used to transfect CAR-T cells to obtain energy. CAR-T cells expressing the SLC1A3 gene. In the mouse model, the efficacy of the modified CAR-T cells and common CAR-T cells may be compared, and the CAR-T cells expressing SLC1A3 may be predicted to have a better tumor suppressing effect. Aspartic acid is a negatively charged amino acid in a physiological pH environment, and its intracellular transport requires a special transporter. In the human body, there are now 7 aspartate transporters from SLC1A1 to SLC1A7, most of which are expressed on the cell membrane of nerve cells. One of the aspartate transporters SLC1A3 can also be abundant in tumor epithelial cells. expression. SLC1A3 has a high aspartic acid affinity and can help tumor cells absorb aspartic acid to maintain nucleic acid synthesis and tumor growth.

Some embodiments relate to the cell that has a reduced amount of Yes-associated protein (YAP) as compared to a corresponding wild-type cell, wherein the modified cell has decreased Treg-mediated suppression of antitumor immunity as compared to the corresponding wild-type cell. In some embodiments, the modified T cell has a disruption in an endogenous gene associated with a biosynthesis or transportation pathway of YAP. In some embodiments, the disruption comprises a disruption of one or more exons of YAP gene. In some embodiments, the disruption of the one or more exons of YAP gene comprises a disruption of an exon of YAP gene having the nucleic acid sequence ID: 7. In some embodiments, the cell further comprises a TALEN targeting the nucleic acid sequence ID: 38. In some embodiments, the TALEN comprise a left arm comprising the nucleic acid sequence ID: 39 and a right arm comprising the nucleic acid SEQ ID NO: 40.

Some embodiments relate to the cell that has a nucleic acid sequence that encodes a modified receptor that directly or indirectly activate YAP activity, the modified receptor lacking a functional intracellular domain, and the modified receptor and the antigen binding molecule are expressed as gene products that are separate polypeptides. In some embodiments, the modified receptor is ERBB4, CD44, or a G12/13-coupled receptor that lacks a functional intracellular domain as compared to the corresponding wild-type receptor.

In some embodiments, the G12/13-coupled receptor comprises one of adrenergic receptor a1B, LPA receptors, purinergic receptors, 5-hydroxytryptamine receptor 4, muscarinic acetylcholine receptor M1, adenosine receptor A1A, angiontensin II receptor, free fatty acid receptor 1, platelet-activating factor receptor, thromboxane A2, frizzled homolog D4, complement component 3a receptor 1, estrogen receptor 1, glutamate receptor metabotropic 2, opioid receptor D1, secretin receptor, thyroid-stimulating hormone receptor, gastrin-releasing peptide receptor, melanocortin receptor 1, somatostatin receptor 1, prostaglandin E receptor 2, and bombesin-like receptor 3. In some embodiments, the modified receptor is a modified ERBB4. In some embodiments, the modified ERBB4 consist essentially of the nucleic acid sequence ID: 11. In some embodiments, the modified receptor is a modified LPAR1. In some embodiments, the modified LPAR1 consist essentially the nucleic acid sequence ID: 14. In some embodiments, the modified receptor is a modified CD44. In some embodiments, the modified CD44 consist essentially the nucleic acid sequence ID: 17. In some embodiments, the modified ERBB4 has a mutant site of tyrosine phosphorylation as compared to the corresponding wild-type receptor. In some embodiments, the modified receptor is a dominant negative of ERBB4 receptor. Dominant negative mutations have an altered gene product that acts antagonistically to the wild-type allele. These mutations usually result in an altered molecular function (often inactive) and are characterized by a dominant or semi-dominant phenotype. In some embodiments, the modified receptor is a dominant negative variant of a receptor of the ERBB4, CD44, or G12/13-coupled receptor.

Some embodiments relate to the cell that has a nucleic acid sequence encoding modified TIGIT that lacks a functional intracellular domain as compared to the corresponding wild-type receptor. In some embodiments, the modified TIGIT is a dominant negative variant of TIGIT such that the cell has an altered molecular function of TIGIT. In some embodiments, an intracellular domain of the modified TIGIT consisting essentially of the amino acid sequence SEQ ID NO: 19 or comprising the amino acid sequence SEQ ID: 20.

Some embodiments relate to the cell that comprises a nucleic acid sequence encoding S1P1. In some embodiments, the cell comprises a nucleic acid sequence SEQ ID NO: Construct of S1P1-CART.

Some embodiments relate to the cell that has a nucleic acid sequence encoding a modified IL-35 receptor that lacks a functional intracellular domain as compared to the corresponding wild-type receptor. In some embodiments, the modified IL-35 receptor is a dominant negative variant of IL-35 receptor such that the cell has an altered molecular function of IL-35 receptor. In some embodiments, the modified receptor is gp130 or IL-12Rβ2 receptor that lacks a functional intracellular domain as compared to the corresponding wild-type receptor. In some embodiments, an intracellular domain of the modified IL-35 receptor consisting essentially of the amino acid sequence SEQ ID NO: 24 or 27 or comprising the amino acid sequence SEQ ID NO: 25 or 28.

In some embodiments, the cell has the disruption in an endogenous gene associated with a biosynthesis or transportation pathway of spry1 and/or spry2 and a reduced amount of spry1 and/or spry2 as compared to the corresponding wild-type of the cell. In some embodiments, the disruption is made by a nuclease. In some embodiments, the disruption is made by a CRISPR associated protein 9 (Cas9). In some embodiments, the disruption is made by a Transcription activator-like effector nuclease (TALEN). In some embodiments, the disruption is made by a zinc finger nuclease (ZFN). In some embodiments, a first target sequence of the ZFN is the amino acid sequence SEQ ID No: 74, and a second target sequence of the ZFN is the amino acid sequence SEQ ID NO: 79. In some embodiments, a first ZFP comprising amino acid sequences SEQ ID NOS.: 75-78 ordered from a N-terminal of the first ZFP to a C-terminal of the first ZFP, and a second ZFP comprising amino acid sequences SEQ ID NOS.: 80-83 ordered from a N-terminal of the first ZFP to a C-terminal of the first ZFP. In some embodiments, a first target sequence of the ZFN is the amino acid sequence SEQ ID No: 85, and a second target sequence of the ZFN is the amino acid sequence SEQ ID NO: 90. In some embodiments, a first ZFP comprising amino acid sequences SEQ ID NOS.: 86-89 ordered from a N-terminal of the first ZFP to a C-terminal of the first ZFP, and a second ZFP comprising amino acid sequences SEQ ID NOS.: 91-94 ordered from a N-terminal of the first ZFP to a C-terminal of the first ZFP.

In some embodiments, an intracellular domain of the modified spry1 and/or spry2 consisting essentially of the amino acid sequence SEQ ID NO: 114 or 115. In some embodiments, the modified ERBB4 has a mutant site of tyrosine phosphorylation as compared to the corresponding wild-type receptor. In some embodiments, the cell has the disruption in an endogenous gene associated with a biosynthesis or transportation pathway of foxo1 and a reduced amount of foxo1 as compared to the corresponding wild-type of the cell. In some embodiments, the disruption is made by a nuclease. In some embodiments, the disruption is made by a CRISPR associated protein 9 (Cas9). In some embodiments, the disruption is made by a Transcription activator-like effector nuclease (TALEN). In some embodiments, the disruption is made by a zinc finger nuclease (ZFN). In some embodiments, a first target sequence of the ZFN is the amino acid sequence SEQ ID No: 96 and a second target sequence of the ZFN is the amino acid sequence SEQ ID NO: 101. In some embodiments, a first ZFP comprising amino acid sequences SEQ ID NOS.: 97-100 ordered from a N-terminal of the first ZFP to a C-terminal of the first ZFP, and a second ZFP comprising amino acid sequences SEQ ID NOS.: 102-105 ordered from a N-terminal of the first ZFP to a C-terminal of the first ZFP.

In some embodiments, the cell overexpresses an endogenous gene associated with a biosynthesis or transportation pathway of phosphatidylinositol-specific phospholipase (PLC)-γ and an increased amount of phosphatidylinositol-specific phospholipase (PLC)-γ as compared to the corresponding wild-type of the cell. In some embodiments, the (PLC)-γ is overexpressed as compared to the corresponding wild-type of the cell. In some embodiments, a level of expression of the (PLC)-γ is greater than the average level of expression of (PLC)-γ on the cell at least about 10%, 20%, 30%, 40%, or 50%. In some embodiments, the genome of the cell comprises a polynucleotide sequence encoding the (PLC)-γ, the polynucleotide sequence operably linked to a promoter polynucleotide sequence. In some embodiments, the overexpression of (PLC)-γ is regulated by a SynNotch polypeptide such that (PLC)-γ is overexpressed in response to binding of a target antigen.

In some embodiments, the cell has the enhancement in an endogenous gene associated with a biosynthesis or transportation pathway of TLR9 and/or MyD88 and an increased amount of TLR9 and/or MyD88 as compared to the corresponding wild-type of the cell. In some embodiments, the TLR9 and/or MyD88 is overexpressed as compared to the corresponding wild-type of the cell. In some embodiments, a level of expression of the TLR9 and/or MyD88 is greater than the average level of expression of TLR9 and/or MyD88 on the cell at least about 10%, 20%, 30%, 40%, or 50%. In some embodiments, the genome of the cell comprises a polynucleotide sequence encoding the TLR9 and/or MyD88, the polynucleotide sequence operably linked to a promoter polynucleotide sequence. In some embodiments, the overexpression of TLR9 and/or MyD88 is regulated by a SynNotch polypeptide such that TLR9 and/or MyD88 is overexpressed in response to binding of a target antigen.

In some embodiments, the intracellular domain of the CAR comprises the intercellular function domain of TLR9 (TIR domain SEQ ID NO: 116. In some embodiments, TLR9 are expressed on cDCs and macrophages, which is infused into a subject who is treated with the cell. In some embodiments, the cell comprises a nucleic acid sequence encoding a constitutively active form of IRAK1/IRAK4 or IRF7 (See SEQ ID NO: 110 and 111). Association with MYD88 leads to IRAK1 phosphorylation by IRAK4 and subsequent autophosphorylation and kinase activation. Following recruitment on the activated receptor complex, phosphorylated on Thr-209, probably by IRAK4, resulting in a conformational change of the kinase domain, allowing further phosphorylations to take place. Thr-387 phosphorylation in the activation loop is required to achieve full enzymatic activity. IRAK4 is rapidly recruited by MYD88 to the receptor-signaling complex upon TLR activation to form the Myddosome together with IRAK2. Phosphorylates initially IRAK1, thus stimulating the kinase activity and intensive autophosphorylation of IRAK1. In response to a viral infection, phosphorylated on Ser-477 and Ser-479 by TBK1 and IKBKE1, phosphorylation, and subsequent activation is inhibited by vaccinia virus protein E3. In TLR7- and TLR9-mediated signaling pathway, phosphorylated by IRAK1.

Phosphatidylinositol-specific phospholipase C (PLC)-γ is a common partner of spry1 and spry2 (reference: Sprouty Proteins Inhibit Receptor-mediated Activation of Phosphatidylinositol-specific Phospholipase C), so (PLC)-γ can be used as a downstream molecule of spry protein. Cells deficient for spry1 or spry2 showed increased production of IP(3) at baseline and further increased in response to growth factor signals. Spry-PLCγ interaction was dependent on the Src homology 2 domain of PLCγ and a conserved N-terminal tyrosine residue in Spry1 and Spry2. In some embodiments, this tyrosine may be mutated to do the dominant negative of the spry protein, Y53A and Y55A, respectively.

TLR9 contributes to tumor regression by inducing cytotoxic T cell response (CTL), reducing the numbers of myeloid-derived suppressor cells (MDSCs), the tumor-associated macrophages (TAMs) and the regulatory T cells (T regs). Upon ligand binding, The TIR domain of TLR9 recruits MyD88 which forms a supramolecular complex with TNF receptor-associated factor 6 (TFAF6), Interleukin-1 receptor-associated kinases 1 and 4 (IRAK1/IRAK4), and Interferon Regulatory Factor 7 (IRF7). Once phosphorylated IRF7 translocates to the nucleus and induces the expression of type I interferon and interferon inducible genes. Stimulation of TLR9 with its ligands leads also to the activation of other transcription factors, including nuclear factor kB (NF-kB) and activator protein-1 (AP-1). (reference: the role of Toll-like receptor 9 in gynecologic cancer, 2016).

In some embodiments, CAR T cells may overexpress for TLR9 and MyD88 and/or the ordinary CAR's intracellular domain may be replaced with the TLR9's intercellular functional domain (TIR domain), which activates the downstream signal. The downstream molecules of TLR9, IRAK1/IRAK4 and IRF7, are both Serine/threonine-protein kinase that plays a critical role in initiating innate immune response against foreign pathogens. A constitutively active form of these receptors may be used to continuously activate downstream signals. TLR9 may be expressed on conventional dendritic cells (cDCs) and macrophages, which may be infused to a subject to enhance CAR T cell therapy.

Some embodiments relate to a vector comprising one or more nucleic acid sequences listed above. In some embodiments, a lymphocyte comprises the one or more nucleic acid sequences listed above. In some embodiments, a pharmaceutical composition comprises the lymphocyte (e.g., a T cell, a NK cell, or a macrophage)

In some embodiments, the disruption in the endogenous gene or the addition of the exogenous gene are controlled by a system. For example, the disruption in the endogenous gene or the addition of the exogenous gene may be antigen-dependent. Notch receptors are transmembrane proteins that mediate cell-cell contact signaling and play a central role in development and other aspects of cell-to-cell communication. Notch receptors expressed in a receiver cell recognize their ligands (the delta family of proteins), expressed on a sending cell. The engagement of notch and delta on these contacting cells leads to two-step proteolysis of the notch receptor that ultimately causes the release of the intracellular portion of the receptor from the membrane into the cytoplasm. This released domain alters receiver cell behavior by functioning as a transcriptional regulator.

In some embodiments, a chimeric Notch receptor polypeptide may include, from N-terminal to C-terminal and in covalent linkage: an extracellular domain comprising a first member of a specific binding pair; a Notch receptor polypeptide. The Notch receptor polypeptide has a length of from 50 amino acids to 1000 amino acids, and comprises one or more ligand-inducible proteolytic cleavage sites. The chimeric Notch receptor polypeptide may further include an intracellular domain such that the first member of the specific binding pair is heterologous to the Notch receptor polypeptide, and binding of the first member of the specific binding pair to a second member of the specific binding pair induces cleavage of the Notch receptor polypeptide at the one or more ligand-inducible proteolytic cleavage sites, thereby releasing the intracellular domain. In some embodiments, the Notch receptor polypeptide has a length of from 300 amino acids to 400 amino acids. In some embodiments, the chimeric Notch receptor polypeptide comprises a linker interposed between the extracellular domain and the Notch receptor polypeptide. In some embodiments, the intracellular domain is a transcriptional activator. In some embodiments, the intracellular domain is a transcriptional repressor. In some embodiments, the intracellular domain is a site-specific nuclease. In some embodiments, the site-specific nuclease is a Cas9 polypeptide. In some embodiments, the intracellular domain is a recombinase. In some embodiments, the intracellular domain is an inhibitory immunoreceptor. In some embodiments, the intracellular domain is an activating immunoreceptor.

In some embodiments, gene overexpression or exogenous gene expression may be under control of the nuclear factor of activated T cell (NFAT)-derived minimal promoter that initiates certain transcription upon TCR- or CAR-mediated T cell activation. In the process, a protein corresponding to the certain gene may be released on CAR signaling in engineered T cells intended to accumulate to high levels in the targeted solid tumor lesion while avoiding substantial increase in a protein corresponding to the certain gene. For example, antigen engagement by the TCR or CAR—both of which utilize the CD3ζ signaling domain for downstream signaling—activated the NFAT-responsive elements, resulting in subsequent the protein transcription and triggered the protein release.

In some embodiments, the antigen binding molecule is a chimeric antigen receptor (CAR) or a T Cell Receptor (TCR). The term "Chimeric Antigen Receptor" or alternatively a "CAR" refers to a recombinant polypeptide construct comprising at least an extracellular antigen binding domain, a transmembrane domain and an intracellular signaling domain (e.g., cytoplasmic domain). In some embodiments, the domains in the CAR polypeptide construct are in the same polypeptide chain (e.g., comprising a chimeric fusion protein) or not contiguous with each other (e.g., in different polypeptide chains).

In some embodiments, the intracellular signaling domain may include a functional signaling domain derived from a stimulatory molecule and/or a co-stimulatory molecule as described above. In certain embodiments, the intracellular signaling domain includes a functional signaling domain derived from a primary signaling domain (e.g., a primary signaling domain of CD3-zeta). In other embodiments, the intracellular signaling domain further includes one or more functional signaling domains derived from at least one co-stimulatory molecule. The co-stimulatory signaling region refers to a portion of the CAR including the intracellular domain of a co-stimulatory molecule. Co-stimulatory molecules are cell surface molecules other than antigens receptors or their ligands that are required for an efficient response of lymphocytes to antigen.

Between the extracellular domain and the transmembrane domain of the CAR, there may be incorporated a spacer domain. As used herein, the term "spacer domain" generally means any oligo- or polypeptide that functions to link the transmembrane domain to, either the extracellular domain or, the cytoplasmic domain in the polypeptide chain. A spacer domain may include up to 300 amino acids, preferably 10 to 100 amino acids, and most preferably 25 to 50 amino acids.

The extracellular domain of a CAR may include an antigen binding domain (e.g., a scFv, a single domain antibody, or TCR (e.g., a TCR alpha binding domain or TCR beta binding domain)) that targets a specific tumor marker (e.g., a tumor antigen). Tumor antigens are proteins that are produced by tumor cells that elicit an immune response, particularly T-cell mediated immune responses. Tumor antigens are well known in the art and include, for example, a glioma-associated antigen, carcinoembryonic antigen (CEA), β-human chorionic gonadotropin, alphafetoprotein (AFP), lectin-reactive AFP, thyroglobulin, RAGE-1, MN-CA IX, human telomerase reverse transcriptase, RU1, RU2 (AS), intestinal carboxyl esterase, mut hsp70-2, M-CSF, prostase, prostate-specific antigen (PSA), PAP, NY-ESO-1, LAGE-1a, p53, prostein, PSMA, Her2/neu, survivin and telomerase, prostate-carcinoma tumor antigen-1 (PCTA-1), MAGE, ELF2M, neutrophil elastase, ephrinB2, CD22, insulin growth factor (IGF)-I, IGF-II, IGF-I receptor and mesothelin. For example, the tumor antigen is CD19, and the CAR thereof may be referred as CD19CAR.

In some embodiments, the extracellular ligand-binding domain comprises a scFv comprising the light chain variable (VL) region and the heavy chain variable (VH) region of a target antigen-specific monoclonal antibody joined by a flexible linker. Single chain variable region fragments are made by linking light and/or heavy chain variable regions by using a short linking peptide (Bird et al., Science 242:423-426, 1988). An example of a linking peptide is the GS linker having the amino acid sequence (GGGGS)3 (SEQ ID NO: 75), which bridges approximately 3.5 nm between the carboxy terminus of one variable region and the amino terminus of the other variable region. Linkers of other sequences have been designed and used (Bird et al., 1988, supra). In general, linkers can be short, flexible polypeptides and preferably comprised of about 20 or fewer amino acid residues. Linkers can, in turn, be modified for additional functions, such as attachment of drugs or attachment to solid supports. The single chain variants can be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as E. coli. Polynucleotides encoding the scFv of interest can be made by routine manipulations such as ligation of polynucleotides. The resultant scFv can be isolated using standard protein purification techniques known in the art.

In embodiments, the CAR molecules described herein comprise one or more complementarity-determining regions (CDRs) for binding an antigen of interest. CDRs are part of the variable domains in immunoglobulins and T cell receptors for binding a specific antigen. There are three CDRs for each variable domain. Since there is a variable heavy domain and a variable light domain, there are six CDRs for binding an antigen. Further since an antibody has two heavy chains and two light chains, an antibody has twelve CDRs altogether for binding antigens. In embodiments, the CAR molecules described herein comprise one or more CDRs for binding a tumor.

In some embodiments, the tumor antigen includes HER2, CD19, CD20, CD22, Kappa or light chain, CD30, CD33, CD123, CD38, ROR1, ErbB3/4, EGFR, EGFRvIII, EphA2, FAP, carcinoembryonic antigen, EGP2, EGP40, mesothelin, TAG72, PSMA, NKG2D ligands, B7-H6, IL-13 receptor α 2, IL-11 receptor α, MUC1, MUC16, CA9, GD2, GD3, HMW-MAA, CD171, Lewis Y, G250/CAIX, HLA-AI MAGE A1, HLA-A2 NY-ESO-1, PSC1, folate receptor-α, CD44v7/8, 8H9, NCAM, VEGF receptors, 5T4, Fetal AchR, NKG2D ligands, CD44v6, TEM1, TEM8, or viral-associated antigens expressed by the tumor.

In some embodiments, the antigen binding molecule is a T Cell Receptor (TCR). In some embodiments, the TCR is modified TCR. In some embodiments, the TCR is derived from spontaneously occurring tumor-specific T cells in patients. In some embodiments, the TCR binds to a tumor antigen. In some embodiments, the tumor antigen comprises CEA, gp100, MART-1, p53, MAGE-A3, or NY-ESO-1. In some embodiments, the TCR comprises TCRγ and TCRδ Chains or TCRα and TCRβ chains. In some embodiments, a T cell clone that expresses a TCR with high affinity for the target antigen may be isolated. In certain embodiments, tumor-infiltrating lymphocytes (TILs) or peripheral blood mononuclear cells (PBMCs) may be cultured in the presence of antigen-presenting cells (APCs) pulsed with a peptide representing an epitope known to elicit a dominant T cell response when presented in the context of a defined HLA allele. High-affinity clones may be then selected on the basis of MHC-peptide tetramer staining and/or the ability to recognize and lyse target cells pulsed with low titrated concentrations of cognate peptide antigen. After the clone has been selected, the TCRα and TCRβ chains or TCRγ and TCRδ Chains are identified and isolated by molecular cloning. For example, for TCRα and TCRβ chains, the TCRα and TCRβ gene sequences are then used to generate an expression construct that ideally promotes stable, high-level expression of both TCR chains in human T cells. The transduction vehicle (e.g., a gammaretrovirus or lentivirus) may be then generated and tested for functionality (antigen specificity and functional avidity) and used to produce a clinical lot of the vector. An aliquot of the final product is then used to transduce the target T cell population (generally purified from patient PBMCs), which is expanded before infusion into the patient.

In some embodiments, the binding element of the CAR may include any antigen binding moiety that when bound to its cognate antigen, affects a tumor cell such that the tumor cell fails to grow, or is promoted to die or diminish.

The nucleic acid sequences coding for the desired molecules can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

The embodiments of the present disclosure further relate to vectors in which a DNA of the present disclosure is inserted. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity.

The expression of natural or synthetic nucleic acids encoding CARs is typically achieved by operably linking a nucleic acid encoding the CAR polypeptide or portions thereof to one or more promoters and incorporating the construct into an expression vector. The vectors can be suitable for replication and integration eukaryotes. Typical cloning vectors contain transcription and translation terminators, initiation sequences, and promoters useful for regulation of the expression of the desired nucleic acid sequence.

Additional information related to expression synthetic nucleic acids encoding CARs and gene transfer into mammalian cells is provided in U.S. Pat. No. 8,906,682, incorporated by reference in its entirety.

Some embodiments relate to a method or use of polynucleotides encoding a CAR, a nuclease (e.g., Crispr cas9), and/or dominant negative mutant (e.g., dDn-TIGIT). The method or use includes: providing a viral particle (e.g., AAV, lentivirus or their variants) comprising a vector genome, the vector genome comprising the polynucleotide, wherein the polynucleotide is operably linked to an expression control element conferring transcription of the polynucleotide; and administering an amount of the viral particle to the subject such that the polynucleotide is expressed in the subject. In embodiments, the AAV preparation may include AAV vector particles, empty capsids and host cell impurities, thereby providing an AAV product substantially free of AAV empty capsids. More information of the administration and preparation of the viral particle may be found at the U.S. Pat. No. 9,840,719 and Milani et al., Sci. Transl. Med. 11, eaav7325 (2019) 22 May 2019, which are incorporated herein by reference.

Pharmaceutical compositions of the present disclosure may be administered in a manner appropriate to the disease to be treated (or prevented). The quantity and frequency of administration will be determined by such factors as the condition of the patient, and the type and severity of the patient's disease, although appropriate dosages may be determined by clinical trials.

When "an immunologically effective amount", "an anti-tumor effective amount", "a tumor-inhibiting effective amount", or "therapeutic amount" is indicated, the precise amount of the compositions of the present disclosure to be administered can be determined by a physician with consideration of individual differences in age, weight, tumor size, extent of infection or metastasis, and condition of the patient (subject). It can be stated that a pharmaceutical composition comprising the T cells described herein may be administered at a dosage of $10^4$ to $10^9$ cells/kg body weight, preferably $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly. In certain embodiments, it may be desired to administer activated T cells to a subject and then subsequently redraw the blood (or have apheresis performed), collect the activated and expanded T cells, and reinfuse the patient with these activated and expanded T cells. This process can be carried out multiple times every few weeks. In certain embodiments, T cells can be activated from blood draws of from 10 cc to 400 cc. In certain embodiments, T cells are activated from blood draws of 20 cc, 30 cc, 40 cc, 50 cc, 60 cc, 70 cc, 80 cc, 90 cc, or 100 cc. Not to be bound by theory, using this multiple blood draw/multiple reinfusion protocols, may select out certain populations of T cells.

The administration of the pharmaceutical compositions described herein may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous (i. v.) injection, or intraperitoneally. In some embodiments, the T cell compositions of the present disclosure are administered to a patient by intradermal or subcutaneous injection. In another embodiment, the T cell compositions of the present disclosure are preferably administered by i.v. injection. The compositions of T cells may be injected directly into a tumor, lymph node, or site of infection. In certain embodiments of the present disclosure, cells activated and expanded using the methods described herein, or other methods known in the art where T cells are expanded to therapeutic levels, are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or natalizumab treatment for MS patients or efalizumab treatment for psoriasis patients or other treatments for PML patients. In further embodiments, the T cells of the present disclosure may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycophenolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin). (Liu et al., Cell 66:807-815, 1991; Henderson et al., Immun 73:316-321, 1991; Bierer et al., Curr. Opin. Immun 5:763-773, 1993; Isoniemi (supra)). In some embodiments, the cell compositions of the present disclosure are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. In other embodiments, the cell compositions of the present disclosure are administered following B-cell ablative therapy such as agents that react with CD20, e.g., Rituxan. For example, in some embodiments, subjects may undergo standard treatment with high dose chemotherapy followed by peripheral blood stem cell transplantation. In certain embodiments, following the transplant, subjects receive an infusion of the expanded immune cells of the present disclosure. In other embodiments, expanded cells are administered before or following surgery.

The dosage of the above treatments to be administered to a patient will vary with the precise nature of the condition being treated and the recipient of the treatment. The scaling of dosages for human administration can be performed according to art-accepted practices by a physician depending on various factors.

Additional information on the methods of cancer treatment using engineered or modified T cells is provided in U.S. Pat. No. 8,906,682, incorporated by reference in its entirety.

Some embodiments relate to an in vitro method for preparing modified cells. The method may include obtaining a sample of cells from the subject. For example, the sample may include T cells or T cell progenitors. The method may further include transfecting the cells with a DNA encoding at least a CAR, culturing the population of CAR cells ex vivo in a medium that selectively enhances proliferation of CAR-expressing T cells.

In embodiments, viruses are used to deliver nucleic acids into a cell in vitro and in vivo (in a subject). Examples of viruses useful for delivery of nucleic acids into cells include retrovirus, adenovirus, herpes simplex virus, vaccinia virus, and adeno-associated virus. In embodiments, non-viral methods are used for deliverying nucleic acids into a cell. Examples of non-viral methods include electroporation, gene gun, sonoporation, magnetofection, and the use of oligonucleotides, lipoplexes, dendrimers, and inorganic nanoparticles.

In some embodiments, the sample of cells is a cryopreserved sample. In some embodiments, the sample of cells is from umbilical cord blood or a peripheral blood sample from the subject. In some embodiments, the sample of cells is obtained by apheresis or venipuncture. In some embodiments, the sample of cells is a subpopulation of T cells.

In embodiments, the sample of cells is a population of cells described herein and is used in autologous CAR T cell therapy. In embodiments, the CAR T cell therapy is allogenic CAR T cell therapy, TCR T cell therapy, and NK cell therapy.

The present disclosure is further described by reference to the following exemplary embodiments and examples. These exemplary embodiments and examples are provided for purposes of illustration only and are not intended to be limiting unless otherwise specified. Thus, the present disclosure should in no way be construed as being limited to the following exemplary embodiments and examples, but rather, should be construed to encompass any and all variations which become evident as a result of the teaching provided herein.

Exemplary Embodiments

The following are exemplary embodiments:
1. A modified cell comprising: an antigen binding molecule; and a disruption in an endogenous gene or an addition of exogenous gene that are associated with a biosynthesis or transportation pathway of at least one of CXCR3, SLC1A3, YAP, TIGIT, S1P1, and IL-35.
2. The cell of embodiment 1, wherein the antigen binding molecule comprises a chimeric antigen receptor (CAR) and/or the second antigen binding molecule is a T Cell Receptor (TCR).
3. The cell of embodiment 2, wherein the antigen binding molecule is the CAR comprising an extracellular domain, a transmembrane domain, and an intracellular domain, the extracellular domain binds an antigen.
4. The cell of embodiment 3, wherein the intracellular domain comprises a co-stimulatory signaling region that comprises an intracellular domain of a co-stimulatory molecule selected from the group consisting of CD27, CD28, 4-1BB, OX40, CD30, CD40, PD-1, ICOS, lymphocyte function-associated antigen-1 (LFA-1), CD2, CD7, LIGHT, NKG2C, B7-H3, and any combination thereof.
5. The cell of embodiment 3, wherein the antigen is Epidermal growth factor receptor (EGFR), Variant III of the epidermal growth factor receptor (EGFRvIII), Human epidermal growth factor receptor 2 (HER2), Mesothelin (MSLN), Prostate-specific membrane antigen (PSMA), Carcinoembryonic antigen (CEA), Disialoganglioside 2 (GD2), Interleukin-13Ra2 (IL13Rα2), Glypican-3 (GPC3), Carbonic anhydrase IX (CAIX), L1 cell adhesion molecule (L1-CAM), Cancer antigen 125 (CA125), Cluster of differentiation 133 (CD133), Fibroblast activation protein (FAP), Cancer/testis antigen 1B (CTAG1B), Mucin 1 (MUC1), Folate receptor-α (FR-α) CD19, FZD10, TSHR, PRLR, Muc 17, GUCY2C, CD207, CD3, CD5, B-Cell Maturation Antigen (BCMA), or CD4.
6. The cell of embodiment 2, wherein the antigen binding molecule is a modified TCR.
7. The cell of embodiment 6, wherein the TCR is derived from spontaneously occurring tumor-specific T cells in patients.
8. The cell of embodiment 6, wherein the TCR binds to a tumor antigen.
9. The cell of embodiment 8, wherein the tumor antigen comprises CEA, gp100, MART-1, p53, MAGE-A3, or NY-ESO-1.
10. The cell of embodiment 8, wherein the TCR comprises TCRγ and TCRδ Chains or TCRα and TCRβ chains, or a combination thereof.
11. The cell of embodiment 1, wherein the cell is a T cell, a dendritic cell, a NK cell, or a macrophage cell.
12. The cell of any of embodiments 1-11, wherein the cell has the disruption in an endogenous gene associated with a biosynthesis or transportation pathway of CXCR2 and a reduced amount of CXCR2 as compared to the corresponding wild-type of the cell.
13. The cell of embodiment 12, wherein the disruption is made by a nuclease.
14. The cell of embodiment 12, wherein the disruption is made by a zinc finger nuclease (ZFN).
15. The cell of embodiment 12, wherein the disruption is made by a CRISPR associated protein 9 (Cas9).
16. The cell of embodiment 12, wherein the disruption is made by a Transcription activator-like effector nuclease (TALEN).
17. The cell of embodiment 16, wherein a target sequence of the TALEN is the amino acid sequence SEQ ID No: 29, or a left arm of the TALEN is the amino acid sequence SEQ ID No: 30, and a right arm of the TALEN is the amino acid sequence SEQ ID No: 31.
18. The cell of embodiment 16, wherein a target sequence of the TALEN is the amino acid sequence SEQ ID No: 32, or a left arm of the TALEN is the amino acid sequence SEQ ID No: 33, and a right arm of the TALEN is the amino acid sequence SEQ ID No: 34.
19. The cell of embodiment 16, wherein a target sequence of the TALEN is the amino acid sequence SEQ ID No: 35, or a left arm of the TALEN is the amino acid sequence SEQ ID No: 36, and a right arm of the TALEN is the amino acid sequence SEQ ID No: 37.
20. The cell of any of embodiments 1-11, wherein the cell has a nucleic acid sequence encoding modified CXCR2 that lacks a functional intracellular domain as compared to the corresponding wild-type receptor.
21. The cell of embodiment 20, wherein the modified CXCR2 is a dominant negative variant of CXCR2 such that the cell has an altered molecular function of CXCR2.
22. The cell of embodiment 20, wherein an intracellular domain of the modified CXCR2 consisting essentially of the amino acid sequence SEQ ID NO: 5 or comprising the amino acid sequence SEQ ID NO: 6.
23. The cell of any of embodiments 1-11, wherein the cell has the enhancement in an endogenous gene associated with a biosynthesis or transportation pathway of CXCR3 and an increased amount of CXCR2 as compared to the corresponding wild-type of the cell.
24. The cell of embodiment 23, wherein the CXCR3 is overexpressed as compared to the corresponding wild-type of the cell.
25. The cell of embodiment 24, wherein a level of expression of the CXCR3 is greater than the average level of expression of CXCR3 on the cell at least about 10%, 20%, 30%, 40%, or 50%.
26. The cell of embodiment 23, wherein the genome of the cell comprises a polynucleotide sequence encoding the CXCR3, the polynucleotide sequence operably linked to a promoter polynucleotide sequence.

27. The cell of embodiment 24, wherein the CAR an extracellular, a transmembrane domain; and an intracellular segment comprising a co-stimulatory domain and a CD3 intracellular signaling domain comprising a CXCL9/CXCL10-CXCR3 signaling motif.

28. The cell of any of embodiments 1-11, wherein the cell comprises a nucleic acid sequence encoding SLC1A3.

29. The cell of embodiment 28, wherein the cell comprises a nucleic acid sequence SEQ ID NO: Construct of SLC1A3-CART.

30. The cell of embodiment 28, wherein the cell has enhanced capability of uptake of glutamate.

31. The cell of any of embodiments 1-11, wherein the cell has a reduced amount of Yes-associated protein (YAP) as compared to a corresponding wild-type cell, wherein the modified cell has decreased Treg-mediated suppression of antitumor immunity as compared to the corresponding wild-type cell.

32. The cell of embodiment 31, wherein the modified T cell has a disruption in an endogenous gene associated with a biosynthesis or transportation pathway of YAP.

33. The cell of embodiment 32, wherein the disruption comprises a disruption of one or more exons of YAP gene.

34. The cell of embodiment 33, wherein the disruption of the one or more exons of YAP gene comprises a disruption of an exon of YAP gene having the nucleic acid sequence ID: 7.

35. The cell of embodiment 33, further comprising a TALEN targeting the nucleic acid sequence ID: 38.

36. The cell of embodiment 35, wherein the TALEN comprise a left arm comprising the nucleic acid sequence ID: 39 and a right arm comprising the nucleic acid SEQ ID NO: 40.

37. The cell of any of embodiments 1-11, wherein the cell has a nucleic acid sequence that encodes a modified receptor that directly or indirectly activate YAP activity, the modified receptor lacking a functional intracellular domain, and the modified receptor and the antigen binding molecule are expressed as gene products that are separate polypeptides.

38. The cell of embodiment 37, wherein the modified receptor is ERBB4, CD44, or a G12/13-coupled receptor that lacks a functional intracellular domain as compared to the corresponding wild-type receptor.

39. The cell of embodiment 38, wherein the G12/13-coupled receptor comprises one of adrenergic receptor a1 B, LPA receptors, purinergic receptors, 5-hydroxytryptamine receptor 4, muscarinic acetylcholine receptor M1, adenosine receptor A1A, angiontensin II receptor, free fatty acid receptor 1, platelet-activating factor receptor, thromboxane A2, frizzled homolog D4, complement component 3a receptor 1, estrogen receptor 1, glutamate receptor metabotropic 2, opioid receptor D1, secretin receptor, thyroid-stimulating hormone receptor, gastrin-releasing peptide receptor, melanocortin receptor 1, somatostatin receptor 1, prostaglandin E receptor 2, and bombesin-like receptor 3.

40. The cell of embodiment 37, wherein the modified receptor is a modified ERBB4.

41. The cell of embodiment 40, wherein the modified ERBB4 consist essentially of the nucleic acid sequence ID: 11.

42. The of embodiment 37, wherein the modified receptor is a modified LPAR1.

43. The cell of embodiment 42, wherein the modified LPAR1 consist essentially the nucleic acid sequence ID: 14.

44. The of embodiment 37, wherein the modified receptor is a modified CD44.

45. The cell of embodiment 44, wherein the modified CD44 consist essentially the nucleic acid sequence ID: 17.

46. The cell of embodiment 44, wherein the modified ERBB4 has a mutant site of tyrosine phosphorylation as compared to the corresponding wild-type receptor.

47. The T lymphocyte cell of embodiment 46, wherein the modified receptor is a dominant negative of ERBB4 receptor.

48. The lymphocyte T cell of embodiment 37, wherein the modified receptor is a dominant negative variant of a receptor of the ERBB4, CD44, or G12/13-coupled receptor.

49. The cell of any of embodiments 1-11, wherein the cell has a nucleic acid sequence encoding modified TIGIT that lacks a functional intracellular domain as compared to the corresponding wild-type receptor.

50. The cell of embodiment 49, wherein the modified TIGIT is a dominant negative variant of TIGIT such that the cell has an altered molecular function of TIGIT.

51. The cell of embodiment 49, wherein an intracellular domain of the modified TIGIT consisting essentially of the amino acid sequence SEQ ID NO: 19 or comprising the amino acid sequence SEQ ID: 20.

52. The cell of any of embodiments 1-11, wherein the cell comprises a nucleic acid sequence encoding S1P1.

53. The cell of embodiment 52, wherein the cell comprises a nucleic acid sequence SEQ ID NO: Construct of S1P1-CART.

49. The cell of any of embodiments 1-11, wherein the cell has a nucleic acid sequence encoding a modified IL-35 receptor that lacks a functional intracellular domain as compared to the corresponding wild-type receptor.

50. The cell of embodiment 49, wherein the modified IL-35 receptor is a dominant negative variant of IL-35 receptor such that the cell has an altered molecular function of IL-35 receptor.

51. The cell of embodiment 50, wherein the modified receptor is gp130 or IL-12Rβ2 receptor that lacks a functional intracellular domain as compared to the corresponding wild-type receptor 51. The cell of embodiment 49, wherein an intracellular domain of the modified IL-35 receptor consisting essentially of the amino acid sequence SEQ ID NO: 24 or 27 or comprising the amino acid sequence SEQ ID NO: 25 or 28.

52. A pharmaceutical composition comprising the population of the CAR cells of any of embodiments 1-51.

53. A method of causing or eliciting T cell response in a subject in need thereof and/or treating a tumor of the subject, the method comprising administering an effective amount of the composition of embodiment 52 to the subject.

54. The modified cell, the method, the pharmaceutical composition, the cell of one of embodiments 1-53, wherein the disruption in an endogenous gene or the addition of exogenous gene is associated with an oxygen-sensitive polypeptide domain.

55. The modified cell, the method, the pharmaceutical composition, the cell of embodiment 54, wherein the oxygen-sensitive polypeptide domain comprises HIF VHL binding domain.

56. The modified cell, the method, the pharmaceutical composition, the cell of one of embodiments 1-53, wherein the disruption in an endogenous gene or the addition of exogenous gene is regulated by a promoter comprising a binding site for a transcription modulator that modulates the expression and/or secretion of the therapeutic agent in the cell.

57. The modified cell, the method, the pharmaceutical composition, the cell of embodiment 56, wherein the transcription modulator is or includes Hif1a, NFAT, FOXP3, and/or NFkB.

58. The cell of any of embodiments 1-11, wherein the cell has the disruption in an endogenous gene associated with a biosynthesis or transportation pathway of spry1 and/or spry2 and a reduced amount of spry1 and/or spry2 as compared to the corresponding wild-type of the cell.

59. The cell of embodiment 58, wherein the disruption is made by a nuclease.

60. The cell of embodiment 58, wherein the disruption is made by a CRISPR associated protein 9 (Cas9).

61. The cell of embodiment 58, wherein the disruption is made by a Transcription activator-like effector nuclease (TALEN).

62. The cell of embodiment 58, wherein the disruption is made by a zinc finger nuclease (ZFN).

63. The cell of embodiment 62, wherein a first target sequence of the ZFN is the amino acid sequence SEQ ID No: 74, and a second target sequence of the ZFN is the amino acid sequence SEQ ID NO: 79.

64. The cell of embodiment 62, wherein a first ZFP comprising amino acid sequences SEQ ID NOS.: 75-78 ordered from a N-terminal of the first ZFP to a C-terminal of the first ZFP, and a second ZFP comprising amino acid sequences SEQ ID NOS.: 80-83 ordered from a N-terminal of the first ZFP to a C-terminal of the first ZFP.

65. The cell of embodiment 62, wherein a first target sequence of the ZFN is the amino acid sequence SEQ ID No: 85, and a second target sequence of the ZFN is the amino acid sequence SEQ ID NO: 90.

66. The cell of embodiment 64, wherein a first ZFP comprising amino acid sequences SEQ ID NOS.: 86-89 ordered from a N-terminal of the first ZFP to a C-terminal of the first ZFP, and a second ZFP comprising amino acid sequences SEQ ID NOS.: 91-94 ordered from a N-terminal of the first ZFP to a C-terminal of the first ZFP.

67. The cell of embodiment 58, wherein the modified spry1 is a dominant negative variant of spry1 such that the cell has an altered molecular function of spry1.

68. The cell of embodiment 58, wherein the modified spry2 is a dominant negative variant of spry2 such that the cell has an altered molecular function of spry2.

69. The cell of embodiment 67, wherein an intracellular domain of the modified spry1 and/or spry2 consisting essentially of the amino acid sequence SEQ ID NO: 114 or 115.

70. The cell of embodiment 67, wherein the modified ERBB4 has a mutant site of tyrosine phosphorylation as compared to the corresponding wild-type receptor.

71. The cell of embodiment 60, wherein the cell has the disruption in an endogenous gene associated with a biosynthesis or transportation pathway of foxo1 and a reduced amount of foxo1 as compared to the corresponding wild-type of the cell.

72. The cell of embodiment 71, wherein the disruption is made by a nuclease.

73. The cell of embodiment 71, wherein the disruption is made by a CRISPR associated protein 9 (Cas9).

74. The cell of embodiment 71, wherein the disruption is made by a Transcription activator-like effector nuclease (TALEN).

75. The cell of embodiment 71, wherein the disruption is made by a zinc finger nuclease (ZFN).

76. The cell of embodiment 75, wherein a first target sequence of the ZFN is the amino acid sequence SEQ ID No: 96 and a second target sequence of the ZFN is the amino acid sequence SEQ ID NO: 101.

77. The cell of embodiment 75, wherein a first ZFP comprising amino acid sequences SEQ ID NOS.: 97-100 ordered from a N-terminal of the first ZFP to a C-terminal of the first ZFP, and a second ZFP comprising amino acid sequences SEQ ID NOS.: 102-105 ordered from a N-terminal of the first ZFP to a C-terminal of the first ZFP.

78. The cell of any of embodiments 1-11, wherein the cell has the enhancement in an endogenous gene associated with a biosynthesis or transportation pathway of phosphatidylinositol-specific phospholipase (PLC)-γ and an increased amount of phosphatidylinositol-specific phospholipase (PLC)-γ as compared to the corresponding wild-type of the cell.

79. The cell of embodiment 78, wherein the (PLC)-γ is overexpressed as compared to the corresponding wild-type of the cell.

80. The cell of embodiment 78, wherein a level of expression of the (PLC)-γ is greater than the average level of expression of (PLC)-γ on the cell at least about 10%, 20%, 30%, 40%, or 50%.

81. The cell of embodiment 78, wherein the genome of the cell comprises a polynucleotide sequence encoding the (PLC)-γ, the polynucleotide sequence operably linked to a promoter polynucleotide sequence.

82. The cell of embodiment 78, wherein the overexpression of (PLC)-γ is regulated by a SynNotch polypeptide such that (PLC)-γ is overexpressed in response to binding of a target antigen.

83. The cell of any of embodiments 1-11, wherein the cell has the enhancement in an endogenous gene associated with a biosynthesis or transportation pathway of TLR9 and/or MyD88 and an increased amount of TLR9 and/or MyD88 as compared to the corresponding wild-type of the cell.

84. The cell of embodiment 83, wherein the TLR9 and/or MyD88 is overexpressed as compared to the corresponding wild-type of the cell.

85. The cell of embodiment 83, wherein a level of expression of the TLR9 and/or MyD88 is greater than the average level of expression of TLR9 and/or MyD88 on the cell at least about 10%, 20%, 30%, 40%, or 50%.

86. The cell of embodiment 83, wherein the genome of the cell comprises a polynucleotide sequence encoding the TLR9 and/or MyD88, the polynucleotide sequence operably linked to a promoter polynucleotide sequence.

87. The cell of embodiment 83, wherein the overexpression of TLR9 and/or MyD88 is regulated by a SynNotch polypeptide such that TLR9 and/or MyD88 is overexpressed in response to binding of a target antigen.

88. The cell of any of embodiments 1-11, wherein the intracellular domain of the CAR comprises the intercellular function domain of TLR9 (TIR domain SEQ ID NO: 116.

89. The cell of any of embodiments 1-11, wherein TLR9 are expressed on cDCs and macrophages, which is infused into a subject who is treated with the cell.

90. The cell of embodiment 83, wherein the cell comprises a nucleic acid sequence encoding a constitutively active form of IRAK1/IRAK4 or IRF7 (See SEQ ID NO: 110 and 111).

91. A modified cell engineered to express an antigen binding molecule, wherein expression and/or function of one or more genes in the modified cell has been 1) enhanced, or 2) reduced or eliminated.

92. The modified cell of embodiment 91, wherein the one or more genes comprise at least one of CXCR3, SLC1A3, YAP, TIGIT, S1P1, and IL-35.

93. The modified cell of embodiment 91, wherein the one or more genes are CXCR3 and/or TIGIT.

94. A modified cell engineered to express an antigen binding molecule, wherein expression and/or function of TIGIT in the modified cell has been reduced or eliminated.

95. A modified cell engineered to express an antigen binding molecule, wherein expression and/or function of CXCR3 in the modified cell has been enhanced.

96. The modified cell of one of embodiments 91-94, wherein the antigen binding molecule is chimeric antigen receptor (CAR), which comprises an antigen-binding domain, a transmembrane domain, and an intracellular signaling domain.

97. The modified cell of embodiment 96, wherein the antigen-binding domain binds to a tumor antigen is selected from a group consisting of: TSHR, CD19, CD123, CD22, CD30, CD171, CS-1, CLL-1, CD33, EGFRvIII, GD2, GD3, BCMA, Tn Ag, PSMA, ROR1, FLT3, FAP, TAG72, CD38, CD44v6, CEA, EPCAM, B7H3, KIT, IL-13Ra2, Mesothelin, IL-11Ra, PSCA, PRSS21, VEGFR2, LewisY, CD24, PDGFR-beta, SSEA-4, CD20, Folate receptor alpha, ERBB2 (Her2/neu), MUC1, EGFR, NCAM, Prostase, PAP, ELF2M, Ephrin B2, IGF-I receptor, CAIX, LMP2, gp100, bcr-abl, tyrosinase, EphA2, Fucosyl GM1, sLe, GM3, TGS5, HMW-MAA, o-acetyl-GD2, Folate receptor beta, TEM1/CD248, TEM7R, CLDN6, GPRC5D, CXORF61, CD97, CD179a, ALK, Polysialic acid, PLAC1, GloboH, NY-BR-1, UPK2, HAVCR1, ADRB3, PANX3, GPR20, LY6K, OR51E2, TARP, WT1, NY-ESO-1, LAGE-1a, MAGE-A1, legumain, HPV E6, E7, MAGE A1, ETV6-AML, sperm protein 17, XAGE1, Tie 2, MAD-CT-1, MAD-CT-2, Fos-related antigen 1, p53, p53 mutant, prostein, survivin and telomerase, PCTA-1/Galectin 8, MelanA/MART1, Ras mutant, hTERT, sarcoma translocation breakpoints, ML-IAP, ERG (TMPRSS2 ETS fusion gene), NA17, PAX3, Androgen receptor, Cyclin B1, MYCN, RhoC, TRP-2, CYP1B1, BORIS, SART3, PAX5, OY-TES1, LCK, AKAP-4, SSX2, RAGE-1, human telomerase reverse transcriptase, RU1, RU2, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, and IGLL1.

98. The modified cell of one of embodiments 96 and 97, wherein the intracellular signaling domain comprises a co-stimulatory signaling domain, or a primary signaling domain and a co-stimulatory signaling domain, wherein the co-stimulatory signaling domain comprises a functional signaling domain of a protein selected from the group consisting of CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRF1), CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, and NKG2D.

99. The modified cell of one of embodiments 91-94, wherein the antigen binding molecule is a modified TCR.

100. The modified cell of embodiment 99, wherein the TCR is derived from spontaneously occurring tumor-specific T cells in patients.

101. The modified cell of embodiment 109 wherein the TCR binds to a tumor antigen.

102. The modified cell of embodiment 101, wherein the tumor antigen comprises CEA, gp100, MART-1, p53, MAGE-A3, or NY-ESO-1.

103. The modified cell of embodiment 102, wherein the TCR comprises TCRγ and TCRδ Chains or TCRα and TCRβ chains, or a combination thereof.

104. The modified cell of any of the preceding embodiments, wherein the cell is an immune effector cell (e.g., a population of immune effector cells).

105. The modified cell of embodiment 104, wherein the immune effector cell is a T cell or an NK cell.

106. The modified cell of embodiment 105, wherein the immune effector cell is a T cell.

107. modified cell of embodiment 106, wherein the T cell is a CD4+ T cell, a CD8+ T cell, or a combination thereof.

108. The modified cell of any of the preceding embodiments, wherein the cell is a human cell.

109. The modified cell of any of the preceding embodiments, wherein the modified cell comprises an inhibitor of expression or function of the one or more genes.

110. The modified cell of embodiment 109, wherein the inhibitor is (1) a gene editing system targeted to one or more sites within the gene encoding the one or more genes or a corresponding regulatory elements; (2) nucleic acid encoding one or more components of a gene editing system of the one or more genes; or (3) combinations thereof.

111. A pharmaceutical composition comprising the population of the cells of any of embodiments 91-110.

112. A method of causing or eliciting T cell response in a subject in need thereof and/or treating a tumor of the subject, the method comprising administering an effective amount of the composition of embodiment 113 to the subject.

113. The modified cell, the method, the pharmaceutical composition, the cell of one of embodiments 58-21, wherein the enhanced expression and/or function of the one or more genes is implemented by introducing a nucleic acid sequence of the one or more genes, which is present in the modified cell in a recombinant DNA construct, in an mRNA, or in a viral vector.

114. The modified cell, the method, the pharmaceutical composition, the cell of one of embodiments 91-112, wherein the reduced expression and/or function of the one or more genes is implemented by introducing a nucleic acid sequence encoding a dominant negative form of the one or more genes, and nucleic acid sequence is present in the modified cell in a recombinant DNA construct, in an mRNA, or in a viral vector.

115. The modified cell, the method, the pharmaceutical composition, the cell of one of embodiments 113 and 114, wherein the nucleic acid sequence is an mRNA, which is not integrated into the genome of the modified cell.
116. The modified cell, the method, the pharmaceutical composition, the cell of one of embodiments 113-115, wherein the nucleic acid sequence is associated with an oxygen-sensitive polypeptide domain.
117. The modified cell, the method, the pharmaceutical composition, the cell of embodiment 116, wherein the oxygen-sensitive polypeptide domain comprises HIF VHL binding domain.
118. The modified cell, the method, the pharmaceutical composition, the cell of one of embodiments 113-115, wherein the nucleic acid sequence is regulated by a promoter comprising a binding site for a transcription modulator that modulates the expression and/or secretion of the therapeutic agent in the cell.
119. The modified cell, the method, the pharmaceutical composition, the cell of embodiment 118, wherein the transcription modulator is or includes Hif1a, NFAT, FOXP3, and/or NFkB.

EXAMPLES

Identification of Cell Lines Overexpressing CXCL9/10

Figure 2:
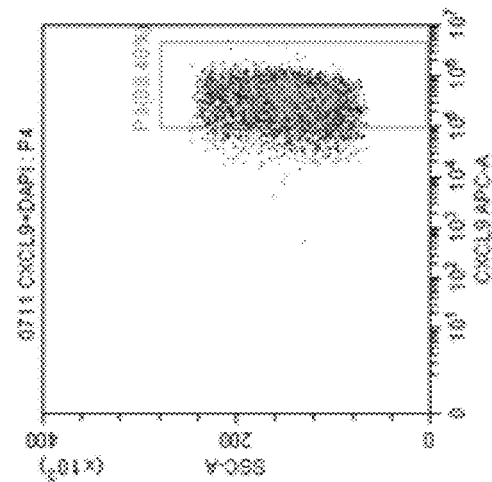
FIG. 2 includes flow cytometry showing identification of cell lines overexpressing CXCL9/10.
Figure 2:
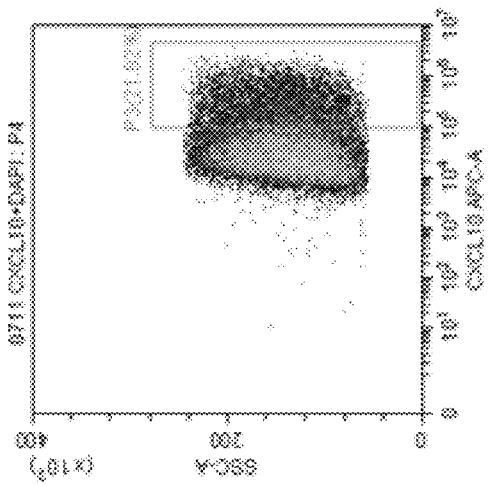
Figure 2:
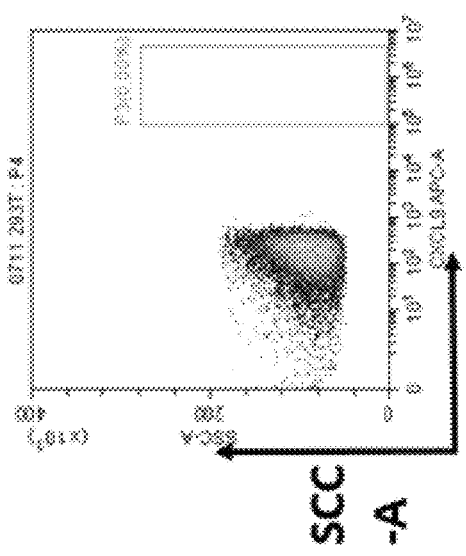
Figure 2:
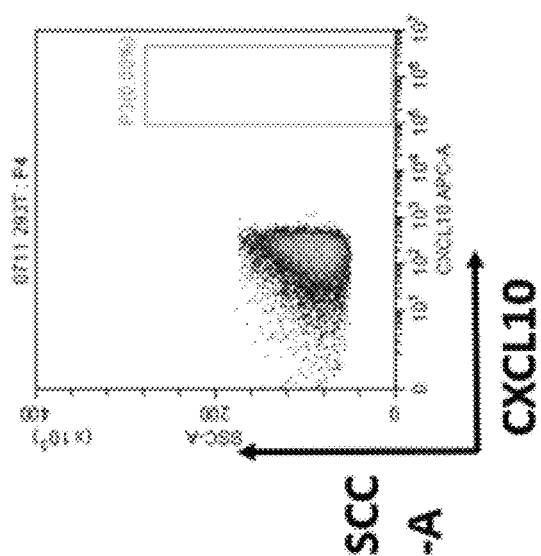

Corresponding sequences described in EXAMPLES are listed in Table 1 below. 293T cells were infected by lentiviruses containing CXCL9/CXCL10 to express CXCL9 and CXCL10. Anti-CXCL9/CXCL10 antibodies were used to detect the expression. These cells were then added as substrate cells for migration assay. Lentiviruses of CXCL9 and CXCL10 were separately packaged with a lentiviral plasmid containing CXCL9 or CXCL10. Fresh $1\times10^6$ 293T-wt cells were infected with CXCL9 or CXCL10 at a ratio of a multiplicity of infection (MOI) 1-50. After neutralizing with 10% DMEM, $5\times10^5$ cells were stained with 1 ug of CXCL9/CXCL10 antibodies. Results are shown in FIG. 2.

CXCR3-CART Cell Migration Assay

Figure 3:
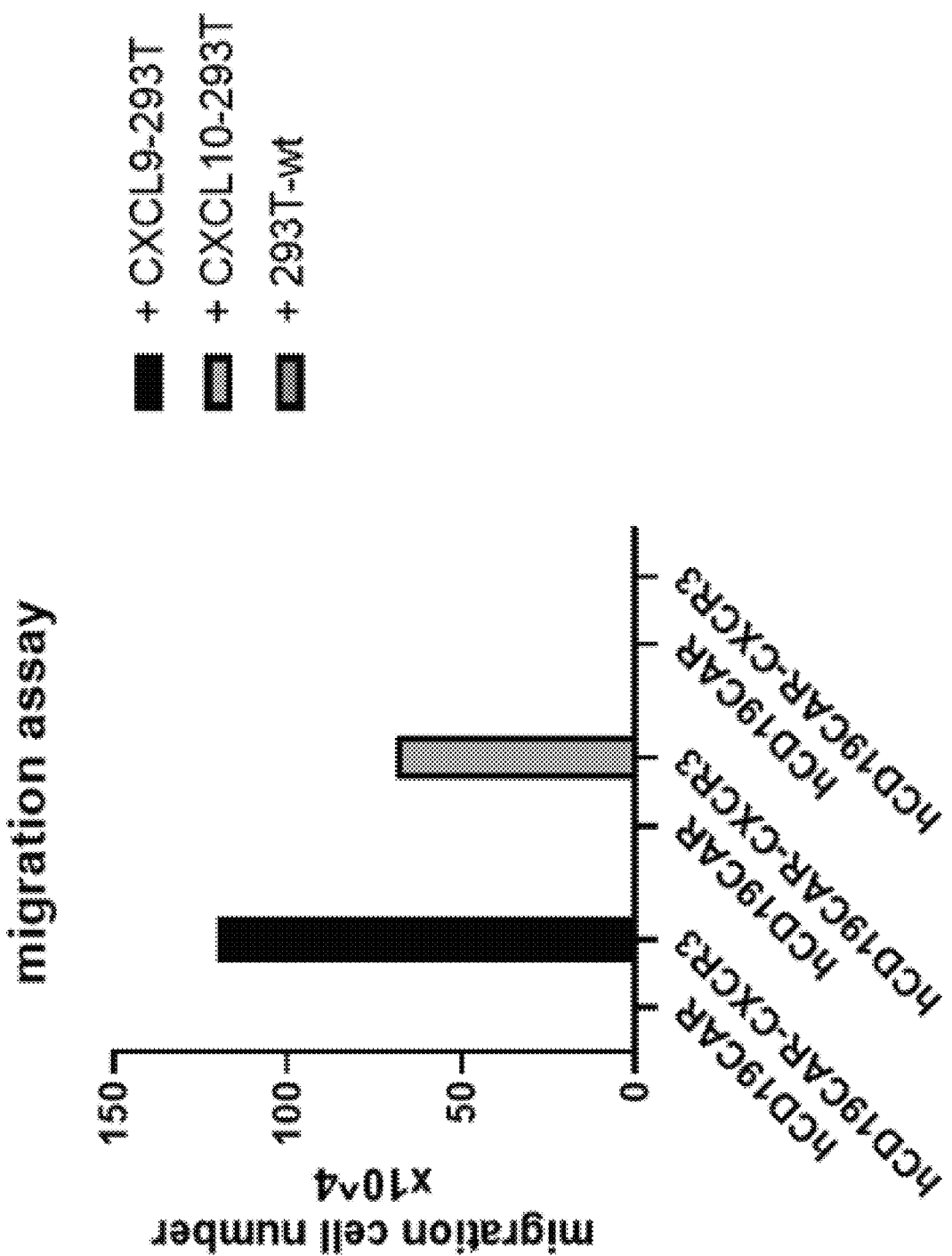
FIG. 3 is a histogram showing CXCR3-CART cell migration assay.

Ligands of CXCR3 include CXCL9 and CXCL10. hCD19CAR and hCD19CAR-CXCR3 cells were prepared from healthy volunteers' fresh cells and cultured to expand to day7. $5\times10^5$ 293T-wt, 293T with CXCL9, 293T with CXCL10 cells (thereafter Testing Cells) were plated to the bottom of the Transwell plate at day 6. At day7, $2\times10^6$ hCD19CAR and hCD19CAR-CXCR3 cells were added to the upper part of transwell containing and not containing Testing Cells. The number of cells migrating to the bottom of each group was counted 24 hours after the CART cells were added. Results are shown in FIG. 3.

Killing Tumor by CXCR3-CART Cells

Figure 4:
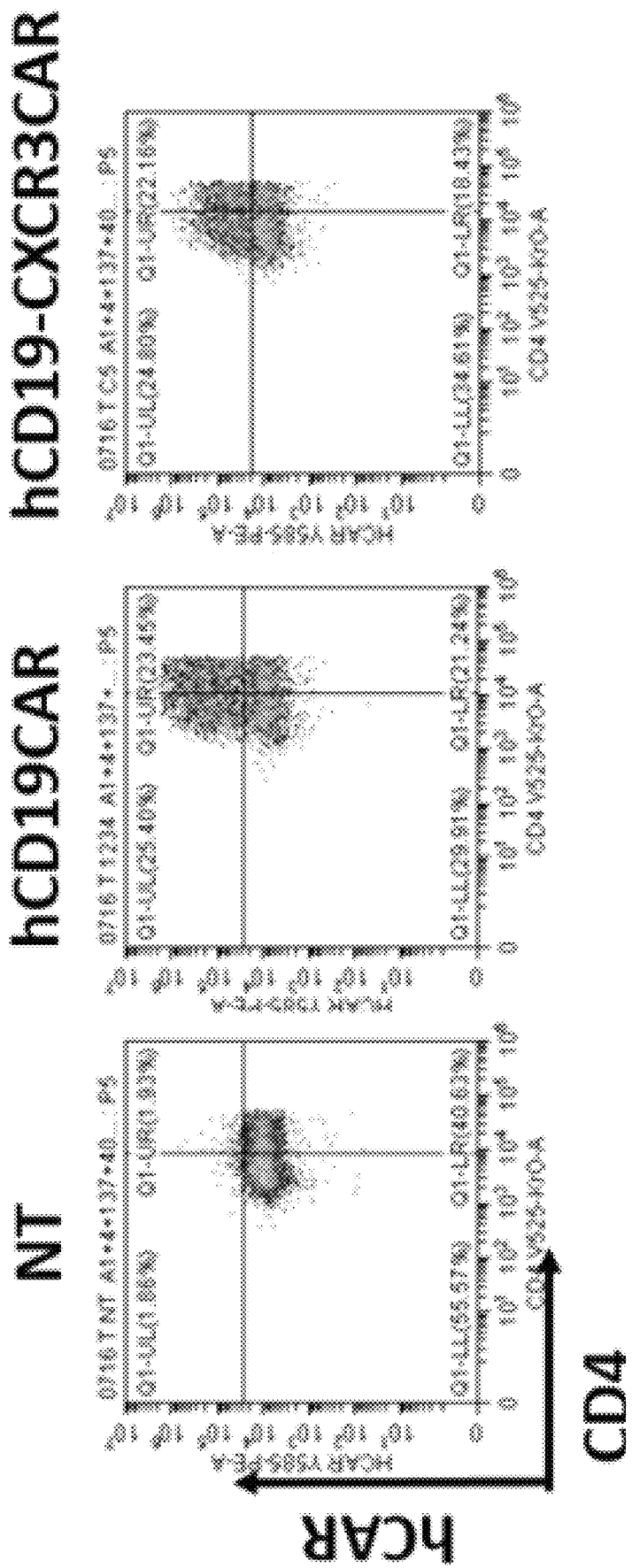
FIGS. 4, 5, and 6 show killing assay of CXCR3-CART cells.
Figure 5:
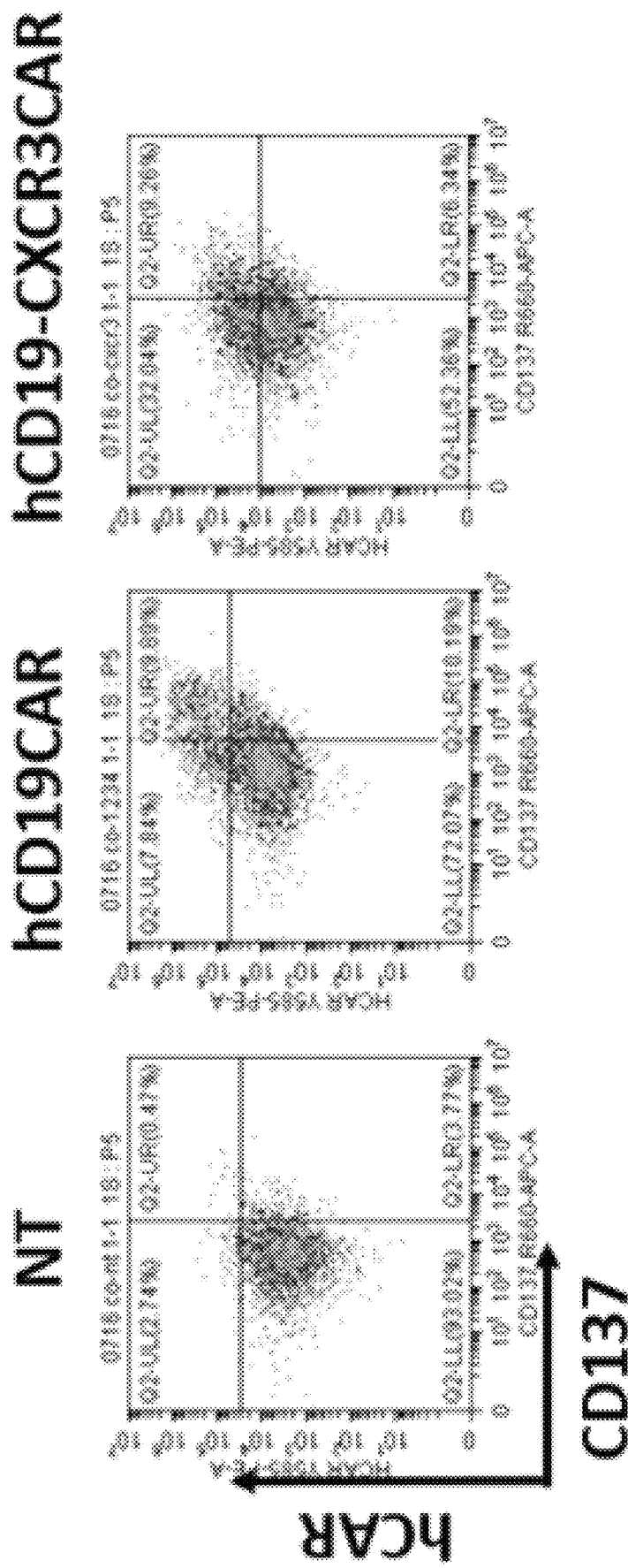
Figure 6:
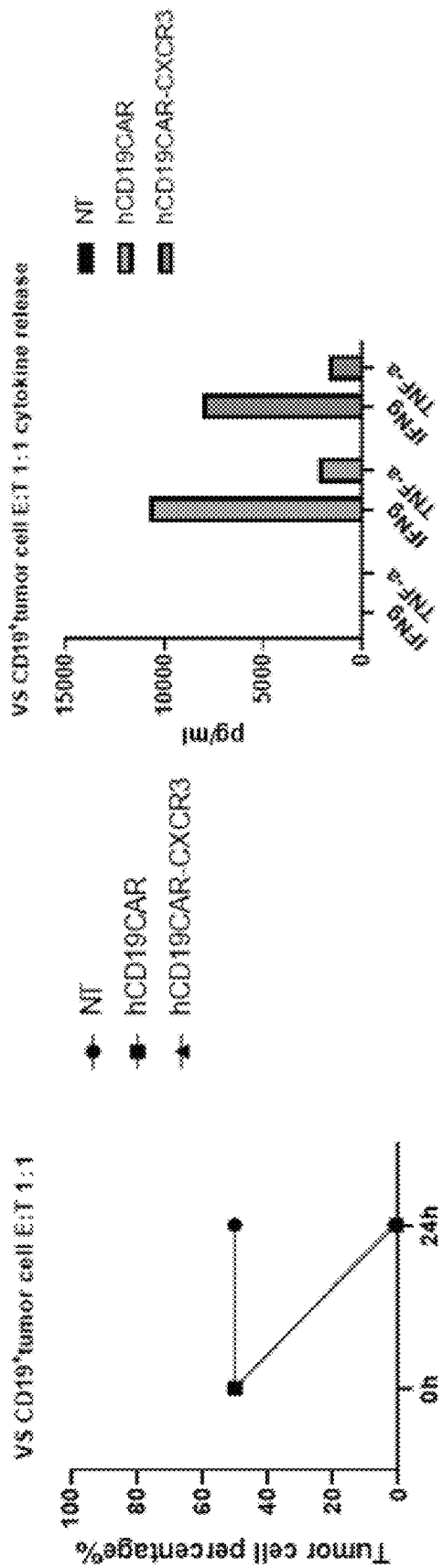

After antigen stimulation, CD19CART cells activate T cells. Activated T cells up-regulate CD137 in a short period and release cytokines such as IFNγ/NFα to cause apoptosis and to kill tumor cells. T cells (NT), hCD19CAR, and hCD19CAR-CXCR3 cells were prepared from healthy volunteers' fresh cells. When cultured and expanded to day7, fresh $2\times10^6$ NT cells, hCD19CAR, and hCD19CAR-CXCR3 were co-cultured with $2\times10^6$ CD19+NALM6 cells. After 24 hours, the cells and supernatant were taken to detect: cell numbers of CD19+ cells, CD137 expression of T cells, expression of CAR, and amounts of IFNγ and TNFα factors released in the supernatant. Results are shown in FIGS. 4-6. The data show that both hCD19CAR-CXCR3 and hCD19CAR T cells inhibited growth of tumor cells, and hCD19CAR-CXCR3 T cells caused more release of IFNγ and TNFα as compared to NT and hCD19CAR T cells.

Identification of Tumor-CD155 Cell Line Overexpressing TIGIT-Ligand (CD155)

Figure 7:
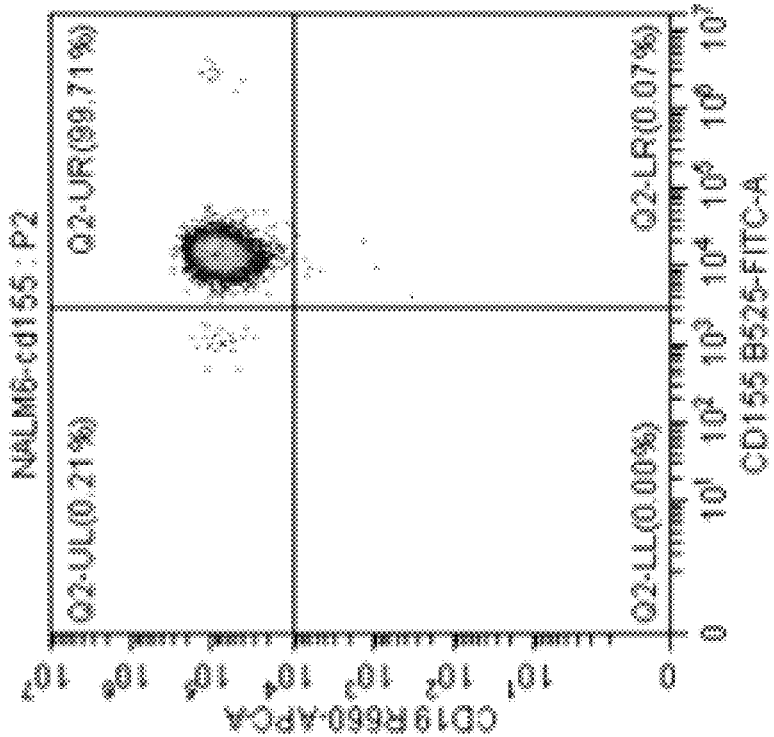
FIG. 7 includes flow cytometry showing identification of tumor-CD155 cell line overexpressing TIGIT-ligand (CD155).
Figure 7:
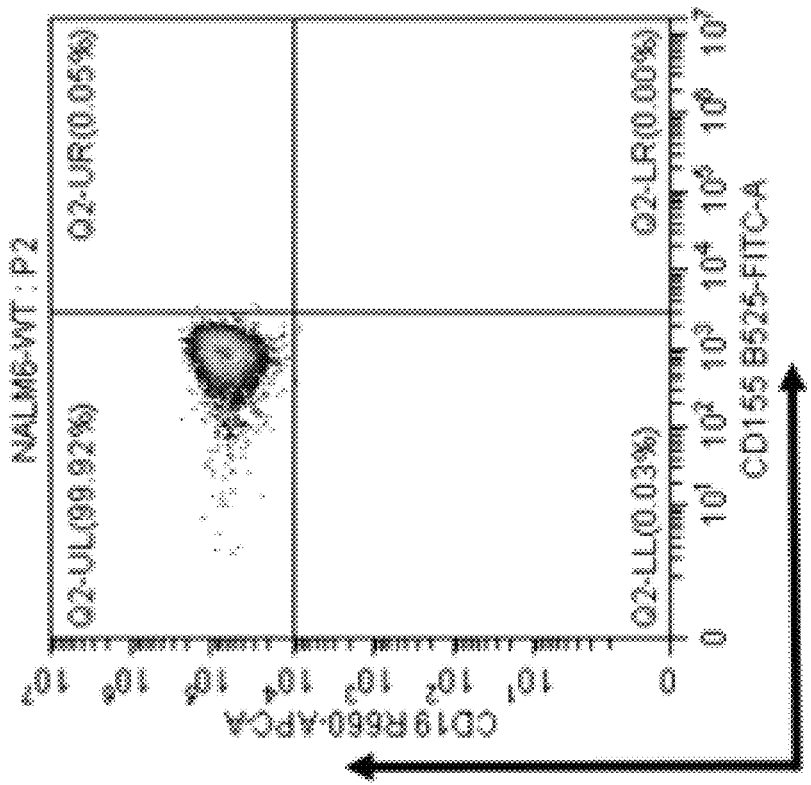

Lentiviral plasmids containing CD155-p2A-GFP were constructed and packaged into lentiviruses using the third-generation lentiviral packaging system and the transfection reagent PEIpro. Fresh $1\times10^6$ nalm6-wt cells were infected with CD155-p2A-GFP lentiviruses at a ratio of MOI 1-50. CD155 antibody was used to detect expression of CD155-p2A-GFPusing flow cytometer. Results are shown in FIG. 7.

Killing Tumor With DN-TIGIT-CART Cells

Figure 8:
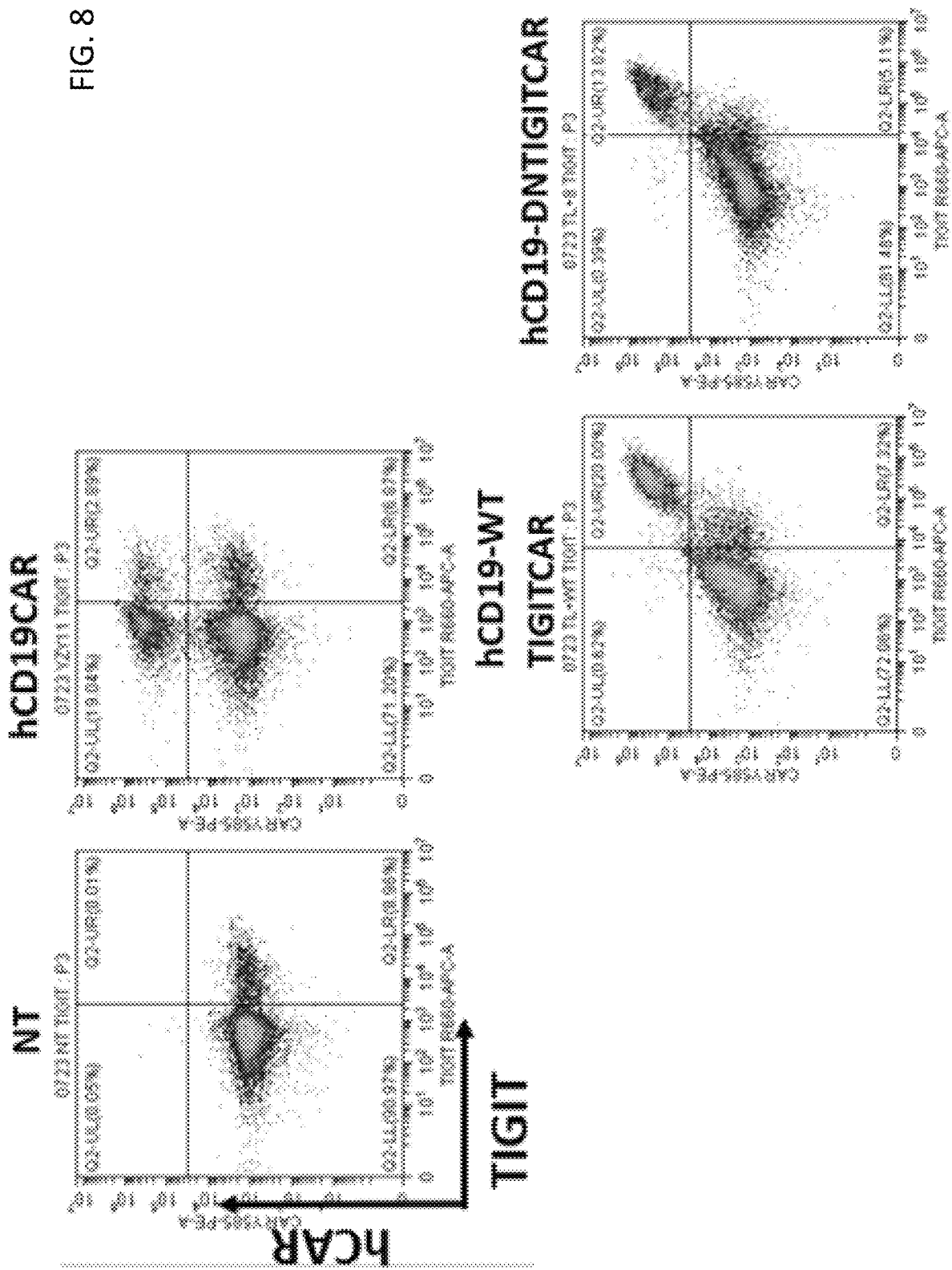
FIGS. 8, 9, and 10 show killing assay of dominant negative (Dn) TIGIT-CART cells.

NT, hCD19CAR, hCD19 CAR-wtTIGIT, and hCD19 CAR-Dn-TIGITCAR cells were prepared from healthy volunteers' fresh cells and cultured and expanded to day7. On day7, fresh $2\times10^6$ NT, hCD19CAR and hCD19 CAR-wt-TIGIT, hCD19 CAR-CAR-Dn-TIGIT cells were co-cultured with NALM6-CD155 cells with a tumor-CART ratio of 3-1 and 1-1. $1\times10^6$ hCD19CAR, hCD19 CAR-wtTIGIT, and hCD19 CAR-Dn-TIGIT cells were taken to measure expression of hCAR and TIGIT using flow cytometry. 24 hours after the coluturing, cells and supernatant to measure killing of tumor cells (CD19 Positive cells), and the IFNγ and TNFα factors release were measured. As shown in FIG. 8, the expression of CAR and TIGIT in NT, hCD19CAR and hCD19 CAR-wtTIGIT, and hCD19-Dn-TIGIT CAR 4 cells was detected by flow cytometry. The results showed that NT, hCD19CAR, hCD19 CAR-wtTIGIT, and hCD19-CAR-Dn-TIGIT had different degrees of TIGIT expression.

Figure 9:
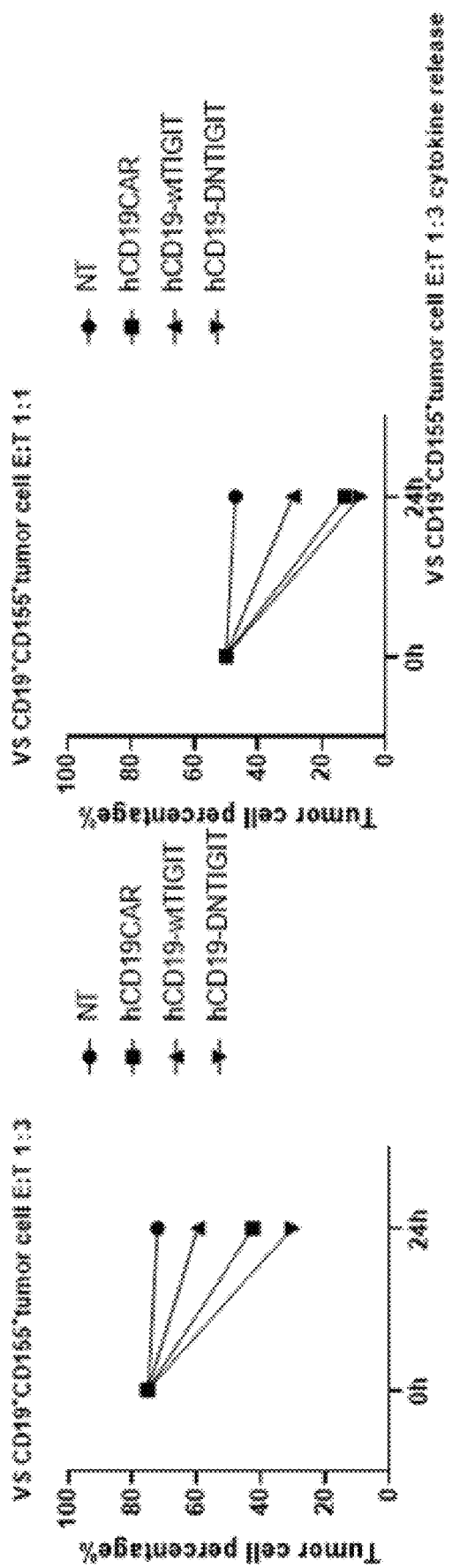
Figure 10:
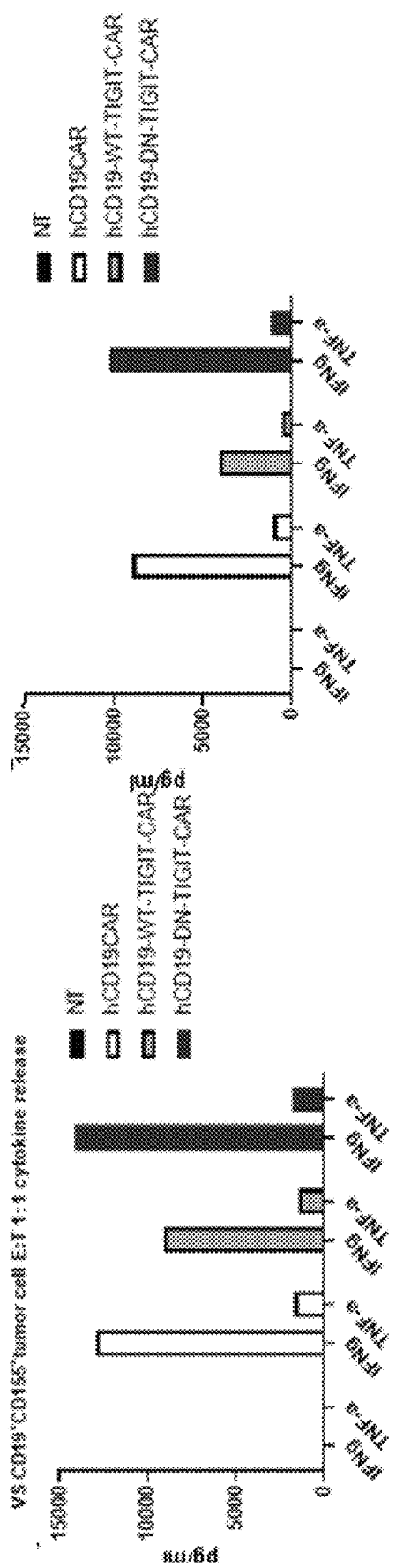

FIG. 9. shows that NT did not significantly reduce the numbers of CD19+ cells, and hCD19-CAR-Dn-TIGIT cells reduced more CD19+ cells as compared to hCD19CAR and hCD19 CAR-wtTIGIT. FIG. 10 shows the release of IFNγ/NFα measured by flow CBAkit after 24 hours of co-culturing with CD19+ cells. The results show that the cytokine release of hCD19-CAR-Dn-TIHT cells was significantly higher than that of h19CAR and hCD19-CAR-WT-TIGIT. Thus, blocking this interaction between CD155 and TIGIT enhanced T cell functions (e.g., cytokine release).

TABLE 1

| SEQ ID NO: | Notes | SEQ ID NO: | Notes | SEQ ID NO: | Notes |
|---|---|---|---|---|---|
| 1 | CDS of CXCR2 | 41 | SP | 81 | ZFN left target spry1 Finger2 |
| 2 | cDNA of SLC1A3 | 42 | Linker | 82 | ZFN left target spry1 Finger3 |

TABLE 1-continued

| SEQ ID NO: | Notes | SEQ ID NO: | Notes | SEQ ID NO: | Notes |
|---|---|---|---|---|---|
| 3 | Construct of SLC1A3-CART | 43 | 4-1BB | 83 | ZFN left target spry1 Finger4 |
| 4 | WT CXCR2 | 44 | CD3-zeta | 84 | cDNA of Spry2 |
| 5 | Truncated CXCR2 | 45 | WT CD3-zeta-aa | 85 | ZFN left arm target spry2 |
| 6 | Modified intracellular domain of CXCR2 | 46 | Group B// Hinge & TM domain | 86 | ZFN left arm target spry2 Finger1 |
| 7 | cDNA of YAP | 47 | Group A// Hinge & TM domain | 87 | ZFN left arm target spry2Finger2 |
| 8 | Amino acid of YAP | 48 | Group D // Hinge & TM domain | 88 | ZFN left arm target spry2 Finger3 |
| 9 | cDNA of ERBB4: | 49 | Group C // Hinge & TM domain | 89 | ZFN left arm target spry2 Finger4 |
| 10 | Amino acid of ERBB4 | 50 | Group D // Hinge domain | 90 | ZFN right arm target spry2 |
| 11 | Truncated Amino acid of ERBB4 | 51 | Group C // Hinge domain | 91 | ZFN right arm target spry2: Finger1 |
| 12 | cDNA of LPA receptor LPAR1 | 52 | Group B Hinge domain | 92 | ZFN right arm target spry2Finger2 |
| 13 | Amino acid of LPA receptor LPAR1 | 53 | Group A // Hinge domain | 93 | ZFN right arm target spry2 Finger3 |
| 14 | Truncated Amino acid of LPA receptor LPAR1 | 54 | Group D // TM domain | 94 | ZFN right arm target spry2Finger4 |
| 15 | cDNA of CD44 | 55 | Group C // TM domain | 95 | cDNA of foxo1 |
| 16 | Amino acid of CD44 | 56 | Group B // domain | 96 | The left arm of ZFN target foxo1 |
| 17 | Truncated Amino acid of CD44 | 57 | Group A // domain | 97 | The left arm of ZFN target foxo1 Finger1 |
| 18 | WT TIGIT | 58 | scFv CD19 | 98 | The left arm of ZFN target foxo1 Finger2 |
| 19 | Truncated TIGIT | 59 | scFv Humanized CD19 | 99 | The left arm of ZFN target foxo1 Finger3 |
| 20 | Modified Intracellular domain of TIGIT | 60 | scFv FZD10 | 100 | The left arm of ZFN target foxo1 Finger4 |
| 21 | cDNA of S1P1 | 61 | scFv TSHR | 101 | ZFN right arm target foxo1 |
| 22 | sequence of S1P1-CART | 62 | scFv PRLR | 102 | ZFN right arm target foxo1 Finger1 |
| 23 | WT gp130 | 63 | scFv Muc 17 | 103 | ZFN right arm target foxo1 Finger2 |
| 24 | Truncated gp130 | 64 | scFv GUCY2C | 104 | ZFN right arm target foxo1 Finger3 |
| 25 | Modified gp130 | 65 | scFv CD207 | 105 | ZFN right arm target foxo1 Finger4 |
| 26 | WT 12Rβ2 | 66 | Prolactin (ligand) | 106 | map and sequence of TLR9-CAR |
| 27 | Truncated 12Rβ2 | 67 | scFv CD3 | 107 | cDNA of MyD88 |
| 28 | Modified 12Rβ2 | 68 | scFv CD4 | 108 | map and sequence of MyD88-CAR |
| 29 | CXCR2 target 1 | 69 | scFv CD4 | 109 | Protein sequence of TLR9 |
| 30 | CXCR2-TALEN left 1 | 70 | scFv CD5 | 110 | constitutively active form of IRAK1/IRAK4以及IRF7 sequence of IRAK1 |
| 31 | CXCR2-TALEN right 1 | 71 | ScFv MUC1-5e5 | 111 | constitutively active form of IRAK1/IRAK4以及IRF7 (2) sequence of IRAK4 |
| 32 | CXCR2 target 2 | 72 | ScFv MUC1-Panko | 112 | Dominant negative Spry1-1 |
| 33 | CXCR2-TALEN left 2 | 73 | cDNA of Spry1 | 113 | Dominant negative Spry2 |
| 34 | CXCR2-TALEN right 2 | 74 | ZFN left target spry1 | 114 | Modified Spry1 |
| 35 | CXCR2 target 3 | 75 | ZFN left target spry1 Finger1 | 115 | Modified Spry2 |
| 36 | CXCR2-TALEN left 3 | 76 | ZFN left target spry1Finger2 | 116 | TIR domain |

TABLE 1-continued

| SEQ ID NO: | Notes | SEQ ID NO: | Notes | SEQ ID NO: | Notes |
|---|---|---|---|---|---|
| 37 | CXCR2-TALEN right 3 | 77 | ZFN left target spry1 Finger3 | 117 | intracellular domain of TLR9 |
| 38 | YAP target | 78 | ZFN left target spry1Finger4 | 118 | TIR domain of TLR9 |
| 39 | YAP TALEN left | 79 | ZFN left target spry1 | 119 | Thr209 and Thr387 substituted with Asp in constitutively active form of IRAK1 |
| 40 | YAP TALEN right | 80 | ZFN left target spry1 Finger1 | 120 | 342T and 345T will be substituted with Asp and 346S substituted with Glu in constitutively active form of IRAK4 |
| 121 | S477 and S479 substituted with Glu in sequence of IRF7 | 122 | Dominant negative Spry1-1 | 123 | Dominant negative Spry1-1 |
| 124 | constitutively active form of IRAK1/IRAK4 以及 IRF7 (3) sequence of IRF7 | 125 | CXCR3 | 126 | CXCL10 |
| 127 | CXCL9 | 128 | hCD19 CAR | 129 | hCD19 CAR-P2A-TIGIT-Dn |
| 130 | CXCL9-P2A-PD1M | 131 | CXCL10-P2A-PD1M | 132 | hCD19 CAR-2PA-CXCR3 |
| 133 | hCD19-P2A-CD155 | | | | |

What is claimed is:

1. A modified cell engineered to express an antigen binding molecule, wherein expression and/or function of CXCR3 in the modified cell has been enhanced, and wherein the modified cell comprises nucleic acid sequence SEQ ID NO: 125.

2. The modified cell of claim 1, wherein the antigen binding molecule is a chimeric antigen receptor (CAR), which comprises an antigen binding domain, a transmembrane domain, and an intracellular signaling domain.

3. The modified cell of claim 2, wherein the antigen binding domain binds to a tumor antigen selected from a group consisting of: TSHR, CD19, CD123, CD22, CD30, CD171, CS-1, CLL-1, CD33, EGFRvIII, GD2, GD3, BCMA, Tn Ag, PSMA, ROR1, FLT3, FAP, TAG72, CD38, CD44v6, CEA, EPCAM, B7H3, KIT, IL-13Ra2, Mesothelin, IL-11Ra, PSCA, PRSS21, VEGFR2, Lewis Y, CD24, PDGFR-beta, SSEA-4, CD20, Folate receptor alpha, ERBB2 (Her2/neu), MUC1, EGFR, NCAM, Prostase, PAP, ELF2M, Ephrin B2, IGF-I receptor, CAIX, LMP2, gp100, bcr-abl, tyrosinase, EphA2, Fucosyl GM1, GM3, TGS5, HMWMAA, o-acetyl-GD2, Folate receptor beta, TEM1/CD248, TEM7R, CLDN6, GPRC5D, CXORF61, CD97, CD179a, ALK, Polysialic acid, PLAC1, GloboH, NY-BR-1, UPK2, HAVCR1, ADRB3, PANX3, GPR20, LY6K, OR51E2, TARP, WT1, NY-ESO-1, LAGE-1a, MAGE-A1, legumain, HPV E6, E7, ETV6-AML, sperm protein 17, XAGE1, Tie 2, MAD-CT-1, MAD-CT-2, Fos-related antigen 1, p53, p53 mutant, prostein, survivin, telomerase (hTERT), PCTA-1/Galectin 8, MelanA/MART1, Ras mutant, ML-IAP, ERG (TMPRSS2 ETS fusion gene), NA17, PAX3, Androgen receptor, Cyclin B1, MYCN, RhoC, TRP-2, CYP1B1, BORIS, SART3, PAX5, OY-TES1, LCK, AKAP-4, SSX2, RAGE-1, human telomerase reverse transcriptase, RU1, RU2, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, GUCY2C, and IGLL1.

4. The modified cell of claim 2, wherein the intracellular signaling domain comprises a co-stimulatory signaling domain or a primary signaling domain, or a combination thereof, wherein the co-stimulatory signaling domain comprises a functional signaling domain of a protein selected from the group consisting of CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRF1), CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11 d, ITGAE, CD103, ITGAL, CD11a, LFA-1, ITGAM, CD11 b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, and NKG2D.

5. The modified cell of claim 1, wherein the modified cell is a T cell.

6. The modified cell of claim 1, wherein the nucleic acid sequence is regulated by a promoter comprising a binding site for a transcription modulator that modulates the expression of the nucleic acid in the cell.

7. The modified cell of claim 6, wherein the transcription modulator is or includes Hif1a, NFAT, FOXP3, and/or NFkB.

8. A method of eliciting a T cell response in a subject in need thereof and/or treating a tumor of in a subject, the method comprising administering an effective amount of a composition comprising a population of the modified cells of claim 1 to the subject.

9. The modified cell of claim 1, wherein the antigen binding molecule is a TCR.

10. The modified cell of claim 9, where the TCR is obtained from spontaneously occurring tumor-specific T cells in a subject.

11. The modified cell of claim 1, wherein the modified cell further comprises a dominant negative TIGIT variant, wherein the TIGIT variant is a truncated TIGIT comprising the amino acid sequence of SEQ ID NO: 19, or a TIGIT having a modified intracellular domain having the amino acid sequence of SEQ ID NO: 20.

12. The modified cell of claim 11, wherein the modified cell further comprises a nucleic acid sequence encoding the dominant negative TIGIT variant.

13. The modified cell of claim 12, wherein the nucleic acid sequence is regulated by a promoter comprising a binding site for a transcription modulator that modulates the expression of the nucleic acid sequence in the cell.

14. The modified cell of claim 13, wherein the transcription modulator is or includes Hif1a, NFAT, FOXP3, and/or NFkB.

* * * * *

SEQUENCE LISTING

<160> NUMBER OF SEQ ID NOS: 133

<210> SEQ ID NO 1
<211> LENGTH: 1083
<212> TYPE: DNA
<213> ORGANISM: Homo sapiens

<400> SEQUENCE: 1

```
atggaagatt ttaacatgga gagtgacagc tttgaagatt tctggaaagg tgaagatctt      60
agtaattaca gttacagctc tacccctgccc ccttttctac tagatgccgc ccatgtgaa     120 ccagaatccc tggaaatcaa caagtatttt gtggtcatta tctatgccct ggtattcctg    180
ctgagcctgc tgggaaactc cctcgtgatg ctggtcatct atacagcag ggtcggccgc     240 tccgtcactg atgtctacct gctgaaccta gccttggccg acctactctt tgccctgacc    300
ttgcccatct gggccgcctc caaggtgaat ggctggattt ttggcacatt cctgtgcaag   360
gtggtctcac tcctgaagga agtcaacttc tatagtggca tcctgctact ggcctgcatc   420
agtgtggacc gttacctggc cattgtccat gccacacgca cactgaccca gaagcgctac   480
ttggtcaaat tcatatgtct cagcatctgg ggtctgtcct tgctcctggc cctgcctgtc    540 ttactttcc gaaggaccgt ctactcatcc aatgttagcc agcctgcta tgaggacatg    600 ggcaacaata tcagcaaactg gcggatgctg ttacggatcc tgccccagtc ctttggcttc    660
atcgtgccac tgctgatcat gctgttctgc tacggattca ccctgcgtac gctgtttaag    720
gcccacatgg gcagaagca ccgggccatg cgggtcatct ttgctgtcgt cctcatcttc    780
ctgctctgct ggctgcccta caaccctggtc ctgctggcag acaccctcat gaggacccag    840
gtgatccagg agacctgtga gcgccgcaat cacatcgacc gggctctgga tgccaccgag    900
```

| | |
|---|---|
| attctgggca tccttcacag ctgcctcaac ccctcatct acgccttcat tggccagaag | 960 |
| tttcgccatg gactcctcaa gattctagct atacatggct tgatcagcaa ggactccctg | 1020 |
| cccaaagaca gcaggccttc ctttgttggc tcttcttcag ggcacacttc cactactctc | 1080 |
| taa | 1083 |

<210> SEQ ID NO 2
<211> LENGTH: 1494
<212> TYPE: DNA
<213> ORGANISM: Homo sapiens

<400> SEQUENCE: 2

| | |
|---|---|
| atgactaaaa gcaatggaga agagcccaag atggggggca ggatggagag attccagcag | 60 |
| ggagtccgta aacgcacact tttggccaag aagaaagtgc agaacattac aaaggaggat | 120 |
| gttaaaagtt acctgtttcg gaatgctttt gtgctgctca cagtcaccgc tgtcattgtg | 180 |
| ggtacaatcc ttggatttac cctccgacca tacagaatga gctaccggga agtcaagtac | 240 |
| ttctcctttc ctggggaact tctgatgagg atgttacaga tgctggtctt accacttatc | 300 |
| atctccagtc ttgtcacagg aatggcggcg ctagatagta aggcatcagg gaagatggga | 360 |
| atgcgagctg tagtctatta tatgactacc accatcattg ctgtggtgat tggcataatc | 420 |
| attgtcatca tcatccatcc tgggaagggc acaaaggaaa acatgcacag agaaggcaaa | 480 |
| attgtacgag tgacagctgc agatgccttc ctggacttga tcaggaacat gttccctcca | 540 |
| aatctggtag aagcctgctt taaacagttt aaaaccaact atgagaagag aagctttaaa | 600 |
| gtgcccatcc aggccaacga aacgcttgtg ggtgctgtga taacaatgt gtctgaggcc | 660 |
| atggagactc ttacccgaat cacagaggag ctggtcccag ttccaggatc tgtgaatgga | 720 |
| gtcaatgccc tgggtctagt tgtcttctcc atgtgcttcg gttttgtgat tggaaacatg | 780 |
| aaggaacagg ggcaggccct gagagagttc tttgattctc ttaacgaagc catcatgaga | 840 |
| ctggtagcag taataatgtg gtatgccccc gtgggtattc tcttcctgat tgctgggaag | 900 |
| attgtggaga tggaagacat gggtgtgatt gggggggcagc ttgccatgta caccgtgact | 960 |
| gtcattgttg gcttactcat tcacgcagtc atcgtcttgc cactcctcta cttcttggta | 1020 |
| acacggaaaa acccttgggt ttttattgga gggttgctgc aagcactcat caccgctctg | 1080 |
| gggacctctt caagttctgc caccctaccc atcaccttca gtgcctggaa agagaacaat | 1140 |
| ggcgtggaca agcgcgtcac cagattcgtg ctccccgtag agccaccat taacatggat | 1200 |
| gggactgccc tctatgaggc tttggctgcc attttcattg ctcaagttaa caactttgaa | 1260 |
| ctgaacttcg gacaaattat tacaatcagg gatcgcctcc ggaccaccac caacgtactg | 1320 |
| ggagactccc tgggagctgg gattgtggag cacttgtcac gacatgaact gaagaacaga | 1380 |
| gatgttgaaa tgggtaactc agtgattgaa gagaatgaaa tgaagaaacc atatcaactg | 1440 |
| attgcacagg acaatgaaac tgagaaaccc atcgacagtg aaaccaagat gtag | 1494 |

<210> SEQ ID NO 3
<211> LENGTH: 9925
<212> TYPE: DNA
<213> ORGANISM: Homo sapiens

<400> SEQUENCE: 3

| | |
|---|---|
| cggctccggt gcccgtcagt gggcagagcg cacatcgccc acagtccccg agaagttggg | 60 |
| gggaggggtc ggcaattgaa ccggtgccta gagaaggtgc gcggggtaa actgggaaag | 120 |
| tgatgtcgtg tactggctcc gccttttttcc cgagggtggg ggagaaccgt atataagtgc | 180 |

```
agtagtcgcc gtgaacgttc tttttcgcaa cgggtttgcc gccagaacac aggatccgcc      240
accatggcct taccagtgac cgccttgctc ctgccgctgg ccttgctgct ccacgccgcc      300
aggccggata tccagatgac ccagagcccg agcagcctga gcgcgagcgt gggtgatcgc      360
gtgaccatta cctgcagggc aagtcaggac attagtaaat atttaaattg gtatcagcag      420
aaaccgggta aagcgccgaa actgttaatt tatcatacat caagattaca ctcaggcgtg      480
ccgtcgcgtt ttagcggctc gggttcgggc accgatttta ccctgaccat ctcgagcttg      540
cagccggagg acttcgccac ctactattgc caacaggcta atacgcttcc gtacacgttc      600
ggtcagggca ccaaagtgga gatcaaaggt ggcggtggct cgggcggtgg tgggtcgggt      660
ggcggcggat ctgaggtgca gctggtggag tctgggggag gcttggtaca gcctgggggg      720
tccctgagac tctcctgtgc agcctctgga gtgtccctgc tgattatgg cgtgtcctgg      780 gtccgccagg ctccagggaa ggggctggag tgggtttcag tgatctgggg cagcgagaca      840
acctactaca cagcgccct gaagtcccga ttcaccatct ccagagacaa tgccaagaac      900
tcactgtatc tgcaaatgaa cagcctgaga gccgaggaca cggctgtgta ttactgtgcg      960
aagcactact actacggcgg cagctacgct atggactact ggggccaagg aaccctggtc     1020
accgtgtcct caaccacgac gccagcgccg cgaccaccaa caccggcgcc caccatcgcg     1080
tcgcagcccc tgtccctgcg cccagaggcg tgccggccag cggcgggggg cgcagtgcac     1140
acgagggggc tggacttcgc ctgtgatatc tacatctggg cgcccttggc cgggacttgt     1200
ggggtccttc tcctgtcact ggttataccc ctttactgca aacggggcag aaagaaactc     1260
ctgtatatat tcaaacaacc atttatgaga ccagtacaaa ctactcaaga ggaagatggc     1320
tgtagctgcc gatttccaga agaagaagaa ggaggatgtg aactgagagt gaagttcagc     1380
aggagcgcag acgccccgc gtaccagcag ggccagaacc agctctataa cgagctcaat     1440
ctaggacgaa gagaggagta cgatgttttg gacaagaggc gtggccggga ccctgagatg     1500 ggggaaagc cgagaaggaa gaaccctcag gaaggcctgt acaatgaact gcagaaagat     1560
aagatggcgg aggcctacag tgagattggg atgaaaggcg agcgccggag gggcaagggg     1620
cacgatggcc tttaccaggg tctcagtaca gccaccaagg acacctacga cgcccttcac     1680
atgcaggccc tgccccctcg ctaagtcgac cccctctccc tcccccccc ctaacgttac     1740 tggccgaagc cgcttggaat aaggccggtg tgcgtttgtc tatatgttat tttccaccat     1800
attgccgtct tttggcaatg tgagggcccg gaaacctggc cctgtcttct tgacgagcat     1860
tcctaggggt ctttcccctc tcgccaaagg aatgcaaggt ctgttgaatg tcgtgaagga     1920
agcagttcct ctggaagctt cttgaagaca acaacgtct gtagcgaccc tttgcaggca     1980
gcggaacccc ccacctggcg acaggtgcct ctgcggccaa agccacgtg tataagatac     2040 acctgcaaag gcggcacaac cccagtgcca cgttgtgagt tggatagttg tggaaagagt     2100
caaatggctc tcctcaagcg tattcaacaa ggggctgaag gatgcccaga aggtaccca     2160 ttgtatggga tctgatctgg ggcctcggta cacatgcttt acatgtgttt agtcgaggtt     2220
aaaaaaacgt ctaggccccc cgaaccacgg gacgtggtt ttcctttgaa aaacacgatg     2280
ataatatggc cacaacccat atgagtgatg actaaaagca atggagaaga gcccaagatg     2340 ggggcagga tggagagatt ccagcaggga gtccgtaaac gcacacttt ggccaagaag     2400 aaagtgcaga acattacaaa ggaggatgtt aaaagttacc tgtttcggaa tgcttttgtg     2460
ctgctcacag tcaccgctgt cattgtgggt acaatccttg gatttaccct ccgaccatac     2520
```

-continued

```
agaatgagct accgggaagt caagtacttc tcctttcctg gggaacttct gatgaggatg    2580
ttacagatgc tggtcttacc acttatcatc tccagtcttg tcacaggaat ggcggcgcta    2640
gatagtaagg catcagggaa gatgggaatg cgagctgtag tctattatat gactaccacc    2700
atcattgctg tggtgattgg cataatcatt gtcatcatca tccatcctgg aagggcaca    2760 aaggaaaaca tgcacagaga aggcaaaatt gtacgagtga cagctgcaga tgccttcctg    2820
gacttgatca ggaacatgtt ccctccaaat ctggtagaag cctgctttaa acagtttaaa    2880
accaactatg agaagagaag ctttaaagtg cccatccagg ccaacgaaac gcttgtgggt    2940
gctgtgataa acaatgtgtc tgaggccatg gagactctta cccgaatcac agaggagctg    3000
gtcccagttc caggatctgt gaatggagtc aatgccctgg gtctagttgt cttctccatg    3060
tgcttcggtt ttgtgattgg aaacatgaag gaacaggggc aggccctgag agagttcttt    3120
gattctctta acgaagccat catgagactg gtagcagtaa taatgtggta tgccccgtg     3180 ggtattctct tcctgattgc tgggaagatt gtggagatgg aagacatggg tgtgattggg    3240
gggcagcttg ccatgtacac cgtgactgtc attgttggct tactcattca cgcagtcatc    3300
gtcttgccac tcctctactt cttggtaaca cggaaaaacc cttgggtttt tattggaggg    3360
ttgctgcaag cactcatcac cgctctgggg acctcttcaa gttctgccac cctacccatc    3420
accttcaagt gcctggaaga gaacaatggc gtggacaagc gcgtcaccag attcgtgctc    3480
cccgtaggag ccaccattaa catggatggg actgccctct atgaggcttt ggctgccatt    3540
ttcattgctc aagttaacaa ctttgaactg aacttcggac aaattattac aatcagggat    3600
cgcctccgga ccaccaccaa cgtactggga gactccctgg gagctgggat tgtggagcac    3660
ttgtcacgac atgaactgaa gaacagagat gttgaaatgg taactcagt gattgaagag    3720 aatgaaatga gaaaccata tcaactgatt gcacaggaca tgaaactgaa gaaacccatc    3780
gacagtgaaa ccaagatgta gactagtaat caacctctgg attacaaaat ttgtgaaaga    3840
ttgactggta ttcttaacta tgttgctcct tttacgctat gtggatacgc tgctttaatg    3900
cctttgtatc atgctattgc ttcccgtatg gctttcattt tctcctcctt gtataaatcc    3960
tggttgctgt ctcttatga ggagttgtgg cccgttgtca ggcaacgtgg cgtggtgtgc    4020 actgtgttg ctgacgcaac ccccactggt tggggcattg ccaccacctg tcagctcctt    4080
tccgggactt tcgcttcc cctcccctatt gccacggcgg aactcatcgc cgcctgcctt    4140
gcccgctgct ggacaggggc tcggctgttg ggcactgaca attccgtggt gttgtcgggg    4200
aagctgacgt cctttccatg gctgctccgcc tgtgttgcca cctggattct cgcgggacg    4260 tccttctgct acgtcccttc ggccctcaat ccagcggacc ttccttcccg cggcctgctg    4320
ccggctctgc ggcctcttcc gcgtcttcgc cttcgccctc agacgagtcg gatctccctt    4380
tgggccgcct cccgcctgc cgcggaattc gagctcggta cctttaagac caatgactta    4440
caaggcagct gtagatctta gccacttttt aaaagaaaag gggggactgg aagggctaat    4500
tcactcccaa cgaagacaag atctgctttt tgcttgtact gggtctctct ggttagacca    4560
gatctgagcc tgggagctct ctggctaact agggaaccca ctgcttaagc ctcaataaag    4620
cttgccttga gtgcttcaag tagtgtgtgc ccgtctgttg tgtgactctg gtaactagag    4680
atccctcaga ccctttagt cagtgtggaa atctctagc agtagtagtt catgtcatct    4740
tattattcag tatttataac ttgcaaagaa atgaatatca gagagtgaga ggaacttgtt    4800
tattgcagct tataatggtt acaaataaag caatagcatc acaaatttca caaataaagc    4860
atttttttca ctgcattcta gttgtggttt gtccaaactc atcaatgtat cttatcatgt    4920
```

```
ctggctctag ctatcccgcc cctaactccg cccatcccgc ccctaactcc gcccagttcc    4980
gcccattctc cgcccatgg ctgactaatt ttttttattt atgcagaggc cgaggccgcc    5040
tcggcctctg agctattcca gaagtagtga ggaggctttt ttggaggcct agggacgtac    5100
ccaattcgcc ctatagtgag tcgtattacg cgcgctcact ggccgtcgtt ttacaacgtc    5160
gtgactggga aaccctggc gttacccaac ttaatcgcct tgcagcacat ccccctttcg    5220 ccagctggc taatagcgaa gaggcccgca ccgatcgccc ttcccaacag ttgcgcagcc    5280
tgaatggcga atgggacgcg ccctgtagcg gcgcattaag cgcggcgggt gtggtggtta    5340
cgcgcagcgt gaccgctaca cttgccacgc cctagcgcc cgctcctttc gctttcttcc    5400
cttcctttct cgccacgttc gccggctttc cccgtcaagc tctaaatcgg ggctcccctt    5460
tagggttccg atttagtgct ttacggcacc tcgacccaa aaacttgat tagggtgatg    5520 gttcacgtag tgggccatcg ccctgataga cggttttcg cccttttgacg ttggagtcca    5580 cgttctttaa tagtggactc ttgttccaaa ctggaacaac actcaaccct atctcggtct    5640 attctttga tttataaggg attttgccga tttcggccta ttggttaaaa aatgagctga    5700
tttaacaaaa attttaacgcg aattttaaca aatattaac gcttacaatt tgaagatcct    5760
ttgatctttt ctacggggtc tgacgctcag tggaacgaaa actcacgtta agggattttg    5820
gtcatgaaca ataaaactgt ctgcttacat aaacagtaat acaaggggtg ttatgagcca    5880
tattcaacgg gaaacgtctt gctctaggcc gcgattaaat tccaacatgg atgctgattt    5940
atatgggtat aaatgggctc gcgataatgt cgggcaatca ggtgcgacaa tctatcgatt    6000
gtatgggaag cccgatgcgc cagagttgtt tctgaaacat ggcaaaggta gcgttgccaa    6060
tgatgttaca gatgagatgg tcagactaaa ctggctgacg gaatttatgc ctcttccgac    6120
catcaagcat tttatccgta ctcctgatga tgcatggtta ctcaccactg cgatccccgg    6180
gaaaacagca ttccaggtat tagaagaata cctgattca ggtgaaaata ttgttgatgc    6240
gctggcagtg ttcctgcgcc ggttgcattc gattcctgtt tgtaattgtc cttttaacag    6300
cgatcgcgta tttcgtctgg ctcaggcgca atcacgaatg aataacggtt tggttgatgc    6360
gagtgatttt gatgacgagc gtaatggctg gcctgttgaa caagtctgga agaaatgca    6420 taaacttttg ccattctcac cggattcagt cgtcactcat ggtgatttct cacttgataa    6480 ccttatttt gacgagggga aattaatagg ttgtattgat gttggacgag tcggaatcgc    6540
agaccgatac caggatcttg ccatcctatg gaactgcctc ggtgagtttt ctccttcatt    6600
acagaaacgg cttttcaaa aatatggtat tgataatcct gatatgaata aattgcagtt    6660
tcatttgatg ctcgatgagt tttctaact gtcagaccaa gtttactcat atatacttta    6720
gattgattta aaacttcatt tttaatttaa aggatctag gtgaagatcc ttttgataa    6780 tctcatgacc aaaatccctt aacgtgagtt ttcgttccac tgagcgtcag accccgtaga    6840
aaagatcaaa ggatcttctt gagatccttt ttttctgcgc gtaatctgct gcttgcaaac    6900
aaaaaaacca ccgctaccag cggtggtttg tttgccggat caagagctac caactctttt    6960
tccgaaggta actggcttca gcagagcgca gataccaaat actgttcttc tagtgtagcc    7020
gtagttaggc caccacttca agaactctgt agcaccgcct acatacctcg ctctgctaat    7080
cctgttacca gtggctgctg ccagtggcga taagtcgtgt cttaccgggt tggactcaag    7140
acgatagtta ccggataagg cgcagcggtc gggctgaacg gggggttcgt gcacacagcc    7200
cagcttggag cgaacgacct acaccgaact gagatacta cagcgtgagc tatgagaaag    7260
```

```
cgccacgctt cccgaaggga gaaaggcgga caggtatccg gtaagcggca gggtcggaac   7320
aggagagcgc acgagggagc ttccaggggg aaacgcctgg tatctttata gtcctgtcgg   7380
gtttcgccac ctctgacttg agcgtcgatt tttgtgatgc tcgtcagggg ggcggagcct   7440
atggaaaaac gccagcaacg cggccttttt acggttcctg ccttttgct ggccttttgc    7500 tcacatgttc tttcctgcgt tatccctga ttctgtggat aaccgtatta ccgcctttga    7560
gtgagctgat accgctcgcc gcagccgaac gaccgagcgc agcgagtcag tgagcgagga   7620
agcggaagag cgcccaatac gcaaaccgcc tctccccgcg cgttggccga ttcattaatg   7680
cagctggcac gacaggtttc ccgactgaaa gcgggcagt gagcgcaacg caattaatgt    7740
gagttagctc actcattagg caccccaggc tttacacttt atgcttccgg ctcgtatgtt   7800
gtgtggaatt gtgagcggat aacaatttca cacaggaaac agctatgacc atgattacgc   7860
caagcgcgca attaaccctc actaaaggga acaaaagctg agctgcaag cttaatgtag    7920 tcttatgcaa tactcttgta gtcttgcaac atggtaacga tgagttagca acatgcctta   7980
caaggagaga aaaagcaccg tgcatgccga ttggtggaag taaggtggta cgatcgtgcc   8040
ttattaggaa ggcaacagac gggtctgaca tggattggac gaaccactga attgccgcat   8100
tgcagagata ttgtatttaa gtgcctagct cgatacataa acgggtctct ctggttagac   8160
cagatctgag cctgggagct ctctggctaa ctagggaacc cactgcttaa gcctcaataa   8220
agcttgcctt gagtgcttca agtagtgtgt gcccgtctgt tgtgtgactc tggtaactag   8280
agatccctca gaccctttta gtcagtgtgg aaaatctcta gcagtggcgc ccgaacaggg   8340
acttgaaagc gaaagggaaa ccagaggagc tctctcgacg caggactcgg cttgctgaag   8400
cgcgcacggc aagaggcgag gggcggcgac tggtgagtac gccaaaaatt ttgactagcg   8460
gaggctagaa ggagagagat gggtgcgaga gcgtcagtat taagcggggg agaattagat   8520
cgcgatggga aaaaattcgg ttaaggccag ggggaaagaa aaatataaa ttaaaacata    8580 tagtatgggc aagcagggag ctagaacgat tcgcagttaa tcctggcctg ttagaaacat   8640
cagaaggctg tagacaaata ctgggacagc tacaaccatc ccttcagaca ggatcagaag   8700
aacttagatc attatataat acagtagcaa ccctctattg tgtgcatcaa aggatagaga   8760
taaaagacac caaggaagct ttagacaaga tagaggaaga gcaaacaaa agtaagacca    8820 ccgcacagca agcggccgct gatcttcaga cctggaggag gagatatgag ggacaattgg   8880
agaagtgaat tatataaata taaagtagta aaaattgaac cattaggagt agcacccacc   8940
aaggcaaaga gaagagtggt gcagagagaa aaaagagcag tgggaatagg agctttgttc   9000
cttgggttct tgggagcagc aggaagcact atgggcgcag cgtcaatgac gctgacggta   9060
caggccagac aattattgtc tggtatagtg cagcagcaga acaatttgct gagggctatt   9120
gaggcgcaac agcatctgtt gcaactcaca gtctggggca tcaagcagct ccaggcaaga   9180
atcctggctg tggaaagata cctaaaggat caacagctcc tggggatttg gggttgctct   9240
ggaaaactca tttgcaccac tgctgtgcct tggaatgcta gttggagtaa taaatctctg   9300
gaacagattt ggaatcacac gacctggatg gagtgggaca gagaaattaa caattacaca   9360
agcttaatac actccttaat tgaagaatcg caaaaccagc aagaaaagaa tgaacaagaa   9420
ttattggaat tagataaatg gcaagtttg tggaattggt ttaacataac aaattggctg    9480
tggtatataa aattattcat aatgatagta ggaggcttgg taggtttaag aatagttttt   9540
gctgtacttt ctatagtgaa tagagttagg cagggatatt caccattatc gtttcagacc   9600
cacctcccaa ccccgagggg acccgacagg cccgaaggaa tagaagaaga aggtggagag   9660
```

-continued

```
agagacagag acagatccat tcgattagtg aacggatctc gacggtatcg atcacgagac    9720
tagcctcgac acaaatggca gtattcatcc acaattttaa aagaaaaggg gggattgggg    9780
ggtacagtgc aggggaaaga atagtagaca taatagcaac agacatacaa actaaagaat    9840
tacaaaaaca aattcaaaaa attcaaaatt ttcgggttta ttacagggac agcagaaatc    9900
cactttggct cgagaagctt gatat                                         9925
```

<210> SEQ ID NO 4
<211> LENGTH: 360
<212> TYPE: PRT
<213> ORGANISM: Homo sapiens

<400> SEQUENCE: 4

| Met | Glu | Asp | Phe | Asn | Met | Glu | Ser | Asp | Ser | Phe | Glu | Asp | Phe | Trp | Lys |
|---|---|---|---|---|---|---|---|---|---|---|---|---|---|---|---|
| 1 | | | | 5 | | | | | 10 | | | | | 15 | |

| Gly | Glu | Asp | Leu | Ser | Asn | Tyr | Ser | Tyr | Ser | Ser | Thr | Leu | Pro | Pro | Phe |
| | | | 20 | | | | | 25 | | | | | 30 | | |

| Leu | Leu | Asp | Ala | Ala | Pro | Cys | Glu | Pro | Glu | Ser | Leu | Glu | Ile | Asn | Lys |
| | | | 35 | | | | 40 | | | | | 45 | | | |

| Tyr | Phe | Val | Val | Ile | Ile | Tyr | Ala | Leu | Val | Phe | Leu | Leu | Ser | Leu | Leu |
| 50 | | | | | 55 | | | | | 60 | | | | | |

| Gly | Asn | Ser | Leu | Val | Met | Leu | Val | Ile | Leu | Tyr | Ser | Arg | Val | Gly | Arg |
| 65 | | | | 70 | | | | | 75 | | | | | 80 | |

| Ser | Val | Thr | Asp | Val | Tyr | Leu | Leu | Asn | Leu | Ala | Leu | Ala | Asp | Leu | Leu |
| | | | | 85 | | | | | 90 | | | | | 95 | |

| Phe | Ala | Leu | Thr | Leu | Pro | Ile | Trp | Ala | Ala | Ser | Lys | Val | Asn | Gly | Trp |
| | | | | 100 | | | | | 105 | | | | | 110 | |

| Ile | Phe | Gly | Thr | Phe | Leu | Cys | Lys | Val | Val | Ser | Leu | Leu | Lys | Glu | Val |
| | | | | 115 | | | | | 120 | | | | | 125 | |

| Asn | Phe | Tyr | Ser | Gly | Ile | Leu | Leu | Leu | Ala | Cys | Ile | Ser | Val | Asp | Arg |
| | | 130 | | | | | 135 | | | | | 140 | | | |

| Tyr | Leu | Ala | Ile | Val | His | Ala | Thr | Arg | Thr | Leu | Thr | Gln | Lys | Arg | Tyr |
| 145 | | | | | 150 | | | | | 155 | | | | | 160 |

| Leu | Val | Lys | Phe | Ile | Cys | Leu | Ser | Ile | Trp | Gly | Leu | Ser | Leu | Leu | Leu |
| | | | | 165 | | | | | 170 | | | | | 175 | |

| Ala | Leu | Pro | Val | Leu | Leu | Phe | Arg | Arg | Thr | Val | Tyr | Ser | Ser | Asn | Val |
| | | | | 180 | | | | | 185 | | | | | 190 | |

| Ser | Pro | Ala | Cys | Tyr | Glu | Asp | Met | Gly | Asn | Asn | Thr | Ala | Asn | Trp | Arg |
| | | 195 | | | | | 200 | | | | | 205 | | | |

| Met | Leu | Leu | Arg | Ile | Leu | Pro | Gln | Ser | Phe | Gly | Phe | Ile | Val | Pro | Leu |
| 210 | | | | | 215 | | | | | 220 | | | | | |

| Leu | Ile | Met | Leu | Phe | Cys | Tyr | Gly | Phe | Thr | Leu | Arg | Thr | Leu | Phe | Lys |
| 225 | | | | | 230 | | | | | 235 | | | | | 240 |

| Ala | His | Met | Gly | Gln | Lys | His | Arg | Ala | Met | Arg | Val | Ile | Phe | Ala | Val |
| | | | | 245 | | | | | 250 | | | | | 255 | |

| Val | Leu | Ile | Phe | Leu | Leu | Cys | Trp | Leu | Pro | Tyr | Asn | Leu | Val | Leu | Leu |
| | | | | 260 | | | | | 265 | | | | | 270 | |

| Ala | Asp | Thr | Leu | Met | Arg | Thr | Gln | Val | Ile | Gln | Glu | Thr | Cys | Glu | Arg |
| | | | 275 | | | | | 280 | | | | | 285 | | |

| Arg | Asn | His | Ile | Asp | Arg | Ala | Leu | Asp | Ala | Thr | Glu | Ile | Leu | Gly | Ile |
| | | | 290 | | | | | 295 | | | | | 300 | | |

| Leu | His | Ser | Cys | Leu | Asn | Pro | Leu | Ile | Tyr | Ala | Phe | Ile | Gly | Gln | Lys |
| 305 | | | | | 310 | | | | | 315 | | | | | 320 |

```
Phe Arg His Gly Leu Leu Lys Ile Leu Ala Ile His Gly Leu Ile Ser
            325                 330                 335

Lys Asp Ser Leu Pro Lys Asp Ser Arg Pro Ser Phe Val Gly Ser Ser
        340                 345                 350

Ser Gly His Thr Ser Thr Thr Leu
        355                 360

<210> SEQ ID NO 5
<211> LENGTH: 265
<212> TYPE: PRT
<213> ORGANISM: Artificial Sequence
<220> FEATURE:
<223> OTHER INFORMATION: Syntheisized

<400> SEQUENCE: 5

Met Glu Asp Phe Asn Met Glu Ser Asp Ser Phe Glu Asp Phe Trp Lys
1               5                   10                  15

Gly Glu Asp Leu Ser Asn Tyr Ser Tyr Ser Ser Thr Leu Pro Pro Phe
            20                  25                  30

Leu Leu Asp Ala Ala Pro Cys Glu Pro Glu Ser Leu Glu Ile Asn Lys
        35                  40                  45

Tyr Phe Val Val Ile Ile Tyr Ala Leu Val Phe Leu Leu Ser Leu Leu
    50                  55                  60

Gly Asn Ser Leu Val Met Leu Val Ile Leu Tyr Ser Arg Val Gly Arg
65                  70                  75                  80

Ser Val Thr Asp Val Tyr Leu Leu Asn Leu Ala Leu Ala Asp Leu Leu
                85                  90                  95

Phe Ala Leu Thr Leu Pro Ile Trp Ala Ala Ser Lys Val Asn Gly Trp
            100                 105                 110

Ile Phe Gly Thr Phe Leu Cys Lys Val Val Ser Leu Leu Lys Glu Val
        115                 120                 125

Asn Phe Tyr Ser Gly Ile Leu Leu Leu Ala Cys Ile Ser Val Asp Arg
    130                 135                 140

Tyr Leu Ala Ile Val His Ala Thr Arg Thr Leu Thr Gln Lys Arg Tyr
145                 150                 155                 160

Leu Val Lys Phe Ile Cys Leu Ser Ile Trp Gly Leu Ser Leu Leu Leu
                165                 170                 175

Ala Leu Pro Val Leu Leu Phe Arg Arg Thr Val Tyr Ser Ser Asn Val
            180                 185                 190

Ser Pro Ala Cys Tyr Glu Asp Met Gly Asn Asn Thr Ala Asn Trp Arg
        195                 200                 205

Met Leu Leu Arg Ile Leu Pro Gln Ser Phe Gly Phe Ile Val Pro Leu
    210                 215                 220

Leu Ile Met Leu Phe Cys Tyr Gly Phe Thr Leu Arg Thr Leu Phe Lys
225                 230                 235                 240

Ala His Met Gly Gln Lys His Arg Ala Met Arg Val Ile Phe Ala Val
                245                 250                 255

Val Leu Ile Phe Leu Leu Cys Trp Leu
            260                 265

<210> SEQ ID NO 6
<211> LENGTH: 95
<212> TYPE: PRT
<213> ORGANISM: Artificial Sequence
<220> FEATURE:
<223> OTHER INFORMATION: Syntheisized

<400> SEQUENCE: 6
```

```
Pro Tyr Asn Leu Val Leu Leu Ala Asp Thr Leu Met Arg Thr Gln Val
1               5                   10                  15

Ile Gln Glu Thr Cys Glu Arg Arg Asn His Ile Asp Arg Ala Leu Asp
            20                  25                  30

Ala Thr Glu Ile Leu Gly Ile Leu His Ser Cys Leu Asn Pro Leu Ile
        35                  40                  45

Tyr Ala Phe Ile Gly Gln Lys Phe Arg His Gly Leu Leu Lys Ile Leu
    50                  55                  60

Ala Ile His Gly Leu Ile Ser Lys Asp Ser Leu Pro Lys Asp Ser Arg
65                  70                  75                  80

Pro Ala Phe Val Gly Ala Ala Ala Gly His Thr Ser Thr Thr Leu
                85                  90                  95

<210> SEQ ID NO 7
<211> LENGTH: 1515
<212> TYPE: DNA
<213> ORGANISM: Homo sapiens

<400> SEQUENCE: 7
atggatcccg ggcagcagcc gccgcctcaa ccggccccccc agggccaagg gcagccgcct      60
tcgcagcccc cgcaggggca gggcccgccg tccggacccg gcaaccggc acccgcggcg      120 acccaggcgg cgccgcaggc accccccgcc gggcatcaga tcgtgcacgt ccgcggggac      180
tcggagaccg acctggaggc gctcttcaac gccgtcatga cccccaagac ggccaacgtg      240
ccccagaccg tgcccatgag gctccggaag ctgcccgact ccttcttcaa gccgccggag      300
cccaaatccc actcccgaca ggccagtact gatgcaggca ctgcaggagc cctgactcca      360
cagcatgttc gagctcattc ctctccagct tctctgcagt tgggagctgt ttctcctggg      420
acactgaccc ccactggagt agtctctggc ccagcagcta cccacagc tcagcatctt      480 cgacagtctt cttttgagat acctgatgat gtacctctgc cagcaggttg ggagatggca      540
aagacatctt ctggtcagag atacttctta aatcacatcg atcagacaac aacatggcag      600
gaccccagga aggccatgct gtcccagatg aacgtcacag cccccaccag tccaccagtg      660
cagcagaata tgatgaactc ggcttcaggt cctcttcctg atggatggga acaagccatg      720
actcaggatg gagaaattta ctatataaac cataagaaca agaccacctc ttggctagac      780
ccaaggcttg accctcgttt tgccatgaac agagaatca gtcagagtgc tccagtgaaa      840
cagccaccac ccctggctcc ccagagccca cagggaggcg tcatgggtgg cagcaactcc      900
aaccagcagc aacagatgcg actgcagcaa ctgcagatgg agaaggagag gctgcggctg      960
aaacagcaag aactgcttcg gcaggcaatg cggaatatca tcccagcac agcaaattct      1020 ccaaaatgtc aggagttagc cctgcgtagc cagttaccaa cactggagca ggatggtggg      1080
actcaaaatc cagtgtcttc tcccgggatg tctcaggaat tgagaacaat gacgaccaat      1140
agctcagatc ctttccttaa cagtggcacc tatcactctc gagatgagag tacagacagt      1200
ggactaagca tgagcagcta cagtgtccct cgaaccccag atgacttcct gaacagtgtg      1260
gatgagatgg atacaggtga tactatcaac caaagcaccc tgccctcaca gcagaaccgt      1320
ttcccagact accttgaagc cattcctggg acaaatgtgg accttggaac actgaaggga      1380
gatggaatga acatagaagg agaggagctg atgccaagtc tgcaggaagc tttgagttct      1440
gacatcctta tgacatgga gtctgttttg gctgccacca agctagataa agaaagcttt      1500
cttacatggt tatag                                                       1515
```

<210> SEQ ID NO 8
<211> LENGTH: 543
<212> TYPE: PRT
<213> ORGANISM: Homo sapiens

<400> SEQUENCE: 8

Met Gly Cys Ile Lys Ser Lys Glu Asn Lys Ser Pro Ala Ile Lys Tyr
1               5                   10                  15

Arg Pro Glu Asn Thr Pro Glu Pro Val Ser Thr Ser Val Ser His Tyr
            20                  25                  30

Gly Ala Glu Pro Thr Thr Val Ser Pro Cys Pro Ser Ser Ser Ala Lys
        35                  40                  45

Gly Thr Ala Val Asn Phe Ser Ser Leu Ser Met Thr Pro Phe Gly Gly
    50                  55                  60

Ser Ser Gly Val Thr Pro Phe Gly Gly Ala Ser Ser Ser Phe Ser Val
65                  70                  75                  80

Val Pro Ser Ser Tyr Pro Ala Gly Leu Thr Gly Gly Val Thr Ile Phe
                85                  90                  95

Val Ala Leu Tyr Asp Tyr Glu Ala Arg Thr Thr Glu Asp Leu Ser Phe
            100                 105                 110

Lys Lys Gly Glu Arg Phe Gln Ile Ile Asn Asn Thr Glu Gly Asp Trp
        115                 120                 125

Trp Glu Ala Arg Ser Ile Ala Thr Gly Lys Asn Gly Tyr Ile Pro Ser
    130                 135                 140

Asn Tyr Val Ala Pro Ala Asp Ser Ile Gln Ala Glu Trp Tyr Phe
145                 150                 155                 160

Gly Lys Met Gly Arg Lys Asp Ala Glu Arg Leu Leu Leu Asn Pro Gly
                165                 170                 175

Asn Gln Arg Gly Ile Phe Leu Val Arg Glu Ser Glu Thr Thr Lys Gly
            180                 185                 190

Ala Tyr Ser Leu Ser Ile Arg Asp Trp Asp Glu Ile Arg Gly Asp Asn
        195                 200                 205

Val Lys His Tyr Lys Ile Arg Lys Leu Asp Asn Gly Gly Tyr Tyr Ile
    210                 215                 220

Thr Thr Arg Ala Gln Phe Asp Thr Leu Gln Lys Leu Val Lys His Tyr
225                 230                 235                 240

Thr Glu His Ala Asp Gly Leu Cys His Lys Leu Thr Thr Val Cys Pro
                245                 250                 255

Thr Val Lys Pro Gln Thr Gln Gly Leu Ala Lys Asp Ala Trp Glu Ile
            260                 265                 270

Pro Arg Glu Ser Leu Arg Leu Glu Val Lys Leu Gly Gln Gly Cys Phe
        275                 280                 285

Gly Glu Val Trp Met Gly Thr Trp Asn Gly Thr Thr Lys Val Ala Ile
    290                 295                 300

Lys Thr Leu Lys Pro Gly Thr Met Met Pro Glu Ala Phe Leu Gln Glu
305                 310                 315                 320

Ala Gln Ile Met Lys Lys Leu Arg His Asp Lys Leu Val Pro Leu Tyr
                325                 330                 335

Ala Val Val Ser Glu Glu Pro Ile Tyr Ile Val Thr Glu Phe Met Ser
            340                 345                 350

Lys Gly Ser Leu Leu Asp Phe Leu Lys Glu Gly Asp Gly Lys Tyr Leu
        355                 360                 365

Lys Leu Pro Gln Leu Val Asp Met Ala Ala Gln Ile Ala Asp Gly Met
    370                 375                 380

```
Ala Tyr Ile Glu Arg Met Asn Tyr Ile His Arg Asp Leu Arg Ala Ala
385                 390                 395                 400

Asn Ile Leu Val Gly Glu Asn Leu Val Cys Lys Ile Ala Asp Phe Gly
            405                 410                 415

Leu Ala Arg Leu Ile Glu Asp Asn Glu Tyr Thr Ala Arg Gln Gly Ala
        420                 425                 430

Lys Phe Pro Ile Lys Trp Thr Ala Pro Glu Ala Ala Leu Tyr Gly Arg
    435                 440                 445

Phe Thr Ile Lys Ser Asp Val Trp Ser Phe Gly Ile Leu Gln Thr Glu
450                 455                 460

Leu Val Thr Lys Gly Arg Val Pro Tyr Pro Gly Met Val Asn Arg Glu
465                 470                 475                 480

Val Leu Glu Gln Val Glu Arg Gly Tyr Arg Met Pro Cys Pro Gln Gly
            485                 490                 495

Cys Pro Glu Ser Leu His Glu Leu Met Asn Leu Cys Trp Lys Lys Asp
        500                 505                 510

Pro Asp Glu Arg Pro Thr Phe Glu Tyr Ile Gln Ser Phe Leu Glu Asp
    515                 520                 525

Tyr Phe Thr Ala Thr Glu Pro Gln Tyr Gln Pro Gly Glu Asn Leu
530                 535                 540

<210> SEQ ID NO 9
<211> LENGTH: 3879
<212> TYPE: DNA
<213> ORGANISM: Homo sapiens

<400> SEQUENCE: 9
atgaagccgg cgacaggact ttgggtctgg gtgagccttc tcgtggcggc ggggaccgtc      60
cagcccagcg attctcagtc agtgtgtgca ggaacggaga ataaactgag ctctctctct     120
gacctggaac agcagtaccg agccttgcgc aagtactatg aaaactgtga ggttgtcatg     180
ggcaacctgg agataaccag cattgagcac aaccgggacc tctccttcct gcggtctgtt     240
cgagaagtca caggctacgt gttagtggct cttaatcagt ttcgttacct gcctctggag     300
aatttacgca ttattcgtgg gacaaaactt tatgaggatc gatatgcctt ggcaatattt     360
ttaaactaca gaaagatgg aaactttgga cttcaagaac ttggattaaa gaacttgaca     420
gaaatcctaa atggtggagt ctatgtagac cagaacaaat ccttttgtta tgcagacacc     480
attcattggc aagatattgt tcggaaccca tggccttcca acttgactct tgtgtcaaca     540
aatggtagtt caggatgtgg acgttgccat aagtcctgta ctggccgttg ctggggaccc     600
acagaaaatc attgccagac tttgacaagg acggtgtgtg cagaacaatg tgacggcaga     660
tgctacggac cttacgtcag tgactgctgc catcgagaat gtgctggagg ctgctcagga     720
cctaaggaca cagactgctt tgcctgcatg aatttcaatg acagtggagc atgtgttact     780
cagtgtcccc aaacctttgt ctacaatcca accaccttc aactggagca atttcaat      840 gcaaagtaca catatggagc attctgtgtc aagaaatgtc cacataactt gtgtagat     900 tccagttctt gtgtgcgtgc ctgccctagt tccaagatgg aagtagaaga aatgggatt     960 aaaatgtgta aaccttgcac tgacatttgc ccaaaagctt gtgatggcat ggcacagga    1020 tcattgatgt cagctcagac tgtggattcc agtaacattg acaaattcat aaactgtacc    1080
aagatcaatg ggaatttgat ctttctagtc actggtattc atgggggaccc ttacaatgca    1140 attgaagcca tagacccaga gaaactgaac gtctttcgga cagtcagaga gataacaggt    1200
```

-continued

```
ttcctgaaca tacagtcatg gccaccaaac atgactgact tcagtgtttt ttctaacctg    1260
gtgaccattg gtggaagagt actctatagt ggcctgtcct tgcttatcct caagcaacag    1320
ggcatcacct ctctacagtt ccagtccctg aaggaaatca gcgcaggaaa catctatatt    1380
actgacaaca gcaacctgtg ttattatcat accattaact ggacaacact cttcagcaca    1440
atcaaccaga gaatagtaat ccgggacaac agaaaagctg aaaattgtac tgctgaagga    1500
atggtgtgca accatctgtg ttccagtgat ggctgttggg gacctgggcc agaccaatgt    1560
ctgtcgtgtc gccgcttcag tagaggaagg atctgcatag agtcttgtaa cctctatgat    1620
ggtgaatttc gggagtttga gaatggctcc atctgtgtgg agtgtgaccc ccagtgtgag    1680
aagatggaag atggcctcct cacatgccat ggaccgggtc ctgacaactg tacaaagtgc    1740
tctcatttta aagatggccc aaactgtgtg gaaaatgtc cagatggctt acagggggca     1800
aacagtttca ttttcaagta tgctgatcca gatcgggagt gccacccatg ccatccaaac    1860
tgcacccaag ggtgtaacgg tcccactagt catgactgca tttactaccc atggacgggc    1920
cattccactt taccacaaca tgctagaact cccctgattg cagctggagt aattggtggg    1980
ctcttcattc tggtcattgt gggtctgaca tttgctgttt atgttagaag gaagagcatc    2040
aaaaagaaaa gagccttgag aagattcttg gaaacagagt tggtggaacc attaactccc    2100
agtggcacag cacccaatca agctcaactt cgtattttga agaaactga gctgaagagg     2160
gtaaaagtcc ttggctcagg tgcttttgga acgttatta aaggtatttg ggtacctgaa      2220
ggagaaactg tgaagattcc tgtggctatt aagattctta atgagacaac tggtcccaag    2280
gcaaatgtga agttcatgga tgaagctctg atcatggcaa gtatggatca tccacaccta    2340
gtccggttgc tgggtgtgtg tctgagccca accatccagc tggttactca acttatgccc    2400
catggctgcc tgttggagta tgtccacgag cacaaggata acattggatc acaactgctg    2460
cttaactggt gtgtccagat agctaaggga atgatgtacc tggaagaaag cgactcgtt     2520
catcgggatt tggcagcccg taatgtctta gtgaaatctc aaaccatgt gaaaatcaca     2580
gattttgggc tagccagact cttggaagga gatgaaaaag agtacaatgc tgatggagga    2640
aagatgccaa ttaaatggat ggctctggag tgtatacatt acaggaaatt cacccatcag    2700
agtgacgttt ggagctatgg agttactata tgggaactga tgacctttgg aggaaaaccc    2760
tatgatggaa ttccaacgcg agaaatccct gatttattag agaaggaga acgtttgcct     2820
cagcctccca tctgcactat tgacgtttac atggtcatgg tcaaatgttg gatgattgat    2880
gctgacagta gacctaaatt taaggaactg gctgctgagt tttcaaggat ggctcgagac    2940
cctcaaagat acctagttat tcagggtgat gatcgtatga agcttcccag tccaaatgac    3000
agcaagttct ttcagaatct cttggatgaa gaggatttgg aagatatgat ggatgctgag    3060
gagtacttgg tccctcaggc tttcaacatc ccacctccca tctatacttc cagagcaaga    3120
attgactcga ataggaacca gtttgtatac cgagatggag ttttgctgc tgaacaagga    3180
gtgtctgtgc cctacagagc cccaactagc acaattccag aagctcctgt ggcacagggt    3240
gctactgctg agattttga tgactcctgc tgtaatggca ccctacgcaa gccagtggca    3300
ccccatgtcc aagaggacag tagcacccag aggtacagtg ctgaccccac cgtgtttgcc    3360
ccagaacgga gcccacgagg agagctggat gaggaaggtt acatgactcc tatgcgagac    3420
aaacccaaac aagaatacct gaatccagtg gaggagaacc cttttgtttc tcggagaaaa    3480
aatggagacc ttcaagcatt ggataatccc gaatatcaca atgcatccaa tggtccaccc    3540
aaggccgagg atgagtatgt gaatgagcca ctgtacctca acaccttgc caacaccttg    3600
```

```
ggaaaagctg agtacctgaa gaacaacata ctgtcaatgc cagagaaggc caagaaagcg    3660
tttgacaacc ctgactactg gaaccacagc ctgccaccte ggagcaccet tcagcaccca    3720 gactacctgc aggagtacag cacaaaatat ttttataaac agaatgggcg gatccggcct    3780 attgtgcag agaatcctga atacctctct gagttctccc tgaagccagg cactgtgctg     3840
ccgcctccac cttacagaca ccggaatact gtggtgtaa                           3879
```

<210> SEQ ID NO 10
<211> LENGTH: 1292
<212> TYPE: PRT
<213> ORGANISM: Homo sapiens

<400> SEQUENCE: 10

```
Met Lys Pro Ala Thr Gly Leu Trp Val Trp Val Ser Leu Leu Val Ala
1               5                   10                  15

Ala Gly Thr Val Gln Pro Ser Asp Ser Gln Ser Val Cys Ala Gly Thr
            20                  25                  30

Glu Asn Lys Leu Ser Ser Leu Ser Asp Leu Glu Gln Gln Tyr Arg Ala
        35                  40                  45

Leu Arg Lys Tyr Tyr Glu Asn Cys Glu Val Val Met Gly Asn Leu Glu
    50                  55                  60

Ile Thr Ser Ile Glu His Asn Arg Asp Leu Ser Phe Leu Arg Ser Val
65                  70                  75                  80

Arg Glu Val Thr Gly Tyr Val Leu Val Ala Leu Asn Gln Phe Arg Tyr
                85                  90                  95

Leu Pro Leu Glu Asn Leu Arg Ile Ile Arg Gly Thr Lys Leu Tyr Glu
            100                 105                 110

Asp Arg Tyr Ala Leu Ala Ile Phe Leu Asn Tyr Arg Lys Asp Gly Asn
        115                 120                 125

Phe Gly Leu Gln Glu Leu Gly Leu Lys Asn Leu Thr Glu Ile Leu Asn
    130                 135                 140

Gly Gly Val Tyr Val Asp Gln Asn Lys Phe Leu Cys Tyr Ala Asp Thr
145                 150                 155                 160

Ile His Trp Gln Asp Ile Val Arg Asn Pro Trp Pro Ser Asn Leu Thr
                165                 170                 175

Leu Val Ser Thr Asn Gly Ser Ser Gly Cys Gly Arg Cys His Lys Ser
            180                 185                 190

Cys Thr Gly Arg Cys Trp Gly Pro Thr Glu Asn His Cys Gln Thr Leu
        195                 200                 205

Thr Arg Thr Val Cys Ala Glu Gln Cys Asp Gly Arg Cys Tyr Gly Pro
    210                 215                 220

Tyr Val Ser Asp Cys Cys His Arg Glu Cys Ala Gly Gly Cys Ser Gly
225                 230                 235                 240

Pro Lys Asp Thr Asp Cys Phe Ala Cys Met Asn Phe Asn Asp Ser Gly
                245                 250                 255

Ala Cys Val Thr Gln Cys Pro Gln Thr Phe Val Tyr Asn Pro Thr Thr
            260                 265                 270

Phe Gln Leu Glu His Asn Phe Asn Ala Lys Tyr Thr Tyr Gly Ala Phe
        275                 280                 285

Cys Val Lys Lys Cys Pro His Asn Phe Val Val Asp Ser Ser Ser Cys
    290                 295                 300

Val Arg Ala Cys Pro Ser Ser Lys Met Glu Val Glu Glu Asn Gly Ile
305                 310                 315                 320
```

-continued

Lys Met Cys Lys Pro Cys Thr Asp Ile Cys Pro Lys Ala Cys Asp Gly
            325                 330                 335

Ile Gly Thr Gly Ser Leu Met Ser Ala Gln Thr Val Asp Ser Ser Asn
            340                 345                 350

Ile Asp Lys Phe Ile Asn Cys Thr Lys Ile Asn Gly Asn Leu Ile Phe
            355                 360             365

Leu Val Thr Gly Ile His Gly Asp Pro Tyr Asn Ala Ile Glu Ala Ile
            370             375                 380

Asp Pro Glu Lys Leu Asn Val Phe Arg Thr Val Arg Glu Ile Thr Gly
385                 390                 395                 400

Phe Leu Asn Ile Gln Ser Trp Pro Pro Asn Met Thr Asp Phe Ser Val
            405                 410                 415

Phe Ser Asn Leu Val Thr Ile Gly Gly Arg Val Leu Tyr Ser Gly Leu
            420                 425                 430

Ser Leu Leu Ile Leu Lys Gln Gln Gly Ile Thr Ser Leu Gln Phe Gln
            435                 440                 445

Ser Leu Lys Glu Ile Ser Ala Gly Asn Ile Tyr Ile Thr Asp Asn Ser
            450                 455                 460

Asn Leu Cys Tyr Tyr His Thr Ile Asn Trp Thr Thr Leu Phe Ser Thr
465                 470                 475                 480

Ile Asn Gln Arg Ile Val Ile Arg Asp Asn Arg Lys Ala Glu Asn Cys
            485                 490                 495

Thr Ala Glu Gly Met Val Cys Asn His Leu Cys Ser Ser Asp Gly Cys
            500                 505                 510

Trp Gly Pro Gly Pro Asp Gln Cys Leu Ser Cys Arg Arg Phe Ser Arg
            515                 520                 525

Gly Arg Ile Cys Ile Glu Ser Cys Asn Leu Tyr Asp Gly Glu Phe Arg
            530                 535                 540

Glu Phe Glu Asn Gly Ser Ile Cys Val Glu Cys Asp Pro Gln Cys Glu
545                 550                 555                 560

Lys Met Glu Asp Gly Leu Leu Thr Cys His Gly Pro Gly Pro Asp Asn
            565                 570                 575

Cys Thr Lys Cys Ser His Phe Lys Asp Gly Pro Asn Cys Val Glu Lys
            580                 585                 590

Cys Pro Asp Gly Leu Gln Gly Ala Asn Ser Phe Ile Phe Lys Tyr Ala
            595                 600                 605

Asp Pro Asp Arg Glu Cys His Pro Cys His Pro Asn Cys Thr Gln Gly
            610                 615                 620

Cys Asn Gly Pro Thr Ser His Asp Cys Ile Tyr Tyr Pro Trp Thr Gly
625                 630                 635                 640

His Ser Thr Leu Pro Gln His Ala Arg Thr Pro Leu Ile Ala Ala Gly
            645                 650                 655

Val Ile Gly Gly Leu Phe Ile Leu Val Ile Gly Leu Thr Phe Ala
            660                 665                 670

Val Tyr Val Arg Arg Lys Ser Ile Lys Lys Arg Ala Leu Arg Arg
            675                 680                 685

Phe Leu Glu Thr Glu Leu Val Glu Pro Leu Thr Pro Ser Gly Thr Ala
            690                 695                 700

Pro Asn Gln Ala Gln Leu Arg Ile Leu Lys Glu Thr Glu Leu Lys Arg
705                 710                 715                 720

Val Lys Val Leu Gly Ser Gly Ala Phe Gly Thr Val Tyr Lys Gly Ile
            725                 730                 735

Trp Val Pro Glu Gly Glu Thr Val Lys Ile Pro Val Ala Ile Lys Ile

```
                740             745             750
Leu Asn Glu Thr Thr Gly Pro Lys Ala Asn Val Glu Phe Met Asp Glu
            755             760             765

Ala Leu Ile Met Ala Ser Met Asp His Pro His Leu Val Arg Leu Leu
            770             775             780

Gly Val Cys Leu Ser Pro Thr Ile Gln Leu Val Thr Gln Leu Met Pro
785             790             795             800

His Gly Cys Leu Leu Glu Tyr Val His Glu His Lys Asp Asn Ile Gly
            805             810             815

Ser Gln Leu Leu Leu Asn Trp Cys Val Gln Ile Ala Lys Gly Met Met
            820             825             830

Tyr Leu Glu Glu Arg Arg Leu Val His Arg Asp Leu Ala Ala Arg Asn
            835             840             845

Val Leu Val Lys Ser Pro Asn His Val Lys Ile Thr Asp Phe Gly Leu
            850             855             860

Ala Arg Leu Leu Glu Gly Asp Glu Lys Glu Tyr Asn Ala Asp Gly Gly
865             870             875             880

Lys Met Pro Ile Lys Trp Met Ala Leu Glu Cys Ile His Tyr Arg Lys
            885             890             895

Phe Thr His Gln Ser Asp Val Trp Ser Tyr Gly Val Thr Ile Trp Glu
            900             905             910

Leu Met Thr Phe Gly Gly Lys Pro Tyr Asp Gly Ile Pro Thr Arg Glu
            915             920             925

Ile Pro Asp Leu Leu Glu Lys Gly Glu Arg Leu Pro Gln Pro Pro Ile
            930             935             940

Cys Thr Ile Asp Val Tyr Met Val Met Val Lys Cys Trp Met Ile Asp
945             950             955             960

Ala Asp Ser Arg Pro Lys Phe Lys Glu Leu Ala Ala Glu Phe Ser Arg
            965             970             975

Met Ala Arg Asp Pro Gln Arg Tyr Leu Val Ile Gln Gly Asp Asp Arg
            980             985             990

Met Lys Leu Pro Ser Pro Asn Asp Ser Lys Phe Phe Gln Asn Leu Leu
            995             1000            1005

Asp Glu Glu Asp Leu Glu Asp Met Met Asp Ala Glu Glu Tyr Leu
    1010            1015            1020

Val Pro Gln Ala Phe Asn Ile Pro Pro Pro Ile Tyr Thr Ser Arg
    1025            1030            1035

Ala Arg Ile Asp Ser Asn Arg Asn Gln Phe Val Tyr Arg Asp Gly
    1040            1045            1050

Gly Phe Ala Ala Glu Gln Gly Val Ser Val Pro Tyr Arg Ala Pro
    1055            1060            1065

Thr Ser Thr Ile Pro Glu Ala Pro Val Ala Gln Gly Ala Thr Ala
    1070            1075            1080

Glu Ile Phe Asp Asp Ser Cys Cys Asn Gly Thr Leu Arg Lys Pro
    1085            1090            1095

Val Ala Pro His Val Gln Glu Asp Ser Ser Thr Gln Arg Tyr Ser
    1100            1105            1110

Ala Asp Pro Thr Val Phe Ala Pro Glu Arg Ser Pro Arg Gly Glu
    1115            1120            1125

Leu Asp Glu Glu Gly Tyr Met Thr Pro Met Arg Asp Lys Pro Lys
    1130            1135            1140

Gln Glu Tyr Leu Asn Pro Val Glu Glu Asn Pro Phe Val Ser Arg
    1145            1150            1155
```

```
Arg Lys Asn Gly Asp Leu Gln Ala Leu Asp Asn Pro Glu Tyr His
    1160                1165                1170

Asn Ala Ser Asn Gly Pro Pro Lys Ala Glu Asp Glu Tyr Val Asn
    1175                1180                1185

Glu Pro Leu Tyr Leu Asn Thr Phe Ala Asn Thr Leu Gly Lys Ala
    1190                1195                1200

Glu Tyr Leu Lys Asn Asn Ile Leu Ser Met Pro Glu Lys Ala Lys
    1205                1210                1215

Lys Ala Phe Asp Asn Pro Asp Tyr Trp Asn His Ser Leu Pro Pro
    1220                1225                1230

Arg Ser Thr Leu Gln His Pro Asp Tyr Leu Gln Glu Tyr Ser Thr
    1235                1240                1245

Lys Tyr Phe Tyr Lys Gln Asn Gly Arg Ile Arg Pro Ile Val Ala
    1250                1255                1260

Glu Asn Pro Glu Tyr Leu Ser Glu Phe Ser Leu Lys Pro Gly Thr
    1265                1270                1275

Val Leu Pro Pro Pro Pro Tyr Arg His Arg Asn Thr Val Val
    1280                1285                1290

<210> SEQ ID NO 11
<211> LENGTH: 709
<212> TYPE: PRT
<213> ORGANISM: Artificial Sequence
<220> FEATURE:
<223> OTHER INFORMATION: Syntheisized

<400> SEQUENCE: 11

Met Lys Pro Ala Thr Gly Leu Trp Val Trp Val Ser Leu Leu Val Ala
1               5                   10                  15

Ala Gly Thr Val Gln Pro Ser Asp Ser Gln Ser Val Cys Ala Gly Thr
                20                  25                  30

Glu Asn Lys Leu Ser Ser Leu Ser Asp Leu Glu Gln Gln Tyr Arg Ala
            35                  40                  45

Leu Arg Lys Tyr Tyr Glu Asn Cys Glu Val Val Met Gly Asn Leu Glu
        50                  55                  60

Ile Thr Ser Ile Glu His Asn Arg Asp Leu Ser Phe Leu Arg Ser Val
65                  70                  75                  80

Arg Glu Val Thr Gly Tyr Val Leu Val Ala Leu Asn Gln Phe Arg Tyr
                85                  90                  95

Leu Pro Leu Glu Asn Leu Arg Ile Ile Arg Gly Thr Lys Leu Tyr Glu
            100                 105                 110

Asp Arg Tyr Ala Leu Ala Ile Phe Leu Asn Tyr Arg Lys Asp Gly Asn
        115                 120                 125

Phe Gly Leu Gln Glu Leu Gly Leu Lys Asn Leu Thr Glu Ile Leu Asn
    130                 135                 140

Gly Gly Val Tyr Val Asp Gln Asn Lys Phe Leu Cys Tyr Ala Asp Thr
145                 150                 155                 160

Ile His Trp Gln Asp Ile Val Arg Asn Pro Trp Pro Ser Asn Leu Thr
                165                 170                 175

Leu Val Ser Thr Asn Gly Ser Ser Gly Cys Gly Arg Cys His Lys Ser
            180                 185                 190

Cys Thr Gly Arg Cys Trp Gly Pro Thr Glu Asn His Cys Gln Thr Leu
        195                 200                 205

Thr Arg Thr Val Cys Ala Glu Gln Cys Asp Gly Arg Cys Tyr Gly Pro
    210                 215                 220
```

```
Tyr Val Ser Asp Cys Cys His Arg Glu Cys Ala Gly Gly Cys Ser Gly
225                 230                 235                 240

Pro Lys Asp Thr Asp Cys Phe Ala Cys Met Asn Phe Asn Asp Ser Gly
                245                 250                 255

Ala Cys Val Thr Gln Cys Pro Gln Thr Phe Val Tyr Asn Pro Thr Thr
            260                 265                 270

Phe Gln Leu Glu His Asn Phe Asn Ala Lys Tyr Thr Tyr Gly Ala Phe
        275                 280                 285

Cys Val Lys Lys Cys Pro His Asn Phe Val Val Asp Ser Ser Ser Cys
    290                 295                 300

Val Arg Ala Cys Pro Ser Ser Lys Met Glu Val Glu Glu Asn Gly Ile
305                 310                 315                 320

Lys Met Cys Lys Pro Cys Thr Asp Ile Cys Pro Lys Ala Cys Asp Gly
                325                 330                 335

Ile Gly Thr Gly Ser Leu Met Ser Ala Gln Thr Val Asp Ser Ser Asn
            340                 345                 350

Ile Asp Lys Phe Ile Asn Cys Thr Lys Ile Asn Gly Asn Leu Ile Phe
        355                 360                 365

Leu Val Thr Gly Ile His Gly Asp Pro Tyr Asn Ala Ile Glu Ala Ile
370                 375                 380

Asp Pro Glu Lys Leu Asn Val Phe Arg Thr Val Arg Glu Ile Thr Gly
385                 390                 395                 400

Phe Leu Asn Ile Gln Ser Trp Pro Pro Asn Met Thr Asp Phe Ser Val
                405                 410                 415

Phe Ser Asn Leu Val Thr Ile Gly Gly Arg Val Leu Tyr Ser Gly Leu
            420                 425                 430

Ser Leu Leu Ile Leu Lys Gln Gln Gly Ile Thr Ser Leu Gln Phe Gln
        435                 440                 445

Ser Leu Lys Glu Ile Ser Ala Gly Asn Ile Tyr Ile Thr Asp Asn Ser
    450                 455                 460

Asn Leu Cys Tyr Tyr His Thr Ile Asn Trp Thr Thr Leu Phe Ser Thr
465                 470                 475                 480

Ile Asn Gln Arg Ile Val Ile Arg Asp Asn Arg Lys Ala Glu Asn Cys
                485                 490                 495

Thr Ala Glu Gly Met Val Cys Asn His Leu Cys Ser Ser Asp Gly Cys
            500                 505                 510

Trp Gly Pro Gly Pro Asp Gln Cys Leu Ser Cys Arg Arg Phe Ser Arg
        515                 520                 525

Gly Arg Ile Cys Ile Glu Ser Cys Asn Leu Tyr Asp Gly Glu Phe Arg
    530                 535                 540

Glu Phe Glu Asn Gly Ser Ile Cys Val Glu Cys Asp Pro Gln Cys Glu
545                 550                 555                 560

Lys Met Glu Asp Gly Leu Leu Thr Cys His Gly Pro Gly Pro Asp Asn
                565                 570                 575

Cys Thr Lys Cys Ser His Phe Lys Asp Gly Pro Asn Cys Val Glu Lys
            580                 585                 590

Cys Pro Asp Gly Leu Gln Gly Ala Asn Ser Phe Ile Phe Lys Tyr Ala
        595                 600                 605

Asp Pro Asp Arg Glu Cys His Pro Cys His Pro Asn Cys Thr Gln Gly
    610                 615                 620

Cys Asn Gly Pro Thr Ser His Asp Cys Ile Tyr Tyr Pro Trp Thr Gly
625                 630                 635                 640
```

-continued

His Ser Thr Leu Pro Gln His Ala Arg Thr Pro Leu Ile Ala Ala Gly
                645                 650                 655

Val Ile Gly Gly Leu Phe Ile Leu Val Ile Val Gly Leu Thr Phe Ala
            660                 665                 670

Val Tyr Val Arg Arg Lys Ser Ile Lys Lys Arg Ala Leu Arg Arg
        675                 680                 685

Phe Leu Glu Thr Glu Leu Val Glu Pro Leu Thr Pro Ser Gly Thr Ala
    690                 695                 700

Pro Asn Gln Ala Gln
705

<210> SEQ ID NO 12
<211> LENGTH: 1095
<212> TYPE: DNA
<213> ORGANISM: Homo sapiens

<400> SEQUENCE: 12

```
atggctgcca tctctacttc catccctgta atttcacagc cccagttcac agccatgaat      60
gaaccacagt gcttctacaa cgagtccatt gccttctttt ataaccgaag tggaaagcat     120
cttgccacag aatggaacac agtcagcaag ctggtgatgg acttggaat cactgtttgt     180
atcttcatca tgttggccaa cctattggtc atggtggcaa tctatgtcaa ccgccgcttc    240
cattttccta tttattacct aatggctaat ctggctgctg cagacttctt tgctgggttg    300
gcctacttct atctcatgtt caacacagga cccaatactc ggagactgac tgttagcaca    360
tggctccttc gtcagggcct cattgacacc agcctgacgg catctgtggc caacttactg    420
gctattgcaa tcgagaggca cattacggtt ttccgcatgc agctccacac acggatgagc    480
aaccggcggg tagtggtggt cattgtggtc atctggacta tggccatcgt tatgggtgct    540
atcccagtg tgggctggaa ctgtatctgt gatattgaaa attgttccaa catggcaccc    600
ctctacagtg actcttactt agtcttctgg gccatttca acttggtgac ctttgtggta    660
atggtggttc tctatgctca catctttggc tatgttcgcc agaggactat gagaatgtct    720
cggcatagtt ctggaccccg gcggaatcgg gataccatga tgagtcttct gaagactgtg    780
gtcattgtgc ttggggcctt tatcatctgc tggactcctg gattggtttt gttacttcta    840
gacgtgtgct gtccacagtg cgacgtgctg gcctatgaga aattcttcct tctccttgct    900
gaattcaact ctgccatgaa ccccatcatt tactcctacc gcacaaaga atgagcgcc     960
accttaggc agatcctctg ctgccagcgc agtgagaacc ccaccggccc cacagaaggc   1020
tcagaccgct cggcttcctc cctcaaccac accatcttgg ctggagttca cagcaatgac   1080
cactctgtgg tttag                                                    1095
```

<210> SEQ ID NO 13
<211> LENGTH: 364
<212> TYPE: PRT
<213> ORGANISM: Homo sapiens

<400> SEQUENCE: 13

Met Ala Ala Ile Ser Thr Ser Ile Pro Val Ile Ser Gln Pro Gln Phe
1               5                   10                  15

Thr Ala Met Asn Glu Pro Gln Cys Phe Tyr Asn Glu Ser Ile Ala Phe
                20                  25                  30

Phe Tyr Asn Arg Ser Gly Lys His Leu Ala Thr Glu Trp Asn Thr Val
            35                  40                  45

Ser Lys Leu Val Met Gly Leu Gly Ile Thr Val Cys Ile Phe Ile Met

```
                50                  55                  60
Leu Ala Asn Leu Leu Val Met Val Ala Ile Tyr Val Asn Arg Arg Phe
 65                  70                  75                  80

His Phe Pro Ile Tyr Tyr Leu Met Ala Asn Leu Ala Ala Ala Asp Phe
                 85                  90                  95

Phe Ala Gly Leu Ala Tyr Phe Tyr Leu Met Phe Asn Thr Gly Pro Asn
                100                 105                 110

Thr Arg Arg Leu Thr Val Ser Thr Trp Leu Leu Arg Gln Gly Leu Ile
                115                 120                 125

Asp Thr Ser Leu Thr Ala Ser Val Ala Asn Leu Leu Ala Ile Ala Ile
                130                 135                 140

Glu Arg His Ile Thr Val Phe Arg Met Gln Leu His Thr Arg Met Ser
145                 150                 155                 160

Asn Arg Arg Val Val Val Ile Val Ile Trp Thr Met Ala Ile
                165                 170                 175

Val Met Gly Ala Ile Pro Ser Val Gly Trp Asn Cys Ile Cys Asp Ile
                180                 185                 190

Glu Asn Cys Ser Asn Met Ala Pro Leu Tyr Ser Asp Ser Tyr Leu Val
                195                 200                 205

Phe Trp Ala Ile Phe Asn Leu Val Thr Phe Val Val Met Val Val Leu
210                 215                 220

Tyr Ala His Ile Phe Gly Tyr Val Arg Gln Arg Thr Met Arg Met Ser
225                 230                 235                 240

Arg His Ser Ser Gly Pro Arg Arg Asn Arg Asp Thr Met Met Ser Leu
                245                 250                 255

Leu Lys Thr Val Val Ile Val Leu Gly Ala Phe Ile Ile Cys Trp Thr
                260                 265                 270

Pro Gly Leu Val Leu Leu Leu Asp Val Cys Cys Pro Gln Cys Asp
                275                 280                 285

Val Leu Ala Tyr Glu Lys Phe Phe Leu Leu Leu Ala Glu Phe Asn Ser
                290                 295                 300

Ala Met Asn Pro Ile Ile Tyr Ser Tyr Arg Asp Lys Glu Met Ser Ala
305                 310                 315                 320

Thr Phe Arg Gln Ile Leu Cys Cys Gln Arg Ser Glu Asn Pro Thr Gly
                325                 330                 335

Pro Thr Glu Gly Ser Asp Arg Ser Ala Ser Ser Leu Asn His Thr Ile
                340                 345                 350

Leu Ala Gly Val His Ser Asn Asp His Ser Val Val
                355                 360

<210> SEQ ID NO 14
<211> LENGTH: 315
<212> TYPE: PRT
<213> ORGANISM: Artificial Sequence
<220> FEATURE:
<223> OTHER INFORMATION: Syntheisized

<400> SEQUENCE: 14

Met Ala Ala Ile Ser Thr Ser Ile Pro Val Ile Ser Gln Pro Gln Phe
 1               5                  10                  15

Thr Ala Met Asn Glu Pro Gln Cys Phe Tyr Asn Glu Ser Ile Ala Phe
                20                  25                  30

Phe Tyr Asn Arg Ser Gly Lys His Leu Ala Thr Glu Trp Asn Thr Val
                35                  40                  45

Ser Lys Leu Val Met Gly Leu Gly Ile Thr Val Cys Ile Phe Ile Met
```

```
                 50                  55                  60
Leu Ala Asn Leu Leu Val Met Val Ala Ile Tyr Val Asn Arg Arg Phe
 65                  70                  75                  80

His Phe Pro Ile Tyr Tyr Leu Met Ala Asn Leu Ala Ala Ala Asp Phe
                 85                  90                  95

Phe Ala Gly Leu Ala Tyr Phe Tyr Leu Met Phe Asn Thr Gly Pro Asn
            100                 105                 110

Thr Arg Arg Leu Thr Val Ser Thr Trp Leu Leu Arg Gln Gly Leu Ile
            115                 120                 125

Asp Thr Ser Leu Thr Ala Ser Val Ala Asn Leu Leu Ala Ile Ala Ile
            130                 135                 140

Glu Arg His Ile Thr Val Phe Arg Met Gln Leu His Thr Arg Met Ser
145                 150                 155                 160

Asn Arg Arg Val Val Val Ile Val Val Ile Trp Thr Met Ala Ile
                165                 170                 175

Val Met Gly Ala Ile Pro Ser Val Gly Trp Asn Cys Ile Cys Asp Ile
            180                 185                 190

Glu Asn Cys Ser Asn Met Ala Pro Leu Tyr Ser Asp Ser Tyr Leu Val
            195                 200                 205

Phe Trp Ala Ile Phe Asn Leu Val Thr Phe Val Met Val Val Leu
210                 215                 220

Tyr Ala His Ile Phe Gly Tyr Val Arg Gln Arg Thr Met Arg Met Ser
225                 230                 235                 240

Arg His Ser Ser Gly Pro Arg Arg Asn Arg Asp Thr Met Met Ser Leu
            245                 250                 255

Leu Lys Thr Val Val Ile Val Leu Gly Ala Phe Ile Ile Cys Trp Thr
            260                 265                 270

Pro Gly Leu Val Leu Leu Leu Asp Val Cys Cys Pro Gln Cys Asp
            275                 280                 285

Val Leu Ala Tyr Glu Lys Phe Phe Leu Leu Leu Ala Glu Phe Asn Ser
            290                 295                 300

Ala Met Asn Pro Ile Ile Tyr Ser Tyr Arg Asp
305                 310                 315

<210> SEQ ID NO 15
<211> LENGTH: 2229
<212> TYPE: DNA
<213> ORGANISM: Homo sapiens

<400> SEQUENCE: 15
atggacaagt tttggtggca cgcagcctgg ggactctgcc tcgtgccgct gagcctggcg      60
cagatcgatt tgaatataac ctgccgcttt gcaggtgtat tccacgtgga aaaaatggt     120 cgctacagca tctctcggac ggaggccgct gacctctgca aggctttcaa tagcaccttg    180
cccacaatgg cccagatgga aaagctctg agcatcggat tgagacctg caggtatggg      240 ttcatagaag ggcacgtggt gattcccgg atccacccca actccatctg tgcagcaaac     300
aacacagggg tgtacatcct cacatccaac acctcccagt atgacacata ttgcttcaat    360
gcttcagctc acctgaaga agattgtaca tcagtcacag acctgcccaa tgcctttgat    420
ggaccaatta ccataactat tgttaaccgt gatggcaccc gctatgtcca gaaaggagaa    480
tacagaacga atcctgaaga catctacccc agcaaccta ctgatgatga cgtgagcagc     540
ggctcctcca gtgaaaggag cagcacttca ggaggttaca tcttttacac ctttttctact   600 gtacacccca tcccagacga agacagtccc tggatcaccg acagcacaga cagaatccct    660
```

```
gctaccactt tgatgagcac tagtgctaca gcaactgaga cagcaaccaa gaggcaagaa    720
acctgggatt ggttttcatg gttgtttcta ccatcagagt caaagaatca tcttcacaca    780
acaacacaaa tggctggtac gtcttcaaat accatctcag caggctggga gccaaatgaa    840
gaaaatgaag atgaaagaga cagacacctc agttttctg gatcaggcat tgatgatgat      900
gaagatttta tctccagcac catttcaacc acaccacggg cttttgacca cacaaaacag    960
aaccaggact ggacccagtg aacccaagc cattcaaatc cggaagtgct acttcagaca     1020
accacaagga tgactgatgt agacagaaat ggcaccactg cttatgaagg aaactggaac    1080
ccagaagcac accctcccct cattcaccat gagcatcatg aggaagaaga ccccacat      1140
tctacaagca caatccaggc aactcctagt agtacaacgg aagaaacagc tacccagaag    1200
gaacagtggt ttggcaacag atggcatgag ggatatcgcc aaacacccaa agaagactcc    1260
cattcgacaa caggacagc tgcagcctca gctcatacca gccatccaat gcaaggaagg      1320
acaacaccaa gcccgagga cagttcctgg actgatttct tcaacccaat ctcacacccc      1380
atgggacgag gtcatcaagc aggaagaagg atggatatgg actccagtca tagtataacg    1440
cttcagccta ctgcaaatcc aaacacaggt ttggtggaag atttggacag acaggacct     1500
cttttcaatga caacgcagca gagtaattct cagagcttct ctacatcaca tgaaggcttg   1560
gaagaagata agaccatcc aacaacttct actctgacat caagcaatag gaatgatgtc    1620
acaggtggaa gaagaccc aaatcattct gaaggctcaa ctactttact ggaaggttat      1680
acctctcatt acccacacac gaaggaaagc aggaccttca tcccagtgac ctcagctaag    1740
actgggtcct ttggagttac tgcagttact gttggagatt ccaactctaa tgtcaatcgt    1800
tccttatcag agaccaaga cacattccac cccagtgggg ggtcccatac cactcatgga    1860
tctgaatcag atggacactc acatgggagt caagaaggtg gagcaaacac aacctctggt    1920
cctataagga caccccaaat tccagaatgg ctgatcatct tggcatccct cttggccttg    1980
gctttgattc ttgcagtttg cattgcagtc aacagtcgaa gaaggtgtgg gcagaagaaa    2040
aagctagtga tcaacagtgg caatggagct gtggaggaca gaaagccaag tggactcaac    2100
ggagaggcca gcaagtctca ggaaatggtg catttggtga acaaggagtc gtcagaaact    2160
ccagaccagt ttatgacagc tgatgagaca aggaacctgc agaatgtgga catgaagatt    2220
ggggtgtaa                                                           2229
```

<210> SEQ ID NO 16
<211> LENGTH: 742
<212> TYPE: PRT
<213> ORGANISM: Homo sapiens

<400> SEQUENCE: 16

Met Asp Lys Phe Trp Trp His Ala Ala Trp Gly Leu Cys Leu Val Pro
1               5                   10                  15

Leu Ser Leu Ala Gln Ile Asp Leu Asn Ile Thr Cys Arg Phe Ala Gly
            20                  25                  30

Val Phe His Val Glu Lys Asn Gly Arg Tyr Ser Ile Ser Arg Thr Glu
        35                  40                  45

Ala Ala Asp Leu Cys Lys Ala Phe Asn Ser Thr Leu Pro Thr Met Ala
    50                  55                  60

Gln Met Glu Lys Ala Leu Ser Ile Gly Phe Glu Thr Cys Arg Tyr Gly
65                  70                  75                  80

Phe Ile Glu Gly His Val Val Ile Pro Arg Ile His Pro Asn Ser Ile

```
                    85                  90                  95
Cys Ala Ala Asn Asn Thr Gly Val Tyr Ile Leu Thr Ser Asn Thr Ser
                100                 105                 110
Gln Tyr Asp Thr Tyr Cys Phe Asn Ala Ser Ala Pro Pro Glu Glu Asp
                115                 120                 125
Cys Thr Ser Val Thr Asp Leu Pro Asn Ala Phe Asp Gly Pro Ile Thr
130                 135                 140
Ile Thr Ile Val Asn Arg Asp Gly Thr Arg Tyr Val Gln Lys Gly Glu
145                 150                 155                 160
Tyr Arg Thr Asn Pro Glu Asp Ile Tyr Pro Ser Asn Pro Thr Asp Asp
                165                 170                 175
Asp Val Ser Ser Gly Ser Ser Glu Arg Ser Ser Thr Ser Gly Gly
                180                 185                 190
Tyr Ile Phe Tyr Thr Phe Ser Thr Val His Pro Ile Pro Asp Glu Asp
                195                 200                 205
Ser Pro Trp Ile Thr Asp Ser Thr Asp Arg Ile Pro Ala Thr Thr Leu
                210                 215                 220
Met Ser Thr Ser Ala Thr Ala Thr Glu Thr Ala Thr Lys Arg Gln Glu
225                 230                 235                 240
Thr Trp Asp Trp Phe Ser Trp Leu Phe Leu Pro Ser Glu Ser Lys Asn
                245                 250                 255
His Leu His Thr Thr Thr Gln Met Ala Gly Thr Ser Ser Asn Thr Ile
                260                 265                 270
Ser Ala Gly Trp Glu Pro Asn Glu Glu Asn Glu Asp Glu Arg Asp Arg
                275                 280                 285
His Leu Ser Phe Ser Gly Ser Gly Ile Asp Asp Asp Glu Asp Phe Ile
                290                 295                 300
Ser Ser Thr Ile Ser Thr Thr Pro Arg Ala Phe Asp His Thr Lys Gln
305                 310                 315                 320
Asn Gln Asp Trp Thr Gln Trp Asn Pro Ser His Ser Asn Pro Glu Val
                325                 330                 335
Leu Leu Gln Thr Thr Thr Arg Met Thr Asp Val Asp Arg Asn Gly Thr
                340                 345                 350
Thr Ala Tyr Glu Gly Asn Trp Asn Pro Glu Ala His Pro Pro Leu Ile
                355                 360                 365
His His Glu His His Glu Glu Glu Thr Pro His Ser Thr Ser Thr
                370                 375                 380
Ile Gln Ala Thr Pro Ser Ser Thr Thr Glu Glu Thr Ala Thr Gln Lys
385                 390                 395                 400
Glu Gln Trp Phe Gly Asn Arg Trp His Glu Gly Tyr Arg Gln Thr Pro
                405                 410                 415
Lys Glu Asp Ser His Ser Thr Thr Gly Thr Ala Ala Ala Ser Ala His
                420                 425                 430
Thr Ser His Pro Met Gln Gly Arg Thr Thr Pro Ser Pro Glu Asp Ser
                435                 440                 445
Ser Trp Thr Asp Phe Phe Asn Pro Ile Ser His Pro Met Gly Arg Gly
                450                 455                 460
His Gln Ala Gly Arg Arg Met Asp Met Asp Ser Ser His Ser Ile Thr
465                 470                 475                 480
Leu Gln Pro Thr Ala Asn Pro Asn Thr Gly Leu Val Glu Asp Leu Asp
                485                 490                 495
Arg Thr Gly Pro Leu Ser Met Thr Thr Gln Gln Ser Asn Ser Gln Ser
                500                 505                 510
```

```
Phe Ser Thr Ser His Glu Gly Leu Glu Glu Asp Lys Asp His Pro Thr
            515                 520                 525

Thr Ser Thr Leu Thr Ser Ser Asn Arg Asn Asp Val Thr Gly Gly Arg
        530                 535                 540

Arg Asp Pro Asn His Ser Glu Gly Ser Thr Thr Leu Leu Glu Gly Tyr
545                 550                 555                 560

Thr Ser His Tyr Pro His Thr Lys Glu Ser Arg Thr Phe Ile Pro Val
                565                 570                 575

Thr Ser Ala Lys Thr Gly Ser Phe Gly Val Thr Ala Val Thr Val Gly
            580                 585                 590

Asp Ser Asn Ser Asn Val Asn Arg Ser Leu Ser Gly Asp Gln Asp Thr
        595                 600                 605

Phe His Pro Ser Gly Gly Ser His Thr Thr His Gly Ser Glu Ser Asp
        610                 615                 620

Gly His Ser His Gly Ser Gln Glu Gly Gly Ala Asn Thr Thr Ser Gly
625                 630                 635                 640

Pro Ile Arg Thr Pro Gln Ile Pro Glu Trp Leu Ile Ile Leu Ala Ser
                645                 650                 655

Leu Leu Ala Leu Ala Leu Ile Leu Ala Val Cys Ile Ala Val Asn Ser
            660                 665                 670

Arg Arg Arg Cys Gly Gln Lys Lys Lys Leu Val Ile Asn Ser Gly Asn
        675                 680                 685

Gly Ala Val Glu Asp Arg Lys Pro Ser Gly Leu Asn Gly Glu Ala Ser
        690                 695                 700

Lys Ser Gln Glu Met Val His Leu Val Asn Lys Glu Ser Ser Glu Thr
705                 710                 715                 720

Pro Asp Gln Phe Met Thr Ala Asp Glu Thr Arg Asn Leu Gln Asn Val
                725                 730                 735

Asp Met Lys Ile Gly Val
                740

<210> SEQ ID NO 17
<211> LENGTH: 671
<212> TYPE: PRT
<213> ORGANISM: Artificial Sequence
<220> FEATURE:
<223> OTHER INFORMATION: Syntheisized

<400> SEQUENCE: 17

Met Asp Lys Phe Trp Trp His Ala Ala Trp Gly Leu Cys Leu Val Pro
1               5                   10                  15

Leu Ser Leu Ala Gln Ile Asp Leu Asn Ile Thr Cys Arg Phe Ala Gly
            20                  25                  30

Val Phe His Val Glu Lys Asn Gly Arg Tyr Ser Ile Ser Arg Thr Glu
        35                  40                  45

Ala Ala Asp Leu Cys Lys Ala Phe Asn Ser Thr Leu Pro Thr Met Ala
    50                  55                  60

Gln Met Glu Lys Ala Leu Ser Ile Gly Phe Glu Thr Cys Arg Tyr Gly
65                  70                  75                  80

Phe Ile Glu Gly His Val Val Ile Pro Arg Ile His Pro Asn Ser Ile
                85                  90                  95

Cys Ala Ala Asn Asn Thr Gly Val Tyr Ile Leu Thr Ser Asn Thr Ser
            100                 105                 110

Gln Tyr Asp Thr Tyr Cys Phe Asn Ala Ser Ala Pro Pro Glu Glu Asp
        115                 120                 125
```

```
Cys Thr Ser Val Thr Asp Leu Pro Asn Ala Phe Asp Gly Pro Ile Thr
    130                 135                 140

Ile Thr Ile Val Asn Arg Asp Gly Thr Arg Tyr Val Gln Lys Gly Glu
145                 150                 155                 160

Tyr Arg Thr Asn Pro Glu Asp Ile Tyr Pro Ser Asn Pro Thr Asp Asp
                165                 170                 175

Asp Val Ser Ser Gly Ser Ser Ser Glu Arg Ser Ser Thr Ser Gly Gly
            180                 185                 190

Tyr Ile Phe Tyr Thr Phe Ser Thr Val His Pro Ile Pro Asp Glu Asp
            195                 200                 205

Ser Pro Trp Ile Thr Asp Ser Thr Asp Arg Ile Pro Ala Thr Thr Leu
    210                 215                 220

Met Ser Thr Ser Ala Thr Ala Thr Glu Thr Ala Thr Lys Arg Gln Glu
225                 230                 235                 240

Thr Trp Asp Trp Phe Ser Trp Leu Phe Leu Pro Ser Glu Ser Lys Asn
                245                 250                 255

His Leu His Thr Thr Thr Gln Met Ala Gly Thr Ser Ser Asn Thr Ile
            260                 265                 270

Ser Ala Gly Trp Glu Pro Asn Glu Glu Asn Glu Asp Glu Arg Asp Arg
    275                 280                 285

His Leu Ser Phe Ser Gly Ser Gly Ile Asp Asp Asp Glu Asp Phe Ile
    290                 295                 300

Ser Ser Thr Ile Ser Thr Thr Pro Arg Ala Phe Asp His Thr Lys Gln
305                 310                 315                 320

Asn Gln Asp Trp Thr Gln Trp Asn Pro Ser His Ser Asn Pro Glu Val
                325                 330                 335

Leu Leu Gln Thr Thr Thr Arg Met Thr Asp Val Asp Arg Asn Gly Thr
            340                 345                 350

Thr Ala Tyr Glu Gly Asn Trp Asn Pro Glu Ala His Pro Pro Leu Ile
            355                 360                 365

His His Glu His His Glu Glu Glu Thr Pro His Ser Thr Ser Thr
    370                 375                 380

Ile Gln Ala Thr Pro Ser Ser Thr Thr Glu Glu Thr Ala Thr Gln Lys
385                 390                 395                 400

Glu Gln Trp Phe Gly Asn Arg Trp His Glu Gly Tyr Arg Gln Thr Pro
                405                 410                 415

Lys Glu Asp Ser His Ser Thr Thr Gly Thr Ala Ala Ala Ser Ala His
            420                 425                 430

Thr Ser His Pro Met Gln Gly Arg Thr Thr Pro Ser Pro Glu Asp Ser
    435                 440                 445

Ser Trp Thr Asp Phe Phe Asn Pro Ile Ser His Pro Met Gly Arg Gly
    450                 455                 460

His Gln Ala Gly Arg Arg Met Asp Met Asp Ser Ser His Ser Ile Thr
465                 470                 475                 480

Leu Gln Pro Thr Ala Asn Pro Asn Thr Gly Leu Val Glu Asp Leu Asp
                485                 490                 495

Arg Thr Gly Pro Leu Ser Met Thr Thr Gln Gln Ser Asn Ser Gln Ser
            500                 505                 510

Phe Ser Thr Ser His Glu Gly Leu Glu Glu Asp Lys Asp His Pro Thr
            515                 520                 525

Thr Ser Thr Leu Thr Ser Ser Asn Arg Asn Asp Val Thr Gly Gly Arg
    530                 535                 540
```

```
Arg Asp Pro Asn His Ser Glu Gly Ser Thr Thr Leu Leu Glu Gly Tyr
545                 550                 555                 560

Thr Ser His Tyr Pro His Thr Lys Glu Ser Arg Thr Phe Ile Pro Val
                565                 570                 575

Thr Ser Ala Lys Thr Gly Ser Phe Gly Val Thr Ala Val Thr Val Gly
            580                 585                 590

Asp Ser Asn Ser Asn Val Asn Arg Ser Leu Ser Gly Asp Gln Asp Thr
        595                 600                 605

Phe His Pro Ser Gly Gly Ser His Thr Thr His Gly Ser Glu Ser Asp
    610                 615                 620

Gly His Ser His Gly Ser Gln Glu Gly Gly Ala Asn Thr Thr Ser Gly
625                 630                 635                 640

Pro Ile Arg Thr Pro Gln Ile Pro Glu Trp Leu Ile Ile Leu Ala Ser
                645                 650                 655

Leu Leu Ala Leu Ala Leu Ile Leu Ala Val Cys Ile Ala Val Asn
                660                 665                 670

<210> SEQ ID NO 18
<211> LENGTH: 244
<212> TYPE: PRT
<213> ORGANISM: Artificial Sequence
<220> FEATURE:
<223> OTHER INFORMATION: Syntheisized

<400> SEQUENCE: 18

Met Arg Trp Cys Leu Leu Ile Trp Ala Gln Gly Leu Arg Gln Ala
1               5                   10                  15

Pro Leu Ala Ser Gly Met Met Thr Gly Thr Ile Glu Thr Thr Gly Asn
                20                  25                  30

Ile Ser Ala Glu Lys Gly Gly Ser Ile Ile Leu Gln Cys His Leu Ser
            35                  40                  45

Ser Thr Thr Ala Gln Val Thr Gln Val Asn Trp Glu Gln Gln Asp Gln
        50                  55                  60

Leu Leu Ala Ile Cys Asn Ala Asp Leu Gly Trp His Ile Ser Pro Ser
65                  70                  75                  80

Phe Lys Asp Arg Val Ala Pro Gly Pro Gly Leu Gly Leu Thr Leu Gln
                85                  90                  95

Ser Leu Thr Val Asn Asp Thr Gly Glu Tyr Phe Cys Ile Tyr His Thr
            100                 105                 110

Tyr Pro Asp Gly Thr Tyr Thr Gly Arg Ile Phe Leu Glu Val Leu Glu
        115                 120                 125

Ser Ser Val Ala Glu His Gly Ala Arg Phe Gln Ile Pro Leu Leu Gly
    130                 135                 140

Ala Met Ala Ala Thr Leu Val Val Ile Cys Thr Ala Val Ile Val Val
145                 150                 155                 160

Val Ala Leu Thr Arg Lys Lys Lys Ala Leu Arg Ile His Ser Val Glu
                165                 170                 175

Gly Asp Leu Arg Arg Lys Ser Ala Gly Gln Glu Glu Trp Ser Pro Ser
            180                 185                 190

Ala Pro Ser Pro Pro Gly Ser Cys Val Gln Ala Glu Ala Pro Ala
        195                 200                 205

Gly Leu Cys Gly Glu Gln Arg Gly Glu Asp Cys Ala Glu Leu His Asp
    210                 215                 220

Tyr Phe Asn Val Leu Ser Tyr Arg Ser Leu Gly Asn Cys Ser Phe Phe
225                 230                 235                 240
```

Thr Glu Thr Gly

<210> SEQ ID NO 19
<211> LENGTH: 162
<212> TYPE: PRT
<213> ORGANISM: Homo sapiens

<400> SEQUENCE: 19

Met Arg Trp Cys Leu Leu Leu Ile Trp Ala Gln Gly Leu Arg Gln Ala
1               5                   10                  15

Pro Leu Ala Ser Gly Met Met Thr Gly Thr Ile Glu Thr Thr Gly Asn
            20                  25                  30

Ile Ser Ala Glu Lys Gly Gly Ser Ile Ile Leu Gln Cys His Leu Ser
        35                  40                  45

Ser Thr Thr Ala Gln Val Thr Gln Val Asn Trp Glu Gln Gln Asp Gln
    50                  55                  60

Leu Leu Ala Ile Cys Asn Ala Asp Leu Gly Trp His Ile Ser Pro Ser
65                  70                  75                  80

Phe Lys Asp Arg Val Ala Pro Gly Pro Gly Leu Gly Leu Thr Leu Gln
                85                  90                  95

Ser Leu Thr Val Asn Asp Thr Gly Glu Tyr Phe Cys Ile Tyr His Thr
            100                 105                 110

Tyr Pro Asp Gly Thr Tyr Thr Gly Arg Ile Phe Leu Glu Val Leu Glu
        115                 120                 125

Ser Ser Val Ala Glu His Gly Ala Arg Phe Gln Ile Pro Leu Leu Gly
    130                 135                 140

Ala Met Ala Ala Thr Leu Val Val Ile Cys Thr Ala Val Ile Val Val
145                 150                 155                 160

Val Ala

<210> SEQ ID NO 20
<211> LENGTH: 82
<212> TYPE: PRT
<213> ORGANISM: Artificial Sequence
<220> FEATURE:
<223> OTHER INFORMATION: Syntheisized

<400> SEQUENCE: 20

Leu Thr Arg Lys Lys Lys Ala Leu Arg Ile His Ser Val Glu Gly Asp
1               5                   10                  15

Leu Arg Arg Lys Ser Ala Gly Gln Glu Glu Trp Ser Pro Ser Ala Pro
            20                  25                  30

Ser Pro Pro Gly Ser Cys Val Gln Ala Glu Ala Ala Pro Ala Gly Leu
        35                  40                  45

Cys Gly Glu Gln Arg Gly Glu Asp Cys Ala Glu Leu His Asp Tyr Phe
    50                  55                  60

Asn Val Leu Ser Phe Arg Ser Leu Gly Asn Cys Ser Phe Phe Thr Glu
65                  70                  75                  80

Thr Gly

<210> SEQ ID NO 21
<211> LENGTH: 1149
<212> TYPE: DNA
<213> ORGANISM: Homo sapiens

<400> SEQUENCE: 21
atggggccca ccagcgtccc gctggtcaag gcccaccgca gctcggtctc tgactacgtc    60

```
aactatgata tcatcgtccg gcattacaac tacacgggaa agctgaatat cagcgcggac    120
aaggagaaca gcattaaact gacctcggtg gtgttcattc tcatctgctg ctttatcatc    180
ctggagaaca tctttgtctt gctgaccatt tggaaaacca agaaattcca ccgacccatg    240
tactatttta ttggcaatct ggccctctca gacctgttgg caggagtagc ctacacagct    300
aacctgctct tgtctggggc caccacctac aagctcactc ccgcccagtg gtttctgcgg    360
gaagggagta tgtttgtggc cctgtcagcc tccgtgttca gtctcctcgc catcgccatt    420
gagcgctata tcacaatgct gaaaatgaaa ctccacaacg ggagcaataa cttccgcctc    480
ttcctgctaa tcagcgcctg ctgggtcatc tccctcatcc tgggtggcct gcctatcatg    540
ggctggaact gcatcagtgc gctgtccagc tgctccaccg tgctgccgct ctaccacaag    600
cactatatcc tcttctgcac cacggtcttc actctgcttc tgctctccat cgtcattctg    660
tactgcagaa tctactcctt ggtcaggact cggagccgcc gcctgacgtt ccgcaagaac    720
atttccaagg ccagccgcag ctctgagaag tcgctggcgc tgctcaagac cgtaattatc    780
gtcctgagcg tcttcatcgc ctgctgggca ccgctcttca tcctgctcct gctggatgtg    840
ggctgcaagg tgaagacctg tgacatcctc ttcagagcgg agtacttcct ggtgttagct    900
gtgctcaact ccggcaccaa ccccatcatt tacactctga ccaacaagga gatgcgtcgg    960
gccttcatcc ggatcatgtc ctgctgcaag tgcccgagcg agactctgc tggcaaattc   1020 aagcgaccca tcatcgccgg catggaattc agccgcagca atcggacaa ttcctcccac   1080 ccccagaaag acgaagggga caacccagag accattatgt cttctggaaa cgtcaactct   1140
tcttcctag                                                          1149

<210> SEQ ID NO 22
<211> LENGTH: 9580
<212> TYPE: DNA
<213> ORGANISM: Artificial Sequence
<220> FEATURE:
<223> OTHER INFORMATION: Syntheisized

<400> SEQUENCE: 22
cggctccggt gcccgtcagt gggcagagcg cacatcgccc acagtccccg agaagttggg     60
gggaggggtc ggcaattgaa ccggtgccta gagaaggtgg cgcggggtaa actgggaaag    120
tgatgtcgtg tactggctcc gccttttttcc cgagggtggg ggagaaccgt atataagtgc    180
agtagtcgcc gtgaacgttc tttttcgcaa cgggtttgcc gccagaacac aggatccgcc    240
accatggcct taccagtgac cgccttgctc ctgccgctgg ccttgctgct ccacgccgcc    300
aggccggata tccagatgac ccagagcccg agcagcctga gcgcgagcgt gggtgatcgc    360
gtgaccatta cctgcagggc aagtcaggac attagtaaat atttaaattg gtatcagcag    420
aaaccgggta aagcgccgaa actgttaatt tatcatacat caagattaca ctcaggcgtg    480
ccgtcgcgtt ttagcggctc gggttcgggc accgatttta ccctgaccat ctcgagcttg    540
cagccggagg acttcgccac ctactattgc caacagggta tacgcttcc gtacacgttc    600 ggtcagggca ccaaagtgga gatcaaaggt ggcggtggct cgggcggtgg tgggtcgggt    660
ggcggcggat ctgaggtgca gctggtggag tctggggga gcttggtaca gcctgggggg    720
tccctgagac tctcctgtgc agcctctgga gtgtccctgc tgattatgg cgtgtcctgg    780 gtccgccagg ctccagggaa ggggctggag tgggtttcag tgatctgggg cagcgagaca    840
acctactaca cagcgccct gaagtcccga ttcaccatct ccagagacaa tgccaagaac    900
tcactgtatc tgcaaatgaa cagcctgaga gccgaggaca cggctgtgta ttactgtgcg    960
```

```
aagcactact actacggcgg cagctacgct atggactact ggggccaagg aaccctggtc   1020
accgtgtcct caaccacgac gccagcgccg cgaccaccaa caccggcgcc caccatcgcg   1080
tcgcagcccc tgtccctgcg cccagaggcg tgccggccag cggcgggggg cgcagtgcac   1140
acgaggggc tggacttcgc ctgtgatatc tacatctggg cgcccttggc cgggacttgt     1200
ggggtccttc tcctgtcact ggttatcacc ctttactgca aacggggcag aaagaaactc   1260
ctgtatatat tcaaacaacc atttatgaga ccagtacaaa ctactcaaga ggaagatggc   1320
tgtagctgcc gatttccaga agaagaagaa ggaggatgtg aactgagagt gaagttcagc   1380
aggagcgcag acgccccgc gtaccagcag ggccagaacc agctctataa cgagctcaat     1440
ctaggacgaa gagaggagta cgatgttttg acaagaggc gtggccggga ccctgagatg     1500
gggggaaagc cgagaaggaa gaaccctcag gaaggcctgt acaatgaact gcagaaagat   1560
aagatggcgg aggcctacag tgagattggg atgaaaggcg agcgccggag gggcaagggg   1620
cacgatggcc tttaccaggg tctcagtaca gccaccaagg acacctacga cgcccttcac   1680
atgcaggccc tgcccctcg ctaagtcgac cccctctccc tccccccccc ctaacgttac     1740
tggccgaagc cgcttggaat aaggccggtg tgcgtttgtc tatatgttat tttccaccat   1800
attgccgtct tttggcaatg tgagggcccg gaaacctggc cctgtcttct tgacgagcat   1860
tcctaggggt ctttcccctc tcgccaaagg aatgcaaggt ctgttgaatg tcgtgaagga   1920
agcagttcct ctggaagctt cttgaagaca aacaacgtct gtagcgaccc tttgcaggca   1980
gcggaaccc ccacctggcg acaggtgcct ctgcggccaa aagccacgtg tataagatac     2040
acctgcaaag gcggcacaac cccagtgcca cgttgtgagt tggatagttg tggaaagagt   2100
caaatggctc tcctcaagcg tattcaacaa ggggctgaag gatgcccaga aggtaccca     2160
ttgtatggga tctgatctgg ggcctcggta cacatgcttt acatgtgttt agtcgaggtt   2220
aaaaaaacgt ctaggccccc cgaaccacgg ggacgtggtt ttcctttgaa aaacacgatg   2280
ataatatggc cacaacccat atgagtgatg gggcccacca gcgtcccgct ggtcaaggcc   2340
caccgcagct cggtctctga ctacgtcaac tatgatatca tcgtccggca ttacaactac   2400
acgggaaagc tgaatatcag cgcggacaag gagaacagca ttaaactgac ctcggtggtg   2460
ttcattctca tctgctgctt tatcatcctg gagaacatct ttgtcttgct gaccatttgg   2520
aaaaccaaga aattccaccg acccatgtac tattttattg gcaatctggc cctctcagac   2580
ctgttggcag gagtagccta cacagctaac ctgctcttgt ctggggccac cacctacaag   2640
ctcactcccg cccagtggtt tctgcgggaa gggagtatgt ttgtggccct gtcagcctcc   2700
gtgttcagtc tcctcgccat cgccattgag cgctatatca caatgctgaa aatgaaactc   2760
cacaacggga gcaataactt ccgcctcttc ctgctaatca gcgcctgctg ggtcatctcc   2820
ctcatcctgg gtggcctgcc tatcatgggc tggaactgca tcagtcgcgt gtccagctgc   2880
tccaccgtgt gccgctcta ccacaagcac tatatcctct tctgcaccac ggtcttcact   2940
ctgcttctgc tctccatcgt cattctgtac tgcagaatct actccttggt caggactcgg   3000
agccgccgcc tgacgttccg caagaacatt tccaaggcca ccgcagctc tgagaagtcg   3060
ctggcgctgc tcaagaccgt aattatcgtc ctgagcgtct tcatcgcctg ctgggcaccg   3120
ctcttcatcc tgctcctgct ggatgtgggc tgcaaggtga agacctgtga catcctcttc   3180
agagcggagt acttcctggt gttagctgtg ctcaactccg gcaccaaccc catcatttac   3240
actctgacca acaaggagat gcgtcgggcc ttcatccgga tcatgtcctg ctgcaagtgc   3300
```

```
ccgagcggag actctgctgg caaattcaag cgacccatca tcgccggcat ggaattcagc   3360
cgcagcaaat cggacaattc ctcccacccc cagaaagacg aagggacaa cccagagacc    3420
attatgtctt ctggaaacgt caactcttct tcctagacta gtaatcaacc tctggattac   3480
aaaatttgtg aaagattgac tggtattctt aactatgttg ctccttttac gctatgtgga   3540
tacgctgctt taatgccttt gtatcatgct attgcttccc gtatggcttt cattttctcc   3600
tccttgtata atcctggtt gctgtctctt tatgaggagt tgtggcccgt tgtcaggcaa     3660
cgtggcgtgg tgtgcactgt gtttgctgac gcaaccccca ctggttgggg cattgccacc   3720
acctgtcagc tcctttccgg gactttcgct ttccccctcc ctattgccac ggcggaactc   3780
atcgccgcct gccttgcccg ctgctggaca ggggctcggc tgttgggcac tgacaattcc   3840
gtggtgttgt cggggaagct gacgtccttt ccatggctgc tcgcctgtgt tgccacctgg   3900
attctgcgcg ggacgtcctt ctgctacgtc ccttcggccc tcaatccagc ggaccttcct   3960
tcccgcggcc tgctgccggc tctgcggcct cttccgcgtc ttcgccttcg ccctcagacg   4020
agtcggatct ccctttgggc cgcctccccg cctgccgcgg aattcgagct cggtaccttt   4080
aagaccaatg acttacaagg cagctgtaga tcttagccac ttttttaaaag aaaaggggg    4140
actgaaggg ctaattcact cccaacgaag acaagatctg cttttttgctt gtactgggtc    4200
tctctggtta gaccagatct gagcctggga gctctctggc taactaggga acccactgct   4260
taagcctcaa taaagcttgc cttgagtgct tcaagtagtg tgtgcccgtc tgttgtgtga   4320
ctctggtaac tagagatccc tcagacccct ttagtcagtg tggaaaatct ctagcagtag   4380
tagttcatgt catcttatta ttcagtattt ataacttgca agaaatgaa tatcagagag    4440
tgagaggaac ttgtttattg cagcttataa tggttacaaa taaagcaata gcatcacaaa   4500
tttcacaaat aaagcatttt tttcactgca ttctagttgt ggtttgtcca aactcatcaa   4560
tgtatcttat catgtctggc tctagctatc ccgcccctaa ctccgcccat cccgccccta   4620
actccgccca gttccgccca ttctccgccc catggctgac taattttttt tatttatgca   4680
gaggccgagg ccgcctcggc ctctgagcta ttccagaagt agtgaggagg cttttttgga   4740
ggcctaggga cgtacccaat tcgccctata gtgagtcgta ttacgcgcgc tcactggccg   4800
tcgttttaca acgtcgtgac tgggaaaacc ctggcgttac ccaacttaat cgccttgcag   4860
cacatccccc tttcgccagc tggcgtaata gcgaagaggc ccgcaccgat cgcccttccc   4920
aacagttgcg cagcctgaat ggcgaatggg acgcgccctg tagcggcgca ttaagcgcgg   4980
cgggtgtggt ggttacgcgc agcgtgaccg ctacacttgc cagcgcccta gcgcccgctc   5040
ctttcgcttt cttcccttcc tttctcgcca cgttcgccgg ctttccccgt caagctctaa   5100
atcgggggct ccctttaggg ttccgattta gtgctttacg gcacctcgac cccaaaaaac   5160
ttgattaggg tgatggttca cgtagtgggc catcgccctg atagacggtt tttcgccctt   5220
tgacgttgga gtccacgttc tttaatagtg gactcttgtt ccaaactgga acaacactca   5280
accctatctc ggtctattct tttgatttat aagggatttt gccgatttcg gcctattggt   5340
taaaaaatga gctgatttaa caaaaattta acgcgaattt taacaaaata ttaacgctta   5400
caatttgaag atcctttgat cttttctacg ggtctgacg ctcagtggaa cgaaaactca    5460
cgttaaggga ttttggtcat gaacaataaa actgtctgct tacataaaca gtaatacaag   5520
gggtgttatg agccatattc aacgggaaac gtcttgctct aggccgcgat taaattccaa   5580
catggatgct gatttatatg ggtataaatg ggctcgcgat aatgtcgggc aatcaggtgc   5640
gacaatctat cgattgtatg ggaagcccga tgcgccagag ttgtttctga acatggcaa    5700
```

```
aggtagcgtt gccaatgatg ttacagatga gatggtcaga ctaaactggc tgacggaatt    5760
tatgcctctt ccgaccatca agcatttat ccgtactcct gatgatgcat ggttactcac    5820
cactgcgatc cccgggaaaa cagcattcca ggtattagaa gaatatcctg attcaggtga    5880
aaatattgtt gatgcgctgg cagtgttcct gcgccggttg cattcgattc ctgtttgtaa    5940
ttgtcctttt aacagcgatc gcgtatttcg tctggctcag gcgcaatcac gaatgaataa    6000
cggtttggtt gatgcgagtg attttgatga cgagcgtaat ggctggcctg ttgaacaagt    6060
ctggaaagaa atgcataaac ttttgccatt ctcaccggat tcagtcgtca ctcatggtga    6120
tttctcactt gataacctta tttttgacga ggggaaatta ataggttgta ttgatgttgg    6180
acgagtcgga atcgcagacc gataccagga tcttgccatc ctatggaact gcctcggtga    6240
gttttctcct tcattacaga aacggctttt tcaaaaatat ggtattgata atcctgatat    6300
gaataaattg cagtttcatt tgatgctcga tgagtttttc taactgtcag accaagttta    6360
ctcatatata ctttagattg atttaaaact tcattttttaa tttaaaagga tctaggtgaa    6420
gatccttttt gataatctca tgaccaaaat cccttaacgt gagttttcgt tccactgagc    6480
gtcagacccc gtagaaaaga tcaaggatc ttcttgagat cctttttttc tgcgcgtaat    6540
ctgctgcttg caaacaaaaa aaccaccgct accagcggtg gtttgtttgc cggatcaaga    6600
gctaccaact cttttttccga aggtaactgg cttcagcaga gcgcagatac caaatactgt    6660
tcttctagtg tagccgtagt taggccacca cttcaagaac tctgtagcac cgcctacata    6720
cctcgctctg ctaatcctgt taccagtggc tgctgccagt ggcgataagt cgtgtcttac    6780
cgggttggac tcaagacgat agttaccgga taaggcgcag cggtcgggct gaacggggggg    6840 ttcgtgcaca gcccagct tggagcgaac gacctacacc gaactgagat acctacagcg    6900
tgagctatga gaaagcgcca cgcttcccga agggagaaag gcggacaggt atccggtaag    6960
cggcagggtc ggaacaggag agcgcacgag ggagcttcca gggggaaacg cctggtatct    7020
ttatagtcct gtcgggtttc gccacctctg acttgagcgt cgatttttgt gatgctcgtc    7080
aggggggcgg agcctatgga aaaacgccag caacgcggcc tttttacggt tcctggcctt    7140
ttgctggcct tttgctcaca tgttctttcc tgcgttatcc cctgattctg tggataaccg    7200
tattaccgcc tttgagtgag ctgataccgc tcgccgcagc cgaacgaccg agcgcagcga    7260
gtcagtgagc gaggaagcgg aagagcgccc aatacgcaaa ccgcctctcc ccgcgcgttg    7320
gccgattcat taatgcagct ggcacgacag gtttcccgac tggaaagcgg gcagtgagcg    7380
caacgcaatt aatgtgagtt agctcactca ttaggcaccc caggctttac actttatgct    7440
tccggctcgt atgttgtgtg gaattgtgag cggataacaa tttcacacag gaaacagcta    7500
tgaccatgat tacgccaagc gcgcaattaa ccctcactaa agggaacaaa agctggagct    7560
gcaagcttaa tgtagtctta tgcaatactc ttgtagtctt gcaacatggt aacgatgagt    7620
tagcaacatg ccttacaagg agagaaaaag caccgtgcat gccgattggt ggaagtaagg    7680
tggtacgatc gtgccttatt aggaaggcaa cagacgggtc tgacatggat tggacgaacc    7740
actgaattgc cgcattgcag agatattgta tttaagtgcc tagctcgata cataaacggg    7800
tctctctggt tagaccagat ctgagcctgg gagctctctg gctaactagg gaacccactg    7860
cttaagcctc aataaagctt gccttgagtg cttcaagtag tgtgtgcccg tctgttgtgt    7920
gactctggta actagagatc cctcagaccc ttttagtcag tgtggaaaat ctctagcagt    7980
ggcgcccgaa cagggacttg aaagcgaaag ggaaaccaga ggagctctct cgacgcagga    8040
```

```
ctcggcttgc tgaagcgcgc acggcaagag gcgaggggcg gcgactggtg agtacgccaa    8100
aaattttgac tagcggaggc tagaaggaga gagatgggtg cgagagcgtc agtattaagc    8160
gggggagaat tagatcgcga tgggaaaaaa ttcggttaag gccaggggga agaaaaaat     8220
ataaattaaa acatatagta tgggcaagca gggagctaga acgattcgca gttaatcctg    8280
gcctgttaga acatcagaa ggctgtagac aaatactggg acagctacaa ccatcccttc     8340
agacaggatc agaagaactt agatcattat ataatacagt agcaaccctc tattgtgtgc    8400
atcaaaggat agagataaaa gacaccaagg aagctttaga caagatagag gaagagcaaa    8460
acaaaagtaa gaccaccgca cagcaagcgg ccgctgatct tcagacctgg aggaggagat    8520
atgagggaca attggagaag tgaattatat aaatataaag tagtaaaaat tgaaccatta    8580
ggagtagcac ccaccaaggc aaagagaaga gtggtgcaga gagaaaaaag agcagtggga    8640
ataggagctt tgttccttgg gttcttggga gcagcaggaa gcactatggg cgcagcgtca    8700
atgacgctga cggtacaggc cagacaatta ttgtctggta tagtgcagca gcagaacaat    8760
ttgctgaggg ctattgaggc gcaacagcat ctgttgcaac tcacagtctg ggcatcaag    8820
cagctccagg caagaatcct ggctgtggaa agatacctaa aggatcaaca gctcctgggg    8880
atttggggtt gctctggaaa actcatttgc accactgctg tgccttggaa tgctagttgg    8940
agtaataaat ctctggaaca gatttggaat cacacgacct ggatggagtg gacagagaa    9000
attaacaatt acacaagctt aatacactcc ttaattgaag aatcgcaaaa ccagcaagaa    9060
aagaatgaac aagaattatt ggaattagat aaatgggcaa gtttgtggaa ttggtttaac    9120
ataacaaatt ggctgtggta tataaaatta ttcataatga tagtaggagg cttggtaggt    9180
ttaagaatag ttttgctgt actttctata gtgaatagag ttaggcaggg atattcacca    9240
ttatcgtttc agacccacct cccaaccccg aggggacccg acaggcccga aggaatagaa    9300
gaagaaggtg gagagagaga cagagacaga tccattcgat tagtgaacgg atctcgacgg    9360
tatcgatcac gagactagcc tcgacacaaa tggcagtatt catccacaat tttaaaagaa    9420
aaggggggat tggggggtac agtgcagggg aaagaatagt agacataata gcaacagaca    9480
tacaaactaa agaattacaa aaacaaatta caaaaattca aaatttcgg gtttattaca    9540
gggacagcag aaatccactt tggctcgaga agcttgatat                         9580
```

<210> SEQ ID NO 23
<211> LENGTH: 918
<212> TYPE: PRT
<213> ORGANISM: Homo sapiens

<400> SEQUENCE: 23

```
Met Leu Thr Leu Gln Thr Trp Leu Val Gln Ala Leu Phe Ile Phe Leu
1               5                   10                  15

Thr Thr Glu Ser Thr Gly Glu Leu Leu Asp Pro Cys Gly Tyr Ile Ser
            20                  25                  30

Pro Glu Ser Pro Val Val Gln Leu His Ser Asn Phe Thr Ala Val Cys
        35                  40                  45

Val Leu Lys Glu Lys Cys Met Asp Tyr Phe His Val Asn Ala Asn Tyr
    50                  55                  60

Ile Val Trp Lys Thr Asn His Phe Thr Ile Pro Lys Glu Gln Tyr Thr
65                  70                  75                  80

Ile Ile Asn Arg Thr Ala Ser Ser Val Thr Phe Thr Asp Ile Ala Ser
                85                  90                  95

Leu Asn Ile Gln Leu Thr Cys Asn Ile Leu Thr Phe Gly Gln Leu Glu
```

```
                100             105             110
Gln Asn Val Tyr Gly Ile Thr Ile Ile Ser Gly Leu Pro Pro Glu Lys
            115             120             125

Pro Lys Asn Leu Ser Cys Ile Val Asn Glu Gly Lys Lys Met Arg Cys
130             135             140

Glu Trp Asp Gly Gly Arg Glu Thr His Leu Glu Thr Asn Phe Thr Leu
145             150             155             160

Lys Ser Glu Trp Ala Thr His Lys Phe Ala Asp Cys Lys Ala Lys Arg
            165             170             175

Asp Thr Pro Thr Ser Cys Thr Val Asp Tyr Ser Thr Val Tyr Phe Val
            180             185             190

Asn Ile Glu Val Trp Val Glu Ala Glu Asn Ala Leu Gly Lys Val Thr
            195             200             205

Ser Asp His Ile Asn Phe Asp Pro Val Tyr Lys Val Lys Pro Asn Pro
            210             215             220

Pro His Asn Leu Ser Val Ile Asn Ser Glu Glu Leu Ser Ser Ile Leu
225             230             235             240

Lys Leu Thr Trp Thr Asn Pro Ser Ile Lys Ser Val Ile Ile Leu Lys
            245             250             255

Tyr Asn Ile Gln Tyr Arg Thr Lys Asp Ala Ser Thr Trp Ser Gln Ile
            260             265             270

Pro Pro Glu Asp Thr Ala Ser Thr Arg Ser Ser Phe Thr Val Gln Asp
            275             280             285

Leu Lys Pro Phe Thr Glu Tyr Val Phe Arg Ile Arg Cys Met Lys Glu
            290             295             300

Asp Gly Lys Gly Tyr Trp Ser Asp Trp Ser Glu Glu Ala Ser Gly Ile
305             310             315             320

Thr Tyr Glu Asp Arg Pro Ser Lys Ala Pro Ser Phe Trp Tyr Lys Ile
            325             330             335

Asp Pro Ser His Thr Gln Gly Tyr Arg Thr Val Gln Leu Val Trp Lys
            340             345             350

Thr Leu Pro Pro Phe Glu Ala Asn Gly Lys Ile Leu Asp Tyr Glu Val
            355             360             365

Thr Leu Thr Arg Trp Lys Ser His Leu Gln Asn Tyr Thr Val Asn Ala
            370             375             380

Thr Lys Leu Thr Val Asn Leu Thr Asn Asp Arg Tyr Leu Ala Thr Leu
385             390             395             400

Thr Val Arg Asn Leu Val Gly Lys Ser Asp Ala Ala Val Leu Thr Ile
            405             410             415

Pro Ala Cys Asp Phe Gln Ala Thr His Pro Val Met Asp Leu Lys Ala
            420             425             430

Phe Pro Lys Asp Asn Met Leu Trp Val Glu Trp Thr Thr Pro Arg Glu
            435             440             445

Ser Val Lys Lys Tyr Ile Leu Glu Trp Cys Val Leu Ser Asp Lys Ala
            450             455             460

Pro Cys Ile Thr Asp Trp Gln Gln Glu Asp Gly Thr Val His Arg Thr
465             470             475             480

Tyr Leu Arg Gly Asn Leu Ala Glu Ser Lys Cys Tyr Leu Ile Thr Val
            485             490             495

Thr Pro Val Tyr Ala Asp Gly Pro Gly Ser Pro Glu Ser Ile Lys Ala
            500             505             510

Tyr Leu Lys Gln Ala Pro Pro Ser Lys Gly Pro Thr Val Arg Thr Lys
            515             520             525
```

Lys Val Gly Lys Asn Glu Ala Val Leu Glu Trp Asp Gln Leu Pro Val
        530                 535                 540

Asp Val Gln Asn Gly Phe Ile Arg Asn Tyr Thr Ile Phe Tyr Arg Thr
545                 550                 555                 560

Ile Ile Gly Asn Glu Thr Ala Val Asn Val Asp Ser Ser His Thr Glu
                565                 570                 575

Tyr Thr Leu Ser Ser Leu Thr Ser Asp Thr Leu Tyr Met Val Arg Met
            580                 585                 590

Ala Ala Tyr Thr Asp Glu Gly Lys Asp Gly Pro Glu Phe Thr Phe
        595                 600                 605

Thr Thr Pro Lys Phe Ala Gln Gly Glu Ile Glu Ala Ile Val Val Pro
    610                 615                 620

Val Cys Leu Ala Phe Leu Leu Thr Thr Leu Leu Gly Val Leu Phe Cys
625                 630                 635                 640

Phe Asn Lys Arg Asp Leu Ile Lys Lys His Ile Trp Pro Asn Val Pro
                645                 650                 655

Asp Pro Ser Lys Ser His Ile Ala Gln Trp Ser Pro His Thr Pro Pro
            660                 665                 670

Arg His Asn Phe Asn Ser Lys Asp Gln Met Tyr Ser Asp Gly Asn Phe
        675                 680                 685

Thr Asp Val Ser Val Val Glu Ile Glu Ala Asn Asp Lys Lys Pro Phe
    690                 695                 700

Pro Glu Asp Leu Lys Ser Leu Asp Leu Phe Lys Lys Glu Lys Ile Asn
705                 710                 715                 720

Thr Glu Gly His Ser Ser Gly Ile Gly Gly Ser Ser Cys Met Ser Ser
                725                 730                 735

Ser Arg Pro Ser Ile Ser Ser Asp Glu Asn Glu Ser Ser Gln Asn
            740                 745                 750

Thr Ser Ser Thr Val Gln Tyr Ser Thr Val Val His Ser Gly Tyr Arg
        755                 760                 765

His Gln Val Pro Ser Val Gln Val Phe Ser Arg Ser Glu Ser Thr Gln
    770                 775                 780

Pro Leu Leu Asp Ser Glu Glu Arg Pro Glu Asp Leu Gln Leu Val Asp
785                 790                 795                 800

His Val Asp Gly Gly Asp Gly Ile Leu Pro Arg Gln Gln Tyr Phe Lys
                805                 810                 815

Gln Asn Cys Ser Gln His Glu Ser Ser Pro Asp Ile Ser His Phe Glu
            820                 825                 830

Arg Ser Lys Gln Val Ser Ser Val Asn Glu Glu Asp Phe Val Arg Leu
        835                 840                 845

Lys Gln Gln Ile Ser Asp His Ile Ser Gln Ser Cys Gly Ser Gly Gln
    850                 855                 860

Met Lys Met Phe Gln Glu Val Ser Ala Ala Asp Ala Phe Gly Pro Gly
865                 870                 875                 880

Thr Glu Gly Gln Val Glu Arg Phe Glu Thr Val Gly Met Glu Ala Ala
                885                 890                 895

Thr Asp Glu Gly Met Pro Lys Ser Tyr Leu Pro Gln Thr Val Arg Gln
            900                 905                 910

Gly Gly Tyr Met Pro Gln
        915

<210> SEQ ID NO 24
<211> LENGTH: 641

-continued

```
<212> TYPE: PRT
<213> ORGANISM: Artificial Sequence
<220> FEATURE:
<223> OTHER INFORMATION: Syntheisized

<400> SEQUENCE: 24
```

Met Leu Thr Leu Gln Thr Trp Leu Val Gln Ala Leu Phe Ile Phe Leu
1               5                   10                  15

Thr Thr Glu Ser Thr Gly Glu Leu Leu Asp Pro Cys Gly Tyr Ile Ser
            20                  25                  30

Pro Glu Ser Pro Val Val Gln Leu His Ser Asn Phe Thr Ala Val Cys
        35                  40                  45

Val Leu Lys Glu Lys Cys Met Asp Tyr Phe His Val Asn Ala Asn Tyr
    50                  55                  60

Ile Val Trp Lys Thr Asn His Phe Thr Ile Pro Lys Glu Gln Tyr Thr
65                  70                  75                  80

Ile Ile Asn Arg Thr Ala Ser Ser Val Thr Phe Thr Asp Ile Ala Ser
                85                  90                  95

Leu Asn Ile Gln Leu Thr Cys Asn Ile Leu Thr Phe Gly Gln Leu Glu
            100                 105                 110

Gln Asn Val Tyr Gly Ile Thr Ile Ile Ser Gly Leu Pro Pro Glu Lys
        115                 120                 125

Pro Lys Asn Leu Ser Cys Ile Val Asn Glu Gly Lys Lys Met Arg Cys
    130                 135                 140

Glu Trp Asp Gly Gly Arg Glu Thr His Leu Glu Thr Asn Phe Thr Leu
145                 150                 155                 160

Lys Ser Glu Trp Ala Thr His Lys Phe Ala Asp Cys Lys Ala Lys Arg
                165                 170                 175

Asp Thr Pro Thr Ser Cys Thr Val Asp Tyr Ser Thr Val Tyr Phe Val
            180                 185                 190

Asn Ile Glu Val Trp Val Glu Ala Glu Asn Ala Leu Gly Lys Val Thr
        195                 200                 205

Ser Asp His Ile Asn Phe Asp Pro Val Tyr Lys Val Lys Pro Asn Pro
    210                 215                 220

Pro His Asn Leu Ser Val Ile Asn Ser Glu Glu Leu Ser Ser Ile Leu
225                 230                 235                 240

Lys Leu Thr Trp Thr Asn Pro Ser Ile Lys Ser Val Ile Ile Leu Lys
                245                 250                 255

Tyr Asn Ile Gln Tyr Arg Thr Lys Asp Ala Ser Thr Trp Ser Gln Ile
            260                 265                 270

Pro Pro Glu Asp Thr Ala Ser Thr Arg Ser Ser Phe Thr Val Gln Asp
        275                 280                 285

Leu Lys Pro Phe Thr Glu Tyr Val Phe Arg Ile Arg Cys Met Lys Glu
    290                 295                 300

Asp Gly Lys Gly Tyr Trp Ser Asp Trp Ser Glu Glu Ala Ser Gly Ile
305                 310                 315                 320

Thr Tyr Glu Asp Arg Pro Ser Lys Ala Pro Ser Phe Trp Tyr Lys Ile
                325                 330                 335

Asp Pro Ser His Thr Gln Gly Tyr Arg Thr Val Gln Leu Val Trp Lys
            340                 345                 350

Thr Leu Pro Pro Phe Glu Ala Asn Gly Lys Ile Leu Asp Tyr Glu Val
        355                 360                 365

Thr Leu Thr Arg Trp Lys Ser His Leu Gln Asn Tyr Thr Val Asn Ala
    370                 375                 380

```
Thr Lys Leu Thr Val Asn Leu Thr Asn Asp Arg Tyr Leu Ala Thr Leu
385                 390                 395                 400

Thr Val Arg Asn Leu Val Gly Lys Ser Asp Ala Ala Val Leu Thr Ile
            405                 410                 415

Pro Ala Cys Asp Phe Gln Ala Thr His Pro Val Met Asp Leu Lys Ala
        420                 425                 430

Phe Pro Lys Asp Asn Met Leu Trp Val Glu Trp Thr Thr Pro Arg Glu
    435                 440                 445

Ser Val Lys Lys Tyr Ile Leu Glu Trp Cys Val Leu Ser Asp Lys Ala
450                 455                 460

Pro Cys Ile Thr Asp Trp Gln Gln Glu Asp Gly Thr Val His Arg Thr
465                 470                 475                 480

Tyr Leu Arg Gly Asn Leu Ala Glu Ser Lys Cys Tyr Leu Ile Thr Val
            485                 490                 495

Thr Pro Val Tyr Ala Asp Gly Pro Gly Ser Pro Glu Ser Ile Lys Ala
        500                 505                 510

Tyr Leu Lys Gln Ala Pro Pro Ser Lys Gly Pro Thr Val Arg Thr Lys
    515                 520                 525

Lys Val Gly Lys Asn Glu Ala Val Leu Glu Trp Asp Gln Leu Pro Val
530                 535                 540

Asp Val Gln Asn Gly Phe Ile Arg Asn Tyr Thr Ile Phe Tyr Arg Thr
545                 550                 555                 560

Ile Ile Gly Asn Glu Thr Ala Val Asn Val Asp Ser Ser His Thr Glu
            565                 570                 575

Tyr Thr Leu Ser Ser Leu Thr Ser Asp Thr Leu Tyr Met Val Arg Met
        580                 585                 590

Ala Ala Tyr Thr Asp Glu Gly Gly Lys Asp Gly Pro Glu Phe Thr Phe
    595                 600                 605

Thr Thr Pro Lys Phe Ala Gln Gly Glu Ile Glu Ala Ile Val Val Pro
610                 615                 620

Val Cys Leu Ala Phe Leu Leu Thr Thr Leu Leu Gly Val Leu Phe Cys
625                 630                 635                 640

Phe

<210> SEQ ID NO 25
<211> LENGTH: 277
<212> TYPE: PRT
<213> ORGANISM: Artificial Sequence
<220> FEATURE:
<223> OTHER INFORMATION: Syntheisized

<400> SEQUENCE: 25

Asn Lys Arg Asp Leu Ile Lys Lys His Ile Trp Pro Asn Val Pro Asp
1               5                   10                  15

Pro Ser Lys Ser His Ile Ala Gln Trp Ser Pro His Thr Pro Pro Arg
            20                  25                  30

His Asn Phe Asn Ser Lys Asp Gln Met Tyr Ser Asp Gly Asn Phe Thr
        35                  40                  45

Asp Val Ser Val Val Glu Ile Glu Ala Asn Asp Lys Lys Pro Phe Pro
    50                  55                  60

Glu Asp Leu Lys Ser Leu Asp Leu Phe Lys Lys Glu Lys Ile Asn Thr
65                  70                  75                  80

Glu Gly His Ser Ser Gly Ile Gly Gly Ser Ser Cys Met Ser Ser Ser
            85                  90                  95

Arg Pro Ser Ile Ser Ser Ser Asp Glu Asn Glu Ser Ser Gln Asn Thr
```

```
            100                 105                 110
Ser Ser Thr Val Gln Tyr Ser Thr Val Val His Ser Gly Tyr Arg His
    115                 120                 125

Gln Val Pro Ser Val Gln Val Phe Ser Arg Ser Glu Ala Thr Gln Pro
    130                 135                 140

Leu Leu Asp Ser Glu Glu Arg Pro Glu Asp Leu Gln Leu Val Asp His
145                 150                 155                 160

Val Asp Gly Gly Asp Gly Ile Leu Pro Arg Gln Gln Tyr Phe Lys Gln
                    165                 170                 175

Asn Cys Ser Gln His Glu Ser Ser Pro Asp Ile Ser His Phe Glu Arg
                180                 185                 190

Ser Lys Gln Val Ser Ser Val Asn Glu Glu Asp Phe Val Arg Leu Lys
                195                 200                 205

Gln Gln Ile Ser Asp His Ile Ser Gln Ser Cys Gly Ser Gly Gln Met
        210                 215                 220

Lys Met Phe Gln Glu Val Ser Ala Ala Asp Ala Phe Gly Pro Gly Thr
225                 230                 235                 240

Glu Gly Gln Val Glu Arg Phe Glu Thr Val Gly Met Glu Ala Ala Thr
                245                 250                 255

Asp Glu Gly Met Pro Lys Ser Tyr Leu Pro Gln Thr Val Arg Gln Gly
                260                 265                 270

Gly Tyr Met Pro Gln
        275

<210> SEQ ID NO 26
<211> LENGTH: 862
<212> TYPE: PRT
<213> ORGANISM: Homo sapiens

<400> SEQUENCE: 26

Met Ala His Thr Phe Arg Gly Cys Ser Leu Ala Phe Met Phe Ile Ile
1               5                   10                  15

Thr Trp Leu Leu Ile Lys Ala Lys Ile Asp Ala Cys Lys Arg Gly Asp
                20                  25                  30

Val Thr Val Lys Pro Ser His Val Ile Leu Leu Gly Ser Thr Val Asn
            35                  40                  45

Ile Thr Cys Ser Leu Lys Pro Arg Gln Gly Cys Phe His Tyr Ser Arg
    50                  55                  60

Arg Asn Lys Leu Ile Leu Tyr Lys Phe Asp Arg Arg Ile Asn Phe His
65                  70                  75                  80

His Gly His Ser Leu Asn Ser Gln Val Thr Gly Leu Pro Leu Gly Thr
                85                  90                  95

Thr Leu Phe Val Cys Lys Leu Ala Cys Ile Asn Ser Asp Glu Ile Gln
                100                 105                 110

Ile Cys Gly Ala Glu Ile Phe Val Gly Val Ala Pro Glu Gln Pro Gln
        115                 120                 125

Asn Leu Ser Cys Ile Gln Lys Gly Glu Gln Gly Thr Val Ala Cys Thr
    130                 135                 140

Trp Glu Arg Gly Arg Asp Thr His Leu Tyr Thr Glu Tyr Thr Leu Gln
145                 150                 155                 160

Leu Ser Gly Pro Lys Asn Leu Thr Trp Gln Lys Gln Cys Lys Asp Ile
                165                 170                 175

Tyr Cys Asp Tyr Leu Asp Phe Gly Ile Asn Leu Thr Pro Glu Ser Pro
                180                 185                 190
```

```
Glu Ser Asn Phe Thr Ala Lys Val Thr Ala Val Asn Ser Leu Gly Ser
            195                 200                 205

Ser Ser Ser Leu Pro Ser Thr Phe Thr Phe Leu Asp Ile Val Arg Pro
210                 215                 220

Leu Pro Pro Trp Asp Ile Arg Ile Lys Phe Gln Lys Ala Ser Val Ser
225                 230                 235                 240

Arg Cys Thr Leu Tyr Trp Arg Asp Glu Gly Leu Val Leu Leu Asn Arg
                245                 250                 255

Leu Arg Tyr Arg Pro Ser Asn Ser Arg Leu Trp Asn Met Val Asn Val
            260                 265                 270

Thr Lys Ala Lys Gly Arg His Asp Leu Leu Asp Leu Lys Pro Phe Thr
        275                 280                 285

Glu Tyr Glu Phe Gln Ile Ser Ser Lys Leu His Leu Tyr Lys Gly Ser
    290                 295                 300

Trp Ser Asp Trp Ser Glu Ser Leu Arg Ala Gln Thr Pro Glu Glu Glu
305                 310                 315                 320

Pro Thr Gly Met Leu Asp Val Trp Tyr Met Lys Arg His Ile Asp Tyr
                325                 330                 335

Ser Arg Gln Gln Ile Ser Leu Phe Trp Lys Asn Leu Ser Val Ser Glu
            340                 345                 350

Ala Arg Gly Lys Ile Leu His Tyr Gln Val Thr Leu Gln Glu Leu Thr
        355                 360                 365

Gly Gly Lys Ala Met Thr Gln Asn Ile Thr Gly His Thr Ser Trp Thr
    370                 375                 380

Thr Val Ile Pro Arg Thr Gly Asn Trp Ala Val Ala Val Ser Ala Ala
385                 390                 395                 400

Asn Ser Lys Gly Ser Ser Leu Pro Thr Arg Ile Asn Ile Met Asn Leu
                405                 410                 415

Cys Glu Ala Gly Leu Leu Ala Pro Arg Gln Val Ser Ala Asn Ser Glu
            420                 425                 430

Gly Met Asp Asn Ile Leu Val Thr Trp Gln Pro Pro Arg Lys Asp Pro
        435                 440                 445

Ser Ala Val Gln Glu Tyr Val Val Glu Trp Arg Glu Leu His Pro Gly
    450                 455                 460

Gly Asp Thr Gln Val Pro Leu Asn Trp Leu Arg Ser Arg Pro Tyr Asn
465                 470                 475                 480

Val Ser Ala Leu Ile Ser Glu Asn Ile Lys Ser Tyr Ile Cys Tyr Glu
                485                 490                 495

Ile Arg Val Tyr Ala Leu Ser Gly Asp Gln Gly Gly Cys Ser Ser Ile
            500                 505                 510

Leu Gly Asn Ser Lys His Lys Ala Pro Leu Ser Gly Pro His Ile Asn
        515                 520                 525

Ala Ile Thr Glu Glu Lys Gly Ser Ile Leu Ile Ser Trp Asn Ser Ile
    530                 535                 540

Pro Val Gln Glu Gln Met Gly Cys Leu Leu His Tyr Arg Ile Tyr Trp
545                 550                 555                 560

Lys Glu Arg Asp Ser Asn Ser Gln Pro Gln Leu Cys Glu Ile Pro Tyr
                565                 570                 575

Arg Val Ser Gln Asn Ser His Pro Ile Asn Ser Leu Gln Pro Arg Val
            580                 585                 590

Thr Tyr Val Leu Trp Met Thr Ala Leu Thr Ala Ala Gly Glu Ser Ser
        595                 600                 605

His Gly Asn Glu Arg Glu Phe Cys Leu Gln Gly Lys Ala Asn Trp Met
```

```
                610                 615                 620
Ala Phe Val Ala Pro Ser Ile Cys Ile Ala Ile Met Val Gly Ile
625                 630                 635                 640

Phe Ser Thr His Tyr Phe Gln Gln Lys Val Phe Val Leu Leu Ala Ala
                645                 650                 655

Leu Arg Pro Gln Trp Cys Ser Arg Glu Ile Pro Asp Pro Ala Asn Ser
                660                 665                 670

Thr Cys Ala Lys Lys Tyr Pro Ile Ala Glu Glu Lys Thr Gln Leu Pro
                675                 680                 685

Leu Asp Arg Leu Leu Ile Asp Trp Pro Thr Pro Glu Asp Pro Glu Pro
                690                 695                 700

Leu Val Ile Ser Glu Val Leu His Gln Val Thr Pro Val Phe Arg His
705                 710                 715                 720

Pro Pro Cys Ser Asn Trp Pro Gln Arg Glu Lys Gly Ile Gln Gly His
                725                 730                 735

Gln Ala Ser Glu Lys Asp Met Met His Ser Ala Ser Ser Pro Pro Pro
                740                 745                 750

Pro Arg Ala Leu Gln Ala Glu Ser Arg Gln Leu Val Asp Leu Tyr Lys
                755                 760                 765

Val Leu Glu Ser Arg Gly Ser Asp Pro Lys Pro Glu Asn Pro Ala Cys
770                 775                 780

Pro Trp Thr Val Leu Pro Ala Gly Asp Leu Pro Thr His Asp Gly Tyr
785                 790                 795                 800

Leu Pro Ser Asn Ile Asp Asp Leu Pro Ser His Glu Ala Pro Leu Ala
                805                 810                 815

Asp Ser Leu Glu Glu Leu Glu Pro Gln His Ile Ser Leu Ser Val Phe
                820                 825                 830

Pro Ser Ser Ser Leu His Pro Leu Thr Phe Ser Cys Gly Asp Lys Leu
                835                 840                 845

Thr Leu Asp Gln Leu Lys Met Arg Cys Asp Ser Leu Met Leu
850                 855                 860

<210> SEQ ID NO 27
<211> LENGTH: 643
<212> TYPE: PRT
<213> ORGANISM: Artificial Sequence
<220> FEATURE:
<223> OTHER INFORMATION: Syntheisized

<400> SEQUENCE: 27

Met Ala His Thr Phe Arg Gly Cys Ser Leu Ala Phe Met Phe Ile Ile
1               5                   10                  15

Thr Trp Leu Leu Ile Lys Ala Lys Ile Asp Ala Cys Lys Arg Gly Asp
                20                  25                  30

Val Thr Val Lys Pro Ser His Val Ile Leu Leu Gly Ser Thr Val Asn
                35                  40                  45

Ile Thr Cys Ser Leu Lys Pro Arg Gln Gly Cys Phe His Tyr Ser Arg
            50                  55                  60

Arg Asn Lys Leu Ile Leu Tyr Lys Phe Asp Arg Arg Ile Asn Phe His
65                  70                  75                  80

His Gly His Ser Leu Asn Ser Gln Val Thr Gly Leu Pro Leu Gly Thr
                85                  90                  95

Thr Leu Phe Val Cys Lys Leu Ala Cys Ile Asn Ser Asp Glu Ile Gln
                100                 105                 110

Ile Cys Gly Ala Glu Ile Phe Val Gly Val Ala Pro Glu Gln Pro Gln
```

```
            115                 120                 125
Asn Leu Ser Cys Ile Gln Lys Gly Glu Gln Gly Thr Val Ala Cys Thr
    130                 135                 140

Trp Glu Arg Gly Arg Asp Thr His Leu Tyr Thr Glu Tyr Thr Leu Gln
145                 150                 155                 160

Leu Ser Gly Pro Lys Asn Leu Thr Trp Gln Lys Gln Cys Lys Asp Ile
                165                 170                 175

Tyr Cys Asp Tyr Leu Asp Phe Gly Ile Asn Leu Thr Pro Glu Ser Pro
            180                 185                 190

Glu Ser Asn Phe Thr Ala Lys Val Thr Ala Val Asn Ser Leu Gly Ser
        195                 200                 205

Ser Ser Ser Leu Pro Ser Thr Phe Thr Phe Leu Asp Ile Val Arg Pro
    210                 215                 220

Leu Pro Pro Trp Asp Ile Arg Ile Lys Phe Gln Lys Ala Ser Val Ser
225                 230                 235                 240

Arg Cys Thr Leu Tyr Trp Arg Asp Glu Gly Leu Val Leu Leu Asn Arg
                245                 250                 255

Leu Arg Tyr Arg Pro Ser Asn Ser Arg Leu Trp Asn Met Val Asn Val
            260                 265                 270

Thr Lys Ala Lys Gly Arg His Asp Leu Leu Asp Leu Lys Pro Phe Thr
        275                 280                 285

Glu Tyr Glu Phe Gln Ile Ser Ser Lys Leu His Leu Tyr Lys Gly Ser
    290                 295                 300

Trp Ser Asp Trp Ser Glu Ser Leu Arg Ala Gln Thr Pro Glu Glu Glu
305                 310                 315                 320

Pro Thr Gly Met Leu Asp Val Trp Tyr Met Lys Arg His Ile Asp Tyr
                325                 330                 335

Ser Arg Gln Gln Ile Ser Leu Phe Trp Lys Asn Leu Ser Val Ser Glu
            340                 345                 350

Ala Arg Gly Lys Ile Leu His Tyr Gln Val Thr Leu Gln Glu Leu Thr
        355                 360                 365

Gly Gly Lys Ala Met Thr Gln Asn Ile Thr Gly His Thr Ser Trp Thr
    370                 375                 380

Thr Val Ile Pro Arg Thr Gly Asn Trp Ala Val Ala Val Ser Ala Ala
385                 390                 395                 400

Asn Ser Lys Gly Ser Ser Leu Pro Thr Arg Ile Asn Ile Met Asn Leu
                405                 410                 415

Cys Glu Ala Gly Leu Leu Ala Pro Arg Gln Val Ser Ala Asn Ser Glu
            420                 425                 430

Gly Met Asp Asn Ile Leu Val Thr Trp Gln Pro Pro Arg Lys Asp Pro
        435                 440                 445

Ser Ala Val Gln Glu Tyr Val Val Glu Trp Arg Glu Leu His Pro Gly
    450                 455                 460

Gly Asp Thr Gln Val Pro Leu Asn Trp Leu Arg Ser Arg Pro Tyr Asn
465                 470                 475                 480

Val Ser Ala Leu Ile Ser Glu Asn Ile Lys Ser Tyr Ile Cys Tyr Glu
                485                 490                 495

Ile Arg Val Tyr Ala Leu Ser Gly Asp Gln Gly Gly Cys Ser Ser Ile
            500                 505                 510

Leu Gly Asn Ser Lys His Lys Ala Pro Leu Ser Gly Pro His Ile Asn
        515                 520                 525

Ala Ile Thr Glu Glu Lys Gly Ser Ile Leu Ile Ser Trp Asn Ser Ile
    530                 535                 540
```

Pro Val Gln Glu Gln Met Gly Cys Leu Leu His Tyr Arg Ile Tyr Trp
545                 550                 555                 560

Lys Glu Arg Asp Ser Asn Ser Gln Pro Gln Leu Cys Glu Ile Pro Tyr
                565                 570                 575

Arg Val Ser Gln Asn Ser His Pro Ile Asn Ser Leu Gln Pro Arg Val
            580                 585                 590

Thr Tyr Val Leu Trp Met Thr Ala Leu Thr Ala Ala Gly Glu Ser Ser
        595                 600                 605

His Gly Asn Glu Arg Glu Phe Cys Leu Gln Gly Lys Ala Asn Trp Met
    610                 615                 620

Ala Phe Val Ala Pro Ser Ile Cys Ile Ala Ile Ile Met Val Gly Ile
625                 630                 635                 640

Phe Ser Thr

<210> SEQ ID NO 28
<211> LENGTH: 219
<212> TYPE: PRT
<213> ORGANISM: Artificial Sequence
<220> FEATURE:
<223> OTHER INFORMATION: Syntheisized

<400> SEQUENCE: 28

His Tyr Phe Gln Gln Lys Val Phe Val Leu Ala Ala Leu Arg Pro
1               5                   10                  15

Gln Trp Cys Ser Arg Glu Ile Pro Asp Pro Ala Asn Ser Thr Cys Ala
                20                  25                  30

Lys Lys Tyr Pro Ile Ala Glu Lys Thr Gln Leu Pro Leu Asp Arg
            35                  40                  45

Leu Leu Ile Asp Trp Pro Thr Pro Glu Asp Pro Glu Pro Leu Val Ile
    50                  55                  60

Ser Glu Val Leu His Gln Val Thr Pro Val Phe Arg His Pro Pro Cys
65                  70                  75                  80

Ser Asn Trp Pro Gln Arg Glu Lys Gly Ile Gln Gly His Gln Ala Ser
                85                  90                  95

Glu Lys Asp Met Met His Ser Ala Ser Ser Pro Pro Pro Arg Ala
                100                 105                 110

Leu Gln Ala Glu Ser Arg Gln Leu Val Asp Leu Tyr Lys Val Leu Glu
    115                 120                 125

Ser Arg Gly Ser Asp Pro Lys Pro Glu Asn Pro Ala Cys Pro Trp Thr
130                 135                 140

Val Leu Pro Ala Gly Asp Leu Pro Thr His Asp Gly Phe Leu Pro Ser
145                 150                 155                 160

Asn Ile Asp Asp Leu Pro Ser His Glu Ala Pro Leu Ala Asp Ser Leu
                165                 170                 175

Glu Glu Leu Glu Pro Gln His Ile Ser Leu Ser Val Phe Pro Ser Ser
            180                 185                 190

Ser Leu His Pro Leu Thr Phe Ser Cys Gly Asp Lys Leu Thr Leu Asp
        195                 200                 205

Gln Leu Lys Met Arg Cys Asp Ser Leu Met Leu
    210                 215

<210> SEQ ID NO 29
<211> LENGTH: 57
<212> TYPE: DNA
<213> ORGANISM: Homo sapiens

```
<400> SEQUENCE: 29
taacatggag agtgacagct ttgaagattt ctggaaaggt gaagatctta gtaatta      57

<210> SEQ ID NO 30
<211> LENGTH: 21
<212> TYPE: DNA
<213> ORGANISM: Artificial Sequence
<220> FEATURE:
<223> OTHER INFORMATION: Syntheisized

<400> SEQUENCE: 30
taacatggag agtgacagct t                                             21

<210> SEQ ID NO 31
<211> LENGTH: 21
<212> TYPE: DNA
<213> ORGANISM: Artificial Sequence
<220> FEATURE:
<223> OTHER INFORMATION: Syntheisized

<400> SEQUENCE: 31
aggtgaagat cttagtaatt a                                             21

<210> SEQ ID NO 32
<211> LENGTH: 53
<212> TYPE: DNA
<213> ORGANISM: Homo sapiens

<400> SEQUENCE: 32
tgacagcttt gaagatttct ggaaaggtga agatcttagt aattacagtt aca          53

<210> SEQ ID NO 33
<211> LENGTH: 18
<212> TYPE: DNA
<213> ORGANISM: Artificial Sequence
<220> FEATURE:
<223> OTHER INFORMATION: Syntheisized

<400> SEQUENCE: 33
tgacagcttt gaagattt                                                 18

<210> SEQ ID NO 34
<211> LENGTH: 21
<212> TYPE: DNA
<213> ORGANISM: Artificial Sequence
<220> FEATURE:
<223> OTHER INFORMATION: Syntheisized

<400> SEQUENCE: 34
atcttagtaa ttacagttac a                                             21

<210> SEQ ID NO 35
<211> LENGTH: 60
<212> TYPE: DNA
<213> ORGANISM: Homo sapiens

<400> SEQUENCE: 35
tggaaaggtg aagatcttag taattacagt tacagctcta ccctgccccc ttttctacta   60

<210> SEQ ID NO 36
<211> LENGTH: 20
<212> TYPE: DNA
<213> ORGANISM: Artificial Sequence
<220> FEATURE:
<223> OTHER INFORMATION: Syntheisized
```

<400> SEQUENCE: 36
ggaaaggtga agatcttagt                                              20

<210> SEQ ID NO 37
<211> LENGTH: 21
<212> TYPE: DNA
<213> ORGANISM: Artificial Sequence
<220> FEATURE:
<223> OTHER INFORMATION: Syntheisized

<400> SEQUENCE: 37
accctgcccc cttttctact a                                            21

<210> SEQ ID NO 38
<211> LENGTH: 57
<212> TYPE: DNA
<213> ORGANISM: Homo sapiens

<400> SEQUENCE: 38
tcgtgcacgt ccgcggggac tcggagaccg acctggaggc gctcttcaac gccgtca     57

<210> SEQ ID NO 39
<211> LENGTH: 20
<212> TYPE: DNA
<213> ORGANISM: Artificial Sequence
<220> FEATURE:
<223> OTHER INFORMATION: Syntheisized

<400> SEQUENCE: 39
cgtgcacgtc cgcggggact                                              20

<210> SEQ ID NO 40
<211> LENGTH: 21
<212> TYPE: DNA
<213> ORGANISM: Artificial Sequence
<220> FEATURE:
<223> OTHER INFORMATION: Syntheisized

<400> SEQUENCE: 40
aggcgctctt caacgccgtc a                                            21

<210> SEQ ID NO 41
<211> LENGTH: 21
<212> TYPE: PRT
<213> ORGANISM: Artificial Sequence
<220> FEATURE:
<223> OTHER INFORMATION: Syntheisized

<400> SEQUENCE: 41

Met Ala Leu Pro Val Thr Ala Leu Leu Leu Pro Leu Ala Leu Leu Leu
1               5                   10                  15

His Ala Ala Arg Pro
            20

<210> SEQ ID NO 42
<211> LENGTH: 15
<212> TYPE: PRT
<213> ORGANISM: Artificial Sequence
<220> FEATURE:
<223> OTHER INFORMATION: Syntheisized

<400> SEQUENCE: 42

Gly Gly Gly Gly Ser Gly Gly Gly Gly Ser Gly Gly Gly Gly Ser
1               5                   10                  15

<210> SEQ ID NO 43
<211> LENGTH: 42
<212> TYPE: PRT
<213> ORGANISM: Artificial Sequence
<220> FEATURE:
<223> OTHER INFORMATION: Syntheisized

<400> SEQUENCE: 43

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 44
<211> LENGTH: 112
<212> TYPE: PRT
<213> ORGANISM: Artificial Sequence
<220> FEATURE:
<223> OTHER INFORMATION: Syntheisized

<400> SEQUENCE: 44

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 45
<211> LENGTH: 339
<212> TYPE: DNA
<213> ORGANISM: Artificial Sequence
<220> FEATURE:
<223> OTHER INFORMATION: Syntheisized

<400> SEQUENCE: 45
agagtgaagt tcagcaggag cgcagacgcc cccgcgtacc agcagggcca gaaccagctc     60
tataacgagc tcaatctagg acgaagagag gagtacgatg ttttggacaa gaggcgtggc    120
cgggaccctg agatggggggg aaagccgaga aggaagaacc ctcaggaagg cctgtacaat    180
gaactgcaga agataagat ggcggaggcc tacagtgaga ttgggatgaa aggcgagcgc     240 cggagggggca aggggcacga tggcctttac cagggtctca gtacagccac caaggacacc    300
tacgacgccc ttcacatgca ggccctgccc cctcgctaa                           339

<210> SEQ ID NO 46
<211> LENGTH: 66
<212> TYPE: PRT
<213> ORGANISM: Artificial Sequence
<220> FEATURE:

<223> OTHER INFORMATION: Syntheisized

<400> SEQUENCE: 46

Thr Thr Thr Pro Ala Pro Arg Pro Pro Thr Pro Ala Pro Thr Ile Ala
1               5                   10                  15
Ser Gln Pro Leu Ser Leu Arg Pro Glu Ala Cys Arg Pro Ala Ala Gly
            20                  25                  30
Gly Ala Val His Thr Arg Gly Leu Asp Phe Ala Cys Asp Ile Tyr Ile
        35                  40                  45
Trp Ala Pro Leu Ala Gly Thr Cys Gly Val Leu Leu Leu Ser Leu Val
    50                  55                  60
Ile Thr
65

<210> SEQ ID NO 47
<211> LENGTH: 69
<212> TYPE: PRT
<213> ORGANISM: Artificial Sequence
<220> FEATURE:
<223> OTHER INFORMATION: Syntheisized

<400> SEQUENCE: 47

Thr Thr Thr Pro Ala Pro Arg Pro Pro Thr Pro Ala Pro Thr Ile Ala
1               5                   10                  15
Ser Gln Pro Leu Ser Leu Arg Pro Glu Ala Cys Arg Pro Ala Ala Gly
            20                  25                  30
Gly Ala Val His Thr Arg Gly Leu Asp Phe Ala Cys Asp Ile Tyr Ile
        35                  40                  45
Trp Ala Pro Leu Ala Gly Thr Cys Gly Val Leu Leu Leu Ser Leu Val
    50                  55                  60
Ile Thr Leu Tyr Cys
65

<210> SEQ ID NO 48
<211> LENGTH: 72
<212> TYPE: PRT
<213> ORGANISM: Artificial Sequence
<220> FEATURE:
<223> OTHER INFORMATION: Syntheisized

<400> SEQUENCE: 48

Ala Lys Pro Thr Thr Thr Pro Ala Pro Arg Pro Pro Thr Pro Ala Pro
1               5                   10                  15
Thr Ile Ala Ser Gln Pro Leu Ser Leu Arg Pro Glu Ala Cys Arg Pro
            20                  25                  30
Ala Ala Gly Gly Ala Val His Thr Arg Gly Leu Asp Phe Ala Cys Asp
        35                  40                  45
Ile Tyr Ile Trp Ala Pro Leu Ala Gly Thr Cys Gly Val Leu Leu Leu
    50                  55                  60
Ser Leu Val Ile Thr Leu Tyr Cys
65                  70

<210> SEQ ID NO 49
<211> LENGTH: 69
<212> TYPE: PRT
<213> ORGANISM: Artificial Sequence
<220> FEATURE:
<223> OTHER INFORMATION: Syntheisized

<400> SEQUENCE: 49

```
Ala Lys Pro Thr Thr Thr Pro Ala Pro Arg Pro Pro Thr Pro Ala Pro
1               5                   10                  15

Thr Ile Ala Ser Gln Pro Leu Ser Leu Arg Pro Glu Ala Cys Arg Pro
            20                  25                  30

Ala Ala Gly Gly Ala Val His Thr Arg Gly Leu Asp Phe Ala Cys Asp
        35                  40                  45

Ile Tyr Ile Trp Ala Pro Leu Ala Gly Thr Cys Gly Val Leu Leu Leu
    50                  55                  60

Ser Leu Val Ile Thr
65
```

<210> SEQ ID NO 50
<211> LENGTH: 50
<212> TYPE: PRT
<213> ORGANISM: Artificial Sequence
<220> FEATURE:
<223> OTHER INFORMATION: Syntheisized

<400> SEQUENCE: 50

```
Ala Lys Pro Thr Thr Thr Pro Ala Pro Arg Pro Pro Thr Pro Ala Pro
1               5                   10                  15

Thr Ile Ala Ser Gln Pro Leu Ser Leu Arg Pro Glu Ala Cys Arg Pro
            20                  25                  30

Ala Ala Gly Gly Ala Val His Thr Arg Gly Leu Asp Phe Ala Cys Asp
        35                  40                  45

Ile Tyr
    50
```

<210> SEQ ID NO 51
<211> LENGTH: 50
<212> TYPE: PRT
<213> ORGANISM: Artificial Sequence
<220> FEATURE:
<223> OTHER INFORMATION: Syntheisized

<400> SEQUENCE: 51

```
Ala Lys Pro Thr Thr Thr Pro Ala Pro Arg Pro Pro Thr Pro Ala Pro
1               5                   10                  15

Thr Ile Ala Ser Gln Pro Leu Ser Leu Arg Pro Glu Ala Cys Arg Pro
            20                  25                  30

Ala Ala Gly Gly Ala Val His Thr Arg Gly Leu Asp Phe Ala Cys Asp
        35                  40                  45

Ile Tyr
    50
```

<210> SEQ ID NO 52
<211> LENGTH: 47
<212> TYPE: PRT
<213> ORGANISM: Artificial Sequence
<220> FEATURE:
<223> OTHER INFORMATION: Syntheisized

<400> SEQUENCE: 52

```
Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr
        35                  40                  45
```

```
<210> SEQ ID NO 53
<211> LENGTH: 47
<212> TYPE: PRT
<213> ORGANISM: Artificial Sequence
<220> FEATURE:
<223> OTHER INFORMATION: Syntheisized

<400> SEQUENCE: 53

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr
        35                  40                  45

<210> SEQ ID NO 54
<211> LENGTH: 22
<212> TYPE: PRT
<213> ORGANISM: Artificial Sequence
<220> FEATURE:
<223> OTHER INFORMATION: Syntheisized

<400> SEQUENCE: 54

Ile Trp Ala Pro Leu Ala Gly Thr Cys Gly Val Leu Leu Leu Ser Leu
1               5                   10                  15

Val Ile Thr Leu Tyr Cys
            20

<210> SEQ ID NO 55
<211> LENGTH: 19
<212> TYPE: PRT
<213> ORGANISM: Artificial Sequence
<220> FEATURE:
<223> OTHER INFORMATION: Syntheisized

<400> SEQUENCE: 55

Ile Trp Ala Pro Leu Ala Gly Thr Cys Gly Val Leu Leu Leu Ser Leu
1               5                   10                  15

Val Ile Thr

<210> SEQ ID NO 56
<211> LENGTH: 19
<212> TYPE: PRT
<213> ORGANISM: Artificial Sequence
<220> FEATURE:
<223> OTHER INFORMATION: Syntheisized

<400> SEQUENCE: 56

Ile Trp Ala Pro Leu Ala Gly Thr Cys Gly Val Leu Leu Leu Ser Leu
1               5                   10                  15

Val Ile Thr

<210> SEQ ID NO 57
<211> LENGTH: 22
<212> TYPE: PRT
<213> ORGANISM: Artificial Sequence
<220> FEATURE:
<223> OTHER INFORMATION: Syntheisized

<400> SEQUENCE: 57

Ile Trp Ala Pro Leu Ala Gly Thr Cys Gly Val Leu Leu Leu Ser Leu
1               5                   10                  15

Val Ile Thr Leu Tyr Cys
            20
```

<210> SEQ ID NO 58
<211> LENGTH: 242
<212> TYPE: PRT
<213> ORGANISM: Artificial Sequence
<220> FEATURE:
<223> OTHER INFORMATION: Syntheisized

<400> SEQUENCE: 58

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Lys Tyr
            20                  25                  30

Leu Asn Trp Tyr Gln Gln Lys Pro Gly Lys Ala Pro Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asn Thr Leu Pro Tyr
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Ser Glu Val Gln Leu Val Glu
            115                 120                 125

Ser Gly Gly Gly Leu Val Gln Pro Gly Gly Ser Leu Arg Leu Ser Cys
130                 135                 140

Ala Ala Ser Gly Val Ser Leu Pro Asp Tyr Gly Val Ser Trp Val Arg
145                 150                 155                 160

Gln Ala Pro Gly Lys Gly Leu Glu Trp Val Ser Val Ile Trp Gly Ser
                165                 170                 175

Glu Thr Thr Tyr Tyr Asn Ser Ala Leu Lys Ser Arg Phe Thr Ile Ser
            180                 185                 190

Arg Asp Asn Ala Lys Asn Ser Leu Tyr Leu Gln Met Asn Ser Leu Arg
        195                 200                 205

Ala Glu Asp Thr Ala Val Tyr Tyr Cys Ala Lys His Tyr Tyr Tyr Gly
    210                 215                 220

Gly Ser Tyr Ala Met Asp Tyr Trp Gly Gln Gly Thr Leu Val Thr Val
225                 230                 235                 240

Ser Ser
```

<210> SEQ ID NO 59
<211> LENGTH: 242
<212> TYPE: PRT
<213> ORGANISM: Artificial Sequence
<220> FEATURE:
<223> OTHER INFORMATION: Syntheisized

<400> SEQUENCE: 59

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60
```

-continued

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Gly Gly Gly Ser
            100                 105                 110

Gly Gly Gly Gly Ser Gly Gly Gly Ser Glu Val Lys Leu Gln Glu
            115                 120                 125

Ser Gly Pro Gly Leu Val Ala Pro Ser Gln Ser Leu Ser Val Thr Cys
            130                 135                 140

Thr Val Ser Gly Val Ser Leu Pro Asp Tyr Gly Val Ser Trp Ile Arg
145                 150                 155                 160

Gln Pro Pro Arg Lys Gly Leu Glu Trp Leu Gly Val Ile Trp Gly Ser
                165                 170                 175

Glu Thr Thr Tyr Tyr Asn Ser Ala Leu Lys Ser Arg Leu Thr Ile Ile
            180                 185                 190

Lys Asp Asn Ser Lys Ser Gln Val Phe Leu Lys Met Asn Ser Leu Gln
            195                 200                 205

Thr Asp Asp Thr Ala Ile Tyr Tyr Cys Ala Lys His Tyr Tyr Tyr Gly
            210                 215                 220

Gly Ser Tyr Ala Met Asp Tyr Trp Gly Gln Gly Thr Ser Val Thr Val
225                 230                 235                 240

Ser Ser

<210> SEQ ID NO 60
<211> LENGTH: 237
<212> TYPE: PRT
<213> ORGANISM: Artificial Sequence
<220> FEATURE:
<223> OTHER INFORMATION: Syntheisized

<400> SEQUENCE: 60

Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Tyr Ser Asn
            20                  25                  30

Leu Ala Trp Tyr Gln Gln Lys Gln Gly Lys Ser Pro Gln Leu Leu Val
        35                  40                  45

Tyr Val Ala Thr Asn Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Ser Tyr Tyr Cys Gln His Phe Trp Gly Thr Pro Tyr
                85                  90                  95

Thr Phe Gly Gly Gly Thr Lys Leu Gly Gly Gly Ser Gly Gly Gly
            100                 105                 110

Gly Ser Gly Gly Gly Gly Ser Glu Val Gln Leu Gln Gln Ser Gly Ala
            115                 120                 125

Glu Leu Val Lys Pro Gly Ala Ser Val Lys Leu Ser Cys Thr Ala Ser
            130                 135                 140

Gly Phe Asn Ile Asn Asp Thr Tyr Met His Trp Val Lys Gln Arg Pro
145                 150                 155                 160

Glu Gln Gly Leu Glu Trp Ile Gly Arg Ile Asp Pro Ala Asn Gly Asn
                165                 170                 175

```
Thr Lys Tyr Asp Pro Lys Phe Gln Gly Lys Ala Thr Ile Thr Ala Asp
            180                 185                 190

Thr Ser Ser Asn Thr Ala Tyr Leu Gln Leu Ser Ser Leu Thr Ser Glu
        195                 200                 205

Asp Thr Ala Val Tyr Tyr Cys Ala Arg Gly Ala Arg Gly Ser Arg Phe
    210                 215                 220

Ala Tyr Trp Gly Gln Gly Thr Leu Val Thr Val Ser Ala
225                 230                 235

<210> SEQ ID NO 61
<211> LENGTH: 244
<212> TYPE: PRT
<213> ORGANISM: Artificial Sequence
<220> FEATURE:
<223> OTHER INFORMATION: Syntheisized

<400> SEQUENCE: 61

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asp Ile Gly Ser Asn
            20                  25                  30

Tyr Val Ser Trp Tyr Gln Gln Phe Pro Gly Thr Ala Pro Lys Leu Leu
        35                  40                  45

Ile Tyr Asp Asn Asn Lys Arg Pro Ser Ala Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Arg Leu
                85                  90                  95

Gly Ile Ala Val Phe Gly Gly Gly Thr Gln Leu Thr Val Leu Gly Gly
            100                 105                 110

Gly Gly Ser Gly Gly Gly Gly Ser Gly Gly Gly Gly Ser Glu Val Gln
        115                 120                 125

Leu Val Gln Ser Gly Ala Glu Val Lys Lys Pro Gly Gln Ser Leu Lys
    130                 135                 140

Ile Ser Cys Lys Ala Ser Gly Tyr Ser Leu Thr Asp Asn Trp Ile Gly
145                 150                 155                 160

Trp Val Arg Gln Lys Pro Gly Lys Gly Leu Glu Trp Met Gly Ile Ile
                165                 170                 175

Tyr Pro Gly Asp Ser Asp Thr Arg Tyr Ser Pro Ser Phe Gln Gly Gln
            180                 185                 190

Val Thr Ile Ser Ala Asp Lys Ser Ile Asn Thr Ala Tyr Leu Gln Trp
        195                 200                 205

Ser Ser Leu Lys Ala Ser Asp Thr Ala Ile Tyr Tyr Cys Val Gly Leu
    210                 215                 220

Asp Trp Asn Tyr Asn Pro Leu Arg Tyr Trp Gly Pro Gly Thr Leu Val
225                 230                 235                 240

Thr Val Ser Ser

<210> SEQ ID NO 62
<211> LENGTH: 252
<212> TYPE: PRT
<213> ORGANISM: Artificial Sequence
<220> FEATURE:
<223> OTHER INFORMATION: Syntheisized

<400> SEQUENCE: 62
```

```
Asp Ile Val Leu Thr Gln Ser Pro Ala Ser Leu Ala Val Ser Leu Gly
1               5                   10                  15

Gln Gly Ala Thr Ile Ser Cys Arg Ala Ser Lys Ser Val Ser Thr Ser
            20                  25                  30

Gly Tyr Thr Tyr Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Gly
                85                  90                  95

Glu Leu Pro Pro Ser Phe Gly Gly Gly Thr Lys Leu Glu Ile Lys Arg
            100                 105                 110

Ala Gly Gly Gly Gly Ser Gly Gly Gly Gly Ser Gly Gly Gly Gly Ser
            115                 120                 125

Glu Val Gln Leu Val Glu Ser Gly Gly Asp Leu Val Lys Pro Gly Gly
        130                 135                 140

Ser Leu Lys Leu Ser Cys Ala Val Ser Gly Phe Thr Phe Ser Ser Tyr
145                 150                 155                 160

Gly Met Ser Trp Val Arg Gln Thr Pro Asp Lys Arg Leu Glu Trp Val
                165                 170                 175

Ala Thr Val Ser Ser Gly Gly Thr Tyr Thr Tyr Tyr Pro Asp Ser Val
            180                 185                 190

Lys Gly Arg Phe Thr Ile Ser Arg Asp Asn Ala Lys Asn Thr Leu Tyr
        195                 200                 205

Leu Gln Met Ser Ser Leu Lys Ser Glu Asp Ser Ala Met Tyr Tyr Cys
    210                 215                 220

Ala Arg His Arg Gly Asn Tyr Tyr Ala Thr Tyr Tyr Ala Met Asp
225                 230                 235                 240

Tyr Trp Gly Gln Gly Thr Ser Val Thr Val Ser Ser
                245                 250

<210> SEQ ID NO 63
<211> LENGTH: 243
<212> TYPE: PRT
<213> ORGANISM: Artificial Sequence
<220> FEATURE:
<223> OTHER INFORMATION: Syntheisized

<400> SEQUENCE: 63

Asp Val Gln Ile Thr Gln Ser Pro Ser Tyr Leu Ala Ala Ser Pro Gly
1               5                   10                  15

Glu Thr Ile Thr Ile Asn Cys Arg Ala Ser Lys Ser Ile Ser Lys Tyr
            20                  25                  30

Leu Ala Trp Tyr Gln Glu Lys Pro Gly Lys Thr Asn Lys Leu Leu Ile
        35                  40                  45

Tyr Ser Gly Ser Thr Leu Gln Ser Gly Ile Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His Asn Glu Tyr Pro Tyr
                85                  90                  95

Thr Phe Gly Gly Gly Thr Lys Leu Glu Ile Lys Gly Gly Gly Gly Ser
            100                 105                 110
```

```
Gly Gly Gly Gly Ser Gly Gly Gly Ser Gln Val Gln Leu Gln Gln
            115                 120                 125
Pro Gly Ala Glu Leu Val Arg Pro Gly Ala Ser Val Lys Leu Ser Cys
    130                 135                 140
Lys Ala Ser Gly Tyr Thr Phe Thr Thr Tyr Trp Met Asn Trp Val Lys
145                 150                 155                 160
Gln Arg Pro Glu Gln Gly Leu Glu Trp Ile Gly Arg Ile Asp Pro Tyr
                165                 170                 175
Asp Ser Glu Thr His Tyr Asn Gln Lys Phe Lys Asp Lys Ala Ile Leu
            180                 185                 190
Thr Val Asp Lys Ser Ser Ser Thr Ala Tyr Met Gln Leu Ser Ser Leu
        195                 200                 205
Thr Ser Glu Asp Ser Ala Val Tyr Tyr Cys Ala Arg Gly Pro Tyr Tyr
    210                 215                 220
Gly Thr Asn Pro Trp Phe Pro Tyr Trp Gly Gln Gly Thr Leu Val Thr
225                 230                 235                 240
Val Ser Ser

<210> SEQ ID NO 64
<211> LENGTH: 241
<212> TYPE: PRT
<213> ORGANISM: Artificial Sequence
<220> FEATURE:
<223> OTHER INFORMATION: Syntheisized

<400> SEQUENCE: 64

Glu Ile Val Met Thr Gln Ser Pro Ala Thr Leu Ser Val Ser Pro Gly
1               5                   10                  15
Glu Arg Ala Thr Leu Ser Cys Arg Ala Ser Gln Ser Val Ser Arg Asn
            20                  25                  30
Leu Ala Trp Tyr Gln Gln Lys Pro Gly Gln Ala Pro Arg Leu Leu Ile
        35                  40                  45
Tyr Gly Ala Ser Thr Arg Ala Thr Gly Ile Pro Ala Arg Phe Ser Gly
    50                  55                  60
Ser Gly Ser Gly Thr Glu Phe Thr Leu Thr Ile Gly Ser Leu Gln Ser
65                  70                  75                  80
Glu Asp Phe Ala Val Tyr Tyr Cys Gln Gln Tyr Lys Thr Trp Pro Arg
                85                  90                  95
Thr Phe Gly Gln Gly Thr Asn Val Glu Ile Lys Gly Gly Gly Gly Ser
            100                 105                 110
Gly Gly Gly Gly Ser Gly Gly Gly Ser Gln Val Gln Leu Gln Gln
            115                 120                 125
Trp Gly Ala Gly Leu Leu Lys Pro Ser Glu Thr Leu Ser Leu Thr Cys
    130                 135                 140
Ala Val Phe Gly Gly Ser Phe Ser Gly Tyr Tyr Trp Ser Trp Ile Arg
145                 150                 155                 160
Gln Pro Pro Gly Lys Gly Leu Glu Trp Ile Gly Glu Ile Asn His Arg
                165                 170                 175
Gly Asn Thr Asn Asp Asn Pro Ser Leu Lys Ser Arg Val Thr Ile Ser
            180                 185                 190
Val Asp Thr Ser Lys Asn Gln Phe Ala Leu Lys Leu Ser Ser Val Thr
        195                 200                 205
Ala Ala Asp Thr Ala Val Tyr Tyr Cys Ala Arg Glu Arg Gly Tyr Thr
    210                 215                 220
Tyr Gly Asn Phe Asp His Trp Gly Gln Gly Thr Leu Val Thr Val Ser
```

-continued

```
                225                 230                 235                 240
Ser

<210> SEQ ID NO 65
<211> LENGTH: 246
<212> TYPE: PRT
<213> ORGANISM: Artificial Sequence
<220> FEATURE:
<223> OTHER INFORMATION: Syntheisized

<400> SEQUENCE: 65

Asp Val Val Met Thr Gln Thr Pro Leu Ser Leu Pro Val Arg Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asn Phe Thr Leu Lys Ile
65                  70                  75                  80

Ser Arg Val Glu Ala Glu Asp Leu Gly Leu Tyr Phe Cys Ser Gln Ser
                85                  90                  95

Thr His Val Pro Tyr Thr Phe Gly Gly Gly Thr Lys Leu Glu Ile Lys
            100                 105                 110

Arg Ala Gly Gly Gly Gly Ser Gly Gly Gly Gly Ser Gly Gly Gly Gly
        115                 120                 125

Ser Gln Val Gln Leu Arg Gln Ser Gly Pro Glu Leu Val Lys Pro Gly
130                 135                 140

Ala Ser Val Lys Met Ser Cys Lys Ala Ser Gly Tyr Thr Phe Thr Asp
145                 150                 155                 160

Tyr Val Ile Ser Trp Val Lys Gln Arg Thr Gly Gln Gly Leu Glu Trp
                165                 170                 175

Ile Gly Asp Ile Tyr Pro Gly Ser Gly Tyr Ser Phe Tyr Asn Glu Asn
            180                 185                 190

Phe Lys Gly Lys Ala Thr Leu Thr Ala Asp Lys Ser Ser Thr Thr Ala
        195                 200                 205

Tyr Met Gln Leu Ser Ser Leu Thr Ser Glu Asp Ser Ala Val Tyr Phe
    210                 215                 220

Cys Ala Thr Tyr Tyr Asn Tyr Pro Phe Ala Tyr Trp Gly Gln Gly Thr
225                 230                 235                 240

Leu Val Thr Val Ser Ala
            245

<210> SEQ ID NO 66
<211> LENGTH: 199
<212> TYPE: PRT
<213> ORGANISM: Artificial Sequence
<220> FEATURE:
<223> OTHER INFORMATION: Syntheisized

<400> SEQUENCE: 66

Leu Pro Ile Cys Pro Gly Gly Ala Ala Arg Cys Gln Val Thr Leu Arg
1               5                   10                  15

Asp Leu Phe Asp Arg Ala Val Val Leu Ser His Tyr Ile His Asn Leu
            20                  25                  30

Ser Ser Glu Met Phe Ser Glu Phe Asp Lys Arg Tyr Thr His Gly Arg
```

```
            35                  40                  45
Gly Phe Ile Thr Lys Ala Ile Asn Ser Cys His Thr Ser Ser Leu Ala
 50                  55                  60

Thr Pro Glu Asp Lys Glu Gln Ala Gln Gln Met Asn Gln Lys Asp Phe
 65                  70                  75                  80

Leu Ser Leu Ile Val Ser Ile Leu Arg Ser Trp Asn Glu Pro Leu Tyr
                 85                  90                  95

His Leu Val Thr Glu Val Arg Gly Met Gln Glu Ala Pro Glu Ala Ile
                100                 105                 110

Leu Ser Lys Ala Val Glu Ile Glu Glu Gln Thr Lys Arg Leu Leu Glu
                115                 120                 125

Gly Met Glu Leu Ile Val Ser Gln Val His Pro Glu Thr Lys Glu Asn
130                 135                 140

Glu Ile Tyr Pro Val Trp Ser Gly Leu Pro Ser Leu Gln Met Ala Asp
145                 150                 155                 160

Glu Glu Ser Arg Leu Ser Ala Tyr Tyr Asn Leu Leu His Cys Leu Arg
                165                 170                 175

Arg Asp Ser His Lys Ile Asp Asn Tyr Leu Lys Leu Leu Lys Cys Arg
                180                 185                 190

Ile Ile His Asn Asn Asn Cys
                195

<210> SEQ ID NO 67
<211> LENGTH: 240
<212> TYPE: PRT
<213> ORGANISM: Artificial Sequence
<220> FEATURE:
<223> OTHER INFORMATION: Syntheisized

<400> SEQUENCE: 67

Asp Ile Val Met Thr Gln Ser Pro Asp Ser Leu Ala Val Ser Leu Gly
 1                   5                  10                  15

Glu Arg Ala Thr Ile Asn Cys Lys Ser Ser Gln Ser Leu Leu Asn Ser
                 20                  25                  30

Arg Thr Arg Lys Asn Tyr Leu Ala Trp Tyr Gln Gln Lys Pro Gly Gln
                 35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Thr Gln
                 85                  90                  95

Ser Phe Ile Leu Arg Thr Phe Gly Gln Gly Thr Lys Val Glu Ile Lys
                100                 105                 110

Gly Gly Gly Gly Gly Ser Gly Gly Gly Gly Ser Gly Gly Gly Gly Ser
                115                 120                 125

Asp Ile Val Met Thr Gln Ser Pro Asp Ser Leu Ala Val Ser Leu Gly
                130                 135                 140

Glu Arg Ala Thr Ile Asn Cys Lys Ser Ser Gln Ser Leu Leu Asn Ser
145                 150                 155                 160

Arg Thr Arg Lys Asn Tyr Leu Ala Trp Tyr Gln Gln Lys Pro Gly Gln
                165                 170                 175

Pro Pro Lys Leu Leu Ile Tyr Trp Ala Ser Thr Arg Glu Ser Gly Val
                180                 185                 190

Pro Asp Arg Phe Ser Gly Ser Gly Ser Gly Thr Asp Phe Thr Leu Thr
```

```
            195                 200                 205
Ile Ser Ser Leu Gln Ala Glu Asp Val Ala Val Tyr Tyr Cys Thr Gln
210                 215                 220

Ser Phe Ile Leu Arg Thr Phe Gly Gln Gly Thr Lys Val Glu Ile Lys
225                 230                 235                 240

<210> SEQ ID NO 68
<211> LENGTH: 281
<212> TYPE: PRT
<213> ORGANISM: Artificial Sequence
<220> FEATURE:
<223> OTHER INFORMATION: Syntheisized

<400> SEQUENCE: 68

Met Asn Val Pro Thr Gln Leu Leu Gly Leu Leu Leu Trp Leu Thr
1               5                   10                  15

Gly Gly Lys Cys Asp Ile Gln Met Thr Gln Ser Pro Ala Ser Leu Ser
                20                  25                  30

Ala Ser Leu Glu Glu Ile Val Thr Ile Thr Cys Lys Ala Ser Gln Ala
            35                  40                  45

Ile Asp Ala Tyr Leu Ser Trp Tyr Gln Gln Lys Pro Gly Lys Ser Pro
50                  55                  60

Gln Leu Leu Ile Tyr Asp Ala Thr Ser Leu Ala Asp Gly Val Pro Ser
65                  70                  75                  80

Arg Phe Ser Gly Ser Arg Ser Gly Thr Gln Tyr Ser Leu Lys Ile Ser
                85                  90                  95

Arg Pro Gln Val Asp Asp Ser Gly Ile Tyr Tyr Cys Leu Gln Ser Tyr
            100                 105                 110

Ser Thr Pro Phe Thr Phe Gly Ser Gly Thr Lys Leu Glu Ile Lys Gly
            115                 120                 125

Gly Gly Gly Gly Ser Gly Gly Gly Ser Gly Gly Gly Ser Met
            130                 135                 140

Ala Val Leu Val Leu Leu Leu Cys Leu Leu Ile Phe Pro Ser Cys Val
145                 150                 155                 160

Leu Ser Gln Val Gln Leu Lys Glu Ser Gly Pro Gly Leu Val Gln Pro
                165                 170                 175

Ser Gln Thr Leu Ser Leu Thr Cys Thr Val Ser Gly Ser Ser Leu Thr
            180                 185                 190

Ser Asn Ser Val Ser Trp Ile Arg Gln Pro Pro Gly Lys Gly Leu Glu
        195                 200                 205

Trp Met Gly Val Ile Trp Ser Asn Gly Asp Ala Asp Tyr Asn Ser Ala
210                 215                 220

Ile Lys Ser Arg Leu Ser Ile Ser Arg Asp Thr Ser Lys Ser Gln Val
225                 230                 235                 240

Phe Leu Lys Met Asn Ser Leu Gln Thr Glu Asp Thr Ala Met Tyr Phe
                245                 250                 255

Cys Ala Ser Pro Tyr Tyr Gly Tyr Tyr Phe Pro Phe Asp Tyr Trp Gly
            260                 265                 270

Gln Gly Val Met Val Thr Val Ser Ser
        275                 280

<210> SEQ ID NO 69
<211> LENGTH: 285
<212> TYPE: PRT
<213> ORGANISM: Artificial Sequence
<220> FEATURE:
<223> OTHER INFORMATION: Syntheisized
```

<400> SEQUENCE: 69

```
Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Ala Leu Ala Val
            20                  25                  30

Ser Leu Gly Gln Arg Ala Thr Ile Ser Cys Arg Ala Ser Gln Ser Val
        35                  40                  45

Ser Ile Ser Ser His Asp Leu Met Gln Trp Tyr Gln Gln Lys Pro Gly
50                  55                  60

Gln Gln Pro Lys Leu Leu Ile Tyr Asp Ala Phe Asn Leu Ala Ser Gly
65                  70                  75                  80

Ile Pro Val Arg Phe Ser Gly Ser Gly Ser Gly Thr Asp Phe Thr Leu
                85                  90                  95

Thr Ile Asp Pro Val Gln Ala Asp Asp Ile Ala Thr Tyr Tyr Cys Gln
            100                 105                 110

Gln Ser Lys Asp Asp Pro Tyr Thr Phe Gly Ala Gly Thr Lys Leu Glu
        115                 120                 125

Leu Lys Gly Gly Gly Gly Ser Gly Gly Gly Ser Gly Gly Gly
130                 135                 140

Gly Ser Met Asp Ile Arg Leu Ser Leu Ala Phe Leu Val Leu Phe Ile
145                 150                 155                 160

Lys Gly Val Gln Cys Glu Val Gln Leu Val Glu Ser Gly Gly Gly Leu
                165                 170                 175

Val Gln Pro Gly Arg Ser Met Lys Leu Ser Cys Ala Ala Ser Gly Phe
            180                 185                 190

Thr Phe Ser Asn Tyr Gly Met Ala Trp Val Arg Gln Ala Pro Thr Lys
        195                 200                 205

Gly Leu Glu Trp Val Ala Thr Ile Ser Tyr Asp Gly Ser Ile Thr Tyr
210                 215                 220

Tyr Arg Asp Ser Val Lys Gly Arg Phe Thr Ile Ser Arg Asp His Ala
225                 230                 235                 240

Lys Ser Thr Leu Tyr Leu Gln Met Asn Ser Leu Arg Ser Glu Asp Thr
                245                 250                 255

Ala Thr Tyr Tyr Cys Thr Arg Glu Glu Gln Tyr Ser Ser Trp Tyr Phe
            260                 265                 270

Asp Phe Trp Gly Pro Gly Ile Met Val Thr Val Ser Ser
        275                 280                 285
```

<210> SEQ ID NO 70
<211> LENGTH: 242
<212> TYPE: PRT
<213> ORGANISM: Artificial Sequence
<220> FEATURE:
<223> OTHER INFORMATION: Syntheisized

<400> SEQUENCE: 70

```
Asn Ile Val Met Thr Gln Ser Pro Ser Ser Leu Ser Ala Ser Val Gly
1               5                   10                  15

Asp Arg Val Thr Ile Thr Cys Gln Ala Ser Gln Asp Val Gly Thr Ala
            20                  25                  30

Val Ala Trp Tyr Gln Gln Lys Pro Asp Gln Ser Pro Lys Leu Leu Ile
        35                  40                  45

Tyr Trp Thr Ser Thr Arg His Thr Gly Val Pro Asp Arg Phe Thr Gly
50                  55                  60
```

```
Ser Gly Ser Gly Thr Asp Phe Thr Leu Thr Ile Ser Ser Leu Gln Pro
 65                  70                  75                  80

Glu Asp Ile Ala Thr Tyr Phe Cys His Gln Tyr Asn Ser Tyr Asn Thr
                 85                  90                  95

Phe Gly Ser Gly Thr Lys Leu Glu Ile Lys Gly Gly Gly Gly Ser
            100                 105                 110

Gly Gly Gly Gly Ser Gly Gly Gly Ser Gln Val Thr Leu Lys Glu
            115                 120                 125

Ser Gly Pro Val Leu Val Lys Pro Thr Glu Thr Leu Thr Leu Thr Cys
130                 135                 140

Thr Phe Ser Gly Phe Ser Leu Ser Thr Ser Gly Met Gly Val Gly Trp
145                 150                 155                 160

Ile Arg Gln Ala Pro Gly Lys Gly Leu Glu Trp Val Ala His Ile Trp
                165                 170                 175

Trp Asp Asp Val Tyr Tyr Asn Pro Ser Leu Lys Ser Arg Leu Thr
                180                 185                 190

Ile Thr Lys Asp Ala Ser Lys Asp Gln Val Ser Leu Lys Leu Ser Ser
            195                 200                 205

Val Thr Ala Ala Asp Thr Ala Val Tyr Tyr Cys Val Arg Arg Arg Ala
210                 215                 220

Thr Gly Thr Gly Phe Asp Tyr Trp Gly Gln Gly Thr Leu Val Thr Val
225                 230                 235                 240

Ser Ser

<210> SEQ ID NO 71
<211> LENGTH: 244
<212> TYPE: PRT
<213> ORGANISM: Artificial Sequence
<220> FEATURE:
<223> OTHER INFORMATION: Syntheisized

<400> SEQUENCE: 71

Asp Ile Val Met Thr Gln Ser Pro Ser Ser Leu Thr Val Thr Ala Gly
 1               5                  10                  15

Glu Lys Val Thr Met Ile Cys Lys Ser Ser Gln Ser Leu Leu Asn Ser
                 20                  25                  30

Gly Asp Gln Lys Asn Tyr Leu Thr Trp Tyr Gln Gln Lys Pro Gly Gln
             35                  40                  45

Pro Pro Lys Leu Leu Ile Phe Trp Ala Ser Thr Arg Glu Ser Gly Val
 50                  55                  60

Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Val Tyr Tyr Cys Gln Asn
                 85                  90                  95

Asp Tyr Ser Tyr Pro Leu Thr Phe Gly Ala Gly Thr Lys Leu Glu Leu
            100                 105                 110

Lys Gly Gly Gly Gly Ser Gly Gly Gly Gly Ser Gly Gly Gly Gly Ser
            115                 120                 125

Gln Val Gln Leu Gln Gln Ser Asp Ala Glu Leu Val Lys Pro Gly Ser
130                 135                 140

Ser Val Lys Ile Ser Cys Lys Ala Ser Gly Tyr Thr Phe Thr Asp His
145                 150                 155                 160

Ala Ile His Trp Val Lys Gln Lys Pro Glu Gln Gly Leu Glu Trp Ile
                165                 170                 175

Gly His Phe Ser Pro Gly Asn Thr Asp Ile Lys Tyr Asn Asp Lys Phe
```

```
            180                 185                 190
Lys Gly Lys Ala Thr Leu Thr Val Asp Arg Ser Ser Thr Ala Tyr
        195                 200                 205

Met Gln Leu Asn Ser Leu Thr Ser Glu Asp Ser Ala Val Tyr Phe Cys
        210                 215                 220

Lys Thr Ser Thr Phe Phe Asp Tyr Trp Gly Gln Gly Thr Thr Leu
225                 230                 235                 240

Thr Val Ser Ser

<210> SEQ ID NO 72
<211> LENGTH: 246
<212> TYPE: PRT
<213> ORGANISM: Artificial Sequence
<220> FEATURE:
<223> OTHER INFORMATION: Syntheisized

<400> SEQUENCE: 72

Asp Ile Val Met Thr Gln Ala Ala Phe Ser Asn Pro Val Thr Leu Gly
1               5                   10                  15

Thr Ser Ala Ser Ile Ser Cys Arg Ser Ser Lys Ser Leu Leu His Ser
            20                  25                  30

Asn Gly Ile Thr Tyr Phe Phe Trp Tyr Leu Gln Lys Pro Gly Leu Ser
        35                  40                  45

Pro Gln Leu Leu Ile Tyr Gln Met Ser Asn Leu Ala Ser Gly Val Pro
    50                  55                  60

Asp Arg Phe Ser Ser Gly Ser Gly Thr Asp Phe Thr Leu Arg Ile
65                  70                  75                  80

Ser Arg Val Glu Ala Glu Asp Val Gly Val Tyr Tyr Cys Ala Gln Asn
                85                  90                  95

Leu Glu Leu Pro Pro Thr Phe Gly Gly Gly Thr Lys Leu Glu Ile Lys
            100                 105                 110

Arg Ala Gly Gly Gly Gly Ser Gly Gly Gly Gly Ser Gly Gly Gly Gly
        115                 120                 125

Ser Glu Val Lys Leu Val Glu Ser Gly Gly Gly Leu Val Gln Pro Gly
    130                 135                 140

Gly Ser Met Lys Leu Ser Cys Val Ala Ser Gly Phe Thr Phe Ser Asn
145                 150                 155                 160

Tyr Trp Met Asn Trp Val Arg Gln Ser Pro Glu Lys Gly Leu Glu Trp
                165                 170                 175

Val Ala Glu Ile Arg Leu Lys Ser Asn Asn Tyr Thr Thr His Tyr Ala
            180                 185                 190

Glu Ser Val Lys Gly Arg Phe Thr Ile Ser Arg Asp Asp Ser Lys Ser
        195                 200                 205

Ser Val Ser Leu Gln Met Asn Asn Leu Arg Val Glu Asp Thr Gly Ile
    210                 215                 220

Tyr Tyr Cys Thr Arg His Tyr Tyr Phe Asp Tyr Trp Gly Gln Gly Thr
225                 230                 235                 240

Thr Leu Thr Val Ser Ser
                245

<210> SEQ ID NO 73
<211> LENGTH: 960
<212> TYPE: DNA
<213> ORGANISM: Homo sapiens

<400> SEQUENCE: 73
```

```
atggatcccc aaaatcaaca tggcagtggc agttcgttag ttgtgatcca gcagccttct      60
ttggatagcc gtcagagatt agactatgag agagagattc agcctactgc tattttgtcc     120
ttagaccaga tcaaggccat aagaggcagc aatgaataca cagaagggcc ttcggtggtg     180
aaaagacctg ctcctcggac agcaccaaga caagaaaagc atgaaaggac tcatgaaatc     240
ataccaatta atgtgaataa taactacgag cacagacaca caagccacct gggacatgca     300
gtactcccaa gtaatgccag gggcccattt tgagcagat caaccagcac tggaagtgca      360
gccagctctg ggagcaacag cagtgcctct tctgaacagg gactgttagg aaggtcacca     420
ccaaccagac cagtccctgg tcataggtct gaaagggcaa tccggaccca gcccaagcaa     480
ctgattgtgg atgacttgaa gggttccttg aaagaggacc tgacacagca caagttcatt     540
tgtgaacagt gtgggaagtg caagtgtgga gaatgcactg ctcccaggac cctaccatcc     600
tgtttggcct gtaaccggca gtgcctttgc tctgctgaga gcatggtgga atatggaacc     660
tgcatgtgct tagtcaaggg catcttctac cactgctcca atgacgacga agggattcc      720
tattcagata atccttgctc ctgttcacaa tcacactgct gctctagata cctgtgtatg     780
ggagccatgt ctttattttt accttgctta ctctgttatc ctcctgctaa aggatgcctg     840
aagctgtgca ggaggtgtta tgactggatc catcgcccag ggtgcagatg taagaactcc     900
aacactgtct attgtaagct ggagagctgc ccctcccggg gtcagggtaa accatcatga     960
```

<210> SEQ ID NO 74
<211> LENGTH: 12
<212> TYPE: DNA
<213> ORGANISM: Homo sapiens

<400> SEQUENCE: 74
gtggtagaag at                                                         12

<210> SEQ ID NO 75
<211> LENGTH: 7
<212> TYPE: PRT
<213> ORGANISM: Artificial Sequence
<220> FEATURE:
<223> OTHER INFORMATION: Syntheisized

<400> SEQUENCE: 75

Ile Ser Ser Asn Leu Gln Arg
1               5

<210> SEQ ID NO 76
<211> LENGTH: 7
<212> TYPE: PRT
<213> ORGANISM: Artificial Sequence
<220> FEATURE:
<223> OTHER INFORMATION: Syntheisized

<400> SEQUENCE: 76

Gln Ser Ser Ser Leu Ile Arg
1               5

<210> SEQ ID NO 77
<211> LENGTH: 7
<212> TYPE: PRT
<213> ORGANISM: Artificial Sequence
<220> FEATURE:
<223> OTHER INFORMATION: Syntheisized

<400> SEQUENCE: 77

Val Ser Ser Ser Leu Arg Arg

```
1               5

<210> SEQ ID NO 78
<211> LENGTH: 7
<212> TYPE: PRT
<213> ORGANISM: Artificial Sequence
<220> FEATURE:
<223> OTHER INFORMATION: Syntheisized

<400> SEQUENCE: 78

Gln Lys Gly Asn Leu Leu Arg
1               5

<210> SEQ ID NO 79
<211> LENGTH: 12
<212> TYPE: DNA
<213> ORGANISM: Homo sapiens

<400> SEQUENCE: 79
aatgacgacg aa                                                           12

<210> SEQ ID NO 80
<211> LENGTH: 7
<212> TYPE: PRT
<213> ORGANISM: Artificial Sequence
<220> FEATURE:
<223> OTHER INFORMATION: Syntheisized

<400> SEQUENCE: 80

Gln Lys Gly Asn Leu Leu Arg
1               5

<210> SEQ ID NO 81
<211> LENGTH: 7
<212> TYPE: PRT
<213> ORGANISM: Artificial Sequence
<220> FEATURE:
<223> OTHER INFORMATION: Syntheisized

<400> SEQUENCE: 81

Cys Pro Ser Asn Leu Arg Arg
1               5

<210> SEQ ID NO 82
<211> LENGTH: 7
<212> TYPE: PRT
<213> ORGANISM: Artificial Sequence
<220> FEATURE:
<223> OTHER INFORMATION: Syntheisized

<400> SEQUENCE: 82

Cys Pro Ser Asn Leu Arg Arg
1               5

<210> SEQ ID NO 83
<211> LENGTH: 7
<212> TYPE: PRT
<213> ORGANISM: Artificial Sequence
<220> FEATURE:
<223> OTHER INFORMATION: Syntheisized

<400> SEQUENCE: 83

Val Ser Ser Asn Leu Asn Val
1               5

<210> SEQ ID NO 84
```

<211> LENGTH: 948
<212> TYPE: DNA
<213> ORGANISM: Homo sapiens

<400> SEQUENCE: 84

```
atggaggcca gagctcagag tggcaacggg tcgcagccct tgctgcagac gccccgtgac    60
ggtggcagac agcgtgggga gcccgacccc agagacgccc tcacccagca ggtacatgtc   120
ttgtctctgg atcagatcag agccatccga aacaccaatg agtacacaga ggggcctact   180
gtcgtcccaa gacctgggct caagcctgct cctcgccect ccactcagca caaacacgag   240
agactccacg gtctgcctga gcaccgccag cctcctaggc tccagcactc gcaggtccat   300
tcttctgcac gagcccctct gtccagatcc ataagcacgg tcagctcagg gtcgcggagc   360
agtacgagga caagtaccag cagcagctcc tctgaacaga gactgctagg atcatccttc   420
tcctccgggc ctgttgctga tggcataatc cgggtgcaac ccaaatctga gctcaagcca   480
ggtgagctta agccactgag caaggaagat ttgggcctgc acgcctacag gtgtgaggac   540
tgtggcaagt gcaaatgtaa ggagtgcacc tacccaaggc ctctgccatc agactggatc   600
tgcgacaagc agtgcctttg ctcggccag aacgtgattg actatgggac ttgtgtatgc   660
tgtgtgaaag gtctcttcta tcactgttct aatgatgatg aggacaactg tgctgacaac   720
ccatgttctt gcagccagtc tcactgttgt acacgatggt cagccatggg tgtcatgtcc   780
ctctttttgc cttgtttatg gtgttacctt ccagccaagg gttgccttaa attgtgccag   840
gggtgttatg accgggttaa caggcctggt tgccgctgta aaaactcaaa cacagtttgc   900
tgcaaagttc ccactgtccc ccctaggaac tttgaaaaac caacatag               948
```

<210> SEQ ID NO 85
<211> LENGTH: 12
<212> TYPE: DNA
<213> ORGANISM: Artificial Sequence
<220> FEATURE:
<223> OTHER INFORMATION: Syntheisized

<400> SEQUENCE: 85

```
ggagaaggat ga                                                         12
```

<210> SEQ ID NO 86
<211> LENGTH: 7
<212> TYPE: PRT
<213> ORGANISM: Artificial Sequence
<220> FEATURE:
<223> OTHER INFORMATION: Syntheisized

<400> SEQUENCE: 86

Gln Ala Gly His Leu Ala Ser
1               5

<210> SEQ ID NO 87
<211> LENGTH: 7
<212> TYPE: PRT
<213> ORGANISM: Artificial Sequence
<220> FEATURE:
<223> OTHER INFORMATION: Syntheisized

<400> SEQUENCE: 87

Gln Arg Ala His Leu Glu Arg
1               5

<210> SEQ ID NO 88
<211> LENGTH: 7

```
<212> TYPE: PRT
<213> ORGANISM: Artificial Sequence
<220> FEATURE:
<223> OTHER INFORMATION: Syntheisized

<400> SEQUENCE: 88

Gln Ser Ser Asn Leu Val Arg
1               5

<210> SEQ ID NO 89
<211> LENGTH: 7
<212> TYPE: PRT
<213> ORGANISM: Artificial Sequence
<220> FEATURE:
<223> OTHER INFORMATION: Syntheisized

<400> SEQUENCE: 89

Gln Arg Ala His Leu Glu Arg
1               5

<210> SEQ ID NO 90
<211> LENGTH: 12
<212> TYPE: DNA
<213> ORGANISM: Homo sapiens

<400> SEQUENCE: 90
cctgttgctg at                                                            12

<210> SEQ ID NO 91
<211> LENGTH: 7
<212> TYPE: PRT
<213> ORGANISM: Artificial Sequence
<220> FEATURE:
<223> OTHER INFORMATION: Syntheisized

<400> SEQUENCE: 91

Thr Ser Gly Asn Leu Val Arg
1               5

<210> SEQ ID NO 92
<211> LENGTH: 7
<212> TYPE: PRT
<213> ORGANISM: Artificial Sequence
<220> FEATURE:
<223> OTHER INFORMATION: Syntheisized

<400> SEQUENCE: 92

Thr Ser Gly Glu Leu Val Arg
1               5

<210> SEQ ID NO 93
<211> LENGTH: 7
<212> TYPE: PRT
<213> ORGANISM: Artificial Sequence
<220> FEATURE:
<223> OTHER INFORMATION: Syntheisized

<400> SEQUENCE: 93

Thr Ser Gly Ser Leu Val Arg
1               5

<210> SEQ ID NO 94
<211> LENGTH: 7
<212> TYPE: PRT
<213> ORGANISM: Artificial Sequence
<220> FEATURE:
<223> OTHER INFORMATION: Syntheisized
```

<400> SEQUENCE: 94

Thr Lys Asn Ser Leu Thr Glu
1               5

<210> SEQ ID NO 95
<211> LENGTH: 1968
<212> TYPE: DNA
<213> ORGANISM: Homo sapiens

<400> SEQUENCE: 95

| | | | | | |
|---|---|---|---|---|---|
| atggccgagg | cgcctcaggt | ggtggagatc | gacccggact | tcgagccgct | gccccggccg | 60 |
| cgctcgtgca | cctggccgct | gcccaggccg | gagtttagcc | agtccaactc | ggccacctcc | 120 |
| agcccggcgc | cgtcgggcag | cgcggctgcc | aaccccgacg | ccgcggcggg | cctgccctcg | 180 |
| gcctcggctg | ccgctgtcag | cgccgacttc | atgagcaacc | tgagcttgct | ggaggagagc | 240 |
| gaggacttcc | cgcaggcgcc | cggctccgtg | gcggcggcgg | tggcggcggc | ggccgccgcg | 300 |
| gccgccaccg | gggggctgtg | cggggacttc | cagggcccgg | aggcgggctg | cctgcaccca | 360 |
| gcgccaccgc | agcccccgcc | gcccgggccg | ctgtcgcagc | accgccggt | gcccccgcc | 420 |
| gccgctgggc | cgctcgcggg | gcagccgcgc | aagagcagct | cgtcccgccg | caacgcgtgg | 480 |
| ggcaacctgt | cctacgccga | cctcatcacc | aaggccatcg | agagctcggc | ggagaagcgg | 540 |
| ctcacgctgt | cgcagatcta | cgagtggatg | gtcaagagcg | tgccctactt | caaggataag | 600 |
| ggtgacagca | acagctcggc | gggctggaag | aattcaattc | gtcataatct | gtccctacac | 660 |
| agcaagttca | ttcgtgtgca | gaatgaagga | actggaaaaa | gttcttggtg | gatgctcaat | 720 |
| ccagagggtg | gcaagagcgg | gaaatctcct | aggagaagag | ctgcatccat | ggacaacaac | 780 |
| agtaaatttg | ctaagagccg | aagccgagct | gccaagaaga | agcatctct | ccagtctggc | 840 |
| caggagggtg | ctggggacag | ccctggatca | cagttttcca | aatggcctgc | aagccctggc | 900 |
| tctcacagca | atgatgactt | tgataactgg | agtacatttc | gccctcgaac | tagctcaaat | 960 |
| gctagtacta | ttagtgggag | actctcaccc | attatgaccg | aacaggatga | tcttggagaa | 1020 |
| ggggatgtgc | attctatggt | gtacccgcca | tctgccgcaa | agatggcctc | tactttaccc | 1080 |
| agtctgtctg | agataagcaa | tcccgaaaac | atggaaaatc | ttttggataa | tctcaacctt | 1140 |
| ctctcatcac | caacatcatt | aactgtttcg | acccagtcct | cacctggcac | catgatgcag | 1200 |
| cagacgccgt | gctactcgtt | tgcgccacca | aacaccagtt | tgaattcacc | cagcccaaac | 1260 |
| taccaaaaat | atacatatgg | ccaatccagc | atgagccctt | gccccagat | gcctatacaa | 1320 |
| acacttcagg | acaataagtc | gagttatgga | ggtatgagtc | agtataactg | tgcgcctgga | 1380 |
| ctcttgaagg | agttgctgac | ttctgactct | cctccccata | atgacattat | gacaccagtt | 1440 |
| gatcctgggg | tagcccagcc | caacagccgg | gttctgggcc | agaacgtcat | gatgggccct | 1500 |
| aattcggtca | tgtcaaccta | tggcagccag | gcatctcata | caaaatgat | gaatcccagc | 1560 |
| tcccataccc | accctggaca | tgctcagcag | acatctgcag | ttaacgggcg | tccccctgccc | 1620 |
| cacacggtaa | gcaccatgcc | ccacacctcg | ggtatgaacc | gcctgaccca | agtgaagaca | 1680 |
| cctgtacaag | tgcctctgcc | ccaccccatg | cagatgagtg | ccctgggggg | ctactcctcc | 1740 |
| gtgagcagct | gcaatggcta | tggcagaatg | ggccttctcc | accaggagaa | gctcccaagt | 1800 |
| gacttggatg | gcatgttcat | tgagcgctta | gactgtgaca | tggaatccat | cattcggaat | 1860 |
| gacctcatgg | atggagatac | attggatttt | aactttgaca | atgtgttgcc | caaccaaagc | 1920 |
| ttcccacaca | gtgtcaagac | aacgacacat | agctgggtgt | caggctga | | 1968 |

```
<210> SEQ ID NO 96
<211> LENGTH: 12
<212> TYPE: DNA
<213> ORGANISM: Homo sapiens

<400> SEQUENCE: 96
acctgaggcg cc                                                            12

<210> SEQ ID NO 97
<211> LENGTH: 7
<212> TYPE: PRT
<213> ORGANISM: Artificial Sequence
<220> FEATURE:
<223> OTHER INFORMATION: Syntheisized

<400> SEQUENCE: 97

Asp Cys Arg Asp Leu Ala Arg
1               5

<210> SEQ ID NO 98
<211> LENGTH: 7
<212> TYPE: PRT
<213> ORGANISM: Artificial Sequence
<220> FEATURE:
<223> OTHER INFORMATION: Syntheisized

<400> SEQUENCE: 98

Asp Pro Gly His Leu Val Arg
1               5

<210> SEQ ID NO 99
<211> LENGTH: 7
<212> TYPE: PRT
<213> ORGANISM: Artificial Sequence
<220> FEATURE:
<223> OTHER INFORMATION: Syntheisized

<400> SEQUENCE: 99

Gln Ala Gly His Leu Ala Ser
1               5

<210> SEQ ID NO 100
<211> LENGTH: 7
<212> TYPE: PRT
<213> ORGANISM: Artificial Sequence
<220> FEATURE:
<223> OTHER INFORMATION: Syntheisized

<400> SEQUENCE: 100

Asp Lys Lys Asp Leu Thr Arg
1               5

<210> SEQ ID NO 101
<211> LENGTH: 12
<212> TYPE: DNA
<213> ORGANISM: Homo sapiens

<400> SEQUENCE: 101
gatcgacccg ga                                                            12

<210> SEQ ID NO 102
<211> LENGTH: 7
<212> TYPE: PRT
<213> ORGANISM: Artificial Sequence
<220> FEATURE:
```

<223> OTHER INFORMATION: Syntheisized

<400> SEQUENCE: 102

Gln Arg Ala His Leu Glu Arg
1               5

<210> SEQ ID NO 103
<211> LENGTH: 7
<212> TYPE: PRT
<213> ORGANISM: Artificial Sequence
<220> FEATURE:
<223> OTHER INFORMATION: Syntheisized

<400> SEQUENCE: 103

Ser Lys Lys His Leu Ala Glu
1               5

<210> SEQ ID NO 104
<211> LENGTH: 7
<212> TYPE: PRT
<213> ORGANISM: Artificial Sequence
<220> FEATURE:
<223> OTHER INFORMATION: Syntheisized

<400> SEQUENCE: 104

Gln Ser Gly His Leu Thr Glu
1               5

<210> SEQ ID NO 105
<211> LENGTH: 7
<212> TYPE: PRT
<213> ORGANISM: Artificial Sequence
<220> FEATURE:
<223> OTHER INFORMATION: Syntheisized

<400> SEQUENCE: 105

Thr Ser Gly Asn Leu Val Arg
1               5

<210> SEQ ID NO 106
<211> LENGTH: 5405
<212> TYPE: DNA
<213> ORGANISM: Artificial Sequence
<220> FEATURE:
<223> OTHER INFORMATION: Syntheisized

<400> SEQUENCE: 106

| | | | | |
|---|---|---|---|---|
| ggctccggtg | cccgtcagtg | ggcagagcgc | acatcgccca | cagtccccga | gaagttgggg | 60 |
| ggaggggtcg | gcaattgaac | cggtgcctag | agaaggtggc | gcggggtaaa | ctgggaaagt | 120 |
| gatgtcgtgt | actggctccg | ccttttttccc | gagggtgggg | gagaaccgta | tataagtgca | 180 |
| gtagtcgccg | tgaacgttct | ttttcgcaac | gggtttgccg | ccagaacaca | ggatccgcca | 240 |
| ccatggcctt | accagtgacc | gccttgctcc | tgccgctggc | cttgctgctc | cacgccgcca | 300 |
| ggccggatat | ccagatgacc | cagagcccga | gcagcctgag | cgcgagcgtg | ggtgatcgcg | 360 |
| tgaccattac | ctgcagggca | agtcaggaca | ttagtaaata | tttaaattgg | tatcagcaga | 420 |
| aaccgggtaa | agcgccgaaa | ctgttaattt | atcatacatc | aagattacac | tcaggcgtgc | 480 |
| cgtcgcgttt | tagcggctcg | ggttcgggca | ccgatttttac | cctgaccatc | tcgagcttgc | 540 |
| agccggagga | cttcgccacc | tactattgcc | aacagggtaa | tacgcttccg | tacacgttcg | 600 |
| gtcagggcac | caaagtggag | atcaaaggtg | gcggtggctc | gggcggtggt | gggtcgggtg | 660 |
| gcggcggatc | tgaggtgcag | ctggtggagt | ctgggggagg | cttggtacag | cctgggggt | 720 |

```
ccctgagact ctcctgtgca gcctctggag tgtccctgcc tgattatggc gtgtcctggg    780
tccgccaggc tccagggaag gggctggagt gggtttcagt gatctgggc agcgagacaa     840 cctactacaa cagcgccctg aagtcccgat tcaccatctc cagagacaat gccaagaact    900
cactgtatct gcaaatgaac agcctgagag ccgaggacac ggctgtgtat tactgtgcga    960
agcactacta ctacggcggc agctacgcta tggactactg gggccaagga accctggtca   1020
ccgtgtcctc aaccacgacg ccagcgccgc gaccaccaac accggcgccc accatcgcgt   1080
cgcagcccct gtccctgcgc ccagaggcgt gccggccagc ggcgggggc gcagtgcaca   1140 cgaggggggct ggacttcgcc tgtgatatct acatctgggc gcccttggcc gggacttgtg  1200
gggtccttct cctgtcactg gttatcaccc tttactgcaa acggggcaga aagaaactcc   1260
tgtatatatt caaacaacca tttatgagac cagtacaaac tactcaagag gaagatggct   1320
gtagctgccg atttccagaa gaagaagaag gaggatgtga actgagagtg aagttcagca   1380
ggagcgcaga cgcccccgcg taccagcagg gccagaacca gctctataac gagctcaatc   1440
taggacgaag agaggagtac gatgttttgg acaagaggcg tggccgggac cctgagatgg   1500
ggggaaagcc gagaaggaag aaccctcagg aaggcctgta caatgaactg cagaaagata   1560
agatggcgga ggcctacagt gagattggga tgaaaggcga gcgccggagg ggcaaggggc   1620
acgatggcct ttaccagggt ctcagtacag ccaccaagga cacctacgac gcccttcaca   1680
tgcaggccct gccccctcgc taagtcgacc cctctccct ccccccccc taacgttact     1740 ggccgaagcc gcttggaata aggccggtgt gcgtttgtct atatgttatt ttccaccata   1800
ttgccgtctt ttggcaatgt gagggcccgg aaacctggcc ctgtcttctt gacgagcatt   1860
cctaggggtc tttcccctct cgccaaagga atgcaaggtc tgttgaatgt cgtgaaggaa   1920
gcagttcctc tggaagcttc ttgaagacaa acaacgtctg tagcgaccct ttgcaggcag   1980
cggaaccccc cacctggcga caggtgcctc tgcggccaaa agccacgtgt ataagataca   2040
cctgcaaagg cggcacaacc ccagtgccac gttgtgagtt ggatagttgt ggaaagagtc   2100
aaatggctct cctcaagcgt attcaacaag gggctgaagg atgcccagaa ggtaccccat   2160
tgtatgggat ctgatctggg gcctcggtac acatgcttta catgtgttta gtcgaggtta   2220
aaaaaacgtc taggcccccc gaaccacggg gacgtggttt tcctttgaaa aacacgatga   2280
taatatggcc acaacccata tgagtgatgg gtttctgccg cagcgccctg cacccgctgt   2340
ctctcctggt gcaggccatc atgctggcca tgaccctggc cctgggtacc ttgcctgcct   2400
tcctaccctg tgagctccag ccccacggcc tggtgaactg caactggctg ttcctgaagt   2460
ctgtgcccca cttctccatg cagcacccc gtggcaatgt caccagcctt tccttgtcct    2520
ccaaccgcat ccaccacctc catgattctg actttgccca cctgcccagc tgcggcatc    2580 tcaacctcaa gtggaactgc cgccggttg gcctcagccc catgcacttc ccctgccaca   2640
tgaccatcga gccagcacc ttcttggctg tgcccaccct ggaagagcta aacctgagct    2700
acaacaacat catgactgtg cctgcgctgc ccaaatccct catatccctg tccctcagcc   2760
ataccaacat cctgatgcta gactctgcca gctcgccgg cctgcatgcc ctgcgcttcc    2820
tattcatgga cggcaactgt tattacaaga acccctgcag gcaggcactg gaggtggccc   2880
cgggtgccct ccttggcctg ggcaacctca cccacctgtc actcaagtac aacaacctca   2940
ctgtggtgcc ccgcaacctg ccttccagcc tggagtatct gctgttgtcc tacaaccgca   3000 tcgtcaaaact ggcgcctgag gacctggcca atctgaccgc cctgcgtgtg ctcgatgtgg   3060
```

```
gcggaaattg ccgccgctgc gaccacgctc ccaacccctg catggagtgc cctcgtcact   3120
tcccccagct acatcccgat accttcagcc acctgagccg tcttgaaggc ctggtgttga   3180
aggacagttc tctctcctgg ctgaatgcca gttggttccg tgggctggga aacctccgag   3240
tgctggacct gagtgagaac ttcctctaca aatgcatcac taaaaccaag gccttccagg   3300
gcctaacaca gctgcgcaag cttaacctgt ccttcaatta ccaaagagg gtgtcctttg    3360
cccacctgtc tctggcccct tccttcggga gcctggtcgc cctgaaggag ctggacatgc   3420
acggcatctt cttccgctca ctcgatgaga ccacgctccg gccactggcc cgcctgccca   3480
tgctccagac tctgcgtctg cagatgaact tcatcaacca ggcccagctc ggcatcttca   3540
gggccttccc tggcctgcgc tacgtggacc tgtcggacaa ccgcatcagc ggagcttcgg   3600
agctgacagc caccatgggg gaggcagatg aggggagaa ggtctggctg cagcctgggg    3660
accttgctcc ggccccagtg gacactccca gctctgaaga cttcaggccc aactgcagca   3720
ccctcaactt caccttggat ctgtcacgga acaacctggt gaccgtgcag ccggagatgt   3780
ttgcccagct ctcgcacctg cagtgcctgc gcctgagcca caactgcatc tcgcaggcag   3840
tcaatggctc ccagttcctg ccgctgaccg gtctgcaggt gctagacctg tcccacaata   3900
agctggacct ctaccacgag cactcattca cggagctacc gcgactggag gccctggacc   3960
tcagctacaa cagccagccc tttggcatgc agggcgtggg ccacaacttc agcttcgtgg   4020
ctcacctgcg caccctgcgc cacctcagcc tgggcccacaa caacatccac agccaagtgt   4080
cccagcagct ctgcagtacg tcgctgcggg ccctggactt cagcggcaat gcactgggcc   4140
atatgtgggc cgagggagac ctctatctgc acttcttcca aggcctgagc ggtttgatct   4200
ggctggactt gtcccagaac cgcctgcaca ccctcctgcc ccaaaccctg cgcaacctcc   4260
ccaagagcct acaggtgctg cgtctccgtg acaattacct ggccttcttt aagtggtgga   4320
gcctccactt cctgcccaaa ctggaagtcc tcgacctggc aggaaaccag ctgaaggccc   4380
tgaccaatgg cagcctgcct gctggcaccc ggctccggag gctggatgtc agctgcaaca   4440
gcatcagctt cgtggccccc ggcttctttt ccaaggccaa ggagctgcga gagctcaacc   4500
ttagcgccaa cgccctcaag acagtggacc actcctggtt tgggcccctg gcgagtgccc   4560
tgcaaatact agatgtaagc gccaaccctc tgcactgcgc ctgtggggcg gcctttatgg   4620
acttcctgct ggaggtgcag gctgccgtgc ccggtctgcc cagccgggtg aagtgtggca   4680
gtccgggcca gctccagggc ctcagcatct ttgcacagga cctgcgcctc tgcctggatg   4740
aggccctctc ctgggactgt ttcgccctct cgctgctggc tgtggctctg ggcctgggtg   4800
tgcccatgct gcatcacctc tgtggctggg acctctggta ctgcttccac ctgtgcctgg   4860
cctggcttcc ctggcggggg cggcaaagtg ggcgagatga ggatgccctg ccctacgatg   4920
ccttcgtggt cttcgacaaa acgcagagcg cagtggcaga ctgggtgtac aacgagcttc   4980
gggggcagct ggaggagtgc cgtgggcgct gggcactccg cctgtgcctg aggaacgcg    5040
actggctgcc tggcaaaacc ctctttgaga acctgtgggc ctcggtctat ggcagccgca   5100
agacgctgtt tgtgctggcc cacacggacc gggtcagtgg tctcttgcgc gccagcttcc   5160
tgctggccca gcagccctg ctggaggacc gcaaggacgt cgtggtgctg gtgatcctga    5220
gccctgacgg ccgccgctcc cgctacgtgc ggctgcgcca gcgcctctgc cgccagagtg   5280
tcctcctctg gccccaccag cccagtggtc agcgcagctt ctgggccag ctgggcatgg    5340
ccctgaccag ggacaaccac cacttctata accggaactt ctgccaggga cccacggccg   5400
aatag                                                              5405
```

<210> SEQ ID NO 107
<211> LENGTH: 480
<212> TYPE: DNA
<213> ORGANISM: Homo sapiens

<400> SEQUENCE: 107

```
atgcgacccg accgcgctga ggctccagga ccgcccgcca tggctgcagg aggtcccggc      60
gcggggtctg cggccccggt ctcctccaca tcctcccttc ccctggctgc tctcaacatg     120
cgagtgcggc gccgcctgtc tctgttcttg aacgtgcgga cacaggtggc ggccgactgg     180
accgcgctgg cggaggagat ggactttgag tacttggaga tccggcaact ggagacacaa     240
gcggacccca ctggcaggct gctggacgcc tggcagggac gccctggcgc tctctaggc      300
cgactgctcg agctgcttac caagctgggc cgcgacgacg tgctgctgga gctgggaccc     360
agcattggtg ccgccggatg tggtggttg tctctgatga ttacctgcag agcaaggaat     420
gtgacttcca gaccaaattt gcactcagcc tctctccagg tgcccatcag aagcgactga     480
```

<210> SEQ ID NO 108
<211> LENGTH: 2786
<212> TYPE: DNA
<213> ORGANISM: Homo sapiens

<400> SEQUENCE: 108

```
ggctccggtg cccgtcagtg ggcagagcgc acatcgccca cagtccccga aagttgggg      60
ggaggggtcg gcaattgaac cggtgcctag agaaggtggc gcggggtaaa ctgggaaagt     120
gatgtcgtgt actggctccg cctttttccc gagggtgggg gagaaccgta tataagtgca     180
gtagtcgccg tgaacgttct ttttcgcaac gggtttgccg ccagaacaca ggatccgcca     240
ccatggcctt accagtgacc gccttgctcc tgccgctggc cttgctgctc cacgccgcca     300
ggccggatat ccagatgacc cagagcccga gcagcctgag cgcgagcgtg ggtgatcgcg     360
tgaccattac ctgcagggca agtcaggaca ttagtaaata tttaaattgg tatcagcaga     420
aaccgggtaa agcgccgaaa ctgttaattt atcatacatc aagattacac tcaggcgtgc     480
cgtcgcgttt tagcggctcg ggttcgggca ccgattttac cctgaccatc tcgagcttgc     540
agccggagga cttcgccacc tactattgcc aacagggtaa tacgcttccg tacacgttcg     600
gtcagggcac caaagtggag atcaaaggtg cggtggctc gggcggtggt gggtcgggtg     660
gcggcggatc tgaggtgcag ctggtggagt ctgggggagg cttggtacag cctggggggt     720
ccctgagact ctcctgtgca gcctctggag tgtccctgcc tgattatggc gtgtcctggg     780
tccgccaggc tccagggaag gggctggagt gggtttcagt gatctgggc agcgagacaa     840
cctactacaa cagcgccctg aagtcccgat tcaccatctc cagagacaat gccaagaact     900
cactgtatct gcaaatgaac agcctgagag ccgaggacac ggctgtgtat tactgtgcga     960
agcactacta ctacgcggc agctacgcta tggactactg gggccaagga acctggtca    1020
ccgtgtcctc aaccacgacg ccagcgccgc gaccaccaac accggcgccc accatcgcgt    1080
cgcagcccct gtccctgcgc ccagaggcgt gccggccagc ggcggggggc gcagtgcaca    1140
cgaggggct ggacttcgcc tgtgatatct acatctgggc gcccttggcc gggacttgtg    1200
gggtccttct cctgtcactg gttatcaccc tttactgcaa acggggcaga aagaaactcc    1260
tgtatatatt caaacaacca tttatgagac cagtacaaac tactcaagag gaagatggct    1320
gtagctgccg atttccagaa gaagaagaag gaggatgtga actgagagtg aagttcagca    1380
```

```
ggagcgcaga cgccccgcg taccagcagg gccagaacca gctctataac gagctcaatc   1440
taggacgaag agaggagtac gatgttttgg acaagaggcg tggccgggac cctgagatgg   1500
ggggaaagcc gagaaggaag aaccctcagg aaggcctgta caatgaactg cagaaagata   1560
agatggcgga ggcctacagt gagattggga tgaaaggcga gcgccggagg ggcaaggggc   1620
acgatggcct ttaccagggt ctcagtacag ccaccaagga cacctacgac gcccttcaca   1680
tgcaggccct gcccctcgc taagtcgacc cctctccct cccccccccc taacgttact     1740
ggccgaagcc gcttggaata aggccggtgt gcgtttgtct atatgttatt ttccaccata   1800
ttgccgtctt ttggcaatgt gagggcccgg aaacctggcc ctgtcttctt gacgagcatt   1860 cctagggtc tttcccctct cgccaaagga atgcaaggtc tgttgaatgt cgtgaaggaa   1920
gcagttcctc tggaagcttc ttgaagacaa acaacgtctg tagcgaccct ttgcaggcag   1980
cggaaccccc cacctggcga caggtgcctc tgcggccaaa agccacgtgt ataagataca   2040
cctgcaaagg cggcacaacc ccagtgccac gttgtgagtt ggatagttgt ggaaagagtc   2100
aaatggctct cctcaagcgt attcaacaag gggctgaagg atgcccagaa ggtacccat    2160 tgtatgggat ctgatctggg gcctcggtac acatgctttta catgtgttta gtcgaggtta   2220
aaaaaacgtc taggcccccc gaaccacggg gacgtggttt tcctttgaaa acacgatga    2280 taatatggcc acaacccata tgagtgatgc gacccgaccg cgctgaggct ccaggaccgc   2340
ccgccatggc tgcaggaggt cccggcgcgg ggtctgcggc cccggtctcc tccacatcct   2400 ccctttcccct ggctgctctc aacatgcgag tgcggcgccg cctgtctctg ttcttgaacg   2460
tgcggacaca ggtggcggcc gactggaccg cgctggcgga ggagatggac tttgagtact   2520
tggagatccg gcaactggag acacaagcgg accccactgg caggctgctg gacgcctggc   2580
agggacgccc tggcgcctct gtaggccgac tgctcgagct gcttaccaag ctgggccgcg   2640
acgacgtgct gctggagctg ggacccagca ttggtgccgc cggatggtgg tggttgtctc   2700
tgatgattac ctgcagagca aggaatgtga cttccagacc aaatttgcac tcagcctctc   2760
tccaggtgcc catcagaagc gactga                                        2786
```

<210> SEQ ID NO 109
<211> LENGTH: 1032
<212> TYPE: PRT
<213> ORGANISM: Homo sapiens

<400> SEQUENCE: 109

```
Met Gly Phe Cys Arg Ser Ala Leu His Pro Leu Ser Leu Val Gln
1               5                   10                  15

Ala Ile Met Leu Ala Met Thr Leu Ala Leu Gly Thr Leu Pro Ala Phe
            20                  25                  30

Leu Pro Cys Glu Leu Gln Pro His Gly Leu Val Asn Cys Asn Trp Leu
        35                  40                  45

Phe Leu Lys Ser Val Pro His Phe Ser Met Ala Ala Pro Arg Gly Asn
    50                  55                  60

Val Thr Ser Leu Ser Leu Ser Ser Asn Arg Ile His His Leu His Asp
65                  70                  75                  80

Ser Asp Phe Ala His Leu Pro Ser Leu Arg His Leu Asn Leu Lys Trp
                85                  90                  95

Asn Cys Pro Pro Val Gly Leu Ser Pro Met His Phe Pro Cys His Met
            100                 105                 110

Thr Ile Glu Pro Ser Thr Phe Leu Ala Val Pro Thr Leu Glu Glu Leu
        115                 120                 125
```

-continued

```
Asn Leu Ser Tyr Asn Asn Ile Met Thr Val Pro Ala Leu Pro Lys Ser
    130                 135                 140

Leu Ile Ser Leu Ser Leu Ser His Thr Asn Ile Leu Met Leu Asp Ser
145                 150                 155                 160

Ala Ser Leu Ala Gly Leu His Ala Leu Arg Phe Leu Phe Met Asp Gly
                165                 170                 175

Asn Cys Tyr Tyr Lys Asn Pro Cys Arg Gln Ala Leu Glu Val Ala Pro
                180                 185                 190

Gly Ala Leu Leu Gly Leu Gly Asn Leu Thr His Leu Ser Leu Lys Tyr
                195                 200                 205

Asn Asn Leu Thr Val Val Pro Arg Asn Leu Pro Ser Ser Leu Glu Tyr
    210                 215                 220

Leu Leu Leu Ser Tyr Asn Arg Ile Val Lys Leu Ala Pro Glu Asp Leu
225                 230                 235                 240

Ala Asn Leu Thr Ala Leu Arg Val Leu Asp Val Gly Gly Asn Cys Arg
                245                 250                 255

Arg Cys Asp His Ala Pro Asn Pro Cys Met Glu Cys Pro Arg His Phe
                260                 265                 270

Pro Gln Leu His Pro Asp Thr Phe Ser His Leu Ser Arg Leu Glu Gly
                275                 280                 285

Leu Val Leu Lys Asp Ser Ser Leu Ser Trp Leu Asn Ala Ser Trp Phe
                290                 295                 300

Arg Gly Leu Gly Asn Leu Arg Val Leu Asp Leu Ser Glu Asn Phe Leu
305                 310                 315                 320

Tyr Lys Cys Ile Thr Lys Thr Lys Ala Phe Gln Gly Leu Thr Gln Leu
                325                 330                 335

Arg Lys Leu Asn Leu Ser Phe Asn Tyr Gln Lys Arg Val Ser Phe Ala
                340                 345                 350

His Leu Ser Leu Ala Pro Ser Phe Gly Ser Leu Val Ala Leu Lys Glu
                355                 360                 365

Leu Asp Met His Gly Ile Phe Phe Arg Ser Leu Asp Glu Thr Thr Leu
                370                 375                 380

Arg Pro Leu Ala Arg Leu Pro Met Leu Gln Thr Leu Arg Leu Gln Met
385                 390                 395                 400

Asn Phe Ile Asn Gln Ala Gln Leu Gly Ile Phe Arg Ala Phe Pro Gly
                405                 410                 415

Leu Arg Tyr Val Asp Leu Ser Asp Asn Arg Ile Ser Gly Ala Ser Glu
                420                 425                 430

Leu Thr Ala Thr Met Gly Glu Ala Asp Gly Gly Glu Lys Val Trp Leu
                435                 440                 445

Gln Pro Gly Asp Leu Ala Pro Ala Pro Val Asp Thr Pro Ser Ser Glu
    450                 455                 460

Asp Phe Arg Pro Asn Cys Ser Thr Leu Asn Phe Thr Leu Asp Leu Ser
465                 470                 475                 480

Arg Asn Asn Leu Val Thr Val Gln Pro Glu Met Phe Ala Gln Leu Ser
                485                 490                 495

His Leu Gln Cys Leu Arg Leu Ser His Asn Cys Ile Ser Gln Ala Val
                500                 505                 510

Asn Gly Ser Gln Phe Leu Pro Leu Thr Gly Leu Gln Val Leu Asp Leu
                515                 520                 525

Ser His Asn Lys Leu Asp Leu Tyr His Glu His Ser Phe Thr Glu Leu
    530                 535                 540
```

-continued

Pro Arg Leu Glu Ala Leu Asp Leu Ser Tyr Asn Ser Gln Pro Phe Gly
545                 550                 555                 560

Met Gln Gly Val Gly His Asn Phe Ser Phe Val Ala His Leu Arg Thr
            565                 570                 575

Leu Arg His Leu Ser Leu Ala His Asn Asn Ile His Ser Gln Val Ser
                580                 585                 590

Gln Gln Leu Cys Ser Thr Ser Leu Arg Ala Leu Asp Phe Ser Gly Asn
    595                 600                 605

Ala Leu Gly His Met Trp Ala Glu Gly Asp Leu Tyr Leu His Phe Phe
610                 615                 620

Gln Gly Leu Ser Gly Leu Ile Trp Leu Asp Leu Ser Gln Asn Arg Leu
625                 630                 635                 640

His Thr Leu Leu Pro Gln Thr Leu Arg Asn Leu Pro Lys Ser Leu Gln
                645                 650                 655

Val Leu Arg Leu Arg Asp Asn Tyr Leu Ala Phe Phe Lys Trp Trp Ser
                660                 665                 670

Leu His Phe Leu Pro Lys Leu Glu Val Leu Asp Leu Ala Gly Asn Gln
                675                 680                 685

Leu Lys Ala Leu Thr Asn Gly Ser Leu Pro Ala Gly Thr Arg Leu Arg
690                 695                 700

Arg Leu Asp Val Ser Cys Asn Ser Ile Ser Phe Val Ala Pro Gly Phe
705                 710                 715                 720

Phe Ser Lys Ala Lys Glu Leu Arg Glu Leu Asn Leu Ser Ala Asn Ala
            725                 730                 735

Leu Lys Thr Val Asp His Ser Trp Phe Gly Pro Leu Ala Ser Ala Leu
            740                 745                 750

Gln Ile Leu Asp Val Ser Ala Asn Pro Leu His Cys Ala Cys Gly Ala
    755                 760                 765

Ala Phe Met Asp Phe Leu Leu Glu Val Gln Ala Ala Val Pro Gly Leu
770                 775                 780

Pro Ser Arg Val Lys Cys Gly Ser Pro Gly Gln Leu Gln Gly Leu Ser
785                 790                 795                 800

Ile Phe Ala Gln Asp Leu Arg Leu Cys Leu Asp Glu Ala Leu Ser Trp
                805                 810                 815

Asp Cys Phe Ala Leu Ser Leu Leu Ala Val Ala Leu Gly Leu Gly Val
                820                 825                 830

Pro Met Leu His His Leu Cys Gly Trp Asp Leu Trp Tyr Cys Phe His
835                 840                 845

Leu Cys Leu Ala Trp Leu Pro Trp Arg Gly Arg Gln Ser Gly Arg Asp
850                 855                 860

Glu Asp Ala Leu Pro Tyr Asp Ala Phe Val Val Phe Asp Lys Thr Gln
865                 870                 875                 880

Ser Ala Val Ala Asp Trp Val Tyr Asn Glu Leu Arg Gly Gln Leu Glu
                885                 890                 895

Glu Cys Arg Gly Arg Trp Ala Leu Arg Leu Cys Leu Glu Glu Arg Asp
            900                 905                 910

Trp Leu Pro Gly Lys Thr Leu Phe Glu Asn Leu Trp Ala Ser Val Tyr
            915                 920                 925

Gly Ser Arg Lys Thr Leu Phe Val Leu Ala His Thr Asp Arg Val Ser
    930                 935                 940

Gly Leu Leu Arg Ala Ser Phe Leu Leu Ala Gln Gln Arg Leu Leu Glu
945                 950                 955                 960

Asp Arg Lys Asp Val Val Val Leu Val Ile Leu Ser Pro Asp Gly Arg

```
                965                 970                 975
Arg Ser Arg Tyr Val Arg Leu Arg Gln Arg Leu Cys Arg Gln Ser Val
            980                 985                 990
Leu Leu Trp Pro His Gln Pro Ser Gly Gln Arg Ser Phe Trp Ala Gln
        995                1000                1005
Leu Gly Met Ala Leu Thr Arg Asp Asn His His Phe Tyr Asn Arg
   1010                1015                1020
Asn Phe Cys Gln Gly Pro Thr Ala Glu
       1025                1030

<210> SEQ ID NO 110
<211> LENGTH: 712
<212> TYPE: PRT
<213> ORGANISM: Homo sapiens

<400> SEQUENCE: 110

Met Ala Gly Gly Pro Gly Pro Gly Glu Pro Ala Ala Pro Gly Ala Gln
1               5                   10                  15
His Phe Leu Tyr Glu Val Pro Pro Trp Val Met Cys Arg Phe Tyr Lys
            20                  25                  30
Val Met Asp Ala Leu Glu Pro Ala Asp Trp Cys Gln Phe Ala Ala Leu
        35                  40                  45
Ile Val Arg Asp Gln Thr Glu Leu Arg Leu Cys Glu Arg Ser Gly Gln
    50                  55                  60
Arg Thr Ala Ser Val Leu Trp Pro Trp Ile Asn Arg Asn Ala Arg Val
65                  70                  75                  80
Ala Asp Leu Val His Ile Leu Thr His Leu Gln Leu Leu Arg Ala Arg
                85                  90                  95
Asp Ile Ile Thr Ala Trp His Pro Pro Ala Pro Leu Pro Ser Pro Gly
            100                 105                 110
Thr Thr Ala Pro Arg Pro Ser Ser Ile Pro Ala Pro Ala Glu Ala Glu
        115                 120                 125
Ala Trp Ser Pro Arg Lys Leu Pro Ser Ser Ala Ser Thr Phe Leu Ser
    130                 135                 140
Pro Ala Phe Pro Gly Ser Gln Thr His Ser Gly Pro Glu Leu Gly Leu
145                 150                 155                 160
Val Pro Ser Pro Ala Ser Leu Trp Pro Pro Pro Ser Pro Ala Pro
                165                 170                 175
Ser Ser Thr Lys Pro Gly Pro Glu Ser Ser Val Ser Leu Leu Gln Gly
            180                 185                 190
Ala Arg Pro Phe Pro Phe Cys Trp Pro Leu Cys Glu Ile Ser Arg Gly
        195                 200                 205
Thr His Asn Phe Ser Glu Glu Leu Lys Ile Gly Glu Gly Gly Phe Gly
    210                 215                 220
Cys Val Tyr Arg Ala Val Met Arg Asn Thr Val Tyr Ala Val Lys Arg
225                 230                 235                 240
Leu Lys Glu Asn Ala Asp Leu Glu Trp Thr Ala Val Lys Gln Ser Phe
                245                 250                 255
Leu Thr Glu Val Glu Gln Leu Ser Arg Phe Arg His Pro Asn Ile Val
            260                 265                 270
Asp Phe Ala Gly Tyr Cys Ala Gln Asn Gly Phe Tyr Cys Leu Val Tyr
        275                 280                 285
Gly Phe Leu Pro Asn Gly Ser Leu Glu Asp Arg Leu His Cys Gln Thr
    290                 295                 300
```

```
Gln Ala Cys Pro Pro Leu Ser Trp Pro Gln Arg Leu Asp Ile Leu Leu
305                 310                 315                 320

Gly Thr Ala Arg Ala Ile Gln Phe Leu His Gln Asp Ser Pro Ser Leu
            325                 330                 335

Ile His Gly Asp Ile Lys Ser Ser Asn Val Leu Leu Asp Glu Arg Leu
        340                 345                 350

Thr Pro Lys Leu Gly Asp Phe Gly Leu Ala Arg Phe Ser Arg Phe Ala
    355                 360                 365

Gly Ser Ser Pro Ser Gln Ser Ser Met Val Ala Arg Thr Gln Thr Val
370                 375                 380

Arg Gly Thr Leu Ala Tyr Leu Pro Glu Glu Tyr Ile Lys Thr Gly Arg
385                 390                 395                 400

Leu Ala Val Asp Thr Asp Thr Phe Ser Phe Gly Val Val Leu Glu
                405                 410                 415

Thr Leu Ala Gly Gln Arg Ala Val Lys Thr His Gly Ala Arg Thr Lys
                420                 425                 430

Tyr Leu Lys Asp Leu Val Glu Glu Ala Glu Ala Gly Val Ala
            435                 440                 445

Leu Arg Ser Thr Gln Ser Thr Leu Gln Ala Gly Leu Ala Ala Asp Ala
    450                 455                 460

Trp Ala Ala Pro Ile Ala Met Gln Ile Tyr Lys Lys His Leu Asp Pro
465                 470                 475                 480

Arg Pro Gly Pro Cys Pro Pro Glu Leu Gly Leu Gly Leu Gly Gln Leu
                485                 490                 495

Ala Cys Cys Cys Leu His Arg Arg Ala Lys Arg Arg Pro Pro Met Thr
            500                 505                 510

Gln Val Tyr Glu Arg Leu Glu Lys Leu Gln Ala Val Val Ala Gly Val
        515                 520                 525

Pro Gly His Ser Glu Ala Ala Ser Cys Ile Pro Pro Ser Pro Gln Glu
    530                 535                 540

Asn Ser Tyr Val Ser Ser Thr Gly Arg Ala His Ser Gly Ala Ala Pro
545                 550                 555                 560

Trp Gln Pro Leu Ala Ala Pro Ser Gly Ala Ser Ala Gln Ala Ala Glu
                565                 570                 575

Gln Leu Gln Arg Gly Pro Asn Gln Pro Val Glu Ser Asp Glu Ser Leu
            580                 585                 590

Gly Gly Leu Ser Ala Ala Leu Arg Ser Trp His Leu Thr Pro Ser Cys
        595                 600                 605

Pro Leu Asp Pro Ala Pro Leu Arg Glu Ala Gly Cys Pro Gln Gly Asp
    610                 615                 620

Thr Ala Gly Glu Ser Ser Trp Gly Ser Gly Pro Gly Ser Arg Pro Thr
625                 630                 635                 640

Ala Val Glu Gly Leu Ala Leu Gly Ser Ser Ala Ser Ser Ser Ser Glu
                645                 650                 655

Pro Pro Gln Ile Ile Ile Asn Pro Ala Arg Gln Lys Met Val Gln Lys
            660                 665                 670

Leu Ala Leu Tyr Glu Asp Gly Ala Leu Asp Ser Leu Gln Leu Leu Ser
        675                 680                 685

Ser Ser Ser Leu Pro Gly Leu Gly Leu Glu Gln Asp Arg Gln Gly Pro
    690                 695                 700

Glu Glu Ser Asp Glu Phe Gln Ser
705                 710
```

<210> SEQ ID NO 111
<211> LENGTH: 460
<212> TYPE: PRT
<213> ORGANISM: Homo sapiens

<400> SEQUENCE: 111

```
Met Asn Lys Pro Ile Thr Pro Ser Thr Tyr Val Arg Cys Leu Asn Val
1               5                   10                  15

Gly Leu Ile Arg Lys Leu Ser Asp Phe Ile Asp Pro Gln Glu Gly Trp
            20                  25                  30

Lys Lys Leu Ala Val Ala Ile Lys Lys Pro Ser Gly Asp Asp Arg Tyr
        35                  40                  45

Asn Gln Phe His Ile Arg Arg Phe Glu Ala Leu Leu Gln Thr Gly Lys
    50                  55                  60

Ser Pro Thr Ser Glu Leu Leu Phe Asp Trp Gly Thr Thr Asn Cys Thr
65                  70                  75                  80

Val Gly Asp Leu Val Asp Leu Ile Gln Asn Glu Phe Phe Ala Pro
                85                  90                  95

Ala Ser Leu Leu Leu Pro Asp Ala Val Pro Lys Thr Ala Asn Thr Leu
            100                 105                 110

Pro Ser Lys Glu Ala Ile Thr Val Gln Gln Lys Gln Met Pro Phe Cys
        115                 120                 125

Asp Lys Asp Arg Thr Leu Met Thr Pro Val Gln Asn Leu Glu Gln Ser
    130                 135                 140

Tyr Met Pro Pro Asp Ser Ser Pro Glu Asn Lys Ser Leu Glu Val
145                 150                 155                 160

Ser Asp Thr Arg Phe His Ser Phe Ser Phe Tyr Glu Leu Lys Asn Val
            165                 170                 175

Thr Asn Asn Phe Asp Glu Arg Pro Ile Ser Val Gly Gly Asn Lys Met
        180                 185                 190

Gly Glu Gly Gly Phe Gly Val Val Tyr Lys Gly Tyr Val Asn Asn Thr
    195                 200                 205

Thr Val Ala Val Lys Lys Leu Ala Ala Met Val Asp Ile Thr Thr Glu
210                 215                 220

Glu Leu Lys Gln Gln Phe Asp Gln Glu Ile Lys Val Met Ala Lys Cys
225                 230                 235                 240

Gln His Glu Asn Leu Val Glu Leu Leu Gly Phe Ser Ser Asp Gly Asp
            245                 250                 255

Asp Leu Cys Leu Val Tyr Val Tyr Met Pro Asn Gly Ser Leu Leu Asp
        260                 265                 270

Arg Leu Ser Cys Leu Asp Gly Thr Pro Pro Leu Ser Trp His Met Arg
    275                 280                 285

Cys Lys Ile Ala Gln Gly Ala Ala Asn Gly Ile Asn Phe Leu His Glu
290                 295                 300

Asn His His Ile His Arg Asp Ile Lys Ser Ala Asn Ile Leu Leu Asp
305                 310                 315                 320

Glu Ala Phe Thr Ala Lys Ile Ser Asp Phe Gly Leu Ala Arg Ala Ser
            325                 330                 335

Glu Lys Phe Ala Gln Thr Val Met Thr Ser Arg Ile Val Gly Thr Thr
        340                 345                 350

Ala Tyr Met Ala Pro Glu Ala Leu Arg Gly Glu Ile Thr Pro Lys Ser
    355                 360                 365

Asp Ile Tyr Ser Phe Gly Val Val Leu Leu Glu Ile Ile Thr Gly Leu
370                 375                 380
```

```
Pro Ala Val Asp Glu His Arg Glu Pro Gln Leu Leu Asp Ile Lys
385                 390                 395                 400

Glu Glu Ile Glu Asp Glu Glu Lys Thr Ile Glu Asp Tyr Ile Asp Lys
            405                 410                 415

Lys Met Asn Asp Ala Asp Ser Thr Ser Val Glu Ala Met Tyr Ser Val
                420                 425                 430

Ala Ser Gln Cys Leu His Glu Lys Lys Asn Lys Arg Pro Asp Ile Lys
            435                 440                 445

Lys Val Gln Gln Leu Leu Gln Glu Met Thr Ala Ser
    450                 455                 460

<210> SEQ ID NO 112
<211> LENGTH: 319
<212> TYPE: PRT
<213> ORGANISM: Artificial Sequence
<220> FEATURE:
<223> OTHER INFORMATION: Syntheisized

<400> SEQUENCE: 112

Met Asp Pro Gln Asn Gln His Gly Ser Gly Ser Ser Leu Val Val Ile
1               5                   10                  15

Gln Gln Pro Ser Leu Asp Ser Arg Gln Arg Leu Asp Tyr Glu Arg Glu
            20                  25                  30

Ile Gln Pro Thr Ala Ile Leu Ser Leu Asp Gln Ile Lys Ala Ile Arg
        35                  40                  45

Gly Ser Asn Glu Tyr Thr Glu Gly Pro Ser Val Val Lys Arg Pro Ala
    50                  55                  60

Pro Arg Thr Ala Pro Arg Gln Glu Lys His Glu Arg Thr His Glu Ile
65                  70                  75                  80

Ile Pro Ile Asn Val Asn Asn Tyr Glu His Arg His Thr Ser His
                85                  90                  95

Leu Gly His Ala Val Leu Pro Ser Asn Ala Arg Gly Pro Ile Leu Ser
            100                 105                 110

Arg Ser Thr Ser Thr Gly Ser Ala Ala Ser Ser Gly Ser Asn Ser Ser
        115                 120                 125

Ala Ser Ser Glu Gln Gly Leu Leu Gly Arg Ser Pro Pro Thr Arg Pro
    130                 135                 140

Val Pro Gly His Arg Ser Glu Arg Ala Ile Arg Thr Gln Pro Lys Gln
145                 150                 155                 160

Leu Ile Val Asp Asp Leu Lys Gly Ser Leu Lys Glu Asp Leu Thr Gln
                165                 170                 175

His Lys Phe Ile Cys Glu Gln Cys Gly Lys Cys Lys Cys Gly Glu Cys
            180                 185                 190

Thr Ala Pro Arg Thr Leu Pro Ser Cys Leu Ala Cys Asn Arg Gln Cys
        195                 200                 205

Leu Cys Ser Ala Glu Ser Met Val Glu Tyr Gly Thr Cys Met Cys Leu
    210                 215                 220

Val Lys Gly Ile Phe Tyr His Cys Ser Asn Asp Asp Glu Gly Asp Ser
225                 230                 235                 240

Tyr Ser Asp Asn Pro Cys Ser Cys Ser Gln Ser His Cys Cys Ser Arg
                245                 250                 255

Tyr Leu Cys Met Gly Ala Met Ser Leu Phe Leu Pro Cys Leu Leu Cys
            260                 265                 270

Tyr Pro Pro Ala Lys Gly Cys Leu Lys Leu Cys Arg Arg Cys Tyr Asp
        275                 280                 285
```

Trp Ile His Arg Pro Gly Cys Arg Cys Lys Asn Ser Asn Thr Val Tyr
290                 295                 300

Cys Lys Leu Glu Ser Cys Pro Ser Arg Gly Gln Gly Lys Pro Ser
305                 310                 315

<210> SEQ ID NO 113
<211> LENGTH: 315
<212> TYPE: PRT
<213> ORGANISM: Artificial Sequence
<220> FEATURE:
<223> OTHER INFORMATION: Syntheisized

<400> SEQUENCE: 113

Met Glu Ala Arg Ala Gln Ser Gly Asn Gly Ser Gln Pro Leu Leu Gln
1               5                   10                  15

Thr Pro Arg Asp Gly Gly Arg Gln Arg Gly Glu Pro Asp Pro Arg Asp
            20                  25                  30

Ala Leu Thr Gln Gln Val His Val Leu Ser Leu Asp Gln Ile Arg Ala
        35                  40                  45

Ile Arg Asn Thr Asn Glu Tyr Thr Glu Gly Pro Thr Val Val Pro Arg
    50                  55                  60

Pro Gly Leu Lys Pro Ala Pro Arg Pro Ser Thr Gln His Lys His Glu
65                  70                  75                  80

Arg Leu His Gly Leu Pro Glu His Arg Gln Pro Pro Arg Leu Gln His
                85                  90                  95

Ser Gln Val His Ser Ser Ala Arg Ala Pro Leu Ser Arg Ser Ile Ser
            100                 105                 110

Thr Val Ser Ser Gly Ser Arg Ser Thr Arg Thr Ser Thr Ser Ser
        115                 120                 125

Ser Ser Ser Glu Gln Arg Leu Leu Gly Ser Ser Phe Ser Ser Gly Pro
130                 135                 140

Val Ala Asp Gly Ile Ile Arg Val Gln Pro Lys Ser Glu Leu Lys Pro
145                 150                 155                 160

Gly Glu Leu Lys Pro Leu Ser Lys Glu Asp Leu Gly Leu His Ala Tyr
                165                 170                 175

Arg Cys Glu Asp Cys Gly Lys Cys Lys Cys Lys Glu Cys Thr Tyr Pro
            180                 185                 190

Arg Pro Leu Pro Ser Asp Trp Ile Cys Asp Lys Gln Cys Leu Cys Ser
        195                 200                 205

Ala Gln Asn Val Ile Asp Tyr Gly Thr Cys Val Cys Val Lys Gly
    210                 215                 220

Leu Phe Tyr His Cys Ser Asn Asp Asp Glu Asp Asn Cys Ala Asp Asn
225                 230                 235                 240

Pro Cys Ser Cys Ser Gln Ser His Cys Cys Thr Arg Trp Ser Ala Met
                245                 250                 255

Gly Val Met Ser Leu Phe Leu Pro Cys Leu Trp Cys Tyr Leu Pro Ala
            260                 265                 270

Lys Gly Cys Leu Lys Leu Cys Gln Gly Cys Tyr Asp Arg Val Asn Arg
        275                 280                 285

Pro Gly Cys Arg Cys Lys Asn Ser Asn Thr Val Cys Cys Lys Val Pro
    290                 295                 300

Thr Val Pro Pro Arg Asn Phe Glu Lys Pro Thr
305                 310                 315

<210> SEQ ID NO 114
<211> LENGTH: 319

```
<212> TYPE: PRT
<213> ORGANISM: Artificial Sequence
<220> FEATURE:
<223> OTHER INFORMATION: Syntheisized

<400> SEQUENCE: 114

Met Asp Pro Gln Asn Gln His Gly Ser Gly Ser Ser Leu Val Val Ile
1               5                   10                  15

Gln Gln Pro Ser Leu Asp Ser Arg Gln Arg Leu Asp Tyr Glu Arg Glu
            20                  25                  30

Ile Gln Pro Thr Ala Ile Leu Ser Leu Asp Gln Ile Lys Ala Ile Arg
        35                  40                  45

Gly Ser Asn Glu Pro Thr Glu Gly Pro Ser Val Val Lys Arg Pro Ala
    50                  55                  60

Pro Arg Thr Ala Pro Arg Gln Glu Lys His Glu Arg Thr His Glu Ile
65                  70                  75                  80

Ile Pro Ile Asn Val Asn Asn Asn Tyr Glu His Arg His Thr Ser His
                85                  90                  95

Leu Gly His Ala Val Leu Pro Ser Asn Ala Arg Gly Pro Ile Leu Ser
            100                 105                 110

Arg Ser Thr Ser Thr Gly Ser Ala Ala Ser Ser Gly Ser Asn Ser Ser
        115                 120                 125

Ala Ser Glu Gln Gly Leu Leu Gly Arg Ser Pro Pro Thr Arg Pro
    130                 135                 140

Val Pro Gly His Arg Ser Glu Arg Ala Ile Arg Thr Gln Pro Lys Gln
145                 150                 155                 160

Leu Ile Val Asp Asp Leu Lys Gly Ser Leu Lys Glu Asp Leu Thr Gln
                165                 170                 175

His Lys Phe Ile Cys Glu Gln Cys Gly Lys Cys Lys Cys Gly Glu Cys
            180                 185                 190

Thr Ala Pro Arg Thr Leu Pro Ser Cys Leu Ala Cys Asn Arg Gln Cys
        195                 200                 205

Leu Cys Ser Ala Glu Ser Met Val Glu Tyr Gly Thr Cys Met Cys Leu
    210                 215                 220

Val Lys Gly Ile Phe Tyr His Cys Ser Asn Asp Glu Gly Asp Ser
225                 230                 235                 240

Tyr Ser Asp Asn Pro Cys Ser Cys Ser Gln Ser His Cys Cys Ser Arg
                245                 250                 255

Tyr Leu Cys Met Gly Ala Met Ser Leu Phe Leu Pro Cys Leu Leu Cys
            260                 265                 270

Tyr Pro Pro Ala Lys Gly Cys Leu Lys Leu Cys Arg Arg Cys Tyr Asp
        275                 280                 285

Trp Ile His Arg Pro Gly Cys Arg Cys Lys Asn Ser Asn Thr Val Tyr
    290                 295                 300

Cys Lys Leu Glu Ser Cys Pro Ser Arg Gly Gln Gly Lys Pro Ser
305                 310                 315

<210> SEQ ID NO 115
<211> LENGTH: 315
<212> TYPE: PRT
<213> ORGANISM: Artificial Sequence
<220> FEATURE:
<223> OTHER INFORMATION: Syntheisized

<400> SEQUENCE: 115

Met Glu Ala Arg Ala Gln Ser Gly Asn Gly Ser Gln Pro Leu Leu Gln
1               5                   10                  15
```

```
Thr Pro Arg Asp Gly Gly Arg Gln Arg Gly Glu Pro Asp Pro Arg Asp
             20                  25                  30

Ala Leu Thr Gln Gln Val His Val Leu Ser Leu Asp Gln Ile Arg Ala
         35                  40                  45

Ile Arg Asn Thr Asn Glu Pro Thr Glu Gly Pro Thr Val Val Pro Arg
 50                  55                  60

Pro Gly Leu Lys Pro Ala Pro Arg Pro Ser Thr Gln His Lys His Glu
 65                  70                  75                  80

Arg Leu His Gly Leu Pro Glu His Arg Gln Pro Pro Arg Leu Gln His
                 85                  90                  95

Ser Gln Val His Ser Ser Ala Arg Ala Pro Leu Ser Arg Ser Ile Ser
            100                 105                 110

Thr Val Ser Ser Gly Ser Arg Ser Ser Thr Arg Thr Ser Thr Ser Ser
        115                 120                 125

Ser Ser Ser Glu Gln Arg Leu Leu Gly Ser Ser Phe Ser Ser Gly Pro
130                 135                 140

Val Ala Asp Gly Ile Ile Arg Val Gln Pro Lys Ser Glu Leu Lys Pro
145                 150                 155                 160

Gly Glu Leu Lys Pro Leu Ser Lys Glu Asp Leu Gly Leu His Ala Tyr
                165                 170                 175

Arg Cys Glu Asp Cys Gly Lys Cys Lys Cys Lys Glu Cys Thr Tyr Pro
            180                 185                 190

Arg Pro Leu Pro Ser Asp Trp Ile Cys Asp Lys Gln Cys Leu Cys Ser
        195                 200                 205

Ala Gln Asn Val Ile Asp Tyr Gly Thr Cys Val Cys Cys Val Lys Gly
    210                 215                 220

Leu Phe Tyr His Cys Ser Asn Asp Asp Glu Asp Asn Cys Ala Asp Asn
225                 230                 235                 240

Pro Cys Ser Cys Ser Gln Ser His Cys Cys Thr Arg Trp Ser Ala Met
                245                 250                 255

Gly Val Met Ser Leu Phe Leu Pro Cys Leu Trp Cys Tyr Leu Pro Ala
            260                 265                 270

Lys Gly Cys Leu Lys Leu Cys Gln Gly Cys Tyr Asp Arg Val Asn Arg
        275                 280                 285

Pro Gly Cys Arg Cys Lys Asn Ser Asn Thr Val Cys Cys Lys Val Pro
    290                 295                 300

Thr Val Pro Pro Arg Asn Phe Glu Lys Pro Thr
305                 310                 315

<210> SEQ ID NO 116
<211> LENGTH: 149
<212> TYPE: PRT
<213> ORGANISM: Homo sapiens

<400> SEQUENCE: 116

Leu Pro Tyr Asp Ala Phe Val Phe Asp Lys Thr Gln Ser Ala Val
1               5                  10                  15

Ala Asp Trp Val Tyr Asn Glu Leu Arg Gly Gln Leu Glu Glu Cys Arg
            20                  25                  30

Gly Arg Trp Ala Leu Arg Leu Cys Leu Glu Glu Arg Asp Trp Leu Pro
        35                  40                  45

Gly Lys Thr Leu Phe Glu Asn Leu Trp Ala Ser Val Tyr Gly Ser Arg
    50                  55                  60

Lys Thr Leu Phe Val Leu Ala His Thr Asp Arg Val Ser Gly Leu Leu
```

```
                65                  70                  75                  80
Arg Ala Ser Phe Leu Leu Ala Gln Gln Arg Leu Leu Glu Asp Arg Lys
                    85                  90                  95

Asp Val Val Leu Val Ile Leu Ser Pro Asp Gly Arg Arg Ser Arg
                    100                 105                 110

Tyr Val Arg Leu Arg Gln Arg Leu Cys Arg Gln Ser Val Leu Leu Trp
                    115                 120                 125

Pro His Gln Pro Ser Gly Gln Arg Ser Phe Trp Ala Gln Leu Gly Met
                    130                 135                 140

Ala Leu Thr Arg Asp
145

<210> SEQ ID NO 117
<211> LENGTH: 193
<212> TYPE: PRT
<213> ORGANISM: Homo sapiens

<400> SEQUENCE: 117

Gly Trp Asp Leu Trp Tyr Cys Phe His Leu Cys Leu Ala Trp Leu Pro
1               5                   10                  15

Trp Arg Gly Arg Gln Ser Gly Arg Asp Glu Asp Ala Leu Pro Tyr Asp
                    20                  25                  30

Ala Phe Val Val Phe Asp Lys Thr Gln Ser Ala Val Ala Asp Trp Val
                    35                  40                  45

Tyr Asn Glu Leu Arg Gly Gln Leu Glu Glu Cys Arg Gly Arg Trp Ala
                50                  55                  60

Leu Arg Leu Cys Leu Glu Arg Asp Trp Leu Pro Gly Lys Thr Leu
65                  70                  75                  80

Phe Glu Asn Leu Trp Ala Ser Val Tyr Gly Ser Arg Lys Thr Leu Phe
                    85                  90                  95

Val Leu Ala His Thr Asp Arg Val Ser Gly Leu Leu Arg Ala Ser Phe
                    100                 105                 110

Leu Leu Ala Gln Gln Arg Leu Leu Glu Asp Arg Lys Asp Val Val Val
                    115                 120                 125

Leu Val Ile Leu Ser Pro Asp Gly Arg Arg Ser Arg Tyr Val Arg Leu
                    130                 135                 140

Arg Gln Arg Leu Cys Arg Gln Ser Val Leu Leu Trp Pro His Gln Pro
145                 150                 155                 160

Ser Gly Gln Arg Ser Phe Trp Ala Gln Leu Gly Met Ala Leu Thr Arg
                    165                 170                 175

Asp Asn His His Phe Tyr Asn Arg Asn Phe Cys Gln Gly Pro Thr Ala
                    180                 185                 190

Glu

<210> SEQ ID NO 118
<211> LENGTH: 149
<212> TYPE: PRT
<213> ORGANISM: Homo sapiens

<400> SEQUENCE: 118

Leu Pro Tyr Asp Ala Phe Val Val Phe Asp Lys Thr Gln Ser Ala Val
1               5                   10                  15

Ala Asp Trp Val Tyr Asn Glu Leu Arg Gly Gln Leu Glu Glu Cys Arg
                    20                  25                  30

Gly Arg Trp Ala Leu Arg Leu Cys Leu Glu Glu Arg Asp Trp Leu Pro
                    35                  40                  45
```

```
Gly Lys Thr Leu Phe Glu Asn Leu Trp Ala Ser Val Tyr Gly Ser Arg
 50                  55                  60

Lys Thr Leu Phe Val Leu Ala His Thr Asp Arg Val Ser Gly Leu Leu
 65                  70                  75                  80

Arg Ala Ser Phe Leu Leu Ala Gln Gln Arg Leu Leu Glu Asp Arg Lys
                 85                  90                  95

Asp Val Val Leu Val Ile Leu Ser Pro Asp Gly Arg Arg Ser Arg
                100                 105                 110

Tyr Val Arg Leu Arg Gln Arg Leu Cys Arg Gln Ser Val Leu Leu Trp
            115                 120                 125

Pro His Gln Pro Ser Gly Gln Arg Ser Phe Trp Ala Gln Leu Gly Met
        130                 135                 140

Ala Leu Thr Arg Asp
145
```

<210> SEQ ID NO 119
<211> LENGTH: 712
<212> TYPE: PRT
<213> ORGANISM: Artificial Sequence
<220> FEATURE:
<223> OTHER INFORMATION: Syntheisized

<400> SEQUENCE: 119

```
Met Ala Gly Gly Pro Gly Pro Gly Glu Pro Ala Pro Gly Ala Gln
 1               5                  10                  15

His Phe Leu Tyr Glu Val Pro Pro Trp Val Met Cys Arg Phe Tyr Lys
                 20                  25                  30

Val Met Asp Ala Leu Glu Pro Ala Asp Trp Cys Gln Phe Ala Ala Leu
             35                  40                  45

Ile Val Arg Asp Gln Thr Glu Leu Arg Leu Cys Glu Arg Ser Gly Gln
 50                  55                  60

Arg Thr Ala Ser Val Leu Trp Pro Trp Ile Asn Arg Asn Ala Arg Val
 65                  70                  75                  80

Ala Asp Leu Val His Ile Leu Thr His Leu Gln Leu Leu Arg Ala Arg
                 85                  90                  95

Asp Ile Ile Thr Ala Trp His Pro Pro Ala Pro Leu Pro Ser Pro Gly
            100                 105                 110

Thr Thr Ala Pro Arg Pro Ser Ser Ile Pro Ala Pro Ala Glu Ala Glu
        115                 120                 125

Ala Trp Ser Pro Arg Lys Leu Pro Ser Ser Ala Ser Thr Phe Leu Ser
130                 135                 140

Pro Ala Phe Pro Gly Ser Gln Thr His Ser Gly Pro Glu Leu Gly Leu
145                 150                 155                 160

Val Pro Ser Pro Ala Ser Leu Trp Pro Pro Pro Ser Pro Ala Pro
                165                 170                 175

Ser Ser Thr Lys Pro Gly Pro Glu Ser Ser Val Ser Leu Leu Gln Gly
                180                 185                 190

Ala Arg Pro Phe Pro Phe Cys Trp Pro Leu Cys Glu Ile Ser Arg Gly
            195                 200                 205

Asp His Asn Phe Ser Glu Glu Leu Lys Ile Gly Glu Gly Gly Phe Gly
        210                 215                 220

Cys Val Tyr Arg Ala Val Met Arg Asn Thr Val Tyr Ala Val Lys Arg
225                 230                 235                 240

Leu Lys Glu Asn Ala Asp Leu Glu Trp Thr Ala Val Lys Gln Ser Phe
                245                 250                 255
```

```
Leu Thr Glu Val Glu Gln Leu Ser Arg Phe Arg His Pro Asn Ile Val
            260                 265                 270

Asp Phe Ala Gly Tyr Cys Ala Gln Asn Gly Phe Tyr Cys Leu Val Tyr
            275                 280                 285

Gly Phe Leu Pro Asn Gly Ser Leu Glu Asp Arg Leu His Cys Gln Thr
            290                 295                 300

Gln Ala Cys Pro Pro Leu Ser Trp Pro Gln Arg Leu Asp Ile Leu Leu
305                 310                 315                 320

Gly Thr Ala Arg Ala Ile Gln Phe Leu His Gln Asp Ser Pro Ser Leu
            325                 330                 335

Ile His Gly Asp Ile Lys Ser Ser Asn Val Leu Leu Asp Glu Arg Leu
            340                 345                 350

Thr Pro Lys Leu Gly Asp Phe Gly Leu Ala Arg Phe Ser Arg Phe Ala
            355                 360                 365

Gly Ser Ser Pro Ser Gln Ser Ser Met Val Ala Arg Thr Gln Thr Val
            370                 375                 380

Arg Gly Asp Leu Ala Tyr Leu Pro Glu Glu Tyr Ile Lys Thr Gly Arg
385                 390                 395                 400

Leu Ala Val Asp Thr Asp Thr Phe Ser Phe Gly Val Val Val Leu Glu
            405                 410                 415

Thr Leu Ala Gly Gln Arg Ala Val Lys Thr His Gly Ala Arg Thr Lys
            420                 425                 430

Tyr Leu Lys Asp Leu Val Glu Glu Ala Glu Ala Gly Val Ala
            435                 440                 445

Leu Arg Ser Thr Gln Ser Thr Leu Gln Ala Gly Leu Ala Ala Asp Ala
450                 455                 460

Trp Ala Ala Pro Ile Ala Met Gln Ile Tyr Lys Lys His Leu Asp Pro
465                 470                 475                 480

Arg Pro Gly Pro Cys Pro Pro Glu Leu Gly Leu Gly Leu Gln Leu
            485                 490                 495

Ala Cys Cys Cys Leu His Arg Arg Ala Lys Arg Arg Pro Pro Met Thr
            500                 505                 510

Gln Val Tyr Glu Arg Leu Glu Lys Leu Gln Ala Val Val Ala Gly Val
            515                 520                 525

Pro Gly His Ser Glu Ala Ala Ser Cys Ile Pro Pro Ser Pro Gln Glu
            530                 535                 540

Asn Ser Tyr Val Ser Ser Thr Gly Arg Ala His Ser Gly Ala Ala Pro
545                 550                 555                 560

Trp Gln Pro Leu Ala Ala Pro Ser Gly Ala Ser Ala Gln Ala Ala Glu
            565                 570                 575

Gln Leu Gln Arg Gly Pro Asn Gln Pro Val Glu Ser Asp Glu Ser Leu
            580                 585                 590

Gly Gly Leu Ser Ala Ala Leu Arg Ser Trp His Leu Thr Pro Ser Cys
            595                 600                 605

Pro Leu Asp Pro Ala Pro Leu Arg Glu Ala Gly Cys Pro Gln Gly Asp
            610                 615                 620

Thr Ala Gly Glu Ser Ser Trp Gly Ser Gly Pro Gly Ser Arg Pro Thr
625                 630                 635                 640

Ala Val Glu Gly Leu Ala Leu Gly Ser Ser Ala Ser Ser Ser Ser Glu
            645                 650                 655

Pro Pro Gln Ile Ile Ile Asn Pro Ala Arg Gln Lys Met Val Gln Lys
            660                 665                 670
```

```
Leu Ala Leu Tyr Glu Asp Gly Ala Leu Asp Ser Leu Gln Leu Leu Ser
            675                 680                 685

Ser Ser Ser Leu Pro Gly Leu Gly Leu Glu Gln Asp Arg Gln Gly Pro
    690                 695                 700

Glu Glu Ser Asp Glu Phe Gln Ser
705                 710

<210> SEQ ID NO 120
<211> LENGTH: 460
<212> TYPE: PRT
<213> ORGANISM: Artificial Sequence
<220> FEATURE:
<223> OTHER INFORMATION: Syntheisized

<400> SEQUENCE: 120

Met Asn Lys Pro Ile Thr Pro Ser Thr Tyr Val Arg Cys Leu Asn Val
1               5                   10                  15

Gly Leu Ile Arg Lys Leu Ser Asp Phe Ile Asp Pro Gln Glu Gly Trp
                20                  25                  30

Lys Lys Leu Ala Val Ala Ile Lys Lys Pro Ser Gly Asp Asp Arg Tyr
            35                  40                  45

Asn Gln Phe His Ile Arg Arg Phe Glu Ala Leu Leu Gln Thr Gly Lys
    50                  55                  60

Ser Pro Thr Ser Glu Leu Leu Phe Asp Trp Gly Thr Thr Asn Cys Thr
65                  70                  75                  80

Val Gly Asp Leu Val Asp Leu Leu Ile Gln Asn Glu Phe Phe Ala Pro
                85                  90                  95

Ala Ser Leu Leu Leu Pro Asp Ala Val Pro Lys Thr Ala Asn Thr Leu
            100                 105                 110

Pro Ser Lys Glu Ala Ile Thr Val Gln Gln Lys Gln Met Pro Phe Cys
    115                 120                 125

Asp Lys Asp Arg Thr Leu Met Thr Pro Val Gln Asn Leu Glu Gln Ser
130                 135                 140

Tyr Met Pro Pro Asp Ser Ser Pro Glu Asn Lys Ser Leu Glu Val
145                 150                 155                 160

Ser Asp Thr Arg Phe His Ser Phe Ser Phe Tyr Glu Leu Lys Asn Val
                165                 170                 175

Thr Asn Asn Phe Asp Glu Arg Pro Ile Ser Val Gly Gly Asn Lys Met
            180                 185                 190

Gly Glu Gly Gly Phe Gly Val Val Tyr Lys Gly Tyr Val Asn Asn Thr
    195                 200                 205

Thr Val Ala Val Lys Lys Leu Ala Ala Met Val Asp Ile Thr Thr Glu
210                 215                 220

Glu Leu Lys Gln Gln Phe Asp Gln Glu Ile Lys Val Met Ala Lys Cys
225                 230                 235                 240

Gln His Glu Asn Leu Val Glu Leu Leu Gly Phe Ser Ser Asp Gly Asp
                245                 250                 255

Asp Leu Cys Leu Val Tyr Val Tyr Met Pro Asn Gly Ser Leu Leu Asp
            260                 265                 270

Arg Leu Ser Cys Leu Asp Gly Thr Pro Pro Leu Ser Trp His Met Arg
    275                 280                 285

Cys Lys Ile Ala Gln Gly Ala Ala Asn Gly Ile Asn Phe Leu His Glu
290                 295                 300

Asn His His Ile His Arg Asp Ile Lys Ser Ala Asn Ile Leu Leu Asp
305                 310                 315                 320
```

```
Glu Ala Phe Thr Ala Lys Ile Ser Asp Phe Gly Leu Ala Arg Ala Ser
                325                 330                 335

Glu Lys Phe Ala Gln Glu Val Met Glu Glu Arg Ile Val Gly Thr Thr
            340                 345                 350

Ala Tyr Met Ala Pro Glu Ala Leu Arg Gly Glu Ile Thr Pro Lys Ser
            355                 360                 365

Asp Ile Tyr Ser Phe Gly Val Val Leu Leu Glu Ile Ile Thr Gly Leu
    370                 375                 380

Pro Ala Val Asp Glu His Arg Glu Pro Gln Leu Leu Asp Ile Lys
385                 390                 395                 400

Glu Glu Ile Glu Asp Glu Glu Lys Thr Ile Glu Asp Tyr Ile Asp Lys
                405                 410                 415

Lys Met Asn Asp Ala Asp Ser Thr Ser Val Glu Ala Met Tyr Ser Val
            420                 425                 430

Ala Ser Gln Cys Leu His Glu Lys Lys Asn Lys Arg Pro Asp Ile Lys
            435                 440                 445

Lys Val Gln Gln Leu Leu Gln Glu Met Thr Ala Ser
            450                 455                 460

<210> SEQ ID NO 121
<211> LENGTH: 503
<212> TYPE: PRT
<213> ORGANISM: Artificial Sequence
<220> FEATURE:
<223> OTHER INFORMATION: Syntheisized

<400> SEQUENCE: 121

Met Ala Leu Ala Pro Glu Arg Ala Pro Arg Val Leu Phe Gly Glu
1               5                   10                  15

Trp Leu Leu Gly Glu Ile Ser Ser Gly Cys Tyr Glu Gly Leu Gln Trp
            20                  25                  30

Leu Asp Glu Ala Arg Thr Cys Phe Arg Val Pro Trp Lys His Phe Ala
        35                  40                  45

Arg Lys Asp Leu Ser Glu Ala Asp Ala Arg Ile Phe Lys Ala Trp Ala
    50                  55                  60

Val Ala Arg Gly Arg Trp Pro Pro Ser Ser Arg Gly Gly Gly Pro Pro
65                  70                  75                  80

Pro Glu Ala Glu Thr Ala Glu Arg Ala Gly Trp Lys Thr Asn Phe Arg
                85                  90                  95

Cys Ala Leu Arg Ser Thr Arg Arg Phe Val Met Leu Arg Asp Asn Ser
            100                 105                 110

Gly Asp Pro Ala Asp Pro His Lys Val Tyr Ala Leu Ser Arg Glu Leu
        115                 120                 125

Cys Trp Arg Glu Gly Pro Gly Thr Asp Gln Thr Glu Ala Glu Ala Pro
    130                 135                 140

Ala Ala Val Pro Pro Gln Gly Gly Pro Gly Pro Phe Leu Ala
145                 150                 155                 160

His Thr His Ala Gly Leu Gln Ala Pro Gly Pro Leu Pro Ala Pro Ala
                165                 170                 175

Gly Asp Lys Gly Asp Leu Leu Leu Gln Ala Val Gln Gln Ser Cys Leu
            180                 185                 190

Ala Asp His Leu Leu Thr Ala Ser Trp Gly Ala Asp Pro Val Pro Thr
        195                 200                 205

Lys Ala Pro Gly Glu Gly Gln Glu Gly Leu Pro Leu Thr Gly Ala Cys
    210                 215                 220
```

```
Ala Gly Gly Pro Gly Leu Pro Ala Gly Glu Leu Tyr Gly Trp Ala Val
225                 230                 235                 240

Glu Thr Thr Pro Ser Pro Gly Pro Gln Pro Ala Ala Leu Thr Thr Gly
                245                 250                 255

Glu Ala Ala Pro Glu Ser Pro His Gln Ala Glu Pro Tyr Leu Ser
            260                 265                 270

Pro Ser Pro Ser Ala Cys Thr Ala Val Gln Glu Pro Ser Pro Gly Ala
        275                 280                 285

Leu Asp Val Thr Ile Met Tyr Lys Gly Arg Thr Val Leu Gln Lys Val
    290                 295                 300

Val Gly His Pro Ser Cys Thr Phe Leu Tyr Gly Pro Asp Pro Ala
305                 310                 315                 320

Val Arg Ala Thr Asp Pro Gln Gln Val Ala Phe Pro Ser Pro Ala Glu
                325                 330                 335

Leu Pro Asp Gln Lys Gln Leu Arg Tyr Thr Glu Glu Leu Leu Arg His
            340                 345                 350

Val Ala Pro Gly Leu His Leu Glu Leu Arg Gly Pro Gln Leu Trp Ala
        355                 360                 365

Arg Arg Met Gly Lys Cys Lys Val Tyr Trp Glu Val Gly Gly Pro Pro
    370                 375                 380

Gly Ser Ala Ser Pro Ser Thr Pro Ala Cys Leu Leu Pro Arg Asn Cys
385                 390                 395                 400

Asp Thr Pro Ile Phe Asp Phe Arg Val Phe Phe Gln Glu Leu Val Glu
                405                 410                 415

Phe Arg Ala Arg Gln Arg Arg Gly Ser Pro Arg Tyr Thr Ile Tyr Leu
            420                 425                 430

Gly Phe Gly Gln Asp Leu Ser Ala Gly Arg Pro Lys Glu Lys Ser Leu
        435                 440                 445

Val Leu Val Lys Leu Glu Pro Trp Leu Cys Arg Val His Leu Glu Gly
    450                 455                 460

Thr Gln Arg Glu Gly Val Ser Ser Leu Asp Ser Ser Glu Leu Glu Leu
465                 470                 475                 480

Cys Leu Ser Ser Ala Asn Ser Leu Tyr Asp Asp Ile Glu Cys Phe Leu
                485                 490                 495

Met Glu Leu Glu Gln Pro Ala
            500

<210> SEQ ID NO 122
<211> LENGTH: 319
<212> TYPE: PRT
<213> ORGANISM: Artificial Sequence
<220> FEATURE:
<223> OTHER INFORMATION: Syntheisized

<400> SEQUENCE: 122

Met Asp Pro Gln Asn Gln His Gly Ser Gly Ser Ser Leu Val Val Ile
1               5                   10                  15

Gln Gln Pro Ser Leu Asp Ser Arg Gln Arg Leu Asp Tyr Glu Arg Glu
                20                  25                  30

Ile Gln Pro Thr Ala Ile Leu Ser Leu Asp Gln Ile Lys Ala Ile Arg
            35                  40                  45

Gly Ser Asn Glu Pro Thr Glu Gly Pro Ser Val Val Lys Arg Pro Ala
        50                  55                  60

Pro Arg Thr Ala Pro Arg Gln Glu Lys His Glu Arg Thr His Glu Ile
65                  70                  75                  80
```

Ile Pro Ile Asn Val Asn Asn Tyr Glu His Arg His Thr Ser His
                85                  90                  95

Leu Gly His Ala Val Leu Pro Ser Asn Ala Arg Gly Pro Ile Leu Ser
            100                 105                 110

Arg Ser Thr Ser Thr Gly Ser Ala Ala Ser Ser Gly Ser Asn Ser Ser
        115                 120                 125

Ala Ser Ser Glu Gln Gly Leu Leu Gly Arg Ser Pro Thr Arg Pro
    130                 135                 140

Val Pro Gly His Arg Ser Glu Arg Ala Ile Thr Gln Pro Lys Gln
145                 150                 155                 160

Leu Ile Val Asp Asp Leu Lys Gly Ser Leu Lys Glu Asp Leu Thr Gln
                165                 170                 175

His Lys Phe Ile Cys Glu Gln Cys Gly Lys Cys Lys Cys Gly Glu Cys
            180                 185                 190

Thr Ala Pro Arg Thr Leu Pro Ser Cys Leu Ala Cys Asn Arg Gln Cys
        195                 200                 205

Leu Cys Ser Ala Glu Ser Met Val Glu Tyr Gly Thr Cys Met Cys Leu
    210                 215                 220

Val Lys Gly Ile Phe Tyr His Cys Ser Asn Asp Asp Glu Gly Asp Ser
225                 230                 235                 240

Tyr Ser Asp Asn Pro Cys Ser Cys Ser Gln Ser His Cys Cys Ser Arg
                245                 250                 255

Tyr Leu Cys Met Gly Ala Met Ser Leu Phe Leu Pro Cys Leu Leu Cys
            260                 265                 270

Tyr Pro Pro Ala Lys Gly Cys Leu Lys Leu Cys Arg Arg Cys Tyr Asp
        275                 280                 285

Trp Ile His Arg Pro Gly Cys Arg Cys Lys Asn Ser Asn Thr Val Tyr
    290                 295                 300

Cys Lys Leu Glu Ser Cys Pro Ser Arg Gly Gln Gly Lys Pro Ser
305                 310                 315

<210> SEQ ID NO 123
<211> LENGTH: 315
<212> TYPE: PRT
<213> ORGANISM: Artificial Sequence
<220> FEATURE:
<223> OTHER INFORMATION: Syntheisized

<400> SEQUENCE: 123

Met Glu Ala Arg Ala Gln Ser Gly Asn Gly Ser Gln Pro Leu Leu Gln
1               5                   10                  15

Thr Pro Arg Asp Gly Gly Arg Gln Arg Gly Glu Pro Asp Pro Arg Asp
                20                  25                  30

Ala Leu Thr Gln Gln Val His Val Leu Ser Leu Asp Gln Ile Arg Ala
            35                  40                  45

Ile Arg Asn Thr Asn Glu Pro Thr Glu Gly Pro Thr Val Val Pro Arg
        50                  55                  60

Pro Gly Leu Lys Pro Ala Pro Arg Pro Ser Thr Gln His Lys His Glu
65                  70                  75                  80

Arg Leu His Gly Leu Pro Glu His Arg Gln Pro Pro Arg Leu Gln His
                85                  90                  95

Ser Gln Val His Ser Ser Ala Arg Ala Pro Leu Ser Arg Ser Ile Ser
            100                 105                 110

Thr Val Ser Ser Gly Ser Arg Ser Ser Thr Arg Thr Thr Ser Ser
        115                 120                 125

```
Ser Ser Ser Glu Gln Arg Leu Leu Gly Ser Ser Phe Ser Ser Gly Pro
    130                 135                 140

Val Ala Asp Gly Ile Ile Arg Val Gln Pro Lys Ser Glu Leu Lys Pro
145                 150                 155                 160

Gly Glu Leu Lys Pro Leu Ser Lys Glu Asp Leu Gly Leu His Ala Tyr
                165                 170                 175

Arg Cys Glu Asp Cys Gly Lys Cys Lys Cys Lys Glu Cys Thr Tyr Pro
                180                 185                 190

Arg Pro Leu Pro Ser Asp Trp Ile Cys Asp Lys Gln Cys Leu Cys Ser
                195                 200                 205

Ala Gln Asn Val Ile Asp Tyr Gly Thr Cys Val Cys Cys Val Lys Gly
    210                 215                 220

Leu Phe Tyr His Cys Ser Asn Asp Asp Glu Asp Asn Cys Ala Asp Asn
225                 230                 235                 240

Pro Cys Ser Cys Ser Gln Ser His Cys Cys Thr Arg Trp Ser Ala Met
                245                 250                 255

Gly Val Met Ser Leu Phe Leu Pro Cys Leu Trp Cys Tyr Leu Pro Ala
                260                 265                 270

Lys Gly Cys Leu Lys Leu Cys Gln Gly Cys Tyr Asp Arg Val Asn Arg
                275                 280                 285

Pro Gly Cys Arg Cys Lys Asn Ser Asn Thr Val Cys Cys Lys Val Pro
    290                 295                 300

Thr Val Pro Pro Arg Asn Phe Glu Lys Pro Thr
305                 310                 315

<210> SEQ ID NO 124
<211> LENGTH: 503
<212> TYPE: PRT
<213> ORGANISM: Homo sapiens

<400> SEQUENCE: 124

Met Ala Leu Ala Pro Glu Arg Ala Ala Pro Arg Val Leu Phe Gly Glu
1               5                   10                  15

Trp Leu Leu Gly Glu Ile Ser Ser Gly Cys Tyr Glu Gly Leu Gln Trp
                20                  25                  30

Leu Asp Glu Ala Arg Thr Cys Phe Arg Val Pro Trp Lys His Phe Ala
                35                  40                  45

Arg Lys Asp Leu Ser Glu Ala Asp Ala Arg Ile Phe Lys Ala Trp Ala
    50                  55                  60

Val Ala Arg Gly Arg Trp Pro Pro Ser Ser Arg Gly Gly Gly Pro Pro
65                  70                  75                  80

Pro Glu Ala Glu Thr Ala Glu Arg Ala Gly Trp Lys Thr Asn Phe Arg
                85                  90                  95

Cys Ala Leu Arg Ser Thr Arg Arg Phe Val Met Leu Arg Asp Asn Ser
                100                 105                 110

Gly Asp Pro Ala Asp Pro His Lys Val Tyr Ala Leu Ser Arg Glu Leu
                115                 120                 125

Cys Trp Arg Glu Gly Pro Gly Thr Asp Gln Thr Glu Ala Glu Ala Pro
    130                 135                 140

Ala Ala Val Pro Pro Gln Gly Gly Pro Gly Pro Phe Leu Ala
145                 150                 155                 160

His Thr His Ala Gly Leu Gln Ala Pro Gly Pro Leu Pro Ala Pro Ala
                165                 170                 175

Gly Asp Lys Gly Asp Leu Leu Leu Gln Ala Val Gln Gln Ser Cys Leu
                180                 185                 190
```

```
Ala Asp His Leu Leu Thr Ala Ser Trp Gly Ala Asp Pro Val Pro Thr
        195                 200                 205
Lys Ala Pro Gly Glu Gly Gln Glu Gly Leu Pro Leu Thr Gly Ala Cys
210                 215                 220
Ala Gly Gly Pro Gly Leu Pro Ala Gly Glu Leu Tyr Gly Trp Ala Val
225                 230                 235                 240
Glu Thr Thr Pro Ser Pro Gly Pro Gln Pro Ala Ala Leu Thr Thr Gly
                245                 250                 255
Glu Ala Ala Ala Pro Glu Ser Pro His Gln Ala Glu Pro Tyr Leu Ser
            260                 265                 270
Pro Ser Pro Ser Ala Cys Thr Ala Val Gln Glu Pro Ser Pro Gly Ala
        275                 280                 285
Leu Asp Val Thr Ile Met Tyr Lys Gly Arg Thr Val Leu Gln Lys Val
    290                 295                 300
Val Gly His Pro Ser Cys Thr Phe Leu Tyr Gly Pro Pro Asp Pro Ala
305                 310                 315                 320
Val Arg Ala Thr Asp Pro Gln Gln Val Ala Phe Pro Ser Pro Ala Glu
                325                 330                 335
Leu Pro Asp Gln Lys Gln Leu Arg Tyr Thr Glu Glu Leu Leu Arg His
            340                 345                 350
Val Ala Pro Gly Leu His Leu Glu Leu Arg Gly Pro Gln Leu Trp Ala
        355                 360                 365
Arg Arg Met Gly Lys Cys Lys Val Tyr Trp Glu Val Gly Pro Pro
    370                 375                 380
Gly Ser Ala Ser Pro Ser Thr Pro Ala Cys Leu Leu Pro Arg Asn Cys
385                 390                 395                 400
Asp Thr Pro Ile Phe Asp Phe Arg Val Phe Phe Gln Glu Leu Val Glu
                405                 410                 415
Phe Arg Ala Arg Gln Arg Arg Gly Ser Pro Arg Tyr Thr Ile Tyr Leu
            420                 425                 430
Gly Phe Gly Gln Asp Leu Ser Ala Gly Arg Pro Lys Glu Lys Ser Leu
        435                 440                 445
Val Leu Val Lys Leu Glu Pro Trp Leu Cys Arg Val His Leu Glu Gly
    450                 455                 460
Thr Gln Arg Glu Gly Val Ser Ser Leu Asp Ser Ser Ser Leu Ser Leu
465                 470                 475                 480
Cys Leu Ser Ser Ala Asn Ser Leu Tyr Asp Asp Ile Glu Cys Phe Leu
                485                 490                 495
Met Glu Leu Glu Gln Pro Ala
            500

<210> SEQ ID NO 125
<211> LENGTH: 1107
<212> TYPE: DNA
<213> ORGANISM: Homo sapiens

<400> SEQUENCE: 125
atggtgctcg aggtgtccga ccatcaagtg ctgaacgatg ccgaggtggc tgctctgctg      60
gagaacttca gctccagcta cgattacgga gagaacgaga gcgacagctg ctgcaccagc     120
cctccttgcc ctcaagactt ctctctgaac ttcgatagag cctttctgcc cgccctctat     180
tctctgctgt ttctgctggg actgctgggc aatggagctg tggctgctgt gctgctgtct     240
aggagaacag ctctcagcag caccgataca tttctgctgc atctggccgt cgctgataca     300
```

```
ctgctggtgc tgacactccc tctctgggct gtggacgctg ctgtgcagtg ggtcttcgga    360
agcggcctct gtaaggtggc tggcgctctg ttcaacatca acttctacgc tggagctctg    420
ctgctggctt gtatttcctt cgatagatac ctcaatatcg tccacgccac ccagctctac    480
agaaggggac cccccgccag agtcacactg acatgtctgg ccgtgtgggg cctctgtctc    540
ctcttcgccc tccccgactt cattttcctg agcgctcacc acgacgagag gctgaacgcc    600
acccactgtc agtacaactt ccctcaagtg gaagaaccg ctctgagggt gctgcaactg     660
gtcgccggat ttctgctgcc tctgctggtc atggcttact gctacgccca cattctggcc    720
gtgctgctgg tgtccagagg acagagaaga ctcagagcca tgaggctcgt ggtggtcgtg    780
gtcgtggcct tcgctctgtg ctggaccect taccatctgg tggtgctggt ggacattctg    840
atggatctgg gcgctctggc tagaaactgc ggcagagagt ctaggtgga tgtggccaag     900 tccgtgacca gcggactggg ctacatgcac tgctgtctga atcctctgct gtacgctttc    960
gtcggcgtca agttcagaga gaggatgtgg atgctgctgc tcagactggg atgccccaac   1020 cagagggac tgcagaggca acccagcagc agcagaaggg attccagctg gagcgagacc   1080
agcgaagcca gctacagcgg cctgtga                                        1107

<210> SEQ ID NO 126
<211> LENGTH: 297
<212> TYPE: DNA
<213> ORGANISM: Homo sapiens

<400> SEQUENCE: 126
atgaaccaga ccgccattct gatctgctgt ctgatctttc tgacactgag cggcattcaa     60
ggcgtgcctc tgtccagaac cgtgagatgc acatgcatca gcatcagcaa ccagcccgtg    120
aaccctagat ctctggagaa gctcgagatc atccccgcta gccagttctg ccctagagtg    180
gagatcatcg ccaccatgaa gaagaagggc gagaagaggt gcctcaaccc cgagagcaag    240
gccatcaaga atctgctgaa agccgtgtcc aaggagagat ccaagaggag ccccggt       297

<210> SEQ ID NO 127
<211> LENGTH: 384
<212> TYPE: DNA
<213> ORGANISM: Homo sapiens

<400> SEQUENCE: 127
gccaccatga agaagagcgg cgtgctgttt ctgctgggca tcattctgct ggtgctgatc     60
ggagtgcaag gcacacccgt ggtgagaaag ggaagatgca gctgcatcag caccaaccaa    120
ggcaccatcc atctgcagtc tctgaaggac ctcaagcagt tcgcccccag ccccagctgc    180
gagaagatcg agatcatcgc cacactgaag aacggcgtgc agacatgtct gaaccccgac    240
agcgctgacg tgaaggagct gatcaagaag tgggagaagc aagtgtccca agaagaagaag    300 cagaagaacg caagaagca ccagaaaaag aaggtgctca agtgaggaa gtcccagaga      360 tccagacaga agaagaccac aggt                                          384

<210> SEQ ID NO 128
<211> LENGTH: 9654
<212> TYPE: DNA
<213> ORGANISM: Homo sapiens

<400> SEQUENCE: 128
gggcagagcg cacatcgccc acagtccccg agaagttggg gggaggggtc ggcaattgaa     60
ccggtgccta gagaaggtgg cgcggggtaa actgggaaag tgatgtcgtg tactggctcc    120
```

-continued

```
gccttttcc cgagggtggg ggagaaccgt atataagtgc agtagtcgcc gtgaacgttc      180
tttttcgcaa cgggtttgcc gccagaacac aggtaagtgc cgtgtgtggt tcccgcgggc      240
ctggcctctt tacgggttat ggcccttgcg tgccttgaat tacttccacc tggctgcagt      300
acgtgattct tgatcccgag cttcggggtg aagtgggtg ggagagttcg aggccttgcg       360
cttaaggagc cccttcgcct cgtgcttgag ttgaggcctg gcctgggcgc tggggccgcc      420
gcgtgcgaat ctggtggcac cttcgcgcct gtctcgctgc tttcgataag tctctagcca      480
tttaaaattt ttgatgacct gctgcgacgc ttttttttctg gcaagatagt cttgtaaatg     540
cgggccaaga tctgcacact ggtatttcgg tttttgggggc cgcgggcggc gacgggccc      600 gtgcgtccca gcgcacatgt tcggcgaggc ggggcctgcg agcgcggcca ccgagaatcg      660 gacggggta gtctcaagct ggccggcctg ctctggtgcc tggcctcgcg ccgccgtgta       720
tcgccccgcc ctgggcggca aggctggccc ggtcggcacc agttgcgtga gcggaaagat      780
ggccgcttcc cggccctgct gcaggagagct caaaatggag gacgcggcgc tcgggagagc     840
gggcgggtga gtcacccaca caaaggaaaa gggcctttcc gtcctcagcc gtcgcttcat      900
gtgactccac ggagtaccgg gcgccgtcca ggcacctcga ttagttctcg agcttttgga      960
gtacgtcgtc tttaggttgg ggggaggggt tttatgcgat ggagtttccc cacactgagt      1020
gggtggagac tgaagttagg ccagcttggc acttgatgta attctccttg gaatttgccc      1080
tttttgagtt tggatcttgg ttcattctca agcctcagac agtggttcaa agtttttttc      1140
ttccatttca ggtgtcgtga ggatccgcca ccatggcctt accagtgacc gccttgctcc      1200
tgccgctggc cttgctgctc cacgccgcca ggccggatat ccagatgacc cagagcccga     1260
gcagcctgag cgcgagcgtg ggtgatcgcg tgaccattac ctgcagggca agtcaggaca     1320
ttagtaaata tttaaattgg tatcagcaga aaccgggtaa agcgccgaaa ctgttaattt     1380
atcatacatc aagattacac tcaggcgtgc cgtcgcgttt tagcggctcg ggttcgggca     1440
ccgattttac cctgaccatc tcgagcttgc agccggagga cttcgccacc tactattgcc     1500
aacagggtaa tacgcttccg tacacgttcg gtcagggcac caaagtggag atcaaaggtg     1560
gcggtggctc gggcggtggt gggtcgggtg gcggcggatc tgaggtgcag ctggtggagt     1620 ctggggggagg cttggtacag cctgggggggt ccctgagact ctcctgtgca gcctctggag    1680
tgtccctgcc tgattatggc gtgtcctggg tccgccaggc tccagggaag gggctggagt     1740
gggtttcagt gatctggggc agcgagacaa cctactacaa cagcgccctg aagtcccgat     1800
tcaccatctc cagagacaat gccaagaact cactgtatct gcaaatgaac agcctgagag    1860
ccgaggacac ggctgtgtat tactgtgcga agcactacta ctacggcggc agctacgcta    1920
tggactactg gggccaagga accctggtca ccgtgtcctc aaccacgacg ccagcgccgc    1980
gaccaccaac accggcgccc accatcgcgt cgcagcccct gtcctgcgc ccagaggcgt      2040 gccgccagc ggcgggggc gcagtgcaca cgaggggggct ggacttcgcc tgtgatatct      2100
acatctgggc gcccttggcc gggacttgtg gggtccttct cctgtcactg gttatcaccc    2160
tttactgctt ttgggtgctg gtggtggttg gtggagtcct ggcttgctat agcttgctag    2220
taacagtggc ctttattatt ttctgggtga ggagtaagag gagcaggctc ctgcacagtg    2280
actacatgaa catgactccc cgccgccccg ggcccacccg caagcattac cagccctatg    2340
ccccaccacg cgacttcgca gcctatcgct ccagagtgaa gttcagcagg agcgcagacg    2400
cccccgcgta ccagcagggc cagaaccagc tctataacga gctcaatcta ggacgaagag    2460
```

```
aggagtacga tgttttggac aagaggcgtg gccgggaccc tgagatgggg ggaaagccga   2520
gaaggaagaa ccctcaggaa ggcctgtaca atgaactgca gaaagataag atggcggagg   2580
cctacagtga gattgggatg aaaggcgagc gccggagggg caaggggcac gatggccttt   2640
accagggtct cagtcagcc accaaggaca cctacgacgc ccttcacatg caggccctgc    2700
cccctcgcgg ttccggagcc acgaacttct ctctgttaaa gcaagcagga gacgtggaag   2760
aaaaccccgg tcctatgagg tggtgtctgc tgctgatctg ggctcaagga ctgagacaag   2820
cccctctggc ctccggcatg atgaccggca ccatcgagac caccggcaac atcagcgccg   2880
agaagggcgg cagcatcatt ctgcagtgtc atctgagctc caccacagcc caagtgacac   2940
aagtgaattg ggagcagcaa gaccaactgc tggccatctg caatgccgat ctgggatggc   3000
atatctcccc ctccttcaaa gatagagtgg ctcccggccc cggactggga ctgaccctcc   3060
agtctctgac agtgaatgat accggcgagt acttctgcat ctaccacaca taccccgacg   3120
gcacctatac cggcagaatc tttctggagg tgctcgagag cagcgtggcc gaacacggag   3180
ccagattcca aatccctctg ctgggagcca tggccgctac actggtggtg atttgcaccg   3240
ccgtgatcgt cgtcgtggct ctgacaagaa agaaaaaggc tctgaggatc cacagcgtgg   3300
agggcgatct cagaaggaaa agcgctggac aagaggaatg gagccctagc gctccttccc   3360 ccccggcag ctgtgtccaa gccgaagctg ctcccgccgg actgtgtgga gagcagagag    3420
gagaggattg cgctgaactg cacgactact tcaacgtgct gagctataga tctctgggca   3480
actgcagctt ctttaccgag accggctgag tcgactctag aactagtaat caacctctgg   3540
attacaaaat ttgtgaaaga ttgactggta ttcttaacta tgttgctcct tttacgctat   3600
gtggatacgc tgctttaatg cctttgtatc atgctattgc ttcccgtatg gctttcattt   3660
tctcctcctt gtataaatcc tggttgctgt ctctttatga ggagttgtgg cccgttgtca   3720
ggcaacgtgg cgtggtgtgc actgtgtttg ctgacgcaac ccccactggt tggggcattg   3780
ccaccacctg tcagctcctt tccgggactt tcgctttccc cctccctatt gccacgcgg    3840 aactcatcgc cgcctgcctt gcccgctgct ggacaggggc tcggctgttg ggcactgaca   3900
attccgtggt gttgtcgggg aaatcatcgt ccttccttg gctgctcgcc tgtgttgcca    3960
cctggattct gcgcgggacg tccttctgct acgtcccttc ggccctcaat ccagcggacc   4020
ttccttcccg cggcctgctg ccggctctgc ggcctcttcc gcgtcttcgc cttcgccctc   4080
agacgagtcg gatctcccct tgggccgcct cccgcctgc gcggaattc gagctcggta    4140 cctttaagac caatgactta caaggcagct gtagatctta gccactttt aaaagaaaag    4200 gggggactgg aagggctaat tcactcccaa cgaagacaag atctgctttt tgcttgtact   4260
gggtctctct ggttagacca gatctgagcc tgggagctct ctggctaact agggaaccca   4320
ctgcttaagc ctcaataaag cttgccttga gtgcttcaag tagtgtgtgc ccgtctgttg   4380
tgtgactctg gtaactagag atccctcaga cccttttagt cagtgtggaa aatctctagc   4440
agtagtagtt catgtcatct tattattcag tatttataac ttgcaaagaa atgaatatca   4500
gagagtgaga ggaacttgtt tattgcagct tataatggtt acaaataaag caatagcatc   4560
acaaatttca caaataaagc attttttca ctgcattcta ttgtggttt gtccaaactc     4620 atcaatgtat cttatcatgt ctggctctag ctatcccgcc cctaactccg cccatcccgc   4680
ccctaactcc gcccagttcc gcccattctc cgccccatgg ctgactaatt ttttttattt   4740
atgcagaggc cgaggccgcc tcggcctctg agctattcca gaagtagtga ggaggctttt   4800
ttggaggcct agggacgtac ccaattcgcc ctatagtgag tcgtattacg cgcgctcact   4860
```

-continued

```
ggccgtcgtt ttacaacgtc gtgactggga aaaccctggc gttacccaac ttaatcgcct   4920
tgcagcacat ccccctttcg ccagctggcg taatagcgaa gaggcccgca ccgatcgccc   4980
ttcccaacag ttgcgcagcc tgaatggcga atgggacgcg ccctgtagcg gcgcattaag   5040
cgcggcgggt gtggtggtta cgcgcagcgt gaccgctaca cttgccagcg ccctagcgcc   5100
cgctcctttc gctttcttcc cttcctttct cgccacgttc gccggctttc cccgtcaagc   5160
tctaaatcgg gggctccctt tagggttccg atttagtgct ttacggcacc tcgaccccaa   5220
aaaacttgat tagggtgatg gttcacgtag tgggccatcg ccctgataga cggttttttcg   5280
cccttttgacg ttggagtcca cgttctttaa tagtggactc ttgttccaaa ctggaacaac   5340
actcaaccct atctcggtct attctttga ttttataaggg attttgccga tttcggccta   5400
ttggttaaaa aatgagctga tttaacaaaa atttaacgcg aattttaaca aaatattaac   5460
gcttacaatt taggtggcac ttttcgggga aatgtgcgcg gaacccctat ttgtttattt   5520
ttctaaatac attcaaatat gtatccgctc atgagacaat aaccctgata aatgcttcaa   5580
taatattgaa aaaggaagag tatgagccat attcaacggg aaacgtcttg ctctaggccg   5640
cgattaaatt ccaacatgga tgctgattta tatgggtata aatgggctcg cgataatgtc   5700
gggcaatcag gtgcgacaat ctatcgattg tatgggaagc ccgatgcgcc agagttgttt   5760
ctgaaacatg gcaaaggtag cgttgccaat gatgttacag atgagatggt cagactaaac   5820
tggctgacgg aatttatgcc tcttccgacc atcaagcatt ttatccgtac tcctgatgat   5880
gcatggttac tcaccactgc gatccccggg aaaacagcat tccaggtatt agaagaatat   5940
cctgattcag gtgaaaatat tgttgatgcg ctggcagtgt tcctgcgccg gttgcattcg   6000
attcctgttt gtaattgtcc ttttaacagc gatcgcgtat ttcgtctggc tcaggcgcaa   6060
tcacgaatga ataacggttt ggttgatgcg agtgattttg atgacgagcg taatggctgg   6120
cctgttgaac aagtctggaa agaaatgcat aaacttttgc cattctcacc ggattcagtc   6180
gtcactcatg gtgatttctc acttgataac cttatttttg acgaggggaa attaataggt   6240
tgtattgatg ttggacgagt cggaatcgca gaccgatacc aggatcttgc catcctatgg   6300
aactgcctcg gtgagttttc tccttcatta cagaaacggc ttttttcaaaa atatggtatt   6360
gataatcctg atatgaataa attgcagttt catttgatgc tcgatgagtt tttctaactg   6420
tcagaccaag tttactcata tatactttag attgatttaa aacttcattt ttaatttaaa   6480
aggatctagg tgaagatcct ttttgataat ctcatgacca aaatccctta acgtgagttt   6540
tcgttccact gagcgtcaga ccccgtagaa aagatcaaag gatcttcttg agatcctttt   6600
tttctgcgcg taatctgctg cttgcaaaca aaaaaaccac cgctaccagc ggtggtttgt   6660
ttgccggatc aagagctacc aactcttttt ccgaaggtaa ctggcttcag cagagcgcag   6720
ataccaaata ctgttcttct agtgtagccg tagttaggcc accacttcaa gaactctgta   6780
gcaccgccta catacctcgc tctgctaatc ctgttaccag tggctgctgc cagtggcgat   6840
aagtcgtgtc ttaccgggtt ggactcaaga cgatagttac cggataaggc gcagcggtcg   6900
ggctgaacgg ggggttcgtg cacacagccc agcttggagc gaacgaccta caccgaactg   6960
agatacctac agcgtgagct atgagaaagc gccacgcttc ccgaagggag aaaggcggac   7020
aggtatccgg taagcggcag ggtcggaaca ggagagcgca cgagggagct tccaggggga   7080
aacgcctggt atctttatag tcctgtcggg tttcgccacc tctgacttga gcgtcgattt   7140
ttgtgatgct cgtcaggggg gcggagccta tggaaaaacg ccagcaacgc ggcctttta   7200
```

```
cggttcctgg cctttttgctg gccttttgct cacatgttct ttcctgcgtt atccctgat    7260
tctgtggata accgtattac cgcctttgag tgagctgata ccgctcgccg cagccgaacg    7320
accgagcgca gcgagtcagt gagcgaggaa gcggaagagc gcccaatacg caaaccgcct    7380
ctccccgcgc gttggccgat tcattaatgc agctggcacg acaggtttcc cgactggaaa    7440
gcgggcagtg agcgcaacgc aattaatgtg agttagctca ctcattaggc accccaggct    7500
ttacacttta tgcttccggc tcgtatgttg tgtggaattg tgagcggata acaatttcac    7560
acaggaaaca gctatgacca tgattacgcc aagcgcgcaa ttaaccctca ctaaagggaa    7620
caaaagctgg agctgcaagc ttaatgtagt cttatgcaat actcttgtag tcttgcaaca    7680
tggtaacgat gagttagcaa catgccttac aaggagagaa aaagcaccgt gcatgccgat    7740
tggtggaagt aaggtggtac gatcgtgcct tattaggaag gcaacagacg ggtctgacat    7800
ggattggacg aaccactgaa ttgccgcatt gcagagatat tgtatttaag tgcctagctc    7860
gatacataaa cgggtctctc tggttagacc agatctgagc ctgggagctc tctggctaac    7920
tagggaaccc actgcttaag cctcaataaa gcttgccttg agtgcttcaa gtagtgtgtg    7980
cccgtctgtt gtgtgactct ggtaactaga tccctcag accctttag tcagtgtgga    8040
aaatctctag cagtggcgcc cgaacaggga cttgaaagcg aaagggaaac cagaggagct    8100
ctctcgacgc aggactcggc ttgctgaagc gcgcacggca agaggcgagg ggcggcgact    8160
ggtgagtacg ccaaaaattt tgactagcgg aggctagaag agagagatg ggtgcgagag    8220
cgtcagtatt aagcggggga gaattagatc gcgatgggaa aaaattcggt taaggccagg    8280
gggaagaaa aatataaat taaaacatat agtatgggca agcagggagc tagaacgatt    8340
cgcagttaat cctggcctgt tagaaacatc agaaggctgt agacaaatac tgggacagct    8400
acaaccatcc cttcagacag gatcagaaga acttagatca ttatataata cagtagcaac    8460
cctctattgt gtgcatcaaa ggatagagat aaaagacacc aaggaagctt tagacaagat    8520
agaggaagag caaaacaaaa gtaagaccac cgcacagcaa gcggccgctg atcttcagac    8580
ctggaggagg agatatgagg gacaattgga gaagtgaatt atataaatat aaagtagtaa    8640
aaattgaacc attaggagta gcacccacca aggcaaagag aagagtggtg cagagagaaa    8700
aaagagcagt gggaatagga gctttgttcc ttgggttctt gggagcagca ggaagcacta    8760
tgggcgcagc gtcaatgacg ctgacggtac aggccagaca attattgtct ggtatagtgc    8820
agcagcagaa caatttgctg agggctattg aggcgcaaca gcatctgttg caactcacag    8880
tctgggcat caagcagctc caggcaagaa tcctggctgt ggaaagatac ctaaaggatc    8940
aacagctcct ggggatttgg ggttgctctg gaaaactcat ttgcaccact gctgtgcctt    9000
ggaatgctag ttggagtaat aaatctctgg aacagatttg gaatcacacg acctggatgg    9060
agtgggacag agaaattaac aattacacaa gcttaataca ctccttaatt gaagaatcgc    9120
aaaaccagca agaaaagaat gaacaagaat tattggaatt agataaatgg gcaagtttgt    9180
ggaattggtt taacataaca aattggctgt ggtatataaa attattcata atgatagtag    9240
gaggcttggt aggtttaaga atagttttttg ctgtactttc tatagtgaat agagttaggc    9300
agggatattc accattatcg tttcagaccc acctcccaac cccgagggga cccgacaggc    9360
ccgaaggaat agaagaagaa ggtggagaga gagacagaga cagatccatt cgattagtga    9420
acggatctcg acggtatcga tcacgagact agcctcgaca caaatggcag tattcatcca    9480
caattttaaa agaaaggggg ggattggggg gtacagtgca ggggaaagaa tagtagacat    9540
aatagcaaca gacatacaaa ctaaagaatt acaaaaacaa attacaaaaa ttcaaaattt    9600
```

```
tcgggtttat tacagggaca gcagaaatcc actttggctc gagaagcttg atat        9654
```

<210> SEQ ID NO 129
<211> LENGTH: 9417
<212> TYPE: DNA
<213> ORGANISM: Homo sapiens

<400> SEQUENCE: 129

```
gggcagagcg cacatcgccc acagtccccg agaagttggg gggagggtc ggcaattgaa     60
ccggtgccta gagaaggtgg cgcggggtaa actgggaaag tgatgtcgtg tactggctcc    120
gccttttcc cgagggtggg ggagaaccgt atataagtgc agtagtcgcc gtgaacgttc    180
tttttcgcaa cgggtttgcc gccagaacac aggtaagtgc cgtgtgtggt tcccgcgggc    240
ctggcctctt tacgggttat ggcccttgcg tgccttgaat tacttccacc tggctgcagt    300
acgtgattct tgatcccgag cttcgggttg aagtgggtg ggagagttcg aggccttgcg    360
cttaaggagc cccttcgcct cgtgcttgag ttgaggcctg gcctgggcgc tggggccgcc    420
gcgtgcgaat ctggtggcac cttcgcgcct gtctcgctgc tttcgataag tctctagcca    480
tttaaaattt ttgatgacct gctgcgacgc ttttttttctg gcaagatagt cttgtaaatg    540
cgggccaaga tctgcacact ggtatttcgg ttttgtgggc cgcgggcggc gacggggccc    600
gtgcgtccca gcgcacatgt tcggcgaggc ggggcctgcg agcgcggcca ccgaaaatcg    660
gacgggggta gtctcaagct ggccggcctg ctctggtgcc tggcctcgcg ccgccgtgta    720
tcgccccgcc ctgggcggca aggctggccc ggtcggcacc agttgcgtga gcggaaagat    780
ggccgcttcc cggccctgct gcagggagct caaaatggag gacgcggcgc tcgggagagc    840
gggcgggtga gtcacccaca caaaggaaaa gggcctttcc gtcctcagcc gtcgcttcat    900
gtgactccac ggagtaccgg cgccgtcca ggcacctcga ttagttctcg agcttttgga    960
gtacgtcgtc tttaggttgg ggggaggggt tttatgcgat ggagtttccc cacactgagt   1020
gggtggagac tgaagttagg ccagcttggc acttgatgta attctccttg gaatttgccc   1080
tttttgagtt tggatcttgg ttcattctca agcctcagac agtggttcaa agttttttc    1140
ttccatttca ggtgtcgtga ggatccgcca ccatggcctt accagtgacc gccttgctcc   1200
tgccgctggc cttgctgctc cacgccgcca ggccggatat ccagatgacc cagagcccga   1260
gcagcctgag cgcgagcgtg ggtgatcgcg tgaccattac ctgcagggca gtcaggaca   1320
ttagtaaata tttaaattgg tatcagcaga accgggtaa agcgccgaaa ctgttaattt    1380
atcatacatc aagattacac tcaggcgtgc cgtcgcgttt tagcggctcg ggttcgggca   1440
ccgattttac cctgaccatc tcgagcttgc agccggagga cttcgccacc tactattgcc   1500
aacagggtaa tacgcttccg tacacgttcg gtcaggcac caaagtggag atcaaaggtg   1560
gcggtggctc gggcggtggt gggtcggtg gcggcggatc tgaggtgcag ctggtggagt   1620
ctgggggagg cttggtacag cctgggggt ccctgagact ctcctgtgca gcctctggag   1680
tgtccctgcc tgattatggc gtgtcctggg tccgccaggc tccagggaag gggctggagt   1740
gggtttcagt gatctggggc agcgagacaa cctactacaa cagcgccctg aagtcccgat   1800
tcaccatctc cagagacaat gccaagaact cactgtatct gcaaatgaac agcctgagag   1860
ccgaggacac ggctgtgtat tactgtgcga agcactacta ctacggcggc agctacgcta   1920
tggactactg gggccaagga accctggtca ccgtgtcctc aaccacgacg ccagcgccgc   1980
gaccaccaac accggcgccc accatcgcgt cgcagcccct gtccctgcgc ccagaggcgt   2040
```

-continued

```
gccggccagc ggcgggggc gcagtgcaca cgagggggct ggacttcgcc tgtgatatct      2100
acatctgggc gcccttggcc gggacttgtg gggtccttct cctgtcactg gttatcaccc      2160
tttactgctt ttgggtgctg gtggtggttg gtggagtcct ggcttgctat agcttgctag      2220
taacagtggc cttttattatt ttctgggtga ggagtaagag gagcaggctc ctgcacagtg     2280
actacatgaa catgactccc cgccgccccg ggcccacccg caagcattac cagccctatg      2340
ccccaccacg cgacttcgca gcctatcgct ccagagtgaa gttcagcagg agcgcagacg      2400
cccccgcgta ccagcagggc cagaaccagc tctataacga gctcaatcta ggacgaagag      2460
aggagtacga tgttttggac aagaggcgtg gccgggaccc tgagatgggg ggaaagccga      2520
gaaggaagaa ccctcaggaa ggcctgtaca atgaactgca gaaagataag atggcggagg      2580
cctacagtga gattgggatg aaaggcgagc gccggagggg caaggggcac gatggccttt      2640
accagggtct cagtacagcc accaaggaca cctacgacgc ccttcacatg caggccctgc      2700
cccctcgcgg ttccggagcc acgaacttct ctctgttaaa gcaagcagga gacgtggaag      2760
aaaaccccgg tcctatgaga tggtgtctgc tgctgatctg ggcccaaggc ctcagacaag      2820
cccctctggc cagcggaatg atgaccggcc catcgagac caccggcaac atctccgccg      2880
agaagggcgg cagcattatt ctgcagtgcc atctgtccag caccaccgcc caagtgaccc      2940
aagtgaactg ggagcagcaa gaccagctgc tggccatctg caacgccgat ctgggctggc      3000
acattagccc ttccttcaag gacagagtcg ctcccggccc cggactggga ctgacactgc      3060
agtctctgac agtcaacgac accggcgagt acttctgcat ctaccacacc taccccgacg      3120
gcacctacac cggcagaatc tttctggagg tgctggagtc cagcgtggcc gaacatggcg      3180
ctagattcca gatccctctg ctgggcgcca tggctgctac actggtggtc atctgcaccg      3240
ccgtgatcgt cgtcgtggct ctgaccagat aagtcgactc tagaactagt aatcaacctc      3300
tggattacaa aatttgtgaa agattgactg gtattcttaa ctatgttgct ccttttacgc      3360
tatgtggata cgctgcttta atgcctttgt atcatgctat tgcttcccgt atggctttca      3420
ttttctcctc cttgtataaa tcctggttgc tgtctcttta tgaggagttg tggcccgttg      3480
tcaggcaacg tggcgtggtg tgcactgtgt ttgctgacgc aacccccact ggttggggca      3540
ttgccaccac ctgtcagctc ctttccggga ctttcgcttt ccccctccct attgccacgg      3600
cggaactcat cgccgcctgc cttgcccgct gctggacagg ggctcggctg ttgggcactg      3660
acaattccgt ggtgttgtcg gggaaatcat cgtcctttcc ttggctgctc gcctgtgttg      3720
ccacctggat tctgcgcggg acgtccttct gctacgtccc ttcggccctc aatccagcgg      3780
accttccttc ccgcggcctg ctgccggctc tgcggcctct tccgcgtctt cgccttcgcc      3840
ctcagacgag tcggatctcc ctttgggccg cctccccgcc tgccgcggaa ttcgagctcg      3900
gtacctttaa gaccaatgac ttacaaggca gctgtagatc ttagccactt tttaaagaa      3960 aagggggac tggaagggct aattcactcc caacgaagac aagatctgct ttttgcttgt       4020
actgggtctc tctggttaga ccagatctga gcctgggagc tctctggcta actagggaac       4080
ccactgctta agcctcaata aagcttgcct tgagtgcttc aagtagtgtg tgcccgtctg      4140
ttgtgtgact ctggtaacta gagatccctc agaccctttt agtcagtgtg gaaaatctct      4200
agcagtagta gttcatgtca tcttattatt cagtatttat aacttgcaaa gaaatgaata     4260
tcagagagtg agaggaactt gtttattgca gcttataatg gttacaaata aagcaatagc     4320
atcacaaatt tcacaaataa agcattttttt tcactgcatt ctagttgtgg tttgtccaaa    4380
ctcatcaatg tatcttatca tgtctggctc tagctatccc gcccctaact ccgcccatcc    4440
```

```
cgcccctaac tccgcccagt tccgcccatt ctccgcccca tggctgacta attttttta    4500
tttatgcaga ggccgaggcc gcctcggcct ctgagctatt ccagaagtag tgaggaggct   4560
tttttggagg cctagggacg tacccaattc gccctatagt gagtcgtatt acgcgcgctc   4620
actggccgtc gttttacaac gtcgtgactg ggaaaaccct ggcgttaccc aacttaatcg   4680
ccttgcagca catccccctt cgccagctg gcgtaatagc gaagaggccc gcaccgatcg    4740
cccttcccaa cagttgcgca gcctgaatgg cgaatgggac gcgccctgta gcggcgcatt   4800
aagcgcggcg ggtgtggtgg ttacgcgcag cgtgaccgct acacttgcca gcgccctagc   4860
gcccgctcct ttcgctttct tcccttcctt tctcgccacg ttcgccggct ttccccgtca   4920
agctctaaat cgggggctcc ctttagggtt ccgatttagt gctttacggc acctcgaccc   4980
caaaaaactt gattagggtg atggttcacg tagtgggcca tcgccctgat agacggtttt   5040
tcgccctttg acgttggagt ccacgttctt taatagtgga ctcttgttcc aaactggaac   5100
aacactcaac cctatctcgg tctattcttt tgatttataa gggattttgc cgatttcggc   5160
ctattggtta aaaaatgagc tgatttaaca aaaatttaac gcgaatttta acaaaatatt   5220
aacgcttaca atttaggtgg cacttttcgg ggaaatgtgc gcggaacccc tatttgttta   5280
tttttctaaa tacattcaaa tatgtatccg ctcatgagac aataaccctg ataaatgctt   5340
caataatatt gaaaaggaa gagtatgagc catattcaac gggaaacgtc ttgctctagg    5400
ccgcgattaa attccaacat ggatgctgat ttatatgggt ataaatgggc tcgcgataat   5460
gtcgggcaat caggtgcgac aatctatcga ttgtatggga agcccgatgc gccagagttg   5520
tttctgaaac atggcaaagg tagcgttgcc aatgatgtta cagatgagat ggtcagacta   5580
aactggctga cggaatttat gcctcttccg accatcaagc attttatccg tactcctgat   5640
gatgcatggt tactcaccac tgcgatcccc gggaaaacag cattccaggt attagaagaa   5700
tatcctgatt caggtgaaaa tattgttgat gcgctggcag tgttcctgcg ccggttgcat   5760
tcgattcctg tttgtaattg tcctttaac agcgatcgcg tatttcgtct ggctcaggcg    5820
caatcacgaa tgaataacgg tttggttgat gcgagtgatt ttgatgacga gcgtaatggc   5880
tggcctgttg aacaagtctg gaaagaaatg cataaacttt tgccattctc accggattca   5940
gtcgtcactc atggtgattt ctcacttgat aaccttattt ttgacgaggg gaaattaata   6000
ggttgtattg atgttggacg agtcggaatc gcagaccgat accaggatct tgccatccta   6060
tggaactgcc tcggtgagtt ttctccttca ttacagaaac ggctttttca aaaatatggt   6120
attgataatc ctgatatgaa taaattgcag tttcatttga tgctcgatga gttttctaa    6180
ctgtcagacc aagtttactc atatatactt tagattgatt taaaacttca tttttaattt   6240
aaaaggatct aggtgaagat cctttttgat aatctcatga ccaaaatccc ttaacgtgag   6300
ttttcgttcc actgagcgtc agaccccgta gaaaagatca aggatcttc ttgagatcct    6360
ttttttctgc gcgtaatctg ctgcttgcaa acaaaaaaac caccgctacc agcggtggtt   6420
tgtttgccgg atcaagagct accaactctt tttccgaagg taactggctt cagcagagcg   6480
cagataccaa atactgttct tctagtgtag ccgtagttag gccaccactt caagaactct   6540
gtagcaccgc ctacatacct cgctctgcta atcctgttac cagtggctgc tgccagtggc   6600
gataagtcgt gtcttaccgg gttggactca agacgatagt taccggataa ggcgcagcgg   6660
tcgggctgaa cggggggttc gtgcacacag cccagcttgg agcgaacgac ctacaccgaa   6720
ctgagatacc tacagcgtga gctatgagaa agcgccacgc ttcccgaagg gagaaaggcg   6780
```

```
gacaggtatc cggtaagcgg cagggtcgga acaggagagc gcacgaggga gcttccaggg    6840
ggaaacgcct ggtatcttta tagtcctgtc gggtttcgcc acctctgact tgagcgtcga    6900 ttttttgtgat gctcgtcagg ggggcggagc ctatggaaaa acgccagcaa cgcggccttt   6960
ttacggttcc tggccttttg ctggcctttt gctcacatgt tctttcctgc gttatcccct    7020
gattctgtgg ataaccgtat taccgccttt gagtgagctg ataccgctcg ccgcagccga   7080
acgaccgagc gcagcgagtc agtgagcgag gaagcggaag agcgcccaat acgcaaaccg    7140
cctctccccg cgcgttggcc gattcattaa tgcagctggc acgacaggtt cccgactgg     7200 aaagcgggca gtgagcgcaa cgcaattaat gtgagttagc tcactcatta ggcaccccag    7260
gctttacact ttatgcttcc ggctcgtatg ttgtgtggaa ttgtgagcgg ataacaattt    7320
cacacaggaa acagctatga ccatgattac gccaagcgcg caattaaccc tcactaaagg    7380
gaacaaaagc tggagctgca agcttaatgt agtcttatgc aatactcttg tagtcttgca    7440
acatggtaac gatgagttag caacatgcct tacaaggaga gaaaaagcac cgtgcatgcc    7500
gattggtgga agtaaggtgg tacgatcgtg ccttattagg aaggcaacag acgggtctga    7560
catggattgg acgaaccact gaattgccgc attgcagaga tattgtattt aagtgcctag    7620
ctcgatacat aaacgggtct ctctggttag accagatctg agcctgggag ctctctggct    7680
aactagggaa cccactgctt aagcctcaat aaagcttgcc ttgagtgctt caagtagtgt    7740
gtgcccgtct gttgtgtgac tctggtaact agagatccct cagacccttt tagtcagtgt    7800
ggaaaatctc tagcagtggc gcccgaacag ggacttgaaa gcgaaaggga accagagga    7860 gctctctcga cgcaggactc ggcttgctga agcgcgcacg gcaagaggcg aggggcggcg    7920
actggtgagt acgccaaaaa ttttgactag cggaggctag aaggagagag atgggtgcga    7980
gagcgtcagt attaagcggg ggagaattag atcgcgatgg gaaaaaattc ggttaaggcc    8040
agggggaaag aaaaaatata aattaaaaca tatagtatgg gcaagcaggg agctagaacg    8100
attcgcagtt aatcctggcc tgttagaaac atcagaaggc tgtagacaaa tactgggaca    8160
gctacaacca tcccttcaga caggatcaga agaacttaga tcattatata atacagtagc    8220
aaccctctat tgtgtgcatc aaaggataga gataaaagac accaaggaag ctttagacaa    8280
gatagaggaa gagcaaaaca aaagtaagac caccgcacag caagcggccg ctgatcttca    8340
gacctggagg aggagatatg agggacaatt ggagaagtga attatataaa tataaagtag    8400
taaaaattga accattagga gtagcaccca ccaaggcaaa gagaagagtg gtgcagagag    8460
aaaaaagagc agtgggaata ggagctttgt tccttgggtt cttgggagca gcaggaagca    8520
ctatgggcgc agcgtcaatg acgctgacgg tacaggccag acaattattg tctggtatag    8580
tgcagcagca gaacaatttg ctgagggcta ttgaggcgca acagcatctg ttgcaactca    8640
cagtctgggg catcaagcag ctccaggcaa gaatcctggc tgtggaaaga tacctaaagg    8700
atcaacagct cctggggatt tggggttgct ctggaaaact catttgcacc actgctgtgc    8760
cttggaatgc tagttggagt aataaatctc tggaacagat ttggaatcac acgacctgga    8820
tggagtggga cagagaaatt aacaattaca caagcttaat acactcctta attgaagaat    8880
cgcaaaacca gcaagaaaag aatgaacaag aattattgga attagataaa tgggcaagtt    8940
tgtggaattg gtttaacata acaaattggc tgtggtatat aaaattattc ataatgatag    9000
taggaggctt ggtaggttta agaatagttt ttgctgtact ttctatagtg aatagagtta    9060
ggcagggata ttcaccatta tcgtttcaga cccacctccc aaccccgagg gacccgaca    9120 ggcccgaagg aatagaagaa gaaggtggag agagagacag agacagatcc attcgattag    9180
```

| | | | |
|---|---|---|---|
| tgaacggatc | tcgacggtat | cgatcacgag actagcctcg acacaaatgg cagtattcat | 9240 |
| ccacaatttt | aaaagaaaag | gggggattgg ggggtacagt gcaggggaaa gaatagtaga | 9300 |
| cataatagca | acagacatac | aaactaaaga attacaaaaa caaattacaa aaattcaaaa | 9360 |
| ttttcgggtt | tattacaggg | acagcagaaa tccactttgg ctcgagaagc ttgatat | 9417 |

<210> SEQ ID NO 130
<211> LENGTH: 8625
<212> TYPE: DNA
<213> ORGANISM: Homo sapiens

<400> SEQUENCE: 130

| | | | |
|---|---|---|---|
| gggcagagcg | cacatcgccc | acagtccccg agaagttggg gggaggggtc ggcaattgaa | 60 |
| ccggtgccta | gagaaggtgg | cgcggggtaa actgggaaag tgatgtcgtg tactggctcc | 120 |
| gccttttcc | cgagggtggg | ggagaaccgt ataagtgc agtagtcgcc gtgaacgttc | 180 |
| tttttcgcaa | cgggtttgcc | gccagaacac aggtaagtgc cgtgtgtggt tcccgcgggc | 240 |
| ctggcctctt | tacgggttat | ggcccttgcg tgccttgaat tacttccacc tggctgcagt | 300 |
| acgtgattct | tgatcccgag | cttcggggttg aagtggggtg ggagagttcg aggccttgcg | 360 |
| cttaaggagc | cccttcgcct | cgtgcttgag ttgaggcctg gcctgggcgc tggggccgcc | 420 |
| gcgtgcgaat | ctggtggcac | cttcgcgcct gtctcgctgc tttcgataag tctctagcca | 480 |
| tttaaatttt | ttgatgacct | gctgcgacgc ttttttctg gcaagatagt cttgtaaatg | 540 |
| cgggccaaga | tctgcacact | ggtatttcgg ttttgggggc cgcgggcggc gacggggccc | 600 |
| gtgcgtccca | gcgcacatgt | tcggcgaggc ggggcctgcg agcgcggcca ccgagaatcg | 660 |
| gacgggggta | gtctcaagct | ggccggcctg tctctggtgcc tggcctcgcg ccgccgtgta | 720 |
| tcgccccgcc | ctgggcggca | aggctggccc ggtcggcacc agttgcgtga gcggaaagat | 780 |
| ggccgcttcc | cggccctgct | gcagggagct caaaatggag gacgcggcgc tcgggagagc | 840 |
| gggcgggtga | gtcacccaca | caaaggaaaa gggccttttcc gtcctcagcc gtcgcttcat | 900 |
| gtgactccac | ggagtaccgg | cgccgtccca ggcacctcga ttagttctcg agcttttgga | 960 |
| gtacgtcgtc | tttaggttgg | ggggaggggt tttatgcgat ggagtttccc cacactgagt | 1020 |
| gggtggagac | tgaagttagg | ccagcttggc acttgatgta attctccttg gaatttgccc | 1080 |
| tttttgagtt | tggatcttgg | ttcattctca agcctcagac agtggttcaa agttttttttc | 1140 |
| ttccatttca | ggtgtcgtga | ggatccgcca ccatgaagaa gagcggcgtg ctgtttctgc | 1200 |
| tgggcatcat | tctgctggtg | ctgatcggag tgcaaggcac acccgtggtg agaaagggaa | 1260 |
| gatgcagctg | catcagcacc | aaccaaggca ccatccatct gcagtctctg aaggacctca | 1320 |
| agcagttcgc | cccagccccc | agctgcgaga gatcgagat catcgccaca ctgaagaacg | 1380 |
| gcgtgcagac | atgtctgaac | cccgacagcg ctgacgtgaa ggagctgatc aagaagtggg | 1440 |
| agaagcaagt | gtcccagaag | aagaagcaga gaacggcaa gaagcaccag aaaaagaagg | 1500 |
| tgctcaaggt | gaggaagtcc | cagagatcca gacagaagaa gaccacaggt tccggagcca | 1560 |
| cgaacttctc | tctgttaaag | caagcaggag acgtggaaga aaaccccggt cctatgcaga | 1620 |
| tcccacaggc | gccctggcca | gtcgtctggg cggtgctaca actgggctgg cggccaggat | 1680 |
| ggttcttaga | ctccccagac | aggccctgga accccccac cttctcccca gccctgctcg | 1740 |
| tggtgaccga | aggggacaac | gccaccttca cctgcagctt ctccaacaca tcggagagct | 1800 |
| tcgtgctaaa | ctggtaccgc | atgagcccca gcaaccagac ggacaagctg gccgccttcc | 1860 |

```
ccgaggaccg cagccagccc ggccaggact gccgcttccg tgtcacacaa ctgcccaacg    1920
ggcgtgactt ccacatgagc gtggtcaggg cccggcgcaa tgacagcggc acctacctct    1980
gtggggccat ctccctggcc cccaaggcgc agatcaaaga gagcctgcgg gcagagctca    2040
gggtgacaga gagaagggca gaagtgccca cagcccaccc cagcccctca cccaggccag    2100
ccggccagtt ccaaaccctg gtggttggtg tcgtgggcgg cctgctgggc agcctggtgc    2160
tgctagtctg ggtcctggcc gtcatctgct cccgggccgc acgagggaca ataggagcca    2220
ggcgcaccgg ccagcccctg aaggaggacc cctcagccgt gcctgtgttc tctgtggacg    2280
ccggggagct ggatttccag tggcgagaga gacccccgga gcccccgtg ccctgtgtcc    2340 ctgagcagac ggaggccgcc accattgtct ttcctagcgg aatgggcacc tcatccccg    2400 cccgcagggg ctcagctgac ggccctcgga gtgcccagcc actgaggcct gaggatggac    2460
actgctcttg gcccctctga gtcgactcta gaactagtaa tcaacctctg gattacaaaa    2520
tttgtgaaag attgactggt attcttaact atgttgctcc ttttacgcta tgtggatacg    2580
ctgctttaat gcctttgtat catgctattg cttcccgtat ggctttcatt ttctcctcct    2640
tgtataaatc ctggttgctg tctctttatg aggagttgtg gcccgttgtc aggcaacgtg    2700
gcgtggtgtg cactgtgttt gctgacgcaa cccccactgg ttggggcatt gccaccacct    2760
gtcagctcct ttccgggact ttcgctttcc cctccctat tgccacggcg gaactcatcg    2820
ccgcctgcct tgcccgctgc tggacagggg ctcggctgtt gggcactgac aattccgtgg    2880
tgttgtcggg gaaatcatcg tcctttcctt ggctgctcgc ctgtgttgcc acctggattc    2940
tgcgcgggac gtccttctgc tacgtccctt cggccctcaa tccagcggac cttccttccc    3000
gcggcctgct gccggctctg cggcctcttc cgcgtcttcg ccttcgccct cagacgagtc    3060
ggatctccct ttgggccgcc tccccgcctg ccgcggaatt cgagctcggt acctttaaga    3120
ccaatgactt acaaggcagc tgtagatctt agccactttt taaaagaaaa ggggggactg    3180
gaagggctaa ttcactccca acgaagacaa gatctgcttt ttgcttgtac tgggtctctc    3240
tggttagacc agatctgagc ctgggagctc tctggctaac tagggaaccc actgcttaag    3300
cctcaataaa gcttgccttg agtgcttcaa gtagtgtgtg cccgtctgtt gtgtgactct    3360
ggtaactaga tccctcag acccttttag tcagtgtgga aaatctctag cagtagtagt    3420
tcatgtcatc ttattattca gtatttataa cttgcaaaga atgaatatc agagagtgag    3480 aggaacttgt ttattgcagc ttataatggt tacaaataaa gcaatagcat cacaaatttc    3540
acaaataaag catttttttc actgcattct agttgtggtt tgtccaaact catcaatgta    3600
tcttatcatg tctggctcta gctatcccgc ccctaactcc gcccatcccg cccctaactc    3660
cgcccagttc cgcccattct ccgccccatg gctgactaat ttttttatt tatgcagagg    3720 ccgaggccgc ctcggcctct gagctattcc agaagtagtg aggaggcttt tttggaggcc    3780
tagggacgta cccaattcgc cctatagtga gtcgtattac gcgcgctcac tggccgtcgt    3840
tttacaacgt cgtgactggg aaaaccctgg cgttacccaa cttaatcgcc ttgcagcaca    3900
tccccctttc gccagctggc gtaatagcga agaggcccgc accgatcgcc cttcccaaca    3960
gttgcgcagc ctgaatggcg aatgggacgc gccctgtagc ggcgcattaa gcgcggcggg    4020
tgtggtggtt acgcgcagcg tgaccgctac acttgccagc gccctagcgc ccgctccttt    4080
cgctttcttc ccttcctttc tcgccacgtt cgccggcttt cccgtcaag ctctaaatcg    4140 ggggctccct ttagggttcc gatttagtgc tttacggcac ctcgacccca aaaaacttga    4200
ttagggtgat ggttcacgta gtgggccatc gccctgatag acggtttttc gccctttgac    4260
```

```
gttggagtcc acgttcttta atagtggact cttgttccaa actggaacaa cactcaaccc    4320
tatctcggtc tattctttg atttataagg gattttgccg atttcggcct attggttaaa    4380
aaatgagctg atttaacaaa aatttaacgc gaattttaac aaaatattaa cgcttacaat    4440
ttaggtggca cttttcgggg aaatgtgcgc ggaacccta tttgtttatt tttctaaata    4500
cattcaaata tgtatccgct catgagacaa taaccctgat aaatgcttca ataatattga    4560 aaaggaaga gtatgagcca tattcaacgg gaaacgtctt gctctaggcc gcgattaaat    4620
tccaacatgg atgctgattt atatgggtat aaatgggctc gcgataatgt cgggcaatca    4680
ggtgcgacaa tctatcgatt gtatgggaag cccgatgcgc cagagttgtt tctgaaacat    4740
ggcaaaggta gcgttgccaa tgatgttaca gatgagatgg tcagactaaa ctggctgacg    4800
gaatttatgc ctcttccgac catcaagcat tttatccgta ctcctgatga tgcatggtta    4860
ctcaccactg cgatccccgg gaaaacagca ttccaggtat tagaagaata tcctgattca    4920
ggtgaaaata ttgttgatgc gctggcagtg ttcctgcgcc ggttgcattc gattcctgtt    4980
tgtaattgtc ctttaacag cgatcgcgta tttcgtctgg ctcaggcgca atcacgaatg    5040
aataacggtt tggttgatgc gagtgatttt gatgacgagc gtaatggctg gcctgttgaa    5100
caagtctgga aagaaatgca taaacttttg ccattctcac cggattcagt cgtcactcat    5160
ggtgatttct cacttgataa ccttattttt gacgagggga aattaatagg ttgtattgat    5220
gttggacgag tcggaatcgc agaccgatac caggatcttg ccatcctatg aactgcctc    5280 ggtgagttt ctccttcatt acagaaacgg ctttttcaaa aatatggtat tgataatcct    5340
gatatgaata aattgcagtt tcatttgatg ctcgatgagt ttttctaact gtcagaccaa    5400
gtttactcat atatacttta gattgattta aaacttcatt tttaatttaa aaggatctag    5460
gtgaagatcc ttttgataa tctcatgacc aaaatccctt aacgtgagtt ttcgttccac    5520
tgagcgtcag accccgtaga aaagatcaaa ggatcttctt gagatccttt ttttctgcgc    5580
gtaatctgct gcttgcaaac aaaaaaacca ccgctaccag cggtggtttg tttgccggat    5640
caagagctac caactctttt tccgaaggta actggcttca gcagagcgca gataccaaat    5700
actgttcttc tagtgtagcc gtagttaggc caccacttca agaactctgt agcaccgcct    5760
acatacctcg ctctgctaat cctgttacca gtggctgctg ccagtggcga taagtcgtgt    5820
cttaccgggt tggactcaag acgatagtta ccggataagg cgcagcggtc gggctgaacg    5880
gggggttcgt gcacacagcc cagcttggag cgaacgacct acaccgaact gagataccta    5940
cagcgtgagc tatgagaaag cgccacgctt cccgaaggga gaaaggcgga caggtatccg    6000
gtaagcggca gggtcggaac aggagagcgc acgagggagc ttccagggg aaacgcctgg    6060 tatctttata gtcctgtcgg gtttcgccac ctctgacttg agcgtcgatt tttgtgatgc    6120
tcgtcagggg gcggagcct atggaaaaac gccagcaacg cggccttttt acggttcctg    6180
gccttttgct ggccttttgc tcacatgttc tttcctgcgt tatcccctga ttctgtggat    6240
aaccgtatta ccgcctttga gtgagctgat accgctcgcc gcagccgaac gaccgagcgc    6300
agcgagtcag tgagcgagga agcggaagag cgcccaatac gcaaaccgcc tctccccgcg    6360
cgttggccga ttcattaatg cagctggcac gacaggtttc ccgactggaa agcgggcagt    6420
gagcgcaacg caattaatgt gagttagctc actcattagg caccccaggc tttacacttt    6480
atgcttccgg ctcgtatgtt gtgtggaatt gtgagcggat aacaatttca cacaggaaac    6540
agctatgacc atgattacgc caagcgcgca attaacccte actaaggga acaaaagctg    6600
```

| | | |
|---|---|---|
| gagctgcaag cttaatgtag tcttatgcaa tactcttgta gtcttgcaac atggtaacga | 6660 | |
| tgagttagca acatgcctta caaggagaga aaaagcaccg tgcatgccga ttggtggaag | 6720 | |
| taaggtggta cgatcgtgcc ttattaggaa ggcaacagac gggtctgaca tggattggac | 6780 | |
| gaaccactga attgccgcat tgcagagata ttgtatttaa gtgcctagct cgatacataa | 6840 | |
| acgggtctct ctggttagac cagatctgag cctgggagct ctctggctaa ctagggaacc | 6900 | |
| cactgcttaa gcctcaataa agcttgcctt gagtgcttca agtagtgtgt gcccgtctgt | 6960 | |
| tgtgtgactc tggtaactag agatccctca gacccttta gtcagtgtgg aaaatctcta | 7020 | |
| gcagtggcgc ccgaacaggg acttgaaagc gaaagggaaa ccagaggagc tctctcgacg | 7080 | |
| caggactcgg cttgctgaag cgcgcacggc aagaggcgag gggcggcgac tggtgagtac | 7140 | |
| gccaaaaatt ttgactagcg gaggctagaa ggagagagat gggtgcgaga gcgtcagtat | 7200 | |
| taagcggggg agaattagat cgcgatggga aaaaattcgg ttaaggccag ggggaaagaa | 7260 | |
| aaaatataaa ttaaaacata tagtatgggc aagcagggag ctagaacgat cgcagttaa | 7320 | |
| tcctggcctg ttagaaacat cagaaggctg tagacaaata ctgggacagc tacaaccatc | 7380 | |
| ccttcagaca ggatcagaag aacttagatc attatataat acagtagcaa ccctctattg | 7440 | |
| tgtgcatcaa aggatagaga taaaagacac caaggaagct ttagacaaga tagaggaaga | 7500 | |
| gcaaaacaaa agtaagacca ccgcacagca agcggccgct gatcttcaga cctggaggag | 7560 | |
| gagatatgag ggacaattgg agaagtgaat tatataaata taaagtagta aaaattgaac | 7620 | |
| cattaggagt agcacccacc aaggcaaaga gaagagtggt gcagagagaa aaaagagcag | 7680 | |
| tgggaatagg agctttgttc cttgggttct tgggagcagc aggaagcact atgggcgcag | 7740 | |
| cgtcaatgac gctgacggta caggccagac aattattgtc tggtatagtg cagcagcaga | 7800 | |
| acaatttgct gagggctatt gaggcgcaac agcatctgtt gcaactcaca gtctgggca | 7860 | |
| tcaagcagct ccaggcaaga atcctggctg tggaaagata cctaaaggat caacagctcc | 7920 | |
| tggggatttg gggttgctct ggaaaactca tttgcaccac tgctgtgcct tggaatgcta | 7980 | |
| gttggagtaa taatctctg gaacagattt ggaatcacac gacctggatg gagtgggaca | 8040 | |
| gagaaattaa caattacaca agcttaatac actccttaat tgaagaatcg caaaaccagc | 8100 | |
| aagaaaagaa tgaacaagaa ttattggaat tagataaatg ggcaagtttg tggaattggt | 8160 | |
| ttaacataac aaattggctg tggtatataa aattattcat aatgatagta ggaggcttgg | 8220 | |
| taggtttaag aatagttttt gctgtacttt ctatagtgaa tagagttagg cagggatatt | 8280 | |
| caccattatc gtttcagacc cacctcccaa ccccgagggg acccgacagg cccgaaggaa | 8340 | |
| tagaagaaga aggtggagag agagacagag acagatccat tcgattagtg aacggatctc | 8400 | |
| gacggtatcg atcacgagac tagcctcgac acaaatggca gtattcatcc acaattttaa | 8460 | |
| aagaaaaggg gggattgggg ggtacagtgc aggggaaaga atagtagaca taatagcaac | 8520 | |
| agacatacaa actaaagaat tacaaaaaca aattacaaaa attcaaaatt ttcgggttta | 8580 | |
| ttacagggac agcagaaatc cactttggct cgagaagctt gatat | 8625 | |

<210> SEQ ID NO 131
<211> LENGTH: 8538
<212> TYPE: DNA
<213> ORGANISM: Homo sapiens

<400> SEQUENCE: 131

| | | |
|---|---|---|
| gggcagagcg cacatcgccc acagtccccg agaagttggg gggaggggtc ggcaattgaa | 60 | |
| ccggtgccta gagaaggtgg cgcggggtaa actgggaaag tgatgtcgtg tactggctcc | 120 | |

```
gccttttcc cgagggtggg ggagaaccgt atataagtgc agtagtcgcc gtgaacgttc    180
tttttcgcaa cgggtttgcc gccagaacac aggtaagtgc cgtgtgtggt tcccgcgggc    240
ctggcctctt tacgggttat ggcccttgcg tgccttgaat tacttccacc tggctgcagt    300
acgtgattct tgatcccgag cttcggggtg aagtgggtg ggagagttcg aggccttgcg    360
cttaaggagc cccttcgcct cgtgcttgag ttgaggcctg gcctgggcgc tggggccgcc    420
gcgtgcgaat ctggtggcac cttcgcgcct gtctcgctgc tttcgataag tctctagcca    480
tttaaaattt ttgatgacct gctgcgacgc ttttttctg gcaagatagt cttgtaaatg    540
cgggccaaga tctgcacact ggtatttcgg tttttgggc cgcgggcggc gacgggccc    600 gtgcgtccca gcgcacatgt tcggcgaggc ggggcctgcg agcgcggcca ccgagaatcg    660 gacggggta gtctcaagct ggccggcctg ctctggtgcc tggcctcgcg ccgccgtgta    720
tcgccccgcc ctgggcggca aggctggccc ggtcggcacc agttgcgtga gcggaaagat    780
ggccgcttcc cggccctgct gcaggagct caaaatggag gacgcggcgc tcgggagagc    840
gggcgggtga gtcacccaca caaaggaaaa gggccttcc gtcctcagcc gtcgcttcat    900
gtgactccac ggagtaccgg gcgccgtcca ggcacctcga ttagttctcg agcttttgga    960
gtacgtcgtc tttaggttgg ggggagggt tttatgcgat ggagtttccc cacactgagt   1020
gggtggagac tgaagttagg ccagcttggc acttgatgta attctccttg gaatttgccc   1080 ttttgagtt tggatcttgg ttcattctca agcctcagac agtggttcaa agtttttc    1140 ttccatttca ggtgtcgtga ggatccatga accagaccgc cattctgatc tgctgtctga   1200
tctttctgac actgagcggc attcaaggcg tgcctctgtc cagaaccgtg agatgcacat   1260
gcatcagcat cagcaaccag cccgtgaacc ctagatctct ggagaagctc gagatcatcc   1320
ccgctagcca gttctgccct agagtggaga tcatcgccac catgaagaag aagggcgaga   1380
agaggtgcct caaccccgag agcaaggcca tcaagaatct gctgaaagcc gtgtccaagg   1440
agagatccaa gaggagcccc ggttccggag ccacgaactt ctctctgtta aagcaagcag   1500
gagacgtgga agaaaacccc ggtcctatgc agatcccaca ggcgcctgg ccagtcgtct   1560 gggcggtgct acaactgggc tggcggccag gatggttctt agactcccca gacaggccc    1620 ggaaccccc caccttctcc ccagccctgc tcgtggtgac cgaaggggac aacgccacct   1680
tcacctgcag cttctccaac acatcggaga gcttcgtgct aaactggtac cgcatgagcc   1740
ccagcaacca gacggacaag ctggccgcct tccccgagga ccgcagccag cccggccagg   1800
actgccgctt ccgtgtcaca caactgccca cgggcgtga cttccacatg agcgtggtca   1860
gggcccggcg caatgacagc ggcacctacc tctgtgggc catctccctg gcccccaagg   1920
cgcagatcaa agagagcctg cgggcagagc tcagggtgac agagagaagg gcagaagtgc   1980
ccacagccca ccccagcccc tcacccaggc cagccggcca gttccaaacc ctggtggttg   2040
gtgtcgtggg cggcctgctg ggcagcctgg tgctgctagt ctgggtcctg gccgtcatct   2100
gctcccgggc cgcacgaggg acaataggag ccaggcgcac cggccagccc ctgaaggagg   2160
acccctcagc cgtgcctgtg ttctctctgt acgccgggga gctggatttc cagtggcgag   2220 agaagaccc ggagccccc gtgccctgtg tccctgagca gacggaggcc gccaccattg   2280
tctttcctag cggaatgggc acctcatccc ccgcccgcag gggctcagct gacggccctc   2340
ggagtgccca gccactgagg cctgaggatg gacactgctc ttggcccctc tgagtcgact   2400
ctagaactag taatcaacct ctggattaca aaatttgtga aagattgact ggtattctta   2460
```

```
actatgttgc tccttttacg ctatgtggat acgctgcttt aatgcctttg tatcatgcta   2520
ttgcttcccg tatggctttc attttctcct ccttgtataa atcctggttg ctgtctcttt   2580
atgaggagtt gtggcccgtt gtcaggcaac gtggcgtggt gtgcactgtg tttgctgacg   2640
caaccccccac tggttggggc attgccacca cctgtcagct cctttccggg actttcgctt   2700
tcccccctccc tattgccacg gcggaactca tcgccgcctg ccttgcccgc tgctggacag   2760
gggctcggct gttgggcact gacaattccg tggtgttgtc ggggaaatca tcgtcctttc   2820
cttggctgct cgcctgtgtt gccacctgga ttctgcgcgg acgtccttc  tgctacgtcc   2880
cttcggccct caatccagcg gaccttcctt cccgcggcct gctgccggct ctgcggcctc   2940
ttccgcgtct tcgccttcgc cctcagacga gtcggatctc cctttgggcc gcctccccgc   3000
ctgccgcgga attcgagctc ggtaccttta agaccaatga cttacaaggc agctgtagat   3060
cttagccact ttttaaaaga aagggggga  ctggaagggc taattcactc ccaacgaaga   3120
caagatctgc ttttgcttg  tactgggtct ctctggttag accagatctg agcctgggag   3180
ctctctggct aactagggaa cccactgctt aagcctcaat aaagcttgcc ttgagtgctt   3240
caagtagtgt gtgcccgtct gttgtgtgac tctggtaact agagatccct cagacccttt   3300
tagtcagtgt ggaaaatctc tagcagtagt agttcatgtc atcttattat tcagtattta   3360
taacttgcaa agaaatgaat atcagagagt gagaggaact tgtttattgc agcttataat   3420
ggttacaaat aaagcaatag catcacaaat ttcacaaata aagcattttt ttcactgcat   3480
tctagttgtg gtttgtccaa actcatcaat gtatcttatc atgtctggct ctagctatcc   3540
cgcccctaac tccgcccatc ccgcccctaa ctccgcccag ttccgcccat tctccgcccc   3600
atggctgact aattttttt  atttatgcag aggccgaggc cgcctcggcc tctgagctat   3660
tccagaagta gtgaggaggc tttttggag  gcctagggac gtacccaatt cgccctatag   3720
tgagtcgtat tacgcgcgct cactggccgt cgttttacaa cgtcgtgact gggaaaaccc   3780
tggcgttacc caacttaatc gccttgcagc acatccccct ttcgccagct ggcgtaatag   3840
cgaagaggcc cgcaccgatc gcccttccca acagttgcgc agcctgaatg gcgaatggga   3900
cgcgccctgt agcggcgcat taagcgcggc gggtgtggtg gttacgcgca gcgtgaccgc   3960
tacacttgcc agcgccctag cgcccgctcc tttcgctttc ttcccttcct ttctcgccac   4020
gttcgccggc tttccccgtc aagctctaaa tcggggggctc cctttagggt tccgatttag   4080
tgctttacgg cacctcgacc ccaaaaaact tgattagggt gatggttcac gtagtgggcc   4140
atcgccctga tagacggttt ttcgcccttt gacgttggag tccacgttct ttaatagtgg   4200
actcttgttc caaactggaa caacactcaa ccctatctcg gtctattctt ttgatttata   4260
agggattttg ccgatttcgg cctattggtt aaaaaatgag ctgatttaac aaaaatttaa   4320
cgcgaatttt aacaaaatat taacgcttac aatttaggtg cacttttcg  gggaaatgtg   4380
cgcggaaccc ctatttgttt attttttctaa atacattcaa atatgtatcc gctcatgaga   4440
caataaccct gataaatgct tcaataatat tgaaaaagga agagtatgag ccatattcaa   4500
cgggaaacgt cttgctctag gccgcgatta aattccaaca tggatgctga tttatatggg   4560
tataaatggg ctcgcgataa tgtcgggcaa tcaggtgcga caatctatcg attgtatggg   4620
aagcccgatg cgccagagtt gtttctgaaa catggcaaag gtagcgttgc caatgatgtt   4680
acagatgaga tggtcagact aaactggctg acggaattta tgcctcttcc gaccatcaag   4740
cattttatcc gtactcctga tgatgcatgg ttactcacca ctgcgatccc cgggaaaaca   4800
gcattccagg tattagaaga atatcctgat tcaggtgaaa atattgttga tgcgctggca   4860
```

```
gtgttcctgc gccggttgca ttcgattcct gtttgtaatt gtccttttaa cagcgatcgc   4920
gtatttcgtc tggctcaggc gcaatcacga atgaataacg gtttggttga tgcgagtgat   4980
tttgatgacg agcgtaatgg ctggcctgtt gaacaagtct ggaaagaaat gcataaactt   5040
ttgccattct caccggattc agtcgtcact catggtgatt tctcacttga taaccttatt   5100
tttgacgagg ggaaattaat aggttgtatt gatgttggac gagtcggaat cgcagaccga   5160
taccaggatc ttgccatcct atggaactgc ctcggtgagt tttctccttc attacagaaa   5220 cggcttttc aaaaatatgg tattgataat cctgatatga ataaattgca gtttcatttg   5280
atgctcgatg agttttcta actgtcagac caagtttact catatatact ttagattgat   5340
ttaaaacttc attttaatt taaaaggatc taggtgaaga tcctttttga taatctcatg   5400
accaaaatcc cttaacgtga gttttcgttc cactgagcgt cagacccgt agaaaagatc   5460 aaaggatctt cttgagatcc ttttttctg cgcgtaatct gctgcttgca acaaaaaaa   5520 ccaccgctac cagcggtggt ttgtttgccg gatcaagagc taccaactct ttttccgaag   5580
gtaactggct tcagcagagc gcagatacca atactgttc ttctagtgta gccgtagtta   5640
ggccaccact tcaagaactc tgtagcaccg cctacatacc tcgctctgct aatcctgtta   5700
ccagtggctg ctgccagtgg cgataagtcg tgtcttaccg ggttggactc aagacgatag   5760
ttaccggata aggcgcagcg tcgggctga acgggggtt cgtgcacaca gcccagcttg   5820
gagcgaacga cctacaccga actgagatac ctacagcgtg agctatgaga aagcgccacg   5880
cttcccgaag ggagaaaggc ggacaggtat ccggtaagcg gcagggtcgg aacaggagag   5940
cgcacgaggg agcttccagg gggaaacgcc tggtatcttt atagtcctgt cgggtttcgc   6000
cacctctgac ttgagcgtcg atttttgtga tgctcgtcag ggggggcgag cctatggaaa   6060
aacgccagca acgcggcctt tttacggttc ctggcctttt gctggccttt tgctcacatg   6120
ttctttcctg cgttatcccc tgattctgtg gataaccgta ttaccgcctt tgagtgagct   6180
gataccgctc gccgcagccg aacgaccgag cgcagcgagt cagtgagcga ggaagcggaa   6240
gagcgcccaa tacgcaaacc gcctctcccc gcgcgttggc cgattcatta atgcagctgg   6300
cacgacaggt ttcccgactg gaaagcgggc agtgagcgca acgcaattaa tgtgagttag   6360
ctcactcatt aggcacccca ggctttacac tttatgcttc cggctcgtat gttgtgtgga   6420
attgtgagcg gataacaatt tcacacagga aacagctatg accatgatta cgccaagcgc   6480
gcaattaacc ctcactaaag ggaacaaaag ctggagctgc aagcttaatg tagtcttatg   6540
caatactctt gtagtcttgc aacatggtaa cgatgagtta gcaacatgcc ttacaaggag   6600
agaaaaagca ccgtgcatgc cgattggtgg aagtaaggtg gtacgatcgt gccttattag   6660
gaaggcaaca gacgggtctg acatggattg gacgaaccac tgaattgccg cattgcagag   6720
atattgtatt taagtgccta gctcgataca taaacgggtc tctctggtta gaccagatct   6780
gagcctggga gctctctggc taactaggga acccactgct taagcctcaa taaagcttgc   6840
cttgagtgct tcaagtagtg tgtgcccgtc tgttgtgtga ctctggtaac tagagatccc   6900 tcagacccctt ttagtcagtg tggaaaatct ctagcagtgg cgcccgaaca gggacttgaa   6960
agcgaaaggg aaaccagagg agctctctcg acgcaggact cggcttgctg aagcgcgcac   7020
ggcaagaggc gaggggcggc gactggtgag tacgccaaaa attttgacta gcggaggcta   7080
gaaggagaga gatgggtgcg agagcgtcag tattaagcgg gggagaatta gatcgcgatg   7140
ggaaaaaatt cggttaaggc cagggggaaa gaaaaaatat aaattaaaac atatagtatg   7200
```

| | |
|---|---|
| ggcaagcagg gagctagaac gattcgcagt taatcctggc ctgttagaaa catcagaagg | 7260 |
| ctgtagacaa atactgggac agctacaacc atcccttcag acaggatcag aagaacttag | 7320 |
| atcattatat aatacagtag caaccctcta ttgtgtgcat caaaggatag agataaaaga | 7380 |
| caccaaggaa gctttagaca agatagagga agagcaaaac aaaagtaaga ccaccgcaca | 7440 |
| gcaagcggcc gctgatcttc agacctggag gaggagatat gagggacaat tggagaagtg | 7500 |
| aattatataa atataaagta gtaaaaattg aaccattagg agtagcaccc accaaggcaa | 7560 |
| agagaagagt ggtgcagaga gaaaaaagag cagtgggaat aggagctttg ttccttgggt | 7620 |
| tcttgggagc agcaggaagc actatgggcg cagcgtcaat gacgctgacg gtacaggcca | 7680 |
| gacaattatt gtctggtata gtgcagcagc agaacaattt gctgagggct attgaggcgc | 7740 |
| aacagcatct gttgcaactc acagtctggg gcatcaagca gctccaggca agaatcctgg | 7800 |
| ctgtggaaag atacctaaag gatcaacagc tcctggggat ttggggttgc tctggaaaac | 7860 |
| tcatttgcac cactgctgtg ccttggaatg ctagttggag taataaatct ctggaacaga | 7920 |
| tttggaatca cacgacctgg atggagtggg acagagaaat taacaattac acaagcttaa | 7980 |
| tacactcctt aattgaagaa tcgcaaaacc agcaagaaaa gaatgaacaa gaattattgg | 8040 |
| aattagataa atgggcaagt ttgtggaatt ggtttaacat aacaaattgg ctgtggtata | 8100 |
| taaaattatt cataatgata gtaggaggct tggtaggttt aagaatagtt tttgctgtac | 8160 |
| tttctatagt gaatagagtt aggcaggat attcaccatt atcgtttcag acccacctcc | 8220 |
| caaccccgag gggacccgac aggcccgaag aatagaagaa gaaggtggag agagagaca | 8280 |
| gagacagatc cattcgatta gtgaacggat ctcgacggta tcgatcacga gactagcctc | 8340 |
| gacacaaatg gcagtattca tccacaattt taaaagaaaa ggggggattg ggggtacag | 8400 |
| tgcagggaa agaatagtag acataatagc aacagacata caaactaaag aattacaaaa | 8460 |
| acaaattaca aaaattcaaa attttcgggt ttattacagg gacagcagaa atccactttg | 8520 |
| gctcgagaag cttgatat | 8538 |

<210> SEQ ID NO 132
<211> LENGTH: 9954
<212> TYPE: DNA
<213> ORGANISM: Homo sapiens

<400> SEQUENCE: 132

| | |
|---|---|
| gggcagagcg cacatcgccc acagtccccg agaagttggg gggaggggtc ggcaattgaa | 60 |
| ccggtgccta gagaaggtgg cgcggggtaa actgggaaag tgatgtcgtg tactggctcc | 120 |
| gcctttttcc cgagggtggg ggagaaccgt atataagtgc agtagtcgcc gtgaacgttc | 180 |
| tttttcgcaa cgggtttgcc gccagaacac aggtaagtgc cgtgtgtggt tcccgcgggc | 240 |
| ctggcctctt tacgggttat ggcccttgcg tgccttgaat tacttccacc tggctgcagt | 300 |
| acgtgattct tgatcccgag cttcggggttg aagtgggtg ggagagttcg aggccttgcg | 360 |
| cttaaggagc cccttcgcct cgtgcttgag ttgaggcctg gcctgggcgc tggggccgcc | 420 |
| gcgtgcgaat ctggtggcac cttcgcgcct gtctcgctgc tttcgataag tctctagcca | 480 |
| tttaaaattt tgatgacct gctgcgacgc ttttttctg gcaagatagt cttgtaaatg | 540 |
| cgggccaaga tctgcacact ggtatttcgg ttttttgggggc cgcgggcggc gacggggccc | 600 |
| gtgcgtccca gcgcacatgt tcggcgaggc ggggcctgcg agcgcggcca ccgagaatcg | 660 |
| gacggggggta gtctcaagct ggccggcctg ctctggtgcc tggcctcgcg ccgccgtgta | 720 |
| tcgccccgcc ctgggcggca aggctggccc ggtcggcacc agttgcgtga gcggaaagat | 780 |

```
ggccgcttcc cggccctgct gcagggagct caaaatggag gacgcggcgc tcgggagagc     840
gggcgggtga gtcacccaca caaaggaaaa gggcctttcc gtcctcagcc gtcgcttcat     900
gtgactccac ggagtaccgg gcgccgtcca ggcacctcga ttagttctcg agcttttgga     960
gtacgtcgtc tttaggttgg ggggaggggt tttatgcgat ggagtttccc cacactgagt    1020
gggtggagac tgaagttagg ccagcttggc acttgatgta attctccttg gaatttgccc    1080
tttttgagtt tggatcttgg ttcattctca agcctcagac agtggttcaa agtttttttc    1140
ttccatttca ggtgtcgtga ggatccgcca ccatggcctt accagtgacc gccttgctcc    1200
tgccgctggc cttgctgctc cacgccgcca ggccggatat ccagatgacc cagagcccga    1260
gcagcctgag cgcgagcgtg ggtgatcgcg tgaccattac ctgcagggca agtcaggaca    1320
ttagtaaata tttaaaattgg tatcagcaga accgggtaa agcgccgaaa ctgttaattt    1380
atcatacatc aagattacac tcaggcgtgc cgtcgcgttt tagcggctcg ggttcgggca    1440
ccgattttac cctgaccatc tcgagcttgc agccggagga cttcgccacc tactattgcc    1500
aacagggtaa tacgcttccg tacacgttcg gtcagggcac caaagtggag atcaaaggtg    1560
gcggtggctc gggcggtggt gggtcgggtg cggcggatc tgaggtgcag ctggtggagt    1620
ctgggggagg cttggtacag cctggggggt ccctgagact ctcctgtgca gcctctggag    1680
tgtccctgcc tgattatggc gtgtcctggg tccgccaggc tccagggaag gggctggagt    1740
gggtttcagt gatctggggc agcgagacaa cctactacaa cagcgccctg aagtcccgat    1800
tcaccatctc cagagacaat gccaagaact cactgtatct gcaaatgaac agcctgagag    1860
ccgaggacac ggctgtgtat tactgtgcga agcactacta ctacggcggc agctacgcta    1920
tggactactg ggccaagga accctggtca ccgtgtcctc aaccacgacg ccagcgccgc    1980
gaccaccaac accggcgccc accatcgcgt cgcagcccct gtccctgcgc ccagaggcgt    2040
gccggccagc ggcgggggc gcagtgcaca cgagggggct ggacttcgcc tgtgattttt    2100
gggtgctggt ggtggttggt ggagtcctgg cttgctatag cttgctagta acagtggcct    2160
ttattatttt ctgggtgagg agtaagagga gcaggctcct gcacagtgac tacatgaaca    2220
tgactccccg ccgccccggg cccacccgca agcattacca gccctatgcc ccaccacgcg    2280
acttcgcagc ctatcgctcc agagtgaagt tcagcaggag cgcagacgcc ccgcgtacc    2340 agcagggcca gaaccagctc tataacgagc tcaatctagg acgaagagag gagtacgatg    2400
ttttggacaa gaggcgtggc cgggaccctg agatgggggg aaagccgaga aggaagaacc    2460
ctcaggaagg cctgtacaat gaactgcaga agataagat ggcggaggcc tacagtgaga    2520
ttgggatgaa aggcgagcgc cggaggggca aggggcacga tggcctttac cagggtctca    2580
gtacagccca caaggacacc tacgacgccc ttcacatgca ggccctgccc ctcgcggtt    2640 ccggagccac gaacttctct ctgttaaagc aagcaggaga cgtggaagaa accccggtc    2700 ctatggtgct cgaggtgtcc gaccatcaag tgctgaacga tgccgaggtg gctgctctgc    2760
tggagaactt cagctccagc tacgattacg agagaacga gagcgacagc tgctgcacca    2820
gccctccttg ccctcaagac ttctctctga acttcgatag agcctttctg cccgccctct    2880
attctctgct gttctgctg ggactgctgg gcaatggagc tgtggctgct gtgctgctgt    2940
ctaggagaac agctctcagc agcaccgata catttctgct gcatctggcc gtcgctgata    3000
cactgctggt gctgacactc cctctctggg ctgtggacgc tgctgtgcag tgggtcttcg    3060
gaagcggcct ctgtaaggtg gctggcgctc tgttcaacat caacttctac gctggagctc    3120
```

```
tgctgctggc ttgtatttcc ttcgatagat acctcaatat cgtccacgcc acccagctct   3180
acagaagggg acccccgcc agagtcacac tgacatgtct ggccgtgtgg ggcctctgtc   3240
tcctcttcgc cctccccgac ttcatttttc tgagcgctca ccacgacgag aggctgaacg   3300
ccacccactg tcagtacaac ttccctcaag tgggaagaac cgctctgagg gtgctgcaac   3360
tggtcgccgg atttctgctg cctctgctgg tcatggctta ctgctacgcc cacattctgg   3420
ccgtgctgct ggtgtccaga ggacagagaa gactcagagc catgaggctc gtggtggtcg   3480
tggtcgtggc cttcgctctg tgctggaccc cttaccatct ggtggtgctg gtggacattc   3540
tgatggatct gggcgctctg gctagaaact gcggcagaga gtctagggtg gatgtggcca   3600
agtccgtgac cagcggactg ggctacatgc actgctgtct gaatcctctg ctgtacgctt   3660
tcgtcggcgt caagttcaga gagaggatgt ggatgctgct gctcagactg ggatgcccca   3720
accagagggg actgcagagg caacccagca gcagcagaag ggattccagc tggagcgaga   3780
ccagcgaagc cagctacagc ggcctgtgag tcgactctag aactagtaat caacctctgg   3840
attacaaaat ttgtgaaaga ttgactggta ttcttaacta tgttgctcct tttacgctat   3900
gtggatacgc tgctttaatg cctttgtatc atgctattgc ttcccgtatg ctttcatttt   3960
tctcctcctt gtataaatcc tggttgctgt ctctttatga ggagttgtgg cccgttgtca   4020
ggcaacgtgg cgtggtgtgc actgtgtttg ctgacgcaac ccccactggt tggggcattg   4080
ccaccacctg tcagctcctt tccgggactt tcgctttccc cctccctatt gccacgcgg   4140 aactcatcgc cgcctgcctt gcccgctgct ggacaggggc tcggctgttg ggcactgaca   4200
attccgtggt gttgtcgggg aaatcatcgt cctttccttg gctgctcgcc tgtgttgcca   4260
cctggattct gcgcgggacg tccttctgct acgtcccttc ggccctcaat ccagcggacc   4320
ttccttcccg cggcctgctg ccggctctgc ggcctcttcc gcgtcttcgc cttcgccctc   4380
agacgagtcg atctcccctt gggccgcct cccgcctgc gcggaattc gagctcggta   4440 cctttaagac caatgactta caaggcagct gtagatctta gccactttt aaaagaaaag   4500 gggggactgg aagggctaat tcactcccaa cgaagacaag atctgctttt tgcttgtact   4560
gggtctctct ggttagacca gatctgagcc tgggagctct ctggctaact agggaaccca   4620
ctgcttaagc ctcaataaag cttgccttga gtgcttcaag tagtgtgtgc ccgtctgttg   4680
tgtgactctg gtaactagag atccctcaga ccctttagt cagtgtggaa aatctctagc   4740
agtagtagtt catgtcatct tattattcag tatttataac ttgcaaagaa atgaatatca   4800
gagagtgaga ggaacttgtt tattgcagct tataatggtt acaaataaag caatagcatc   4860
acaaatttca caaataaagc attttttca ctgcattcta gttgtggttt gtccaaactc   4920
atcaatgtat cttatcatgt ctggctctag ctatcccgcc cctaactccg cccatcccgc   4980
ccctaactcc gcccagttcc gcccattctc cgccccatgg ctgactaatt ttttttattt   5040
atgcagaggc cgaggccgcc tcggcctctg agctattcca gaagtagtga ggaggctttt   5100
ttggaggcct agggacgtac ccaattcgcc ctatagtgag tcgtattacg cgcgctcact   5160
ggccgtcgtt ttacaacgtc gtgactggga aaaccctggc gttacccaac ttaatcgcct   5220
tgcagcacat ccccctttcg ccagctggcg taatagcgaa gaggcccgca ccgatcgccc   5280
ttcccaacag ttgcgcagcc tgaatggcga atgggacgcg ccctgtagcg gcgcattaag   5340
cgcggcgggt gtggtggtta cgcgcagcgt gaccgctaca cttgccagcg ccctagcgcc   5400
cgctcctttc gctttcttcc cttcctttct cgccacgttc gccggctttc ccgtcaagc   5460 tctaaatcgg gggctccctt tagggttccg atttagtgct ttacggcacc tcgaccccaa   5520
```

```
aaaacttgat tagggtgatg gttcacgtag tgggccatcg ccctgataga cggttttcg    5580
cccttgacg ttggagtcca cgttcttaa tagtggactc ttgttccaaa ctggaacaac    5640
actcaaccct atctcggtct attcttttga tttataaggg attttgccga tttcggccta    5700
ttggttaaaa aatgagctga tttaacaaaa atttaacgcg aattttaaca aaatattaac    5760
gcttacaatt taggtggcac ttttcgggga aatgtgcgcg gaaccccctat tgtttattt    5820
ttctaaatac attcaaatat gtatccgctc atgagacaat aaccctgata aatgcttcaa    5880
taatattgaa aaggaagag tatgagccat attcaacggg aaacgtcttg ctctaggccg    5940
cgattaaatt ccaacatgga tgctgattta tgggtata aatgggctcg cgataatgtc    6000
gggcaatcag gtgcgacaat ctatcgattg tatgggaagc ccgatgcgcc agagttgttt    6060
ctgaaacatg gcaaaggtag cgttgccaat gatgttacag atgagatggt cagactaaac    6120
tggctgacgg aatttatgcc tcttccgacc atcaagcatt ttatccgtac tcctgatgat    6180
gcatggttac tcaccactgc gatcccggg aaaacagcat tccaggtatt agaagaatat    6240
cctgattcag gtgaaaatat tgttgatgcg ctggcagtgt tcctgcgccg gttgcattcg    6300
attcctgttt gtaattgtcc ttttaacagc gatcgcgtat ttcgtctggc tcaggcgcaa    6360
tcacgaatga ataacggttt ggttgatgcg agtgattttg atgacgagcg taatggctgg    6420
cctgttgaac aagtctggaa agaaatgcat aaacttttgc cattctcacc ggattcagtc    6480
gtcactcatg gtgatttctc acttgataac cttatttttg acgagggaa attaataggt    6540
tgtattgatg ttggacgagt cggaatcgca gaccgatacc aggatcttgc catcctatgg    6600
aactgcctcg gtgagttttc tccttcatta cagaaacggc ttttcaaaa atatggtatt    6660
gataatcctg atatgaataa attgcagttt catttgatgc tcgatgagtt tttctaactg    6720
tcagaccaag tttactcata tatactttag attgatttaa aacttcattt ttaatttaaa    6780
aggatctagg tgaagatcct ttttgataat ctcatgacca aaatccctta acgtgagttt    6840
tcgttccact gagcgtcaga ccccgtagaa aagatcaaag gatcttcttg agatcctttt    6900
tttctgcgcg taatctgctg cttgcaaaca aaaaaaccac cgctaccagc ggtggttttgt    6960
ttgccggatc aagagctacc aactcttttt ccgaaggtaa ctggcttcag cagagcgcag    7020
ataccaaata ctgttcttct agtgtagccg tagttaggcc accacttcaa gaactctgta    7080
gcaccgccta catacctcgc tctgctaatc ctgttaccag tggctgctgc cagtggcgat    7140
aagtcgtgtc ttaccgggtt ggactcaaga cgatagttac cggataaggc gcagcggtcg    7200
ggctgaacgg ggggttcgtg cacacagccc agcttggagc gaacgaccta caccgaactg    7260
agatacctac agcgtgagct atgagaaagc gccacgcttc ccgaagggag aaaggcggac    7320
aggtatccgg taagcggcag ggtcggaaca ggagagcgca cgagggagct tccaggggga    7380
aacgcctggt atctttatag tcctgtcggg tttcgccacc tctgacttga gcgtcgattt    7440
ttgtgatgct cgtcaggggg gcggagccta tggaaaaacg ccagcaacgc ggccttttta    7500
cggttcctgg ccttttgctg gccttttgct cacatgttct ttcctgcgtt atcccctgat    7560
tctgtggata accgtattac cgcctttgag tgagctgata ccgctcgccg cagccgaacg    7620
accgagcgca gcgagtcagt gagcgaggaa gcggaagagc gcccaatacg caaaccgcct    7680
ctccccgcgc gttggccgat tcattaatgc agctggcacg acaggtttcc cgactggaaa    7740
gcgggcagtg agcgcaacgc aattaatgtg agttagctca ctcattaggc accccaggct    7800
ttacacttta tgcttccggc tcgtatgttg tgtggaattg tgagcggata acaatttcac    7860
```

```
acaggaaaca gctatgacca tgattacgcc aagcgcgcaa ttaaccctca ctaaagggaa    7920
caaaagctgg agctgcaagc ttaatgtagt cttatgcaat actcttgtag tcttgcaaca    7980
tggtaacgat gagttagcaa catgccttac aaggagagaa aaagcaccgt gcatgccgat    8040
tggtggaagt aaggtggtac gatcgtgcct tattaggaag gcaacagacg ggtctgacat    8100
ggattggacg aaccactgaa ttgccgcatt gcagagatat tgtatttaag tgcctagctc    8160
gatacataaa cgggtctctc tggttagacc agatctgagc ctgggagctc tctggctaac    8220
tagggaaccc actgcttaag cctcaataaa gcttgccttg agtgcttcaa gtagtgtgtg    8280
cccgtctgtt gtgtgactct ggtaactaga tccctcag acccttttag tcagtgtgga    8340
aaatctctag cagtggcgcc cgaacaggga cttgaaagcg aaagggaaac cagaggagct    8400
ctctcgacgc aggactcggc ttgctgaagc gcgcacggca agaggcgagg ggcggcgact    8460
ggtgagtacg ccaaaaattt tgactagcgg aggctagaag gagagagatg ggtgcgagag    8520
cgtcagtatt aagcggggga gaattagatc gcgatgggaa aaaattcggt taaggccagg    8580
gggaaagaaa aaatataaat taaaacatat agtatgggca agcagggagc tagaacgatt    8640
cgcagttaat cctggcctgt tagaaacatc agaaggctgt agacaaatac tgggacagct    8700
acaaccatcc cttcagacag gatcagaaga acttagatca ttatataata cagtagcaac    8760
cctctattgt gtgcatcaaa ggatagagat aaaagacacc aaggaagctt tagacaagat    8820
agaggaagag caaaacaaaa gtaagaccac cgcacagcaa gcggccgctg atcttcagac    8880
ctggaggagg agatatgagg gacaattgga gaagtgaatt atataaatat aaagtagtaa    8940
aaattgaacc attaggagta gcacccacca aggcaaagag aagagtggtg cagagagaaa    9000
aaagagcagt gggaatagga gctttgttcc ttgggttctt gggagcagca ggaagcacta    9060
tgggcgcagc gtcaatgacg ctgacggtac aggccagaca attattgtct ggtatagtgc    9120
agcagcagaa caatttgctg agggctattg aggcgcaaca gcatctgttg caactcacag    9180
tctggggcat caagcagctc caggcaagaa tcctggctgt ggaaagatac ctaaaggatc    9240
aacagctcct ggggatttgg ggttgctctg gaaaactcat ttgcaccact gctgtgcctt    9300
ggaatgctag ttggagtaat aaatctctgg aacagatttg gaatcacacg acctggatgg    9360
agtgggacag agaaattaac aattacacaa gcttaataca ctccttaatt gaagaatcgc    9420
aaaaccagca agaaaagaat gaacaagaat tattggaatt agataaatgg gcaagtttgt    9480
ggaattggtt taacataaca aattggctgt ggtatataaa attattcata atgatagtag    9540
gaggcttggt aggtttaaga atagtttttg ctgtactttc tatagtgaat agagttaggc    9600
agggatattc accattatcg tttcagaccc acctcccaac cccgagggga cccgacaggc    9660
ccgaaggaat agaagaagaa ggtggagaga gagacagaga cagatccatt cgattagtga    9720
acggatctcg acggtatcga tcacgagact agcctcgaca caaatggcag tattcatcca    9780
caatttaaaa agaaaagggg ggattggggg gtacagtgca ggggaaagaa tagtagacat    9840
aatagcaaca gacatacaaa ctaaagaatt acaaaaacaa attacaaaaa ttcaaaattt    9900
tcgggtttat tacagggaca gcagaaatcc actttggctc gagaagcttg atat        9954
```

<210> SEQ ID NO 133
<211> LENGTH: 10914
<212> TYPE: DNA
<213> ORGANISM: Homo sapiens

<400> SEQUENCE: 133

```
gggcagagcg cacatcgccc acagtccccg agaagttggg gggaggggtc ggcaattgaa      60
```

```
ccggtgccta gagaaggtgg cgcggggtaa actgggaaag tgatgtcgtg tactggctcc      120 gccttttttcc cgagggtggg ggagaaccgt atataagtgc agtagtcgcc gtgaacgttc     180
tttttcgcaa cgggtttgcc gccagaacac aggtaagtgc cgtgtgtggt tcccgcgggc     240
ctggcctctt tacgggttat ggcccttgcg tgccttgaat tacttccacc tggctgcagt     300
acgtgattct tgatcccgag cttcgggttg aagtgggtg ggagagttcg aggccttgcg      360
cttaaggagc cccttcgcct cgtgcttgag ttgaggcctg gcctgggcgc tggggccgcc     420
gcgtgcgaat ctggtggcac cttcgcgcct gtctcgctgc tttcgataag tctctagcca     480
tttaaaattt ttgatgacct gctgcgacgc ttttttttctg gcaagatagt cttgtaaatg    540
cgggccaaga tctgcacact ggtatttcgg tttttgggc cgcgggcggc gacggggccc      600
gtgcgtccca gcgcacatgt tcggcgaggc ggggcctgcg agcgcggcca ccgagaatcg     660
gacgggggta gtctcaagct ggccggcctg ctctggtgcc tggcctcgcg ccgccgtgta     720
tcgccccgcc ctgggcggca aggctggccc ggtcggcacc agttgcgtga gcggaaagat     780
ggccgcttcc cggccctgct gcagggagct caaaatggag gacgcggcgc tcgggagagc     840
gggcgggtga gtcacccaca caaaggaaaa gggccttttcc gtcctcagcc gtcgcttcat    900
gtgactccac ggagtaccgg gcgccgtcca ggcacctcga ttagttctcg agcttttgga    960
gtacgtcgtc tttaggttgg ggggagggggt tttatgcgat ggagtttccc cacactgagt   1020
gggtggagac tgaagttagg ccagcttggc acttgatgta attctccttg gaatttgccc    1080 ttttgagtt tggatcttgg ttcattctca agcctcagac agtggttcaa agttttttc      1140 ttccatttca ggtgtcgtga ggatccgcca ccatggcctt accagtgacc gccttgctcc    1200
tgccgctggc cttgctgctc cacgccgcca ggccggatat ccagatgacc cagagcccga   1260
gcagcctgag cgcgagcgtg ggtgatcgcg tgaccattac ctgcagggca agtcaggaca   1320
ttagtaaata tttaaattgg tatcagcaga aaccgggtaa agcgccgaaa ctgttaattt    1380
atcatacatc aagattacac tcaggcgtgc cgtcgcgttt tagcggctcg ggttcgggca    1440
ccgattttac cctgaccatc tcgagcttgc agcggagga cttcgccacc tactattgcc    1500
aacagggtaa tacgcttccg tacacgttcg gtcagggcac caaagtggag atcaaaggtg    1560
gcggtggctc gggcggtggt gggtcgggtg gcggcggatc tgaggtgcag ctggtggagt   1620
ctgggggagg cttggtacag cctggggggt ccctgagact ctcctgtgca gcctctggag   1680
tgtccctgcc tgattatggc gtgtcctggg tccgccaggc tccagggaag gggctggagt    1740
gggtttcagt gatctggggc agcgagacaa cctactacaa cagcgccctg aagtcccgat    1800
tcaccatctc cagagacaat gccaagaact cactgtatct gcaaatgaac agcctgagag    1860
ccgaggacac ggctgtgtat tactgtgcga agcactacta ctacggcggc agctacgcta   1920
tggactactg gggccaagga accctggtca ccgtgtcctc aaccacgacg ccagcgccgc   1980
gaccaccaac accggcgccc accatcgcgt cgcagcccct gtccctgcgc ccagaggcgt   2040
gccggccagc ggcggggggc gcagtgcaca cgagggggct ggacttcgcc tgtgattttt   2100
gggtgctggt ggtggttggt ggagtcctgg cttgctatag cttgctagta acagtggcct   2160
ttattatttt ctgggtgagg agtaagagga gcaggctcct gcacagtgac tacatgaaca   2220
tgactccccg ccgccccggg cccacccgca agcattacca gccctatgcc ccaccacgcg   2280
acttcgcagc ctatcgctcc agagtgaagt tcagcaggag cgcagacgcc cccgcgtacc    2340
agcagggcca gaaccagctc tataacgagc tcaatctagg acgaagagag gagtacgatg   2400
```

```
ttttggacaa gaggcgtggc cgggaccctg agatgggggg aaagccgaga aggaagaacc    2460
ctcaggaagg cctgtacaat gaactgcaga aagataagat ggcggaggcc tacagtgaga    2520
ttgggatgaa aggcgagcgc cggaggggca aggggcacga tggcctttac cagggtctca    2580
gtacagccac caaggacacc tacgacgccc ttcacatgca ggccctgccc cctcgcggtt    2640
ccggagccac gaacttctct ctgttaaagc aagcaggaga cgtggaagaa aaccccggtc    2700
ctggatccgc caccatggcc agagctatgg ctgccgcttg gcctctgctg ctcgtcgctc    2760
tgctcgtgct gagctggcct ccccccggca ccggcgatgt ggtcgtgcaa gcccctaccc    2820
aagtgcccgg ctttctgggc gactccgtca cactgccttg ctacctccaa gtgcccaaca    2880
tggaggtcac ccacgtgagc cagctcacat gggccagaca tggcgaaagc ggaagcatgg    2940
ccgtgttcca ccagacccaa ggcccctcct acagcgaaag caagagactc gagtttgtgg    3000
ccgctagact cggagctgag ctcagaaacg cttctctgag gatgtttgga ctgagagtcg    3060
aagacgaagg caactacaca tgcctctttg tgaccttttcc tcaaggctcc agaagcgtcg    3120
atatttggct cagagtgctc gccaagcccc aaaacacagc cgaggtccaa aaagtgcagc    3180
tcaccggcga accgtgccc atggctagat gtgtctccac cggcggcaga ccccccgccc    3240
aaattacatg gcacagcgat ctgggcggca tgcctaacac aagccaagtg cccggctttc    3300
tgagcggcac agtgacagtg acaagcctct ggattctggt gcccagctcc caagtggacg    3360
gcaagaacgt gacatgcaag gtggaacacg aatccttcga gaaacccag ctgctcaccg    3420
tgaacctcac agtctactat ccccccgagg tgagcatcag cggctacgac aacaattggt    3480
acctcggcca gaacgaggct accctcacat gcgacgctag aagcaacccc gagcccaccg    3540
gctacaactg gtccaccacc atgggccccc tccctcccct tgctgtggcc aaggcgctc    3600
agctgctgat taggcccgtg ataagcccca tcaacaccac actgatctgc aacgtgacca    3660
atgctctggg agctaggcaa gccgaactga ccgtccaagt gaaggaaggc cctccctccg    3720
agcattccgg catctctagg aacgctatta tcttttctggt cctcggcatc ctcgtgtttc    3780
tgattctgct cggcatcggc atctacttct actggagcaa gtgttctagg gaggtgctgt    3840
ggcactgtca tctgtgcccc tccagcaccg aacatgcctc cgctagcgct aatggccacg    3900
tgagctacag cgctgtgtct agggaaaaca gcagctccca agacccccag acagaaggaa    3960
caagaggaag cggcgccacc aacttctctc tgctgaaaca agccggcgac gtggaggaaa    4020
atcccggccc tatggtgtcc aagggcgagg aactctttac cggagtggtc cctatcctcg    4080
tggagctgga cggcgatgtg aacggccaca aatttagcgt ctccggcgaa ggcgagggag    4140
atgccaccta cggcaaactc acactgaagt tcatctgcac caccggaaaa ctgcccgtgc    4200
cttggcccac actggtgaca accctcacct acggagtgca gtgcttttct aggtaccccg    4260
accacatgaa gcagcacgac ttttttaagt ccgccatgcc cgagggatac gtccaagaga    4320
gaaccatctt tttcaaggat gacggcaact acaagacaag agccgaagtc aagttcgagg    4380
gcgataccct cgtgaataga atcgagctga agggaatcga cttcaaagag gacggaaata    4440
ttctgggcca caaactggag tacaactaca acagccataa tgtctacatt atggctgata    4500
agcagaagaa tggaattaag gtgaatttta agatcagaca caatatcgag gacggctccg    4560
tgcagctggc tgaccactat caacagaaca cccctattgg agacggaccc gtgctgctcc    4620
ccgacaatca ctacctctcc acacagagcg ctctcagcaa agaccccaat gagaagaggg    4680
accatatggt gctgctcgaa tttgtcaccg ccgctggcat taccctcggc atggacgagc    4740
tctataagtg agtcgactct agaactagtg tcgactctag aactagtaat caacctctgg    4800
```

```
attacaaaat tgtgaaaga ttgactggta ttcttaacta tgttgctcct tttacgctat    4860
gtggatacgc tgctttaatg cctttgtatc atgctattgc ttcccgtatg gctttcattt    4920
tctcctcctt gtataaatcc tggttgctgt ctctttatga ggagttgtgg cccgttgtca    4980
ggcaacgtgg cgtggtgtgc actgtgtttg ctgacgcaac ccccactggt tggggcattg    5040
ccaccacctg tcagctcctt tccgggactt tcgctttccc cctccctatt gccacggcgg    5100
aactcatcgc cgcctgcctt gcccgctgct ggacaggggc tcggctgttg ggcactgaca    5160
attccgtggt gttgtcgggg aaatcatcgt cctttccttg gctgctcgcc tgtgttgcca    5220
cctggattct gcgcgggacg tccttctgct acgtcccttc ggcctcaat ccagcggacc     5280
ttccttcccg cggcctgctg ccggctctgc ggcctcttcc gcgtcttcgc cttcgccctc    5340
agacgagtcg gatctccctt gggccgcct ccccgcctgc cgcggaattc gagctcggta     5400
cctttaagac caatgactta caaggcagct gtagatctta gccactttt aaaagaaaag     5460
gggggactaa aagggctaat tcactcccaa cgaagacaag atctgctttt tgcttgtact    5520
gggtctctct ggttagacca gatctgagcc tgggagctct ctggctaact agggaaccca    5580
ctgcttaagc ctcaataaag cttgccttga gtgcttcaag tagtgtgtgc ccgtctgttg    5640
tgtgactctg gtaactagag atccctcaga ccctttagt cagtgtggaa aatctctagc     5700
agtagtagtt catgtcatct tattattcag tatttataac ttgcaaagaa atgaatatca    5760
gagagtgaga ggaacttgtt tattgcagct tataatggtt acaaataaag caatagcatc    5820
acaaatttca caaataaagc attttttca ctgcattcta gttgtggttt gtccaaactc     5880
atcaatgtat cttatcatgt ctggctctag ctatcccgcc cctaactccg cccatcccgc    5940
ccctaactcc gcccagttcc gcccattctc cgccccatgg ctgactaatt ttttttattt    6000
atgcagaggc cgaggccgcc tcggcctctg agctattcca gaagtagtga ggaggctttt    6060
ttggaggcct agggacgtac ccaattcgcc ctatagtgag tcgtattacg cgcgctcact    6120
ggccgtcgtt ttacaacgtc gtgactggga aaaccctggc gttacccaac ttaatcgcct    6180
tgcagcacat ccccctttcg ccagctggcg taatagcgaa gaggcccgca ccgatcgccc    6240
ttcccaacag ttgcgcagcc tgaatggcga atgggacgcg ccctgtagcg cgcattaag    6300
cgcggcgggt gtggtggtta cgcgcagcgt gaccgctaca cttgccagcg ccctagcgcc    6360
cgctcctttc gctttcttcc cttcctttct cgccacgttc gccggctttc cccgtcaagc    6420
tctaaatcgg gggctccctt tagggttccg atttagtgct ttacggcacc tcgaccccaa    6480
aaaacttgat tagggtgatg gttcacgtag tgggccatcg ccctgataga cggttttcg     6540
cccttttgacg ttggagtcca cgttctttaa tagtggactc ttgttccaaa ctggaacaac    6600
actcaaccct atctcggtct attctttga tttataaggg attttgccga tttcggccta     6660
ttggttaaaa aatgagctga tttaacaaaa atttaacgcg aattttaaca aaatattaac    6720
gcttacaatt taggtggcac ttttcgggga aatgtgcgcg gaacccctat tgtttatttt    6780
ttctaaatac attcaaatat gtatccgctc atgagacaat aaccctgata aatgcttcaa    6840
taatattgaa aaaggaagag tatgagccat attcaacggg aaacgtcttg ctctaggccg    6900
cgattaaatt ccaacatgga tgctgattta tatgggtata aatgggctcg cgataatgtc    6960
gggcaatcag gtgcgacaat ctatcgattg tatgggaagc ccgatgcgcc agagttgttt    7020
ctgaaacatg gcaaaggtag cgttgccaat gatgttacag atgagatggt cagactaaac    7080
tggctgacgg aatttatgcc tcttccgacc atcaagcatt ttatccgtac tcctgatgat    7140
```

```
gcatggttac tcaccactgc gatccccggg aaaacagcat tccaggtatt agaagaatat   7200
cctgattcag gtgaaaatat tgttgatgcg ctggcagtgt tcctgcgccg gttgcattcg   7260
attcctgttt gtaattgtcc ttttaacagc gatcgcgtat ttcgtctggc tcaggcgcaa   7320
tcacgaatga ataacggttt ggttgatgcg agtgattttg atgacgagcg taatggctgg   7380
cctgttgaac aagtctggaa agaaatgcat aaacttttgc cattctcacc ggattcagtc   7440
gtcactcatg gtgatttctc acttgataac cttatttttg acgaggggaa attaataggt   7500
tgtattgatg ttggacgagt cggaatcgca gaccgatacc aggatcttgc catcctatgg   7560
aactgcctcg gtgagttttc tccttcatta cagaaacggc ttttcaaaa atatggtatt    7620 gataatcctg atatgaataa attgcagttt catttgatgc tcgatgagtt tttctaactg   7680
tcagaccaag tttactcata tactttag attgatttaa aacttcattt ttaatttaaa      7740
aggatctagg tgaagatcct ttttgataat ctcatgacca aaatccctta acgtgagttt   7800
tcgttccact gagcgtcaga ccccgtagaa aagatcaaag gatcttcttg agatcctttt   7860
tttctgcgcg taatctgctg cttgcaaaca aaaaaaccac cgctaccagc ggtggtttgt   7920
ttgccggatc aagagctacc aactcttttt ccgaaggtaa ctggcttcag cagagcgcag   7980
ataccaaata ctgttcttct agtgtagccg tagttaggcc accacttcaa gaactctgta   8040
gcaccgccta catacctcgc tctgctaatc ctgttaccag tggctgctgc cagtggcgat   8100
aagtcgtgtc ttaccgggtt ggactcaaga cgatagttac cggataaggc gcagcggtcg   8160
ggctgaacgg ggggttcgtg cacacagccc agcttggagc gaacgaccta caccgaactg   8220
agatacctac agcgtgagct atgagaaagc gccacgcttc ccgaagggag aaaggcggac   8280
aggtatccgg taagcggcag ggtcggaaca ggagagcgca cgagggagct tccaggggga   8340
aacgcctggt atctttatag tcctgtcggg tttcgccacc tctgacttga gcgtcgattt   8400
ttgtgatgct cgtcaggggg gcggagccta tggaaaaacg ccagcaacgc ggccttttta   8460
cggttcctgg ccttttgctg ccttttgct cacatgttct ttcctgcgtt atcccctgat    8520
tctgtggata accgtattac cgcctttgag tgagctgata ccgctcgccg cagccgaacg   8580
accgagcgca gcgagtcagt gagcgaggaa gcggaagagc gcccaatacg caaaccgcct   8640
ctccccgcgc gttggccgat tcattaatgc agctggcacg acaggtttcc cgactggaaa   8700 gcggcagtg agcgcaacgc aattaatgtg agttagctca ctcattaggc accccaggct    8760
ttacacttta tgcttccggc tcgtatgttg tgtggaattg tgagcggata acaatttcac   8820
acaggaaaca gctatgacca tgattacgcc aagcgcgcaa ttaaccctca ctaaagggaa   8880
caaaagctgg agctgcaagc ttaatgtagt cttatgcaat actcttgtag tcttgcaaca   8940
tggtaacgat gagttagcaa catgccttac aaggagagaa aaagcaccgt gcatgccgat   9000
tggtggaagt aaggtggtac gatcgtgcct tattaggaag gcaacagacg ggtctgacat   9060
ggattggacg aaccactgaa ttgccgcatt gcagagatat tgtatttaag tgcctagctc   9120
gatacataaa cgggtctctc tggttagacc agatctgagc ctgggagctc tctggctaac   9180
tagggaaccc actgcttaag cctcaataaa gcttgccttg agtgcttcaa gtagtgtgtg   9240
cccgtctgtt gtgtgactct ggtaactaga gatccctcag accctttag tcagtgtgga    9300 aaatctctag cagtggcgcc cgaacaggga cttgaaagcg aaagggaaac cagaggagct   9360
ctctcgacgc aggactcggc ttgctgaagc gcgcacggca agaggcgagg ggcggcgact   9420
ggtgagtacg ccaaaaattt tgactagcgg aggctagaag gagagagatg ggtgcgagag   9480
cgtcagtatt aagcggggga gaattagatc gcgatgggaa aaaattcggt taaggccagg   9540
```

```
gggaaagaaa aaatataaat taaaacatat agtatgggca agcagggagc tagaacgatt    9600
cgcagttaat cctggcctgt tagaaacatc agaaggctgt agacaaatac tgggacagct    9660
acaaccatcc cttcagacag gatcagaaga acttagatca ttatataata cagtagcaac    9720
cctctattgt gtgcatcaaa ggatagagat aaaagacacc aaggaagctt tagacaagat    9780
agaggaagag caaaacaaaa gtaagaccac cgcacagcaa gcggccgctg atcttcagac    9840
ctggaggagg agatatgagg gacaattgga gaagtgaatt atataaatat aaagtagtaa    9900
aaattgaacc attaggagta gcacccacca aggcaaagag aagagtggtg cagagagaaa    9960
aaagagcagt gggaatagga gctttgttcc ttgggttctt gggagcagca ggaagcacta   10020
tgggcgcagc gtcaatgacg ctgacggtac aggccagaca attattgtct ggtatagtgc   10080
agcagcagaa caatttgctg agggctattg aggcgcaaca gcatctgttg caactcacag   10140 tctgggcat caagcagctc caggcaagaa tcctggctgt ggaaagatac ctaaaggatc   10200
aacagctcct ggggatttgg ggttgctctg gaaaactcat ttgcaccact gctgtgcctt   10260
ggaatgctag ttggagtaat aaatctctgg aacagatttg gaatcacacg acctggatgg   10320
agtgggacag agaaattaac aattacacaa gcttaataca ctccttaatt gaagaatcgc   10380
aaaaccagca agaaaagaat gaacaagaat tattggaatt agataaatgg gcaagtttgt   10440
ggaattggtt taacataaca aattggctgt ggtatataaa attattcata atgatagtag   10500
gaggcttggt aggtttaaga atagtttttg ctgtactttc tatagtgaat agagttaggc   10560
agggatattc accattatcg tttcagaccc acctcccaac cccgagggga cccgacaggc   10620
ccgaaggaat agaagaagaa ggtggagaga gagacagaga cagatccatt cgattagtga   10680
acggatctcg acggtatcga tcacgagact agcctcgaca caaatggcag tattcatcca   10740
caattttaaa agaaaagggg ggattggggg gtacagtgca ggggaaagaa tagtagacat   10800
aatagcaaca gacatacaaa ctaaagaatt acaaaaacaa attacaaaaa ttcaaaattt   10860
tcgggtttat tacagggaca gcagaaatcc actttggctc gagaagcttg atat         10914
```